United States Patent
Hassanein et al.

(10) Patent No.: US 8,535,934 B2
(45) Date of Patent: Sep. 17, 2013

(54) SYSTEMS AND METHODS FOR EX VIVO ORGAN CARE

(75) Inventors: Waleed Hassanein, North Andover, MA (US); Tamer Khayal, North Andover, MA (US); Robert Havener, Lynnfield, MA (US); Stanley Kyi, Andover, MA (US); Ihab Abdel Fattah, North Andover, MA (US); Hesham Saleh, S. Lawrence, MA (US); Jon Trachtenberg, Andover, MA (US)

(73) Assignee: TransMedics, Inc., Andover, MA (US)

( * ) Notice: Subject to any disclaimer, the term of this patent is extended or adjusted under 35 U.S.C. 154(b) by 909 days.

(21) Appl. No.: 11/788,865

(22) Filed: Apr. 19, 2007

(65) Prior Publication Data

US 2008/0017194 A1    Jan. 24, 2008

Related U.S. Application Data

(60) Provisional application No. 60/793,472, filed on Apr. 19, 2006.

(51) Int. Cl.
| | | |
|---|---|---|
| *A01N 1/00* | (2006.01) | |
| *A01N 1/02* | (2006.01) | |
| *C12M 1/36* | (2006.01) | |
| *C12M 1/38* | (2006.01) | |
| *C12M 3/00* | (2006.01) | |
| *C12M 1/00* | (2006.01) | |
| *C12M 1/12* | (2006.01) | |

(52) U.S. Cl.
USPC ............ 435/284.1; 435/286.5; 435/286.6; 435/307.1; 435/297.2

(58) Field of Classification Search
USPC ..................................... 435/283.1–309.4
See application file for complete search history.

(56) References Cited

U.S. PATENT DOCUMENTS

| 3,388,803 A | 6/1968 | Scott |
| 3,537,956 A | 11/1970 | Falcone |
| 3,738,914 A | 6/1973 | Thorne et al. |
| 3,995,444 A | 12/1976 | Clark et al. |
| 4,231,354 A | 11/1980 | Kurtz et al. |
| 4,415,556 A | 11/1983 | Bretschneider et al. |
| 4,598,697 A | 7/1986 | Numazawa et al. |
| 4,605,644 A | 8/1986 | Foker |
| 4,666,425 A | 5/1987 | Fleming |
| 4,719,201 A | 1/1988 | Foker |

(Continued)

FOREIGN PATENT DOCUMENTS

| DE | 4201259 A1 | 7/1993 |
| DE | 10121159 | 11/2002 |

(Continued)

OTHER PUBLICATIONS

Brandes, H. et al. "Influence of high molecular dextrans on lung function in an ex vivo porcine lung model," J. of Surgical Research, 101:2, 225-231 (2001).

(Continued)

*Primary Examiner* — Nathan Bowers
*Assistant Examiner* — Lydia Edwards
(74) *Attorney, Agent, or Firm* — Wilmer Cutler Pickering Hale and Dorr LLP

(57) ABSTRACT

The invention, in various embodiments, provides systems, methods and solutions using an organ ex vivo.

19 Claims, 89 Drawing Sheets

(56) References Cited

U.S. PATENT DOCUMENTS

| | | |
|---|---|---|
| 4,759,371 A | 7/1988 | Franetzki |
| 4,847,470 A | 7/1989 | Bakke |
| 4,920,044 A | 4/1990 | Bretan, Jr. |
| 5,051,352 A | 9/1991 | Martindale et al. |
| 5,066,578 A | 11/1991 | Wikman-Coffelt |
| 5,141,847 A | 8/1992 | Sugimachi et al. |
| 5,145,771 A | 9/1992 | Lemasters et al. |
| 5,200,398 A | 4/1993 | Strasberg et al. |
| 5,217,860 A | 6/1993 | Fahy et al. |
| 5,285,657 A | 2/1994 | Bacchi et al. |
| 5,306,711 A | 4/1994 | Andrews |
| 5,326,706 A | 7/1994 | Yland et al. |
| 5,338,662 A | 8/1994 | Sadri |
| 5,356,593 A | 10/1994 | Heiberger et al. |
| 5,356,771 A | 10/1994 | O'Dell |
| 5,362,622 A | 11/1994 | O'Dell et al. |
| 5,370,989 A | 12/1994 | Stern et al. |
| 5,381,510 A | 1/1995 | Ford et al. |
| 5,385,821 A | 1/1995 | O'Dell et al. |
| 5,405,742 A | 4/1995 | Taylor |
| 5,407,669 A | 4/1995 | Lindstrom et al. |
| 5,407,793 A | 4/1995 | Del Nido et al. |
| 5,472,876 A | 12/1995 | Fahy |
| 5,494,822 A | 2/1996 | Sadri |
| 5,498,427 A | 3/1996 | Menasche et al. |
| 5,505,709 A | 4/1996 | Funderburk et al. |
| 5,514,536 A | 5/1996 | Taylor |
| 5,552,267 A | 9/1996 | Stern et al. |
| 5,554,497 A | 9/1996 | Raymond |
| 5,571,801 A | 11/1996 | Segall et al. |
| 5,586,438 A | 12/1996 | Fahy |
| 5,588,816 A | 12/1996 | Abbott et al. |
| 5,599,173 A | 2/1997 | Chen et al. |
| 5,599,659 A | 2/1997 | Brasile et al. |
| 5,613,944 A | 3/1997 | Segall et al. |
| 5,643,712 A | 7/1997 | Brasile |
| 5,656,420 A | 8/1997 | Chien |
| 5,679,565 A | 10/1997 | Mullen et al. |
| 5,693,462 A | 12/1997 | Raymond |
| 5,698,536 A | 12/1997 | Segall et al. |
| 5,699,793 A | 12/1997 | Brasile |
| 5,702,881 A | 12/1997 | Brasile et al. |
| 5,716,378 A | 2/1998 | Minten |
| 5,723,281 A | 3/1998 | Segall et al. |
| 5,733,894 A | 3/1998 | Segall et al. |
| 5,747,071 A | 5/1998 | Segall et al. |
| 5,770,149 A | 6/1998 | Raible |
| 5,786,136 A | 7/1998 | Mayer et al. |
| 5,807,737 A | 9/1998 | Schill et al. |
| 5,823,799 A | 10/1998 | Tor et al. |
| 5,843,024 A | 12/1998 | Brasile |
| 6,024,698 A | 2/2000 | Brasile |
| 6,042,550 A | 3/2000 | Haryadi et al. |
| 6,046,046 A * | 4/2000 | Hassanein ............. 435/284.1 |
| 6,100,082 A | 8/2000 | Hassanein |
| 6,110,139 A | 8/2000 | Loubser |
| 6,110,504 A | 8/2000 | Segall et al. |
| 6,144,444 A | 11/2000 | Haworth et al. |
| 6,168,877 B1 | 1/2001 | Pedicini et al. |
| 6,365,338 B1 | 4/2002 | Bull et al. |
| 6,375,611 B1 | 4/2002 | Voss et al. |
| 6,375,613 B1 | 4/2002 | Brasile |
| 6,389,308 B1 | 5/2002 | Shusterman |
| 6,475,716 B1 | 11/2002 | Seki |
| 6,490,880 B1 | 12/2002 | Walsh |
| 6,492,103 B1 | 12/2002 | Taylor |
| 6,492,745 B1 | 12/2002 | Colley, III et al. |
| 6,524,785 B1 | 2/2003 | Cozzone et al. |
| 6,569,615 B1 | 5/2003 | Thatte et al. |
| 6,582,953 B2 | 6/2003 | Brasile |
| 6,600,941 B1 | 7/2003 | Khuri |
| 6,609,987 B1 | 8/2003 | Beardmore |
| 6,642,045 B1 | 11/2003 | Brasile |
| 6,673,594 B1 | 1/2004 | Owen et al. |
| 6,696,238 B2 | 2/2004 | Murphy et al. |
| 6,783,328 B2 | 8/2004 | Lucke et al. |
| 6,794,124 B2 | 9/2004 | Steen et al. |
| 6,811,965 B2 | 11/2004 | Vodovotz et al. |
| 6,925,324 B2 | 8/2005 | Shusterman |
| 7,238,165 B2 | 7/2007 | Vincent et al. |
| 7,316,666 B1 | 1/2008 | Entenman et al. |
| 7,452,711 B2 | 11/2008 | Daykin |
| 2001/0003652 A1 | 6/2001 | Freeman |
| 2002/0012988 A1* | 1/2002 | Brasile ............... 435/284.1 |
| 2002/0102720 A1 | 8/2002 | Steen |
| 2002/0164795 A1 | 11/2002 | Gen |
| 2002/0177117 A1 | 11/2002 | Wolf |
| 2003/0011604 A1 | 1/2003 | Capers |
| 2003/0040665 A1 | 2/2003 | Khuri et al. |
| 2003/0050689 A1 | 3/2003 | Matson |
| 2003/0053998 A1 | 3/2003 | Daemen et al. |
| 2003/0073227 A1 | 4/2003 | Hull et al. |
| 2003/0086830 A1 | 5/2003 | Haywood et al. |
| 2003/0135152 A1 | 7/2003 | Kollar et al. |
| 2003/0147466 A1 | 8/2003 | Liang |
| 2004/0018966 A1 | 1/2004 | Segall et al. |
| 2004/0029096 A1 | 2/2004 | Steen |
| 2004/0038192 A1 | 2/2004 | Brasile |
| 2004/0058432 A1 | 3/2004 | Owen et al. |
| 2004/0082057 A1 | 4/2004 | Alford et al. |
| 2004/0086578 A1 | 5/2004 | Segall et al. |
| 2004/0102415 A1 | 5/2004 | Thatte et al. |
| 2004/0102678 A1 | 5/2004 | Haindl |
| 2004/0110800 A1 | 6/2004 | Bril et al. |
| 2004/0115689 A1 | 6/2004 | Augello et al. |
| 2004/0138542 A1 | 7/2004 | Khuri et al. |
| 2004/0168341 A1 | 9/2004 | Petersen et al. |
| 2004/0170950 A1 | 9/2004 | Prien |
| 2004/0171138 A1 | 9/2004 | Hassanein et al. |
| 2004/0202993 A1 | 10/2004 | Poo et al. |
| 2004/0224298 A1 | 11/2004 | Brassil et al. |
| 2004/0235142 A1 | 11/2004 | Schein et al. |
| 2004/0236170 A1* | 11/2004 | Kim ............... 600/16 |
| 2004/0248281 A1 | 12/2004 | Wright et al. |
| 2005/0010118 A1 | 1/2005 | Toyoda et al. |
| 2005/0019917 A1 | 1/2005 | Toledo-Pereyra et al. |
| 2005/0142532 A1 | 6/2005 | Poo et al. |
| 2005/0153271 A1 | 7/2005 | Wenrich |
| 2005/0187469 A1 | 8/2005 | Phillips |
| 2006/0039870 A1 | 2/2006 | Turner |
| 2006/0121438 A1 | 6/2006 | Toledo-Pereyra et al. |
| 2006/0154357 A1 | 7/2006 | Hassanein et al. |
| 2006/0160204 A1 | 7/2006 | Hassanein et al. |
| 2011/0136096 A1 | 6/2011 | Hassanein et al. |

FOREIGN PATENT DOCUMENTS

| | | |
|---|---|---|
| DK | 4201259 | 7/1993 |
| EP | 0347923 | 12/1989 |
| EP | 0376763 | 7/1990 |
| JP | 04-099701 A | 3/1992 |
| JP | 2004513889 A | 5/2004 |
| JP | 2004525290 A | 8/2004 |
| WO | WO-8805261 | 7/1988 |
| WO | WO-9531897 | 11/1995 |
| WO | WO-9618293 | 6/1996 |
| WO | WO-9629865 | 10/1996 |
| WO | WO 9746091 | 12/1997 |
| WO | WO-9915011 | 4/1999 |
| WO | WO-2004026031 | 4/2004 |
| WO | WO-2006042138 A2 | 4/2006 |

OTHER PUBLICATIONS

Macchiarini, P. et al. "Ex vivo lung model of pig-to-human hyperacute xenograft rejection," J. of Thoracic and Cardiovascular Surgery, 114:3, 315-325 (2000).

PCT 07/009652 International Search Report, mailed Apr. 18, 2008.

Voiglio, E. et al. "Rat multiple organ blocks: microsurgical technique of removal for ex vivo aerobic organ preservation using a fluorcarbon emulsion," Microsurgery 20:3, 109-115 (2000).

Wright, N. et al. "A porcine ex vivo paracorporeal model of lung transplantation," Laboratory Animals, 34:1, 56-62 (2000).

"2002 Design & Engineering Awards, Portable Organ Preservation System," Science (2002).

Ahmad, et al., "A Pathophysiologic Study of the Kidney Tubule to Optimize Organ Preservation Solutions," Kidney Int. 66(1):77-90 (2004).

Anathaswamy, "Machine Keeps Organs Alive for Longer," New Scientist.com (2002).

Aoki, M. et al. "Anti-CD18 Attenuates Deleterious Effects of Cardiopulmonary Bypass and Hypothermic Circulatory Arrest in Piglets," J. Card. Surg. 10:407-17 (1995).

Bando, et al., "Oxygenated Perfluorocarbon, Recombinant Human Superoxide Dismutase, and Catalase Ameliorate Free Radical Incuded Myocardial Injury During Heart Preservation and Transplantation," J. Thorac Cardiovasc Surb. 96:930-8 (Dec. 1988).

Belzer, "Formula for Belzer MPS Solution," University of Wisconsin-Madison Organ Preservation (internet reference) (2003).

Benichou, et al., "Canine and Human Liver Preservation for 6 to 18 Hours by Cold Infusion," Transplantation, 24(6):407-411 (Dec. 1977).

Birkett et al., "The Fatty Acid Content and Drug Binding Characteristics of Commercial Albumin Preparations," Clin. Chem. Acta. 85:253-58 (1978).

Blanchard, et al., "Techniques for Perfusion and Storage of Heterotopic Heart Transplants in Mice," Microsurgery, 6:169-174 (1985).

Boggi, et al., "Pancreas Preservation with University of Wisconsin and Celsior Solutions," Transplant Proc. 36(3):563-5 (2004).

Boggi, et al., "Pancreas Preservation with University of Wisconsin and Celsior Solutions: A Single-Center Prospective, Randomized Pilot Study," Transplantation 27:77(8):1186-90 (2004).

Boyle, Jr. et al., "Ischemia-Reperfusion Injury," Ann. Thorac. Surg. 64:524-30 (1997).

Burt, et al, "Myocardial Function After Preservation for 24 Hours," Jour. Thorac. and Cardiovascular Surg., 92(2):238-46 (1986).

Brasile, et al., "Organ Preservation Without Extreme Hypothermia Using an Oxygen Supplemented Perfusate," Art. Cells. Blood Subs. and Immob. Biotech., 22(4):1463-68 (1994).

Calhoon, et al., "Twelve-Hour Canine Heart Preservation With a Simple, Portable Hypothermic Organ Perfusion Device," Ann. Thorac. Surg., 62:91-3 (1996).

Canelo R., et al., "Experience with Hystidine Tryptophan Ketoglutarate Versus University Wisconsin Preservation Solutions in Transplatation," Int. Surg. 88(3):145-51 (2003).

"CELSIOR Cold Storage Solution," Sangstat Medical Corporation (internet reference) (1999).

Chambers, et al., "Long-Term Preservation of the Heart: The Effect of Infusion Pressure During Continuous Hypothermic Cardioplegia," Jour. of Heart and Lung Transp., 11(4):665-75 (1992).

Chen, et al., "Development of New Organ Preservation Solutions in Kyoto University," Yonsei Medical Journal, 46(6):1107-40 (2004).

Chien, et al., "A Simple Technique for Multiorgan Preservation," Jour. of Thor. and Card. Surg., 95(1):55-61 (1988).

Chien, et al., Canine Lung Transplantation After More Than Twenty-four Hours of Normothermic Preservation, J. Heart Lung Transplant, 16:3340-51 (1997).

Chien, et al., "Functional Studies of the Heart During a 24-Hour Preservation Using a New Autoperfusion Preparation," The Journal of Heart and Lung Transplantation, 10(3):401-8 (1991).

Cimino, Adria, "Doctor Develops Device to Preserve Donated Organs," Mass High Tech (2001).

Christophi, et al., "A Comparison of Standard and Rapid Infusion Methods of Liver Preservation During Multi-Organ Procurement," Aust. N.Z.J. Surg., 61(9):692-94 (1991).

Collins, B.H., "Organ Transplantation: What Is the State of the Art?," Ann. Surg., 238(6 Suppl):S72-89 (2003).

Cronin, et al., "Liver Transplantation at the University of Chicago," Clin. Transpl. 231-8 (1999).

Daemen, et al., "Short-Term Outcome of Kidney Transplants Fron Non-Heart-Beating Donors After Preservation by Machine Perfusion," Transpl. Int. 9(Supp 1):S76-S80 (1996).

Demertzis et al., "University of Wisconsin Versus St. Thomas' Hospital Solution for Human Donor Heart Preservation," Ann. Thorac. Surg. 55:1131-7 (1993).

Den Butter, et al., "Comparison of Solutions for Preservation of the Rabbit Liver as Tested by Isolated Perfusion," Transpl. Int. 8(6):466-71 (1995).

Denham, et al., "Twenty-Four Hour Canine Renal Preservation by Pulsatile Perfusion, Hypothermic Storage, and Combinations of the Two Methods," Transplant Proc. 9(3):1553-56 (1977).

Dobrian, et al., "In vitro formation of oxidatively-modified and reassembled human low-density lipoproteins," Biochimica et Biophysica Acta (BBA) 1169:12-24 (1993).

Drexler et al., "Effect of L-Arginine on Coronary Endothelial Function in Cardiac Transplant Recipients," Circulation.89(4):1615-23 (1994).

Eiseman, et al., "A Disposable Liver Perfusion Chamber," Surgery 6:1163-66 (1966).

Engelman et al. "Influence of Steroids on Complement and Cytokine Generation After Cardiopulmonary Bypass," Ann. Thorac. Surg. 60(3):801-04 (1995).

Fabregas, Luis, "UPMC Tests Machine to Aid Heart Transplants," Pittsburg Tribune-Review (2002).

Faggian, et al., "Donor Organ Preservation in High-Risk Cardiac Transplantation," Transplant Proc. 36:617-19 (2004).

Fehrenberg, et al., "Protective Effects of B2 Preservation Solution in Comparison to a Standard Solution (Histidine-Tryptophan-Ketoglutarate/Bretschneider) in a Model of Isolated Autologous Hemoperfused Porcine Kidney," Nephron. Physiol. 96:52-58 (2004).

Ferrera et al., "Comparison of Different Techniques of Hypothermic Pig Heart Preservation," Ann. Thorac. Surg. 57(5):1233-39 (1994).

Finn et al., Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass. J. Thorac. Cardiovasc. Surg. 111(2):451-49 (1996).

Fourcade, et al., "A New Method of Kidney Preservation with Collins' Solution," Biomed. 21(7):308-11 (1974).

Fraser, et al., "Evaluation of Current Organ Preservation Methods for Heart-Lung Transplantation," Transplant. Proc. 20(1 Suppl. 1):987-90 (1988).

Guarrera, et al., "Pulsatile Machine Perfusion with Vasosol Solution Improves Early Graft Function After Cadaveric Renal Transplantation," Transplantation 77(8):1264-68 (2004).

Gundry et al., "Successful Transplantation of Hearts Harvested 30 Minutes After Death From Exsanguination," Ann. Thorac. Surg. 53(5):772-75 (1992).

Habazetti et al., "Improvement in Functional Recovery of the Isolated Guinea Pig Heart After Hyperkalemic Reperfusion with Adenosine," J. Thorac. Cardiovasc. Surg. 111(1):74-84 (1996).

Hachida, et al., Abstract "Efficacy of Myocardial Preservation using HTK Solution in Continuous 120 Min. Cross-Clamping Method-a Comparative Study with GIK Method," Nippon Kyobu Geka Gakkai Zasshi 41(9):1495-1501 (1993).

Hartman, J.C. "The Role of Bradykinin and Nitric Oxide in the Cardioprotective Action of ACE Inhibitors," Ann Thor. Surg. 60:789-92 (1995).

Hassanein, et al., "A Novel Approach for 12-Hour Donor Heart Preservation, Presented at the 70th Scientific Session of the American Heart Association," Abstract was published in Circulation (1977).

Hassanein, et al., "Continuous Perfusion of Donor Hearts in the Beating State Extends Preservation Time and Improves Recovery of Function," The Journal of Thoracic and Cardiovascular Surgery, pp. 821-830 (1988).

"Heart Kept Beating Outside Body," Associated Press, CNN.com (2001).

Heil, et al., "A Controlled Comparison of Kidney Preservation by Two Methods: Machine Perfusion and Cold Storage," Transplant. Proc. 19(1):2046 (1987).

History of Transplantation and Organ Preservation, Barr Laboratories,Inc. (internet reference) (2004).

"Human Heart Beats on its own Outside Body," USA Today (2001).

"Human Heart Kept Alive Outside Body for First Time in Study of Portable Organ Preservation System™ at University of Pittsburgh Medical Center," UPMC, McGowan Institute for Regenerative Medicine (2001).

Imber, et al., "Advantages of Normothermic Perfusion Over Cold Storage in Liver Preservation," Transplantation, 73(5):701-09 (2002).

Janssen, et al., "UW is Superior to Celsior and HTK in the Protection of Human Liver Endothelial Cells Against Preservation Injury," Liver Transpl., 10(12):1514-23 (2004).

Kawamura, et al., "Long-Term Preservation of Canine Pancreas by a New Simple Cold Storage Method Using Perfluorochemical—The Two-Layer Cold Storage Method (Euro-Collins' Solution/Perfluorochemical)," Kobe J. Med. Sci., 38(2):135-45 (1992).

Kelly, "Current Strategies in Lung Preservation," J. Lab Clin. Med., 136:427-40 (2000).

Keshavjee, et al., "A Method for Safe Twelve-Hour Pulmonary Preservation," J. Thorac. Cardiovasc Surg., 98:529-34 (1989).

Kioka, et al., "Twenty-Four-Hour Isolated Heart Preservation by Perfusion Method With Oxygenated Solution Containing Perfluorochemicals and Albumin," J. Heart Transplant., 5:437-43 (1986).

Kozaki, et al., "Usefulness of a Combination of Machine Perfusion and Pentoxifylline for Porcine Liver Transplantation From Non-Heart-Beating Donors With Prolonged Hypotension," Transplant Proc., 29:3476-77 (1997).

Kuroda, et al., "A New, Simple Method for Cold Storage of the Pancreas Using Perfluorochemical," Transplantation, 46(3):457-60 (1988).

Lasley, et al., "Protective Effects of Adenosine in the Reversibly Injured Heart," Ann. Thorac. Surg., 60(3):843-46 (1995).

Lawrence, "Machine Preserves Organs Outside Body," Chicago Sun Times (2001).

Lefer, A.M., "Attenuation of Myocardial Ischemia-Reperfusion Injury With Nitric Oxide Replacement Therapy." Ann. Thorac. Surg. 60(3):847-51 (1995).

Li, et al., "Insulin in University of Wisconsin Solution Exacerbates the Ischemic Injury and Decreases the Graft Survival Rate in Rat Liver Transplantation," Transplantation, 15:76(1):44-49 (2003).

Li, et al., "Insulin in UW Solution Exacerbates Hepatic Ischemia/Reperfusion Injury by Energy Depletion Through the IRS-2/SREBP-1C Pathway," Liver Transp., 10(9):1173-82 (2004).

Li, G. et al., "Functional Recovery in Rabbit Heart after Preservation with a Blood Cardioplegic Solution and Perfusion," J. Herat Lung Transplant. 12(2)263-70 (1993).

Liu, et al., "Annexin V Assay-proven Anti-apopototic Effect of Ascorbic Acid 2-glucoside after Cold Ischemia/Reperfusion Injury in Rat Liver Transplantation," Acta Med. Okayama, 57(5):209-16 (2003).

"Machine Keeps Human Kidney Alive for 24-Hours," 222.worldhealth.net, Aug. 25, 2001.

"Machine May Be Organ Transplant Breakthrough," USA Today (2001).

Mankad et al., "Endothelial dysfunction caused by University of Wisconsin preservation solution in the rat heart," J. Thorac. Cardiovasc. Surg. 104(6): 1618-24 (1992).

Matsuno et al., "Effectiveness of Machine Perfusion Preservation as a Viability Determination Method for Kidneys Procured from Non-Heart-Beating Donors," Transplant. Proc. 26(4):2421-22 (1994).

Matsuno et al., "The Effect of Machine Perfusion Preservation Versus Cold Storage on the Function of Kidneys from Non-Heart-Beating Donors," Transplantation. 57(2):293-94 (1994).

Menasche et al., "Experimental evaluation of Celsior® . a new heart preservation solution," Eur. J. Cardiothor. Surg. 8:207-13 (1994).

Menasche, et al., "Improved Recovery of Heart Transplants With a Specific Kit of Preservation Solutions," J. Thorac. Cardiovasc. Surg., 105(2):353-63 (1993).

Menasche, P., "The inflammatory response to cardiopulmonary bypass and its impact on postoperative myocardial function", Curr. Opin. Cardiology. 10:597-604 (1995).

Moisiuk, et al., "Histidine-Tryptophan-Ketoglutarate Versus Euro-Collins for Preservation of Kidneys from Non-Heart-Beating Donors," Transplant Proc., 28(1):202 (1996).

Moller-Pedersen, et al., "Evaluation of Potential Organ Culture Media for Eye Banking Using Human Donor Corneas," Br. J. Ophthamol, 85(9):1075-79 (2001).

Morimoto, et al., "A Simple Method for Extended Heart-Lung Preservation by Autoperfusion," Trans. Am. Soc. Artif Intern Organs., 30:320-24 (1984).

"New Discovery in Organ Transplantation," MSNBC (2001).

Innovations—Report "New Organ Preservation Solution Easier to Use," (internet reference) (2003).

Nicholson, et al., "A Comparison of Renal Preservation by Cold Storage and Machine Perfusion Using a Procine Autotransplant Model," Transplantation 78(3):333-37 (2004).

Opelz, et al., "Advantage of Cold Storage Over Machine Perfusion for Preservation of Cadaver Kidneys," Transplantation, 33(1):64-68 (1982).

Opelz, et al., "Comparative Analysis of Kidney Preservation Methods, Collaborative Transplant Study," Transplant Proc. 28(1):87-90 (1996).

Pearl et al., "Loss of endothelium-dependent vasodilation and nitric oxide release after myocardial protection with University of Wisconnsin solution," J. Thorac. Cardiovasc. Surg., 107(1):257-64 (1994).

Petrovsky, et al., Justification and Application of a New Method for Transorganic Oxygen Preservation of the Kidneys, Vestn. Akad. Med. Nauk, SSSR., (2):69-82 (1989).

Pinsky et al., "Restoration of the cAMP Second Messenger Pathway Enhances Cardiac Preservation for Transplantation in a Heterotopic Rat Model," J. Clin. Invest. 92(6):2944-3002 (1993).

Ploeg, et al., "Successful 72-Hour Cold Storage of Dog Kidneys with UW Solution," Transplantation, 46(2):191-96 (1988).

Pokorny, et al., "Histidine-Tryptophan-Ketoglutarate Solution for Organ Preservation in Human Liver Transplantation—A Prospective Multi-Centre Observation Study," Transpl. Int. 17(5):256-60 (2004).

Potdar, et al., "Initial Experience Using Histidine-Tryptophan-Ketoglutarate Solution in Clinical Pancreas Transplantation," Clin. Transplant., 18(6):661-65 (2004).

Pozniak, "Keeping Hearts Alive: Doctors Develop a High-Tech System to Salvage Donated Organs," ABC News.com (2001).

Rao et al., "Donor blood Perfusion Improves Myocardial Recovery After Heart Transplantaion," J. Heart Lung Transplant, 16(6):667-73 (1997).

Reddy, et al., "Preservation of Porcine Non-Heart Beating Donor Livers by Sequential Cold Storage and Warm Perfusion," Transplantation, 77(9):1328-32 (2004).

Richens et al., "Clinical Study of Crystalloid Cardioplegia vs Aspartate-Enriched Cardioplegia Plus Warm Reperfusion for Donor Heart Preservation," Transplant. Proc. 24(1): 1608-10 (1993).

Rinder et al., "Blockade of C5a and C5b-9 Generation Inhibits Leukocyte and Platelet Activation during Extracorporeal Circulation," J. Clin. Invest. 96:3(1564-72). 1995.

Rossi, "Portable Organ Preservation System™ Keeps Human Heart Alive Outside Body," PITT Campaign Chronicle (2001).

Rosenkranz, E.R. "Substrate Enhancement of Cardioplegic Solution: Experimental Studies and Clinical Evaluation," Ann. Thorac. Surg. 60:797-800 (1995).

Sato, H. et al., "Supplemental L-Arginine During Cardioplegic Arrest and Reperfusion Avoids Regional Postischemic Injury," J. Thorac. Cardiovasc. Surg. 110(2):302-14 (1995).

Schmid, et al., "The Use of Myocytes as a Model for Developing Successful Heart Preservation Solutions," Transplantation, 52(1):20-6 (Jul. 1991).

Schon, et al., "Liver Transplantation After Organ Preservation by Normothermic Extracorporeal Perfusion," Ann. Surg. 233(1):114-23 (2001).

Schwalb et al., "New Solution for Prolonged Myocardial Preservation for Transplantation," J. Heart Lung Transplant. 17(2):222-29 (1998).

Seccombe et al., "Coronary Artery Endothelial Function After Myocardial Ischemia and Reperfusion," Ann. Thorac. Surg. 60(3):778-88 (1995).

Segel et al., "Posttransplantation Function of Hearts Preserved with Fluorochemical Emulsion", J. Heart Lung Transplant. 13(4):669-80 (1994).

Segel, et al., "Recovery of Sheep Hearts After Perfusion Preservation or Static Storage With Crystalloid Media," The Journal of Heart and Lung Transplantation, 17:211-21 (1998).

Shimokawa, et al., "A New Lung Preservation Method of Topical Cooling by Ambient Cold Air Combined with High-Frequency Oscillation: An Experimental Study," Transplant. Proc., 26(4):2364-66 (1994).

Shimokawa, et al., "A New Lung Preservation Method of Topical Cooling by Ambient Cold Air: An Experimental Study," Transplant. Proc., 23 (1 Pt 1):653-54 (1991).

Shirakura et al., "Multiorgan Procurement from Non-Heart-Beating Donors by use of Osaka University Cocktail, Osaka Rinse Solution, and the Portable Cardiopulmonary Bypasss Machine," Transplant. Proc. 25(6):3093-94 (1993).

Southard, "The Right Solution for Organ Preservation", Business Briefings: Global Surgery, 79-84 (2004).

Stubenitsky, et al., "Kidney Preservation in the Next Millenium," Transpl. Int., 12:83-91 (1999).

Sunamori et al., "Relative Advantages of Nondepolarizing Solution to Depolarizing University of Wisconsin Solution in Donor Heart Preservation," Transplant. Proc. 25(1): 1613-17 (1993).

Tang, et al., "Warm Ischemia Lung Protection with Pinacidil: An ATP Regulated Potassium Channel Opener," Ann. Thorac. Surg., 76:385-9 (2003).

Tesi et al., "Pulsatile Kidney Perfusion for Preservation and Evaluation: Use of High-Risk Kidney Donors to Expand the Donor Pool," Transplant. Proc. 25(6):3099-100 (1993).

The Merck Index, 11th ed. Entry 4353 (pp. 699-700) (1989).

"The Nation Warm-Storage Device May Aid Organ Transplants," Dow Jones Publications Library (2001).

Turpin, et al., "Perfusion of Isolated Rat Adipose Cells," The Journal of Clinical Investigation, 60:442-448 (1977).

"ViaSpan (Belzer UW) Cold Storage Solution," Barr Laboratories, Inc. (2002).

Vinten-Johansen, et al., "Reduction in Surgical Ischemic-Reperfusion Injury With Adenosine and Nitric Oxide Therapy," Ann. Thorac. Surg. 60(3):852-57 (1995).

"Warm-Storage for Donor Organs," Univ. of Chicago Magazine (2001).

Watanabe, et al., "Effects of free fatty acids on the binding of bovine and human serum albumin with steroid hormones," Biochimica et Biophysica Acta (BGBA), 1289:385-96 (1996).

Wicomb et al., "24-Hour Rabbit Heart Storage with UW Solution," Transplantation. 48(1):6-9 (1989).

Zhengquang, et al., "A Study on the Preservation of Rat Kidney with HX-III Solution," WCUMS, 31(3):347-49 (2000).

Wicomb, et al., "Cardiac Transplantation Following Storage of the Donor Heart by a Portable Hypothermic Perfusion System," The Annals of Thoracic Surgery, 37(3):243-48 (1984).

Wicomb, et al., "Orthotopic Transplantation of the Baboon Heart After 20 to 24 Hours Preservation by Continuous Hypothermic Perfusion With an Oxygenated Hyperosmolar Solution," The Journal of Thoracic and Cardiovascular Surgery, 83(1):133-40 (1982).

Yland, et al., "New Pulsatile Perfusion Method for Non-Heart-Beating Cadaveric Donor Organs: A Preliminary Report," Transplantation Proceedings, 25(6):3087-90 (1993).

Zhang, et al., "Research Progress on Preservation of Severed Limbs," Chinese Journal of Reparative and Reconstructive Surgery, 14(3):189-192 (2000).

Definition of Examine. Merriam-Webster Dictionary oneline. www.m-w.com/dictionary/examine. Printed Feb. 9, 2011. 1 page.

http://dictionary.reference.com/browse/synchrony. Randon House Unabridged Dictionary. 2006. 1 page.

File History for U.S. Appl. No. 60/616,835, filed Oct. 7, 2004. 82 pages.

File History for U.S. Appl. No. 60/694,971, filed Jun. 28, 2005. 280 pages.

File History for U.S. Appl. No. 60/725,168, filed Oct. 6, 2005. 699 pages.

\* cited by examiner

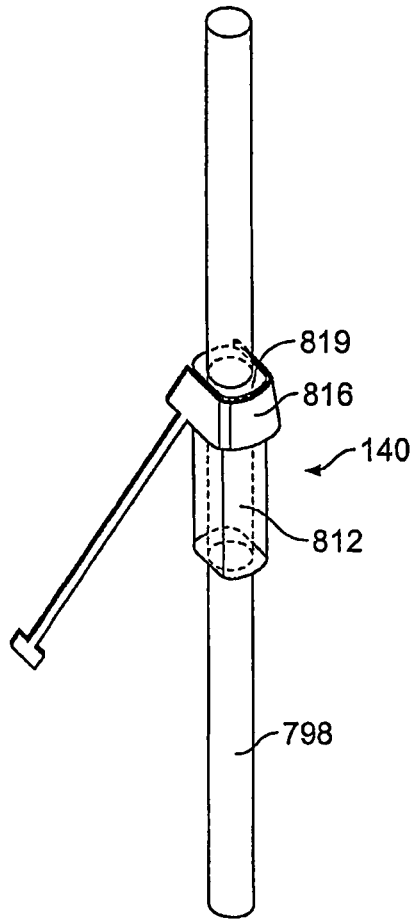
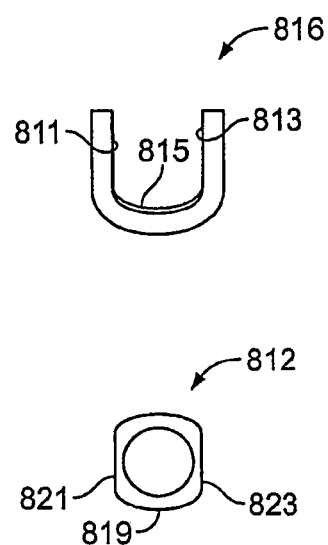
FIG. 28A
FIG. 28C
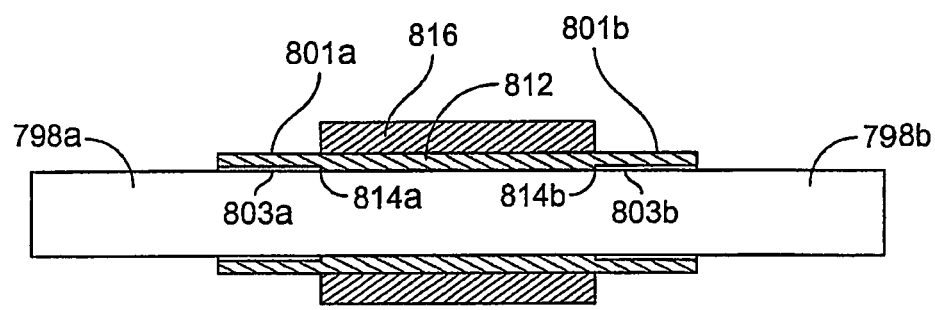
FIG. 28B

4000

| RADIOMETER ABL800 FLEX | | |
|---|---|---|
| ABL835 Patient Report | Syringe-S 95uL | 04:39 PM 3/16/ Sample # |

Identifications
Patient ID          L-03-16-07
Patient Last Name   5:00
Patient First Name  PF 2.15
Sample Type         Arterial
T                   36.9°C

Blood Gas Values
pH              7.247        [ - ]
$[pCO_2]$       43.8  mmHg}  [ - ]
$cHCO_3^-(P)_c$ 18.4  mmol/L         ─4000a
$[pO_2]$        84.5  mmHg}  [ - ]
                                     ─4000b
Oximetry Values
ctHb            7.6   g/dL   [ - ]
$FO_2Hb$        93.5  %      [ - ]
$Hct_c$         23.7  %
FCOHb           0.5   %      [ - ]
$sO_2$          95.3  %
FHHb            4.6   %      [ - ]
FMetHb          1.4   %      [ - ]

Electrolyte Values
$cNa^+$         149   mmol/L
$cK^+$          4.2   mmol/L [ - ]
$cCl^-$         107   mmol/L [ - ]
$cCa^{2+}$      3.39  mg/dL

Metabolite Values
cGlu            446   mg/dL  [ - ]
cLac            14.3  mmol/L [ - ]
ctBil           12    µmol/L [ - ]

Temperature Corrected Values
$pH(T)_c$       7.248
$pCO_2(T)_c$    43.8  mmHg
$pO_2(T)_c$     84.0  mmHg

Oxygen Status
$ctO_{2c}$      10.1  Vol%
$p50_c$         29.39 mmHg

Acid Base Status
$cBase(Ecf)_c$       -7.6  mmol/L
$cHCO_3^-(P.st)_c$   18.0  mmol/L

Notes
C   Calculated value(s)
    0712: FHbF measurement not possible

Printed   4:41:24PM   07-03-16

---

4002

| RADIOMETER ABL800 FLEX | | |
|---|---|---|
| ABL835 Patient Report | Syringe-S 95uL | 04:43 PM 3/16/2007 Sample # 2035 |

Identifications
Patient ID          L-03-16-07
Patient Last Name   5:00
Patient First Name  PF 2.15
Sample Type         Venous
T                   36.9°C

Blood Gas Values
pH              7.239        [ - ]
$[pCO_2]$       44.6  mmHg}  [ - ]
$cHCO_3^-(P)_c$ 18.4  mmol/L         ─4002a
$[pO_2]$        83.9  mmHg}  [ - ]
                                     ─4002b
Oximetry Values
ctHb            7.5   g/dL   [ - ]
$FO_2Hb$        93.2  %      [ - ]
$Hct_c$         23.5  %
FCOHb           0.4   %      [ - ]
$sO_2$          94.7  %
FHHb            5.2   %      [ - ]
FMetHb          1.2   %      [ - ]

Electrolyte Values
$cNa^+$         149   mmol/L
$cK^+$          4.2   mmol/L [ - ]
$cCl^-$         106   mmol/L [ - ]
$cCa^{2+}$      3.39  mg/dL

Metabolite Values
cGlu            456   mg/dL  [ - ]
cLac            14.5  mmol/L [ - ]
ctBil           13    µmol/L [ - ]

Temperature Corrected Values
$pH(T)_c$       7.240
$pCO_2(T)_c$    44.4  mmHg
$pO_2(T)_c$     83.4  mmHg

Oxygen Status
$ctO_{2c}$      10.0  Vol%
$p50_c$         30.78 mmHg

Acid Base Status
$cBase(Ecf)_c$       -7.7  mmol/L
$cHCO_3^-(P.st)_c$   17.9  mmol/L

Notes
C   Calculated value(s)
    0712: FHbF measurement not possible

Printed   4:45:51PM   07-03-16

FIG. 39

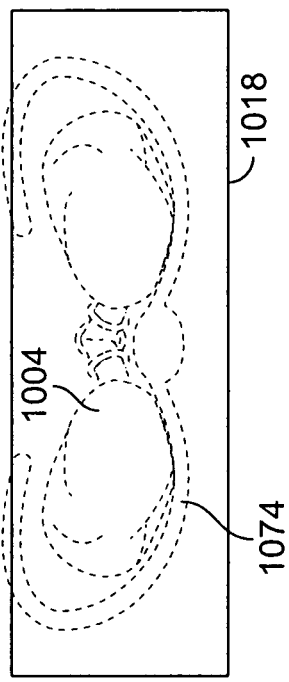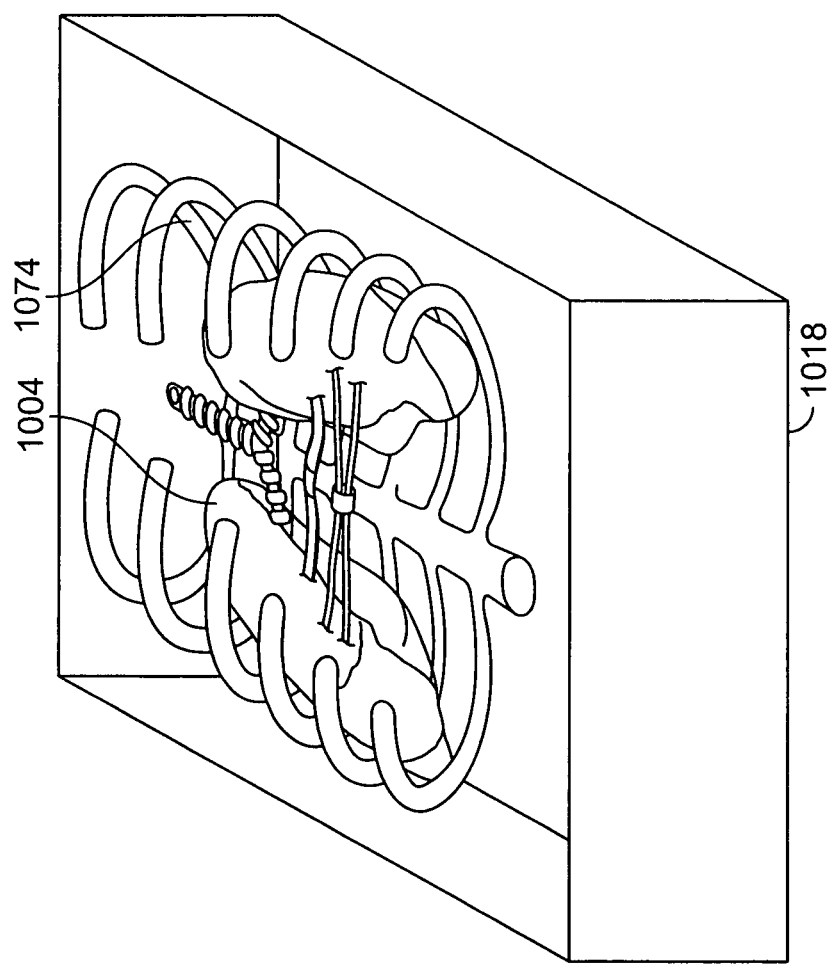
FIG. 46

SYSTEMS AND METHODS FOR EX VIVO ORGAN CARE

REFERENCE TO RELATED APPLICATIONS

This application claims the benefit of U.S. Provisional Application Ser. No. 60/793,472, filed on Apr. 19, 2006, the specification of which is incorporated by reference herein in its entirety.

FIELD OF THE INVENTION

The invention generally relates to systems, methods, and devices for ex vivo organ care. More particularly, in various embodiments, the invention relates to caring for an organ ex vivo at physiologic or near-physiologic conditions.

BACKGROUND OF THE INVENTION

Current organ preservation techniques typically involve hypothermic storage of the organ in a chemical preservation solution on ice. These techniques utilize a variety of solutions, none of which sufficiently protect the organ from damage resulting from ischemia. Such injuries are particularly undesirable when an organ is intended to be transplanted from a donor into a recipient.

Using conventional approaches, such injuries increase as a function of the length of time an organ is maintained ex vivo. For example, in the case of a lung, typically it may be preserved ex vivo for only about 6 to about 8 hours before it becomes unusable for transplantation. A heart typically may be preserved ex vivo for only about 4 to about 6 hours before it becomes unusable for transplantation. These relatively brief time periods limit the number of recipients who can be reached from a given donor site, thereby restricting the recipient pool for a harvested organ. Even within the time limits, the organs may nevertheless be significantly damaged. A significant issue is that there may not be any observable indication of the damage. Because of this, less-than-optimal organs may be transplanted, resulting in post-transplant organ dysfunction or other injuries. Thus, it would be desirable to develop techniques that can extend the time during which an organ can be preserved in a healthy state ex vivo. Such techniques would reduce the risk of post-transplant organ failure and enlarge potential donor and recipient pools.

Effective preservation of an ex vivo organ would also provide numerous other benefits. For instance, prolonged ex vivo preservation would permit more careful monitoring and functional testing of the harvested organ. This would in turn allow earlier detection and potential repair of defects in the harvested organ, further reducing the likelihood of post-transplant organ failure. The ability to perform simple repairs on the organ would also allow many organs with minor defects to be saved, whereas current transplantation techniques require them to be discarded.

In addition, more effective matching between the organ and a particular recipient may be achieved, further reducing the likelihood of eventual organ rejection. Current transplantation techniques rely mainly on matching donor and recipient blood types, which by itself is a relatively unreliable indicator of whether or not the organ will be rejected by the recipient. A more preferred test for organ compatibility is a Human Leukocyte Antigen (HLA) matching test, but current cold ischemic organ preservation approaches preclude the use of this test, which can often require 12 hours or more to complete.

Prolonged and reliable ex vivo organ care would also provide benefits outside the context of organ transplantation. For example, a patient's body, as a whole, can typically tolerate much lower levels of chemo-, bio- and radiation therapy than many particular organs. An ex vivo organ care system would permit an organ to be removed from the body and treated in isolation, reducing the risk of damage to other parts of the body.

In view of the foregoing, improved systems, methods, and devices for caring for an organ ex vivo are needed.

SUMMARY OF THE INVENTION

The invention addresses the deficiencies in the state of the art by, in various embodiments, providing improved systems, methods, solutions and devices relating to portable ex vivo organ care.

In one aspect of the invention, the invention includes a method for perfusing one or more lungs ex vivo for an extended period of time in a "steady" or "equilibrium" state maintenance mode. The method generally includes the step of connecting the lungs within a fluid perfusion circuit, which includes a pump, a fluid source, and a fluid flow interface that allows the fluid to flow in and out of the lungs. The method also includes the steps of flowing a perfusion fluid into the lungs through a pulmonary artery interface and flowing the perfusion fluid away from the lungs through a pulmonary vein interface, ventilating the lungs through a tracheal interface, which provides periodic breaths that include alternating inspiration and expiration of gas in and out of the lungs, similar to inspiration and expiration by lungs in-vivo, and providing a respiratory gas, having a pre-determined composition of gas components, to the lungs for use in metabolism by the lungs. In this method, the perfusion system is brought to a steady state, wherein the perfusion fluid flowing into the lungs includes gas components in a first composition that is substantially constant over time, and the perfusion fluid flowing away from the lungs includes gas components in a second composition that is substantially constant over time. Because the lungs are separated from the rest of the donor's body, they do not need to supply metabolic requirements for the rest of the body, such that during perfusion in the systems described herein less gas exchange is used than lungs in-vivo, and the oxygen and carbon dioxide exchange requirement is reduced. The composition of gas components in the respiratory gas is thus selected so as to provide adequate oxygen and carbon dioxide to the lungs for metabolism and control of perfusion fluid pH in an amount that approximates physiologic levels.

In one embodiment, a tracheal oxygen delivery approach is used to implement the maintenance mode. According to this approach, one or more explanted lungs are instrumented within the perfusion circuit and are perfused by a perfusion fluid that is oxygenated to a desired level prior to initiating the perfusion of the lungs. During perfusion, the oxygenated perfusion fluid flows into the explanted lungs via the pulmonary artery interface and flows away from the lungs via the pulmonary vein interface. In addition, the respiratory gas is delivered to the lungs by the first gas source through the tracheal interface, such that the explanted lungs are ventilated by a respiratory gas in periodic breaths through the tracheal interface with alternating inspiration and expiration periods. In particular, the ventilating/respiratory gas delivers a pre-determined composition of gas components through the tracheal interface. In certain implementations, the gas flowing through the tracheal interface is a combination having at least oxygen, carbon dioxide and nitrogen. In certain embodiments, oxygen is about 10% to about 20% and carbon dioxide is about 2% to about 8% of the combination. In one embodiment, the ventilating/respiratory gas combination is about 14% oxygen and about 5% carbon dioxide, and the balance is nitrogen. In this mode, gas leaving the lungs is removed from the lungs via the tracheal interface, for example, through an outlet valve located along a conduit extending from the tracheal interface. After perfusing the lungs for a period of time in this mode, steady state occurs when the first and second gas compositions are substantially the same. Upon reaching the steady-state, the oxygen and carbon dioxide components in the perfusion fluid flowing into the lungs and in the perfusion fluid flowing away from the lungs reach a substantially constant composition. Moreover, the lungs are perfused with the perfusion fluid and ventilated through the tracheal conduit, while the oxygen, carbon dioxide and other gases are maintained in the perfusion fluid at a substantially constant gas component composition, and the gas delivered to the lungs through the tracheal interface differs from the second gas composition in an amount sufficient to supply the lungs' metabolic requirement, and, in certain embodiments, the two gas compositions differ by an amount approximate to support the metabolic requirement.

In another embodiment, an isolated tracheal volume re-breathing approach is used to implement the maintenance mode. In this embodiment, one or more explanted lungs are first instrumented within the perfusion circuit and are perfused with a perfusion fluid that flows into the lungs via the pulmonary artery interface and flows away from the lungs via the pulmonary vein interface. A ventilating gas source is provided to the lungs through the tracheal interface, and one or more respiratory gas mixtures, each containing a pre-determined composition of gas components, are supplied to the perfusion fluid via a gas exchange device (e.g., an oxygenator) in the perfusion circuit. In one exemplary embodiment, a gas supplied to the gas exchange device is pre-mixed to include a desired gas composition for infusion into the perfusion fluid. In another embodiment, gases having different compositions are controllably released from the appropriate gas sources to the oxygenator 1042 at rates and volumes that allow the desired gas mixture composition to be obtained.

In certain embodiments, a respiratory gas source may be supplied to the gas exchange device that includes a gas composition of about 3% to about 7% carbon dioxide, about 11% to about 14% oxygen, and the balance being nitrogen. In this mode, the ventilating gas source is provided in an isolated volume that interfaces with other fluids and exchanges with other gases only through the alveoli of the lungs. In certain embodiments, the isolated gas volume is provided by a flexible bag. In certain embodiments, the isolated gas volume is provided by a hose. The gas components in the isolated gas volume are able to reach a constant composition by exchanging with the gas components in the perfusion fluid. Exhaled carbon dioxide is carried away from the lungs by the circulating perfusion fluid and substantially removed from the perfusion fluid by mixing with the one or more oxygen-containing gas mixtures supplied through the gas exchange device. In operation, the lungs are ventilated during perfusion in this mode by applying a compression force to the isolated volume. As the isolated volume compresses, its components flow through the tracheal interface and into the lungs, where the lungs inflate and the gas components exchange with gas components in the perfusion fluid through the alveoli in the inflated lungs. As the compression force is withdrawn from the hose or flexible bag, the lungs exhale. The application and withdrawal of the compression force is repeated until the gas components flowing into the tracheal interface reach equilibrium with the components in the perfusion fluid.

Upon reaching a steady state in the isolated tracheal volume re-breathing approach, the oxygen and carbon dioxide components in the perfusion fluid flowing into the lungs includes a substantially constant composition and the gas components in the perfusion fluid flowing away from the lungs also include a substantially constant composition. In certain embodiments, a constant composition of a component is achieved when the composition of the component varies over time by an amount less than about 3%, less than about 2%, less than about 1% over time in a given sampling location within the system. Although at a steady state, in the isolated tracheal volume technique, the composition of oxygen and carbon dioxide in the perfusion fluid flowing into the lungs may differ from the composition of such components in the perfusion fluid flowing away from the lungs. In certain embodiments, the compositions of such components in the in-bound fluid differ from the compositions in the out-bound fluid by amounts substantially equivalent to the quantity resulting from lung metabolism. In certain embodiments, the oxygen component is maintained during perfusion at a steady-state partial pressure that is greater in the perfusion fluid flowing into the lungs than in the perfusion fluid flowing away from the lungs. In certain embodiments, the carbon dioxide component is maintained during perfusion at a steady state partial pressure that is lower in the perfusion fluid flowing into the lungs than in the perfusion fluid flowing out of the lungs.

In certain embodiments of the maintenance mode, the composition of gas components in the perfusion fluid is chosen to provide steady-state partial pressures of the gas components within the circulating fluid in a range between a pre-determined arterial gas composition and pre-determined venous gas composition. In certain embodiments, the pre-determined arterial gas composition is physiologic arterial blood gas composition, and the pre-determined venous gas composition is physiologic venous blood gas composition. For example, the composition of the oxygen component in the perfusion fluid may be at a partial pressure that is greater than a composition of the oxygen component in physiologic venous blood and less than a composition of the oxygen component in physiologic arterial blood. More specifically, this partial pressure of the oxygen component in the perfusion fluid may be between about 60 mmHg to about 100 mmHg, between about 80 mmHg to about 90 mmHg, or between about 83 mmHg to about 85 mmHg. In addition, the composition of the carbon dioxide component in the perfusion fluid is at a partial pressure that is less than a composition of the carbon dioxide component in physiologic venous blood and greater than a composition of the carbon dioxide component in physiologic arterial blood. More specifically, this partial pressure of the carbon dioxide component in the perfusion fluid may be between about 40 mmHg to about 50 mmHg or between about 42 mmHg to about 50 mmHg.

In certain embodiments of the maintenance mode, one or more therapeutics is delivered to the lungs during perfusion. The one or more therapeutics may be selected from antimicrobials, vasodilators, and anti-inflammatory drugs. The one or more therapeutics may also be selected from isuprel, flolan, prostacycline and nitric oxide donors. In addition, the one or more therapeutics may be delivered to the lungs through the tracheal interface via a nebulizer, or to the perfusion fluid through a maintenance solution bag, or by injection directly into the perfusion fluid reservoir at the point of use.

In certain embodiments of the maintenance mode, the perfusion fluid is maintained and provided to the lungs at a near physiologic temperature. According to one implementation, the perfusion fluid employs a blood product-based perfusion fluid to more accurately mimic normal physiologic conditions. In alternative embodiments, a synthetic blood substitute solution is used, while in other embodiments, the solution may contain a blood product in combination with a blood substitute product. The perfusion fluid may include a blood product, such as whole blood, and it may be partially or completely depleted of leukocytes and/or platelets.

In certain embodiments, one or more tests can be performed on the lungs while they are maintained in the perfusion circuit for ex vivo care. For example, levels of an arterial-venous (AV) oxygen gradient between the perfusion fluid flowing into the lungs and flowing away from the lungs can be measured. Levels of oxygen saturation of blood hemoglobin in the perfusion fluid flowing into the lungs and flowing away from the lungs can also be measured, as can pulmonary vascular resistance ventilation rate, tidal volume, peak respiratory pressure and positive end-expiratory pressure (PEEP).

According to another aspect of the invention, the invention includes a lung care system for perfusing one or more lungs ex vivo. The exemplary system includes a portable multiple use module and a single use disposable structure that is sized and shaped for interlocking with the multiple use module. The single use module also includes a lung chamber assembly mounted to the disposable structure. The exemplary system also includes a pump adapted to deliver a perfusion fluid to the lung chamber assembly. The lung chamber assembly includes a pulmonary artery interface for allowing a flow of the perfusion fluid into the lungs, a tracheal interface for allowing ventilation of the lungs, and a pulmonary vein interface for allowing the perfusion fluid to flow away from the lungs. In addition, the single use module may include a respiratory gas source having a predetermined gas component composition. In certain embodiments, the respiratory gas source is included in the multiple-use module.

In certain embodiments, the pulmonary vein interface of the lung care system includes a portion of the donor's left atrium, which is severed from the donor upon explanting the lungs. A portion of the left atrium, known as the left atrial cuff, is left to hang freely from the lungs and is exposed to the lung chamber assembly for allowing the perfusion fluid to flow from the lungs to the lung chamber assembly. In certain embodiments, the pulmonary vein interface includes a cannulation to the left atrial cuff. In one example of cannulation to the left atrial cuff, a semi-sealable connection between the left atrial cuff and a cannula is formed that directs the perfusion fluid to a reservoir. The semi-sealable connection may be formed by a connector device that mates the cannula with the left atrial cuff, and the connection may be releasable. In one instance, the connector device includes a first surface for engaging the left atrial cuff and a second surface for engaging the cannula. In one instance, the first surface of the connector device includes a plurality of perforations for engaging a plurality portions of the left atrial cuff. The left atrial cuff may also extend vertically above the lungs and fit semi-sealably within a vertically extending cannula, wherein the cannula has a cross-section with a diameter that is larger than a diameter of the left atrial cuff. The cannula can be loosely fitted around the left atrial cuff. In other practices, cannulation to the left atrial cuff can be formed by sealing a tip portion of the cannula substantially within a pocket formed by the left atrial cuff. In yet another embodiment, the pulmonary vein interface includes the left atrial cuff disposed in a cup-shaped interface inside of the lung camber assembly for allowing the perfusion fluid to flow from the lungs and away from the lung chamber assembly via an outlet conduit coupled to the cup-shaped interface. The cup-shaped interface may additionally include multiple openings at respective heights along a sidewall of the interface, and the openings are in fluid communication with a selector valve. The selector value is used to controllably draw the perfusion fluid in the cup-shaped interface away from the lung chamber assembly through a selected one of the multiple openings and through the outlet conduit. Hence, the perfusion fluid is able to fill the cup-shaped interface to a height where the select opening is located in order to create a desired level of back pressure on the pulmonary veins.

In certain embodiments of the lung chamber assembly, a housing is mounted inside of the lung chamber assembly for supporting the lungs. The housing substantially prevents the lungs from contacting at least one wall of the lung chamber assembly. The housing may be stiff or flexible, and is configured to distribute the weight of the lungs as evenly as possible about the surface of the lungs. In this manner it is believed that pressure upon the alveoli of the lungs can be reduced. In one practice, the housing includes a flexible membrane, such as a cloth, a netting or other fabric, that suspends the lungs within the lung chamber assembly. In another practice, the housing has a shape of a stiff or flexible ribcage having, optionally, a diaphragm structure and/or padding.

The system may also include a heater for maintaining the perfusion fluid provided to the lung chamber assembly at a near physiologic temperature. The system may additionally include a gas exchange device in fluid communication with at least one gas supply and the perfusion fluid, the gas exchange device being adapted to controllably modulate the composition of a gas component in the perfusion fluid. In certain embodiments, the gas exchange device (e.g., an oxygenator) includes a gas select switch for selecting from a plurality of gas supplies to modulate the composition of a gas component in the perfusion fluid. The system may further include a respiration device for providing a gas supply through the tracheal interface. To operate the system in the isolated tracheal mode, a volume compartment may be cannulated to a tracheal conduit of the lungs and adapted to ventilate the lungs during perfusion.

In another aspect of the invention, the invention includes a method for operating a perfusion circuit in an evaluation mode. One or more lungs may be evaluated for transplant suitability during the evaluation mode. The method includes positioning the lungs in an ex vivo perfusion circuit, flowing a perfusion fluid into the lungs through a pulmonary artery interface, and flowing the perfusion fluid away from the lungs through a pulmonary vein interface, the perfusion fluid being at a physiologic temperature. In addition, the method includes providing gas containing oxygen to the lungs through a tracheal interface. The oxygen level in the gas can be adjusted to allow for evaluation at various oxygen composition levels. The gas may comprise about 100% oxygen, less than 100% oxygen, less than about 75% oxygen, less than about 50% oxygen, less than about 25% oxygen, or no oxygen. In certain embodiments, this gas may be the same composition as ambient air.

The evaluation mode is useful, for example, for performing tests to evaluate the gas-transfer capacity of the lungs by determining the oxygen or carbon dioxide saturation or partial pressure of oxygen in the perfusion fluid both before and after it flows through the lungs. To perform this test in the evaluation mode, a low-oxygen content gas source is used to adjust the gas content of the perfusion fluid such that the fluid resembles that of physiologic venous blood. The blood gas composition of the perfusion fluid is then monitored by taking sample measurements of oxygen saturation or partial pressure of gas components in the perfusion fluid flowing into the lungs via the pulmonary artery interface and flowing away from the lungs via the pulmonary vein interface. The resulting pulmonary artery and pulmonary vein oxygen saturation or partial pressure measurements, collected over a period of time after ventilation begins, are then compared with each other to identify a maximum difference that is representative of the gas-transfer capacity of the lungs.

Other evaluations can be performed on the instrumented lungs. These evaluations include measuring a fractional inspired oxygen concentration, measuring an arterial-venous (AV) oxygen gradient between the perfusion fluid flowing into the lungs and the perfusion fluid flowing away from the lungs, measuring an alveolar arterial (AA) oxygen gradient, measuring a tidal volume, measuring oxygen saturation of blood hemoglobin or partial pressure of oxygen in the perfusion fluid flowing into and away from the lungs, and measuring the PEEP.

In certain embodiments of the evaluation mode, a suction force is applied through the tracheal interface to clear lungs alveoli of debris. The lung alveoli debris may also be cleared by causing the lungs to inhale breaths that are of variable volume. For example, in sigh breathing, the breaths include a first breath having a volume that is larger than the volume of at least two next breaths.

In another aspect of the invention, the invention includes compositions and solutions for infusion into a perfusion fluid that is used to perfuse the lungs prior to transplantation. The solutions include a substantially cell-free composition, where the compositions comprise one or more carbohydrates that include dextran, and a plurality of amino acids that do not include asparagine, glutamine, or cysteine.

According to various aspects, the systems and/or devices of the invention include, and/or the methods of the invention employ, one or more of: an lung chamber assembly sized and configured for containing one or more lungs during ex vivo care; a reservoir for containing and optionally, defoaming and/or filtering a volume of perfusion fluid; a perfusion fluid pump for pumping/circulating perfusion fluid to and from the harvested lungs; a heater assembly for maintaining the temperature of the perfusion fluid at or near to physiologic temperatures; a gas exchange device for exchanging gases with the perfusion fluid in the system; a nutritional subsystem for replenishing nutrients in the perfusion fluid as they are metabolized by the lungs and for providing preservatives to the perfusion fluid to reduce, for example, ischemia, edema and/or other reperfusion related injuries to the lungs; a sensor subsystem for monitoring, for example, temperature, pressure, flow rate and/or oxygenation of the perfusion fluid, and/or the various components employed to maintain suitable flow conditions to and from the lungs; an operator interface for assisting an operator in monitoring system operation and/ or the condition of the lungs, and/or for enabling the operator to set various operating parameters; a power subsystem for providing fault tolerant power to the organ care system; and a control subsystem for controlling operation of the organ care system.

Operationally, in one practice, the lungs are harvested from a donor and is instrumented to the lung chamber assembly by processes described above. The perfusion fluid pump pumps perfusion fluid from a reservoir to the heater assembly. The heater assembly heats the perfusion fluid to or near a normal physiologic temperature. According to one embodiment, the heater assembly heats the perfusion fluid to between about 30° C. and about 37° C., or in between about 34° C. and 37° C. From the heater assembly, the perfusion fluid flows to a first interface on the lung chamber assembly. Also referred to as a pulmonary artery interface, the first interface is cannulated to vascular tissue of the pulmonary artery via a conduit located within the lung chamber assembly. The perfusion fluid then flows out of the lungs through the pulmonary vein via a second interface on the lung chamber assembly. The second interface, also referred to as a pulmonary vein interface, connects to the remainder of the perfusion circuit as described above. Optionally, the pulmonary vein is allowed to drain directly into the lung chamber assembly without cannulation. From the pulmonary vein interface, the perfusion fluid flows back to a fluid reservoir, where it may be infused with nutrients prior to recirculation through the perfusion circuit.

When applicable (e.g., during the isolated tracheal volume mode), a gas exchange device is positioned within the perfusion circuit between the fluid reservoir and the lung chamber assembly. The gas exchange device receives a gas from an external or onboard gas source and applies gas (e.g., oxygen, a mixture of oxygen and carbon dioxide, or a mixture of oxygen, carbon dioxide and nitrogen) to the perfusion fluid prior to flowing the fluid into the lungs. Alternatively, oxygen and other blood gas levels may be determined by drawing fluid samples from the perfusion fluid and analyzing the samples in a commercially available blood gas analyzer or using partial pressure sensors onboard the system. The system may include one or more oxygen saturation sensors to measure the oxygen saturation level of the perfusion fluid to ensure that the perfusion fluid is maintained at physiologic or other user-defined oxygen levels. In the embodiments where the perfusion fluid is blood-product based, it contains red blood cells (i.e., oxygen carrying cells). Optionally, the oxygen sensors also provide a hematocrit measurement of the concentration of red blood cells in the perfusion fluid.

The nutritional subsystem infuses the perfusion fluid with a supply of maintenance solutions as the perfusion fluid flows through the system, and in some embodiments, while it is in the reservoir. According to one feature, the maintenance solutions include nutrients, such as glucose. According to another feature, the maintenance solutions include a supply of therapeutics, vasodilators, endothelial stabilizers, and/or preservatives for reducing edema and providing endothelial support to the lungs.

According to another practice, the perfusion fluid includes blood removed from the donor through a process of exsanguination during harvesting of the lungs. Initially, the blood from the donor is loaded into the reservoir and the cannulation locations in the lung chamber assembly are bypassed with a bypass conduit to enable normal mode flow of perfusion fluid through the system without a lung being present. Prior to cannulating the harvested lungs, the system may be primed by circulating the exsanguinated donor blood through the system to heat and/or filter it, and, if desired, oxygenate it.

In one embodiment, the portable multiple use module includes a portable housing constructed on a portable chassis, and the single use disposable module includes a disposable structure, such as a housing or a frame. To reduce weight, in one configuration, the disposable structure along with various components of the single use module are formed from molded plastic such as polycarbonate, and the multiple use module chassis is formed from molded materials such as polycarbonate or carbon fiber composites. According to one feature, the unloaded single use disposable structure weighs less than about 12 pounds and the loaded single use module weighs less than about 18 pounds. According to another feature, the multiple use housing and chassis unloaded with components weighs less than about 50 pounds, and when loaded with a multiple use module, batteries, gas, maintenance solutions, perfusion fluid and an organ, weighs about 85 pounds or less. According to another advantage, the system of the invention including both single and multiple use modules, exclusive of any perfusion, nutrient, preservative or other fluids, batteries and gas supply, weighs less than about 65 pounds.

The single use disposable structure (e.g., frame or housing) is sized and shaped for interlocking with the portable chassis of the multiple use module for electrical, mechanical, gas and fluid interoperation with the multiple use module. According to one feature, the multiple and single use modules communicate with each other via an optical interface, which comes into optical alignment automatically upon the single use disposable module being installed into the portable multiple use module. According to another feature, the portable multiple use module provides power to the single use disposable module via spring loaded connections, which also automatically connect upon the single use disposable module being installed into the portable multiple use module. According to one feature, the optical interface and spring loaded connections ensure that power and data connection between the single and multiple modules is not lost due to jostling, for example, during transport over rough terrain.

In various embodiments, the lung chamber assembly mounts to the disposable structure.

In one configuration, the various sensors associated with the heater assembly, the gas exchange device and/or the perfusion fluid pump are included on the disposable single use module. However, this need not be the case, for example, with regard to non-perfusion fluid contacting sensors. According to one embodiment, the single use disposable module employs an oxygen sensor including in-line cuvette through which the perfusion fluid passes, an optical source for directing light at the perfusion fluid passing through the cuvette, and an optical sensor for measuring an optical quality of the perfusion fluid passing through the cuvette. Preferably, the in-line cuvette seamlessly or substantially seamlessly attaches to a perfusion fluid flow conduit to reduce turbulence in the perfusion fluid and provide one or more accurate measurements. The seamless or substantially seamless configuration also reduces damage to any blood based components of the perfusion fluid.

According to a further configuration, the disposable single-use module includes the above-mentioned plurality of inline compliance chambers located, for example, at an outlet of the perfusion fluid pump, an outlet of the gas exchange device or an outlet of the heater assembly. In a further embodiment, the disposable single-use module includes a plurality of ports for sampling fluids from the lung chamber assembly.

In a further aspect, the invention is directed to a method of transporting one or more lungs ex vivo, including the steps of placing the lungs for transplantation in a protective chamber of a portable organ care system, pumping a perfusion fluid into the lungs via a pulmonary artery of the lungs, providing a flow of the perfusion fluid away from the lungs via a pulmonary vein of the lungs, and transporting the lungs in the portable organ care system from a donor site to a recipient site while pumping the perfusion fluid into an artery of the lungs.

These and other features and advantages of the invention are described in further detail below with regard to illustrative embodiments of the invention.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting, the scope of the invention instead being defined by the appended claims.

FIGS. 28A-28C show various views of an exemplary hematocrit and oxygen saturation sensor of the type employed in the illustrative single use disposable module of FIGS. 19A-19C.

FIG. 39 shows exemplary measurement data collected during a maintenance mode operation of the lung care system.

FIG. 46 depicts a top view and a profile view of another exemplary lung chamber assembly employed in the illustrative single use disposable module of FIGS. 41-43.

DETAILED DESCRIPTION

Figure 1:
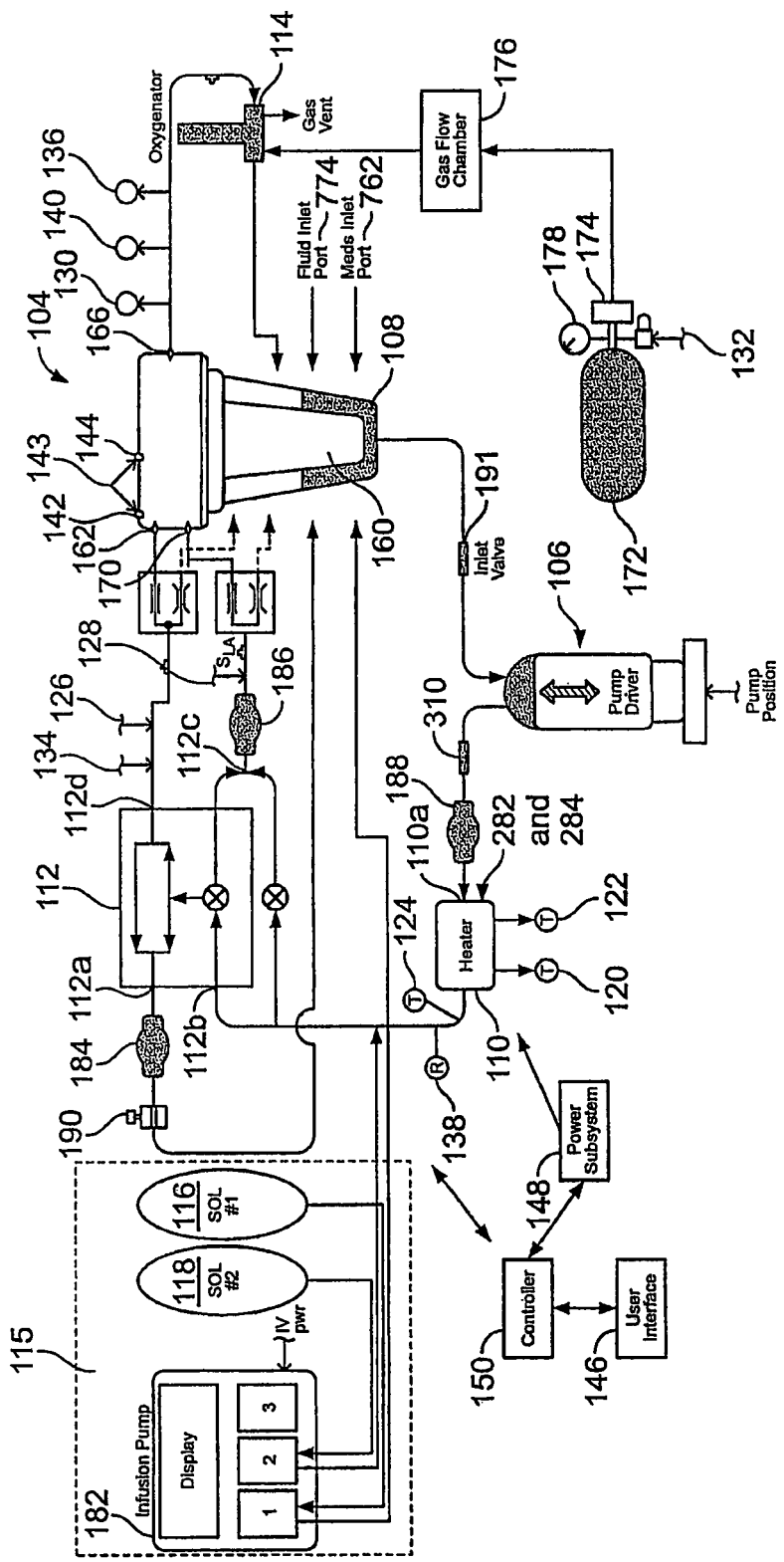
FIG. 1 is a schematic diagram of a portable organ care system according to an illustrative embodiment of the invention.

As described above in summary, the invention generally provides improved approaches to ex vivo organ care. More particularly, in various embodiments, the invention is directed to improved systems, methods and devices relating to maintaining an organ in an ex vivo portable environment. According to one improvement, the organ maintenance system of the invention maintains a heart beating at or near normal physiologic conditions. To this end, the system circulates an oxygenated, nutrient enriched perfusion fluid to the heart at near physiologic temperature, pressure and flow rate.

In other embodiments the system maintains other organs, such as one or more lungs, at or near normal physiologic conditions. According to one implementation, the system employs a perfusion fluid solution that more accurately mimics normal physiologic conditions. In one embodiment, the perfusion fluid is blood-product based. In alternative embodiments, the solution is synthetic blood substitute based. In other embodiments the solution may contain a blood product in combination with a blood substitute product. The blood product may be derived from donor blood or blood from a blood bank.

According to various illustrative embodiments, the improvements of the invention enable an organ to be maintained ex vivo for extended periods of time, for example, exceeding 3, 4, 5, 6, 8, 10, 12, 14, 16, 18, 20, 22, 24 or more hours. Such extended ex vivo maintenance times expand the pool of potential recipients for donor organs, making geographic distance between donors and recipients less important. Extended ex vivo maintenance times of the invention also provide the time needed for better genetic and HLA matching between donor organs and organ recipients, increasing the likelihood of a favorable outcome. The ability to maintain the organ in a near physiologic functioning condition also enables a clinician to evaluate the organ's function ex vivo, further increasing the likelihood of transplantation success. In some instances, the extended maintenance time enables medical operators to perform repairs on donor organs with minor defects. According to another advantage, the increased ex vivo organ maintenance times of the invention enable an organ to be removed from a patient, treated in isolation ex vivo, and then put back into the body of a patient. Such treatment may include, without limitation, pharmaceutical treatments, gas therapies, surgical treatments, chemo-, bio-, gene and/or radiation therapies.

The illustrative systems, methods and devices of the invention are described below in the following order. First, the components of an illustrative organ care system 100 for use with a heart are described. Second, illustrative operation of the system 100 is discussed. Third, a subset of the components of the system 100 are described in further detail. Fourth, illustrative control systems and methods for the system 100 are discussed. Fifth, an illustrative user interface is described. Sixth, mechanical features of the system 100 are discussed in further detail with regard to an exemplary implementation. Seventh, exemplary methods for employing the system 100 during an organ harvest, transport, and transplantation procedure are described. Eighth, illustrative implementations of a system 1000 adapting the system 100 for preserving lungs are described, and ninth illustrative perfusion, nutritional and preservative solutions suitable for use with the system 1000 are presented.

Figure 2:
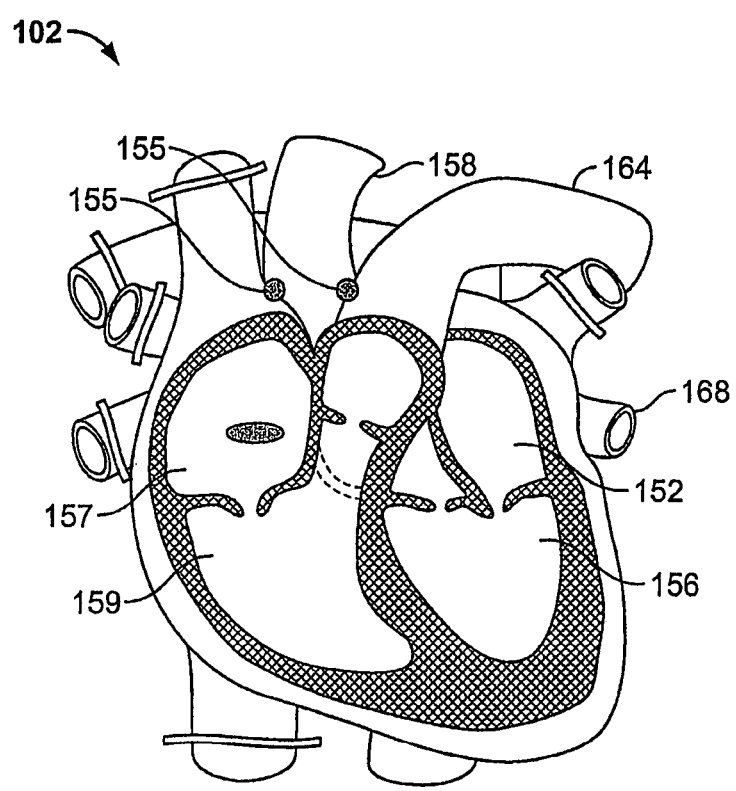
FIG. 2 is a diagram depicting a harvested heart.

Turning to the illustrative embodiments, FIG. 1 depicts a schematic diagram of a portable organ care system 100 according to an illustrative embodiment of the invention. FIG. 2 shows a conceptual drawing of a heart 102, which may be preserved/maintained ex vivo by the organ care system 100 of the invention. Referring to FIGS. 1 and 2, the illustrative system 100 includes an organ chamber assembly 104 for containing the heart 102 during ex vivo maintenance, a reservoir 160 for holding, defoaming and filtering the perfusion fluid 108, portal 774 for loading perfusion fluid 108 into the reservoir 160 and a portal 762 for applying therapeutics to the fluid 108 contained in the reservoir 160, a perfusion fluid pump 106 for pumping/circulating perfusion fluid 108 to and from the harvested heart 102; a heater assembly 110 for maintaining the temperature of the perfusion fluid 108 at or near physiological temperatures; a flow mode selector valve 112 for switching between normal and retrograde aortic flow modes (also referred to as "normal flow mode" and "retrograde flow mode," respectively); an oxygenator 114 for re-oxygenating the perfusion fluid 108 subsequent to it being expelled by the heart 102; a nutritional subsystem 115 for replenishing nutrients 116 in the perfusion fluid 108 as they are metabolized by the heart 102 and for providing additional preservatives 118 to the perfusion fluid to reduce, for example, ischemia and/or other re-perfusion related injuries to the heart 102. The illustrative system 100 also includes a plurality of sensors, including without limitation: temperature sensors 120, 122 and 124; pressure sensors 126, 128, 130 and 132; perfusion flow rate sensors 134, 136 and 138; a perfusion fluid oxygenation sensor 140; and sensor electrodes 142 and 144, and defibrillation source 143. The system 100 further includes: various components employed for maintaining suitable flow conditions to and from the heart 102; an operator interface 146 for assisting an operator in monitoring operation of the system 100, and the condition of the heart 102, and for enabling the operator to select various operating parameters; a power subsystem 148 for providing fault tolerant power to the system 100; and a controller 150 for controlling operation of the organ care system 100.

Figure 3:
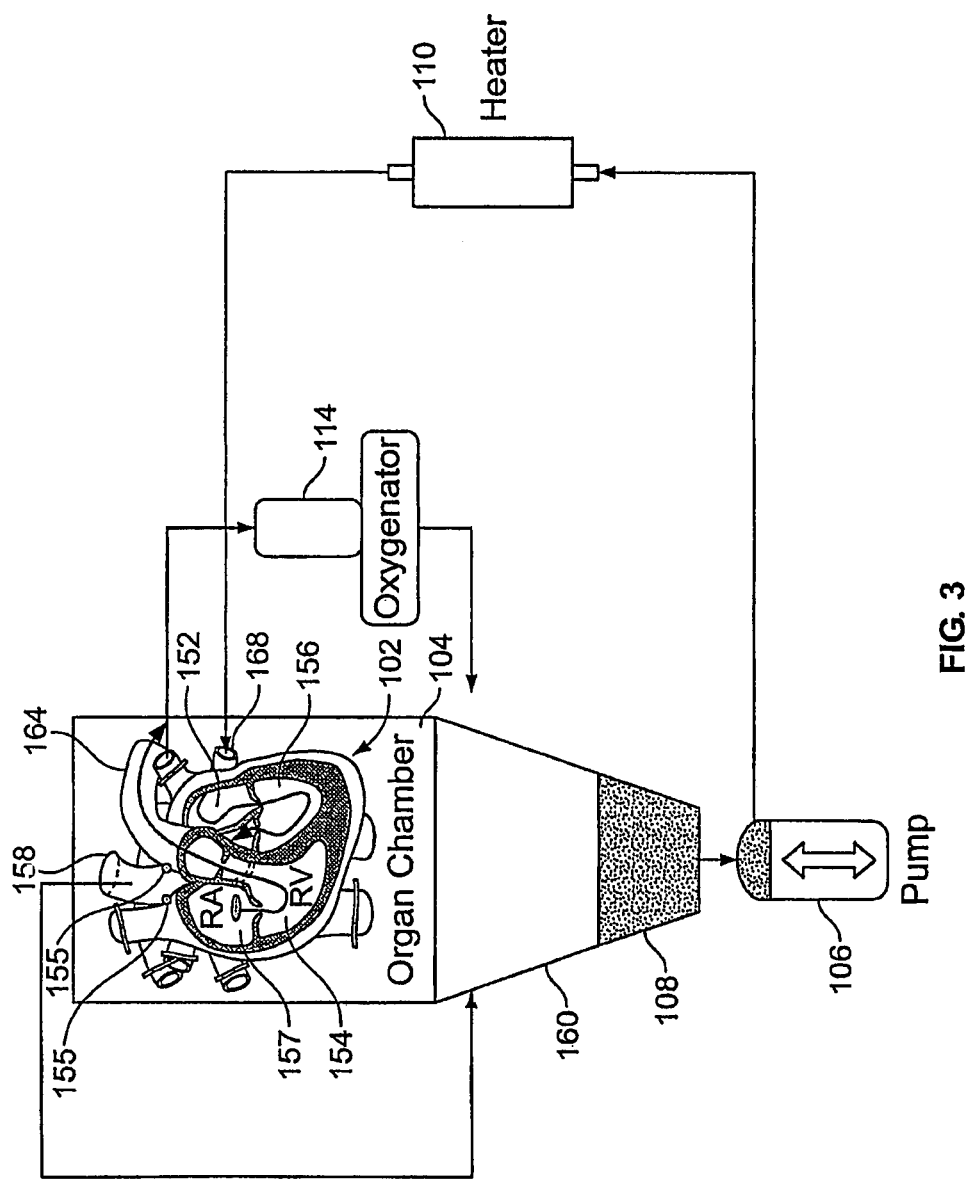
FIG. 3 is a conceptual diagram depicting the harvested heart of FIG. 2 interconnected with the organ care system of FIG. 1 in a normal flow mode configuration according to an illustrative embodiment of the invention.
Figure 4:
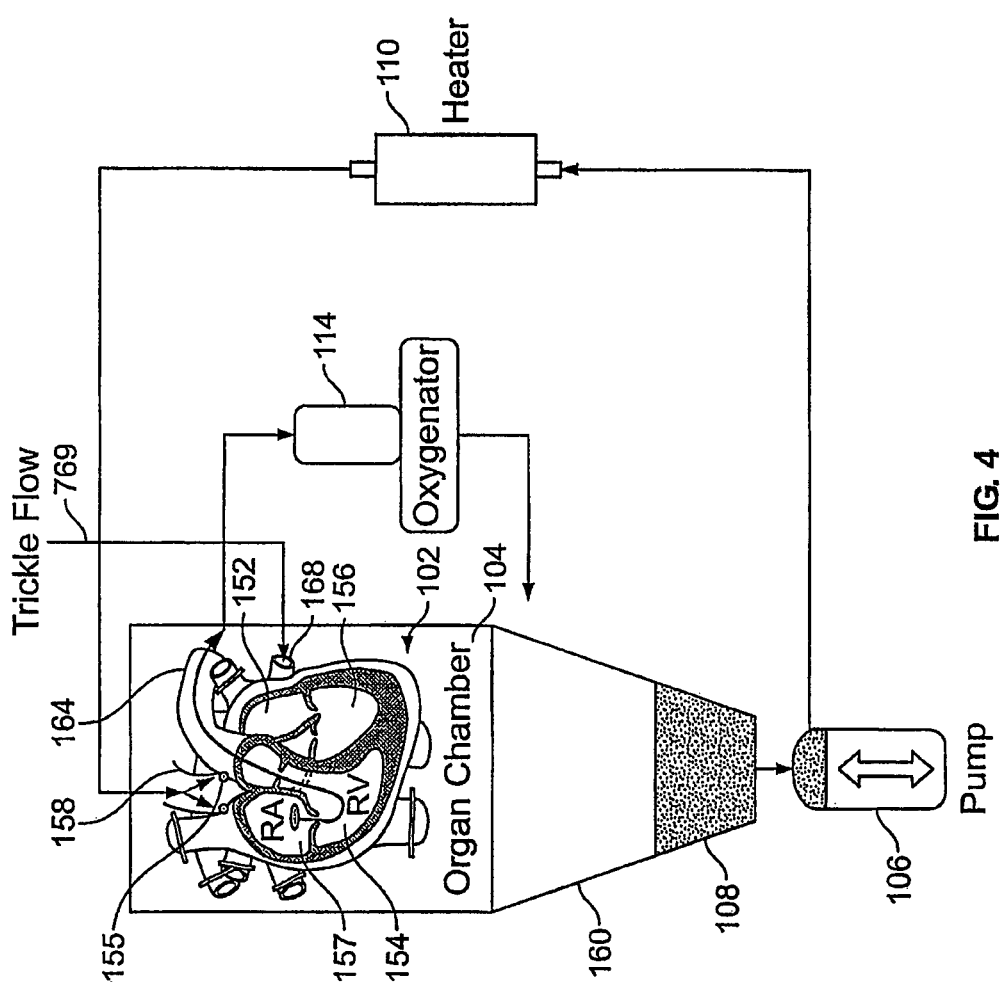
FIG. 4 is a conceptual diagram depicting the harvested heart of FIG. 2 interconnected with the organ care system of FIG. 1 in a retrograde flow mode configuration according to an illustrative embodiment of the invention.

Referring also to FIGS. 3 and 4, according to the illustrative embodiment, the system 100 can maintain the heart 102 in two modes of operation—a normal flow mode, shown in FIG. 3, and a retrograde flow mode shown in FIG. 4. Generally, in the normal flow mode of FIG. 3, the system 100 circulates the perfusion fluid 108 to the heart 102 in the same manner as blood would circulate in the human body. More particularly, referring to FIGS. 1-3, the perfusion fluid enters the left atrium 152 of the heart 102 via the pulmonary vein 168. The perfusion fluid 108 is flowed away from the right ventricle 154 via the pulmonary artery 164 and away from the left 156 ventricle via the aorta 158. In normal flow mode, the system 100 pumps the perfusion fluid to the heart 102 at a near physiological rate of between about 1 liter/min and about 5 liters/minute. This mode is useful, for example, for performing functional testing to verify that the heart 102 is defect free, both prior and subsequent to transportation to a donor location.

Alternatively, in retrograde flow mode, shown in FIG. 4, the system 100 flows the perfusion fluid 108 into the heart 102 via the aorta 158, through the coronary sinus 155 and other coronary vasculature of the heart, and out of the right ventricle 154 of the heart 102 via the pulmonary artery 164. As discussed in further detail below with regard to FIGS. 24A and 24B, the system 100 also provides a trickle flow 769 to the left atrium 152 through trickle valve 768. The trickle flow is provided in an amount sufficient to moisten the left atrium 152 and left ventricle 156. In certain applications the trickle flow is less than about 5 ml/min, less than about 1 ml/min, or less than about 0.1 ml/min. In this mode of operation, the system 100 reduces the flow rate of the perfusion fluid 108 to between about 300 milliliters/minute and about 1 liter/minute. The inventors have found that the retrograde flow path of FIG. 4, along with the reduced flow rate, reduces damage to the heart 102 during extended periods of ex vivo maintenance. Thus, according to one feature of the invention, the heart 102 is transported to a donor site in retrograde flow mode.

Having briefly described the normal and retrograde flow modes, the system 100 will next be described in further detail operationally. Referring once again to FIGS. 1-4, in one practice, the heart 102 is harvested from a donor and cannulated into the organ chamber assembly 104. The perfusion fluid 108 is prepared for use within system 100 by being loaded into the reservoir 160 via portal 774 and, optionally, being treated with therapeutics via portal 762. The pump 106 pumps the loaded perfusion fluid 108 from a reservoir 160 to the heater assembly 110. The heater assembly 110 heats the perfusion fluid 108 to or near a normal physiological temperature. According to one embodiment, the heater assembly 110 heats the perfusion fluid to between about 32° C. and about 37° C. The heater assembly 110 has an internal flow channel with a cross-sectional flow area that is approximately equal to the inside cross-sectional area of fluid conduits that carry the perfusion fluid 108 into and/or away from the heater assembly 110, so as to minimize disturbance of fluid flow. From the heater assembly 110, the perfusion fluid 108 flows to the flow mode selector valve 112.

Figure 5A:
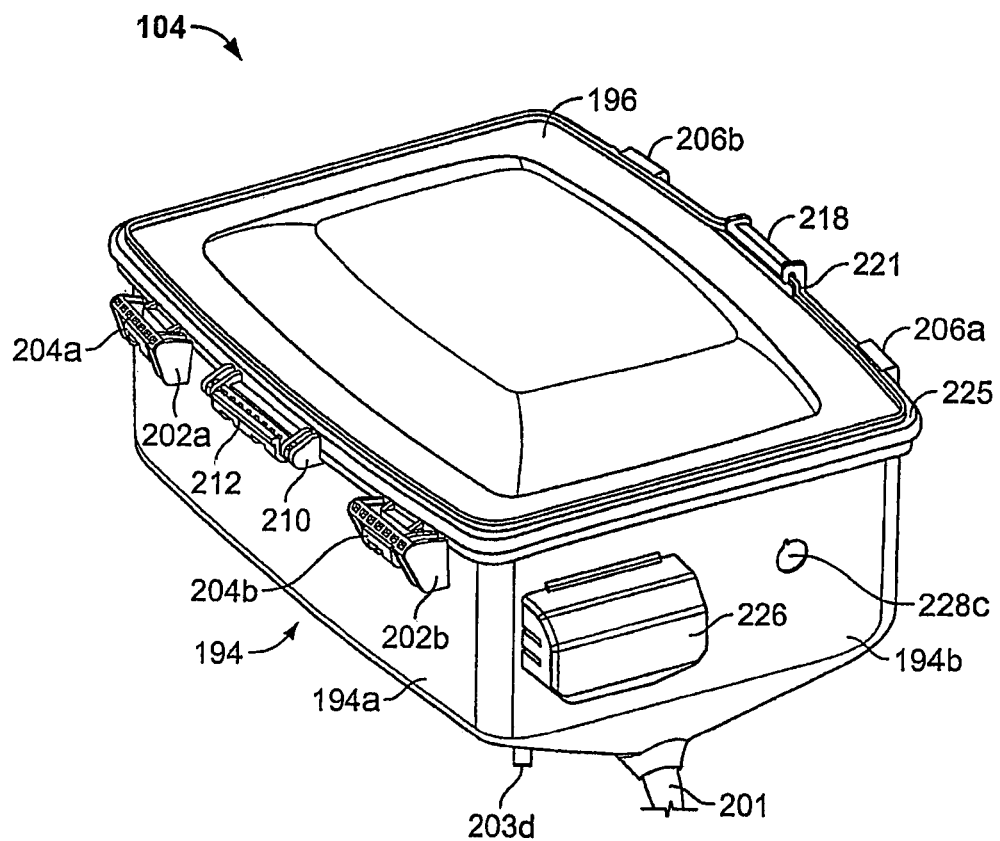
FIGS. 5A-5F show various views of an organ chamber assembly of the type employed in the organ care system of FIG. 1 according to an illustrative embodiment of the invention.
Figure 5B:
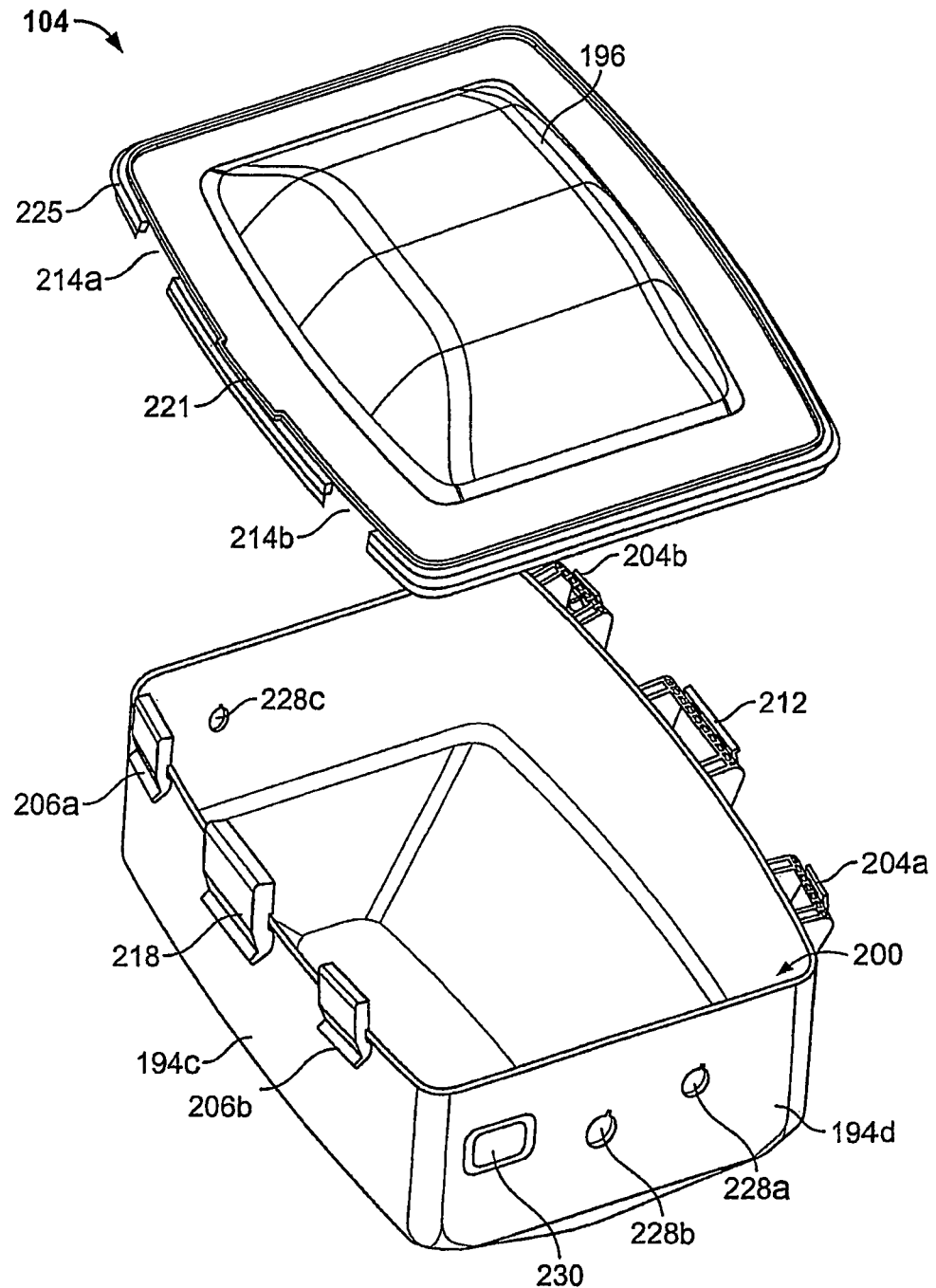

Initially, the flow mode selector valve 112 is positioned in retrograde mode to direct the perfusion fluid 108 from the heater assembly 110 into the organ chamber assembly 104 via a first interface 162. Also referred to as an aorta interface or left ventricle interface, the interface 162 includes cannulation to vascular tissue of the left ventricle via an aperture 228b located on the organ chamber assembly 104 (as shown in FIGS. 5A-5B). As the heart 102 warms, it begins to beat which causes the heart 102 to pump the perfusion fluid 108 through the coronary vasculature 155 and out of the heart 102 through the right ventricle 154 via a second interface 166. The second interface 166, also referred to as a pulmonary artery interface or a right ventricle interface, includes cannulation to vascular tissue of the right ventricle via an aperture 228c located on the organ chamber assembly 104 (as shown in FIGS. 5A-5B). As mentioned above, in retrograde flow mode, fluid is not actively pumped into or out of the left side of the heart, except for a relatively small trickle 769 of perfusion fluid, which is delivered to moisten the left atrium 152 and left ventricle 156, as described below in reference to FIGS. 24A-24E.

In response to the flow mode selector valve 112 being placed in the normal mode position, it directs the perfusion fluid 108 into the left atrium 152 of the heart 102 via a third interface 170. The third interface 170, also referred to as a pulmonary vein interface or left atrium interface, includes cannulation to vascular tissue of the left atrium 152 via an aperture 228a located on the organ chamber assembly 104 (as shown in FIGS. 5A-5B). The heart 102 then expels the perfusion fluid 108 through the left ventricle 156 via the aorta interface 162 and through the right ventricle 154 via the pulmonary artery interface 166.

Each of the interfaces 162, 166 and 170 may be cannulated to the heart 102 by pulling vascular tissue (e.g., an aorta stub) over the end of the interface, then tying or otherwise securing the tissue to the interface. The vascular tissue is preferably a short segment of a blood vessel (e.g., an aorta stub 158) that remains connected to the heart 102 after the heart 102 is severed and explanted from the donor. For example, the aorta interface 162 is cannulated to a small segment of the severed aorta 158 which has been formed by severing the aorta 158 in a location down-stream from the coronary sinus 155. In certain applications, the short vessel segments may be about 5 to about 10 inches in length or longer. The segments may also be shorter than about 5 inches. The segments may be about 2 to about 4 inches in length, or about 1 to about 2 inches in length; in other applications the segments may be less than about ½ inch, or less than about ¼ inch.

Alternatively, the cannulation may occur by affixing the interface directly to the applicable atrium or ventricle, as may be preferred in applications where the heart 102 is prepared for explantation by severing an entire blood vessel without leaving any stub portion of the vessel connected to the heart 102. For example, a left atrium 152 cannulation can be formed by inserting the interface 170 directly into the left atrium 152 and clamping the interface 170 in place, without the need to tie to any pulmonary vein 168 tissue.

With continued reference to FIG. 1, in both flow modes the perfusion fluid 108 flows from the pulmonary artery interface 166 into the oxygenator 114. The oxygenator 114 receives gas from an external or onboard source 172 through a gas regulator 174 and a gas flow chamber 176, which can be a pulse-width modulated solenoid valve that controls gas flow, or any other gas control device that allows for precise control of gas flow rate. A gas pressure gauge 178 provides a visual indication of how full the gas supply 172 is. The transducer 132 provides similar information to the controller 150. The controller 150 can regulate automatically the gas flow into the oxygenator 114 in dependence, for example, on the perfusion fluid oxygen content measured at the sensor 140. According to various illustrative embodiments, the oxygenator 114 is a standard membrane oxygenator, such as the Liliput 2 manufactured by Dideco, a division of Sorin Biomedical, or the MINIMAX PLUS™ manufactured by Medtronic, Inc. In the illustrative embodiment, the gas includes an oxygen and carbon dioxide mixture. An exemplary composition of such a mixture contains about 85% $O_2$, about 1% $CO_2$, with the balance being $N_2$. Subsequent to re-oxygenation, the oxygenator 114 returns the perfusion fluid 108 to the reservoir 160. According to the illustrative embodiment, the sensor 140 measures the amount of light absorbed or reflected by the perfusion fluid 108 when applied at a multi-wavelength to provide an optical-based measurement of oxygen saturation. Since the perfusion fluid 108 is blood product based in certain embodiments, it may contain red blood cells (i.e., oxygen carrying cells). Accordingly, the sensor 140 also provides a signal 145 indicative of a hematocrit measurement of the perfusion fluid 108. In alternative embodiments the solution 108 is formed of a synthetic blood substitute, while in other embodiments, the solution 108 may contain a blood product in combination with a blood substitute product.

Also, in both flow modes, the nutritional subsystem 115, including a supply of maintenance solutions 116/118 and an infusion pump 182, infuses the perfusion fluid 108 with nutrients 116, such as glucose, as the perfusion 108 solution flows through the system 100, and in some embodiments, while it is in the reservoir 160. The maintenance solutions 116/118 also include a supply of therapeutics and preservatives 118 for reducing ischemia and other re-perfusion related injuries to the heart 102.

Both normal and retrograde flow modes are described in further detail below with reference to FIGS. 24A-26B.

According to the illustrative embodiment, the system 100 is primed prior to introducing an organ into the organ chamber assembly 104. During priming, a priming solution (described below) is inserted into the organ chamber 160 and pumped through the system 100. In one exemplar application, the priming occurs for a period of between about 5 and about 20 minutes. The cannulation interfaces 162, 166 and 170 in the organ chamber assembly 104 are bypassed to enable normal mode flow of perfusion fluid 108 through the system 100, without the donor heart 102 being present. Blood (or a synthetic blood substitute) is then loaded into the reservoir 160. The blood may be the blood exsanguinated from the donor during harvesting of the heart 102 or obtained from typed and cross-matched banked blood. The system 100 then circulates the blood (or blood substitute) through the system 100 to heat, oxygenate, and filter it. Nutrients, preservatives and/or other therapeutics are provided via the infusion pump 182 of the nutritional subsystem 115. Various parameters may also be initialized and calibrated via the operator interface 146 during priming. Once the system 100 is running appropriately, the pump rate can be decreased or brought to zero, and the heart 102 can be cannulated into the organ chamber assembly 104. The pump rate can then be increased. Priming of the system 100 is described in further detail below with reference to the flow diagram of FIG. 29A.

As shown in FIG. 1, the system 100 also includes a plurality of compliance chambers 184, 186 and 188. The compliance chambers 184, 186 and 188 are essentially small inline fluid accumulators with flexible, resilient walls designed to simulate the human body's vascular compliance by aiding the system in more accurately mimicking blood flow in the human body, for example, by providing flow back-pressure and/or by filtering/reducing fluid pressure spikes due, for example, to flow rate changes and/or the pumping of the pump 106. According to the illustrative embodiment, the compliance chamber 184 is located between an output 112a of the mode valve 112 and the reservoir 160 and operates in combination with an adjustable clamp 190 during normal flow mode to provide back pressure to the aorta 158 to cause perfusion fluid to flow into the coronary sinus 155 to feed the heart 102. In the illustrative embodiment, the fluid back-pressure provided to the aorta 158 is between about 55 mmHg and about 85 mmHg, which is within an acceptable near-physiologic range of mean aortic blood pressure (which is typically between about 80 mmHg and about 100 mmHg). The back pressure to the aorta 158 aids the system 100 in simulating normal physiologic conditions. The compliance chamber 186 is located between an output 112b of the mode valve 112 and the pulmonary vein cannulation interface 170 of the organ chamber assembly 104. The primary function of the compliance chamber 186 is to provide back-pressure to the left atrium 152 and to smooth pressure/flow spikes caused from the pumping action of the perfusion fluid pump 106, which delivers blood to the heart without causing substantial fluid pressure spikes. In the illustrative embodiment, the fluid back-pressure provided to the left atrium 152 is between about 0 mmHg to about 14 mmHg, which is approximately the same as the left atrial pressure under normal physiologic conditions. The compliance chamber 188 is located between an output of a one way valve 310 and an inlet 110a of the heater 110. The primary function of the compliance chamber 188 is also to smooth pressure/flow spikes caused by the pumping action of the perfusion fluid pump 106 and to provide fluid back-pressure to the pulmonary artery 164. In the illustrative embodiment, the fluid back-pressure provided to the pulmonary artery 164 is between about 0 mmHg and about 25 mmHg, which is within an acceptable near-physiologic range of mean arterial blood pressure (between about 0 mmHg and about 12 mmHg).

The compliance chambers 184, 186 and 188 provide the benefits described above through their size and shape and the materials used in their design. The chambers 184, 186 and 188 are sized to contain about 20 ml to about 100 ml of fluid 108, and they are shaped in an oval configuration to allow them to receive fluid 108 and expand to dampen pressure spikes and to provide back-pressure to the heart 102. In certain applications, the material used for the chambers 184, 186 and 188 includes at least one flexible membrane, selected so that the chambers have a Shore A durametric hardness (ASTM D2240 00) of about 10 (more flexible) to about 60 (less flexible), with certain preferred embodiments having a hardness of between about 30 (+/−about 8) and about 50 (+/−about 8). In the illustrative embodiment, the compliance chamber 184 has a Shore A hardness of about 50 (+/−about 8) and the compliance chamber 186 has a Shore A hardness of about 30 (+/−about 8). In the illustrative embodiment, the compliance chamber 188 has a dual-layered configuration, with an inner chamber having a Shore A hardness of about 50 (+/−about 8) and an outer sleeve having a Shore A hardness of about 30 (+/−about 8). Alternatively, the inner chamber can have a lower hardness (e.g., about 30, +/−about 8) and outer sleeve can have a higher hardness (e.g., about 50, +/−about 8)).

Figure 5C:
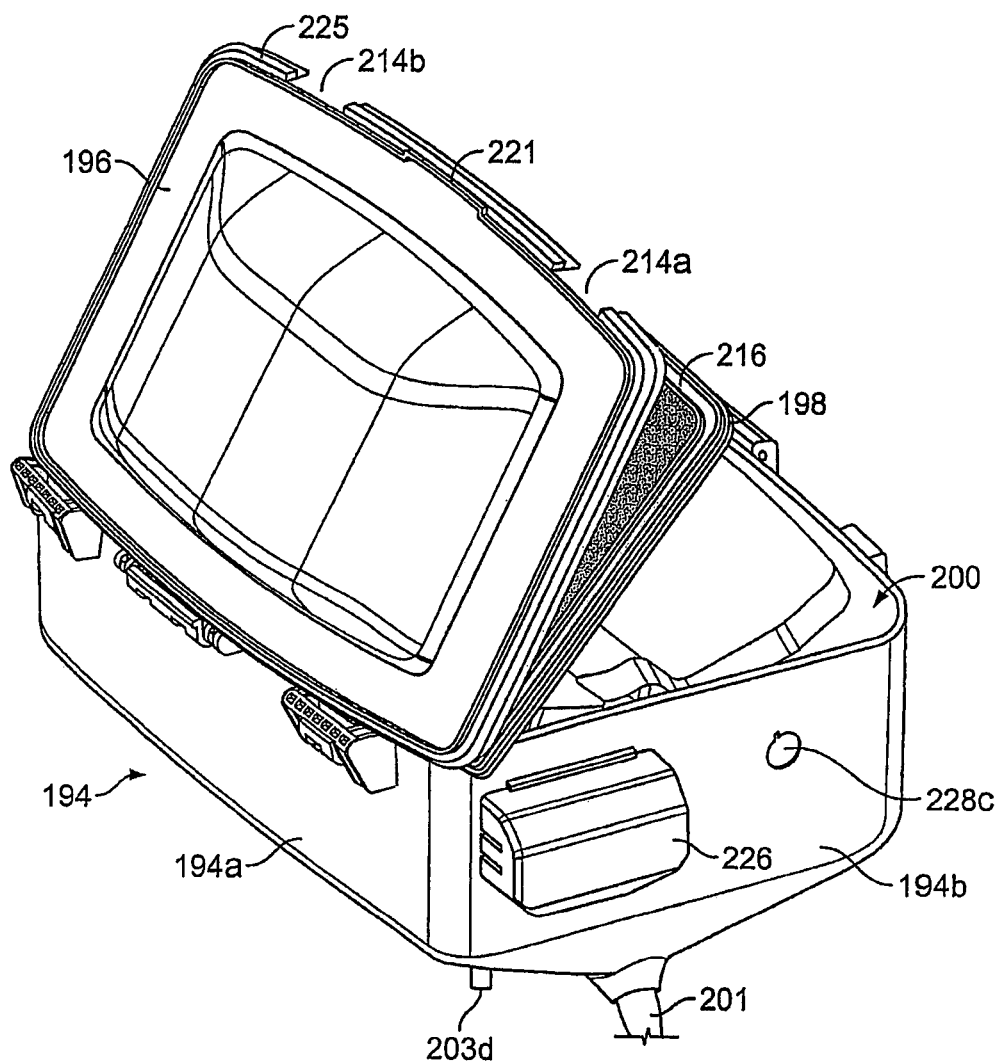

Having provided an operational overview of the system 100, the organ chamber assembly 104, the perfusion heater assembly 110, and a pump head interface assembly 192 for interfacing with the pump 106 are next described in further detail. FIGS. 5A-5F depict various views of the illustrative organ chamber assembly 104 of FIG. 1. As shown most clearly in FIGS. 5A-5D, the organ chamber assembly 104 includes a housing 194, a outer lid 196 and an intermediate lid 198. The housing includes a bottom 194e and one or more walls 194a-194d for containing the heart 102. The intermediate lid 198 covers an opening 200 to the housing 194 for substantially enclosing the heart 102 within the housing 194. As most clearly shown in FIGS. 5E and 5F, the intermediate lid 198 includes a frame 198a and a flexible membrane 198b suspended within the frame 198a. The flexible membrane 198b, preferably, is transparent but may be opaque, translucent, or substantially transparent. According to one feature, the flexible membrane includes sufficient excess membrane material to contact the heart 102 when contained within the housing 195. This feature enables a medical operator to touch/examine the heart 102 indirectly through the membrane 198b, or apply an ultrasound probe to the heart 102 through the membrane 198b, while maintaining sterility of the housing 195. The membrane 198b may be made, for example, from any suitable flexible polymer plastic, for example polyurethane. The membrane 198b may also have integrated electrically conductive pads/contacts 199a and 199b through which electrical activity of the heart may be sensed via electrodes such as the electrodes 142 and 144, and/or for through which defibrillation or pacing signals may be delivered, as described more fully below. Alternatively, the contacts 199a and 199b may be electrodes including all or a portion of the functionality of the electrodes 142 and 144. As shown in FIG. 5C, the outer lid 196 opens and closes over the intermediate lid 198 independently from the intermediate lid 198. Preferably, the outer lid 196 is rigid enough to protect the heart 102 from physical contact, indirect or indirect. The outer lid 196 and the chamber 194 may also be made from any suitable polymer plastic, for example polycarbonate.

Figure 5D:
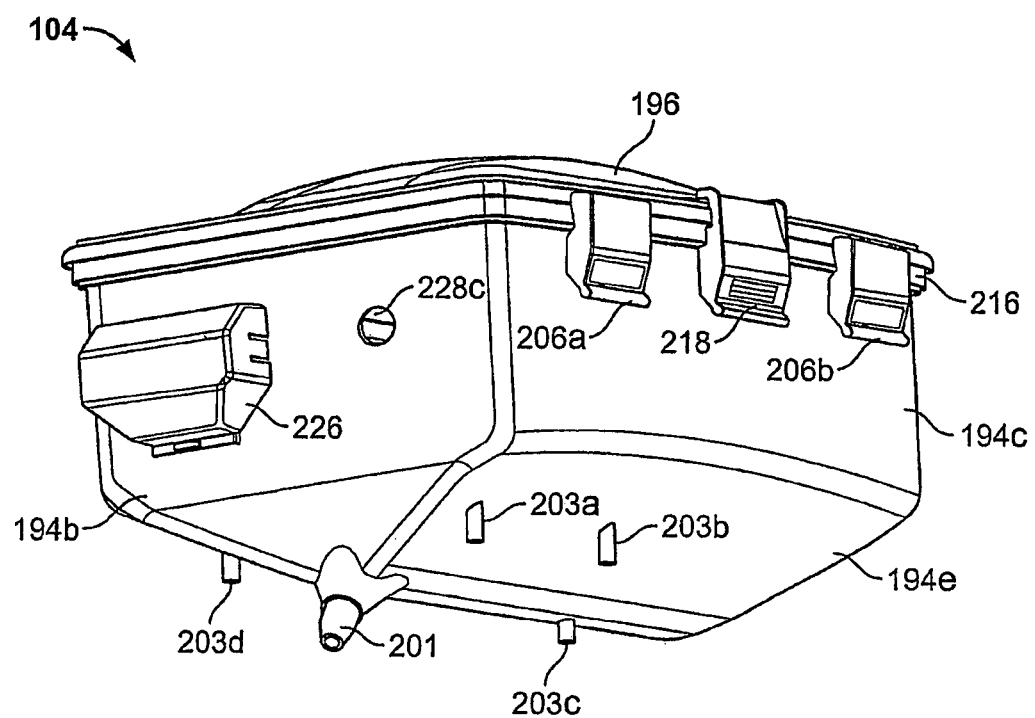
Figure 5E:
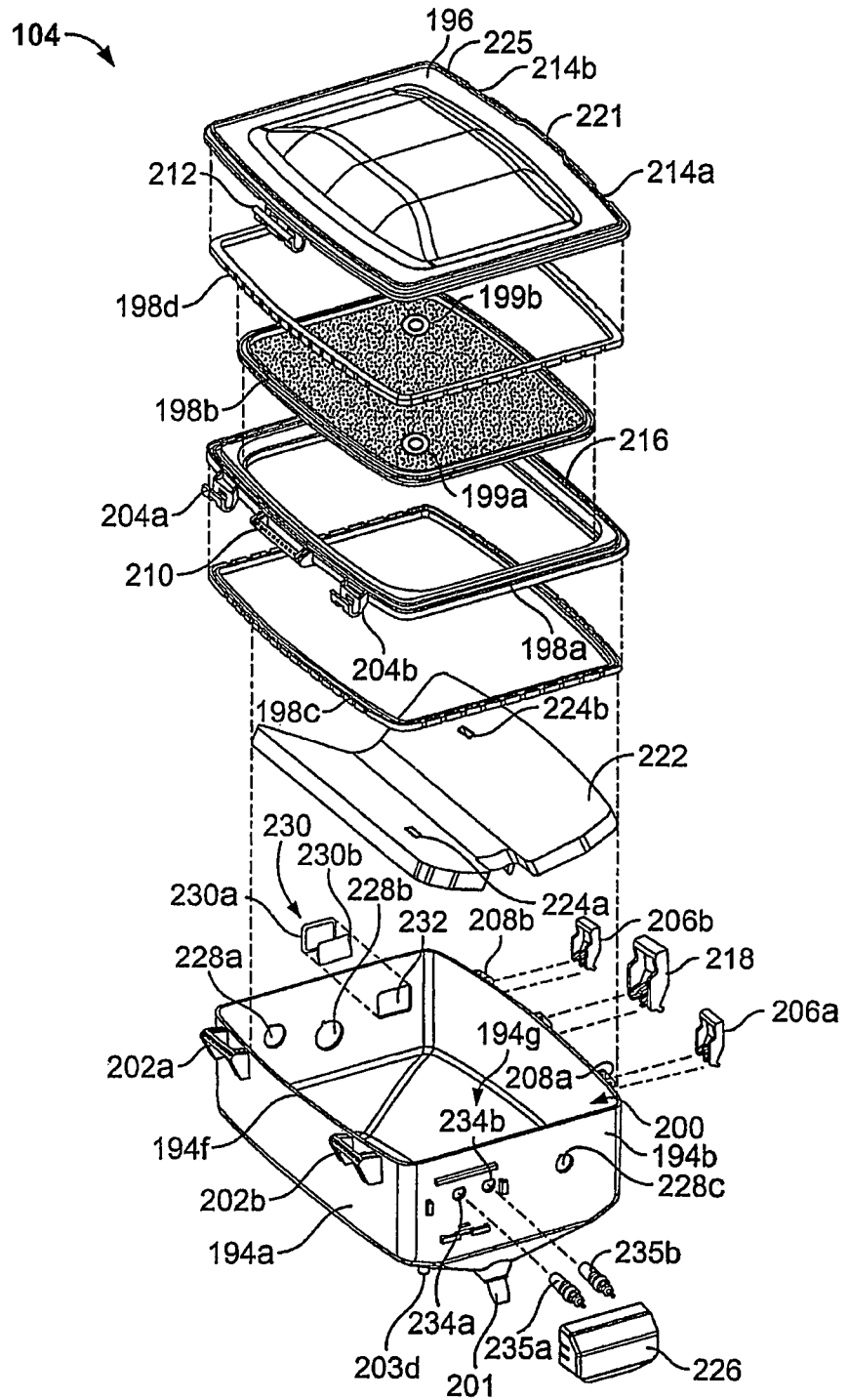
Figure 5F:
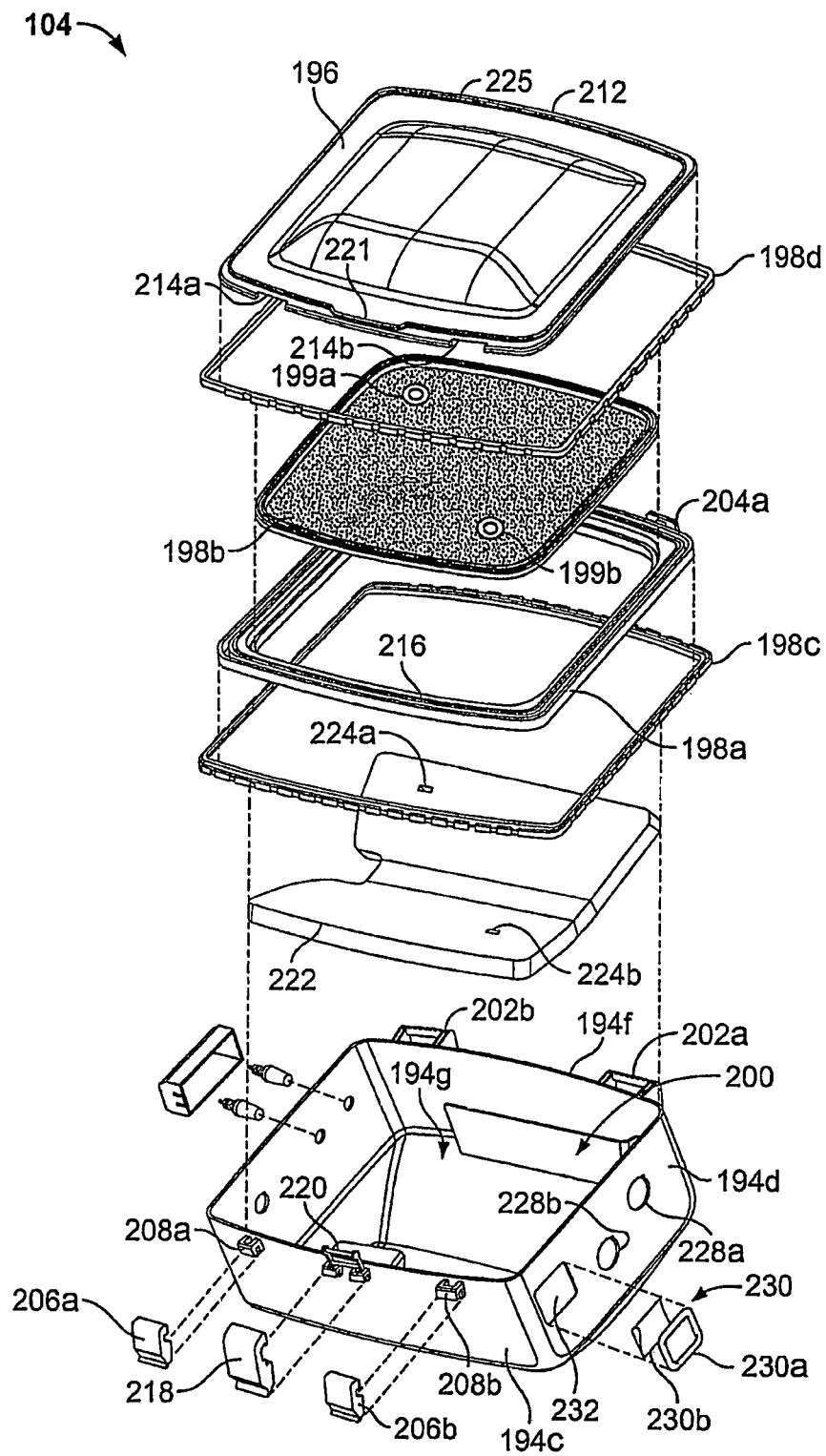

According to one implementation, the housing 194 includes two hinge sections 202a and 202b, and the intermediate lid frame 198a includes two corresponding mating hinge sections 204a and 204b, respectively. The hinge sections 202a and 202b on the housing 194 interfit with the hinge sections 204a and 204b on the intermediate lid frame 198a to enable the intermediate lid 198 to open and close relative to the opening 200 of the housing 194. As shown most clearly in FIGS. 5D and 5F, the organ chamber assembly 104 also includes two latches 206a and 206b for securing the intermediate lid 198 closed over the opening 200. As shown in FIGS. 5E and 5F, the latches 206a and 206b rotatably snap fit onto latch hinge section 208a and 208b, respectively, on the wall 194c of the housing 194. As shown most clearly in FIGS. 5A and 5E, the intermediate lid frame 198a also includes a hinge section 210. The hinge section 210 rotatably snap fits with a mating hinge section 212 on the outer lid 196 to enable the outer lid 196 to open without opening the intermediate lid 198. As shown best in FIGS. 5B, 5D and 5F, the outer lid 196 also includes two cutouts 214a and 214b for enabling the latches 206a and 206b to clamp down on the edge 216 of the intermediate lid frame 198a. As shown in FIGS. 5B, 5D and 5F, the organ chamber assembly 104 also includes a latch 218, which rotatably snap fits onto a hinge part 220 on the wall 194c of the housing 194. In operation, the latch 218 engages a tab 221 on the edge 225 of the outer lid 196 to secure the outer lid 196 closed over the intermediate lid 198.

As shown most clearly in FIGS. 5E and 5F, the intermediate lid also includes two gaskets 198c and 198d. The gasket 198d interfits between a periphery of the intermediate lid frame 198a and a periphery of the outer lid 196 to form a fluid seal between the intermediate lid 198 and the outer lid 196 when the outer lid 196 is closed. The gasket 198c interfits between an outer rim 194f of the housing 194 and the intermediate lid frame 198a to form a fluid seal between the intermediate lid 198 and the periphery 194f of the housing 194 when the intermediate lid 198 is closed.

Optionally, the organ chamber assembly 104 includes a pad 222 or a sac assembly sized and shaped for interfitting over an inner bottom surface 194g of the housing 194. Preferably, the pad 222 is formed from a material resilient enough to cushion the heart 102 from mechanical vibrations and shocks during transport, for example a closed-cell foam. According to one feature, the pad 222 includes a mechanism for adjustably positioning a pair of electrodes, such as the electrodes 142 and 144 of FIG. 1. According to the illustrative embodiment, the mechanism includes two through-apertures 224a and 224b for passing electrical leads from the under side of the pad 222 to corresponding electrodes 142 and 144 on the heart-contacting surface of the pad. Passing the electrical leads through the pad 222 to the electrodes 142 and 144 enables the electrodes 142 and 144 to be adjustably positioned within the pad 222 to accommodate variously sized hearts. In other embodiments, the mechanism may include, without limitation, one or more differently oriented slots, indentations, protrusions, through apertures, partially through apertures, hooks, eyelets, adhesive patches, or the like. In certain embodiments, the pad 222 may be configured with one or more sleeve-like structures that allow an electrode to be inserted within the pad 222, thus providing a membrane-like surface of the pad 222 positioned between the electrode and the heart 102.

In some illustrative embodiments, the pad 222 is configured as a pad assembly, with the assembly including one or more electrodes, such as the electrodes 142 and 144, adjustably located in or on the pad 222. According to one advantage, the pad/electrode configuration of the invention facilitates contact between the electrodes and the heart 102 placed on the pad 222, without temporarily or permanently suturing or otherwise mechanically connecting the electrodes to the heart 102. The weight of the heart 102 itself can also help stabilize the electrodes during transport. According to the illustrative embodiment, the electrodes 142 and 144 include one or more sensors for monitoring one or more electrical signals from the heart and/or defibrillators for providing an electrical signal to the heart. As shown in FIGS. 1 and 5C, the organ chamber assembly 104 includes electrical interface connections 235a-235b, which mount into the apertures 234a-234b, respectively, in the wall 194b of the housing 194. A cover 226 is provided for protecting the electrical interface connections 235a-235b when not being used.

Figure 15:
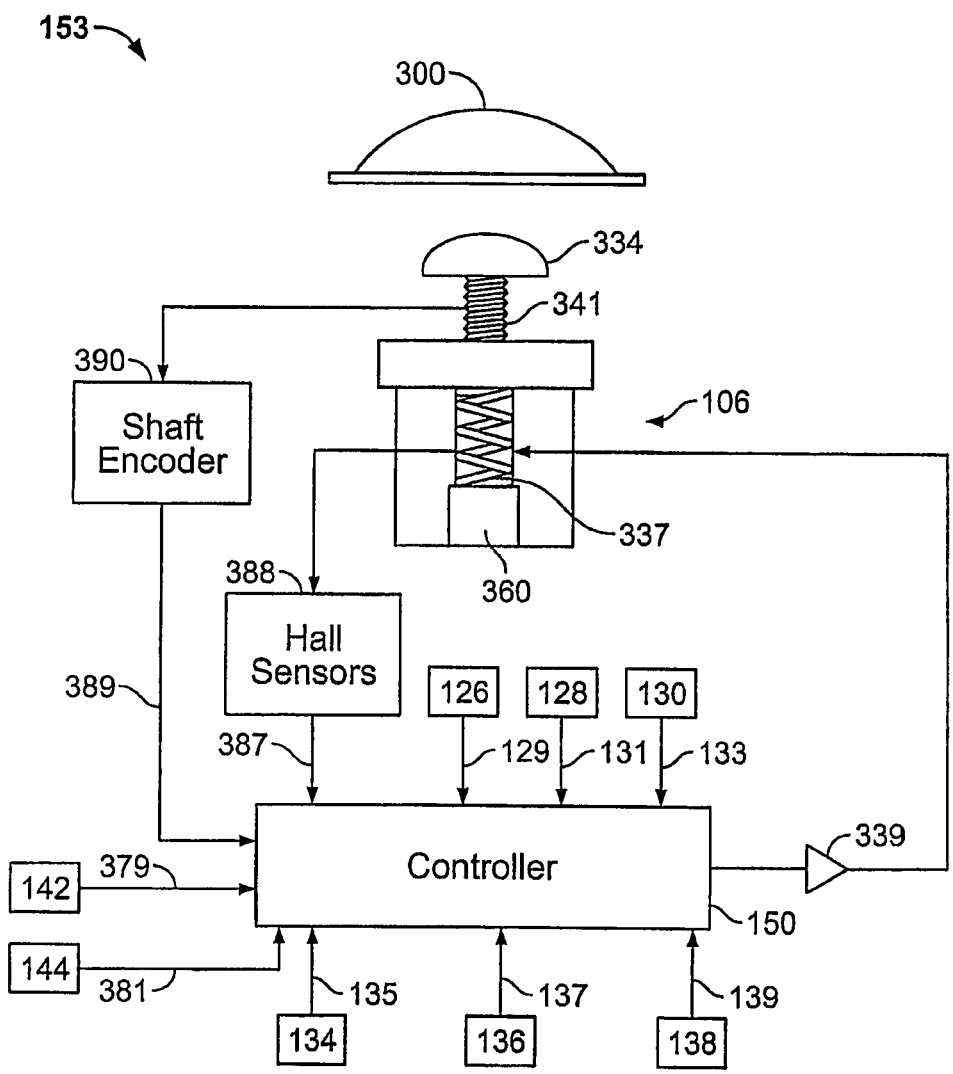
FIG. 15 is a block diagram of an exemplary pumping control subsystem of the type that may be employed for controlling operation of a perfusion fluid pump assembly in the illustrative organ care system of FIG. 1.

As described below in further detail with reference to FIG. 15, the interface connections 235a and 235b couple electrical signals, such as ECG signals, from the electrodes 142 and 144 out of the housing 194, for example, to the controller 194 and/or the operator interface 146. As described in further detail below with reference to FIG. 22A, the interface connections 235a and 235b may also couple to a defibrillation source, which may be either provided by external instrumentation or through circuitry within the system 100, and which can send a defibrillation or pacing signal 143 through electrodes 142 and 144 to the heart 102.

As shown most clearly in FIGS. 5E and 5F, the organ chamber assembly 104 includes a resealable membrane interface 230, which mounts in an interface aperture 232. The interface 230 includes a frame 230a and a resealable polymer membrane 230b mounted in the frame 230a. The membrane 230b may be made of silicone or any other suitable polymer. In operation, the interface 230 is used to provide pacing leads, when necessary, to the heart 102, without having to open the chamber lids 196 and 198. The membrane 230b seals around the pacing leads to maintain a closed environment around the heart 102. The membrane 230b also reseals in response to removing the pacing leads.

As shown in FIGS. 5A and 5B, the organ chamber assembly 104 includes apertures 228a-228c for receiving the aorta interface 162, the pulmonary artery interface 166 and the pulmonary vein interface 170, described above with reference to FIGS. 1-4, and below with reference to FIGS. 24A-28C. As shown in FIG. 5D, the organ chamber assembly 104 also includes a drain 201 for draining perfusion fluid 108 out of the housing 194 back into the reservoir 160, and mounting receptacles 203A-203d for mounting the organ chamber assembly 104 onto the single use module (shown at 634 in FIG. 19A).

Figure 6A:
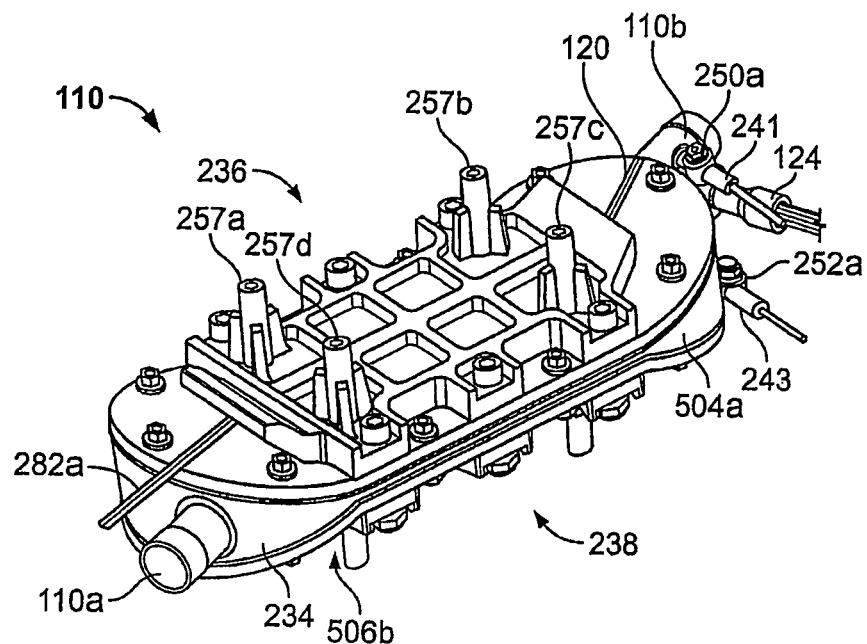
FIGS. 6A-6F show various views of a perfusion heater assembly of the type employed in the organ care system of FIG. 1 according to an illustrative embodiment of the invention.
Figure 6B:
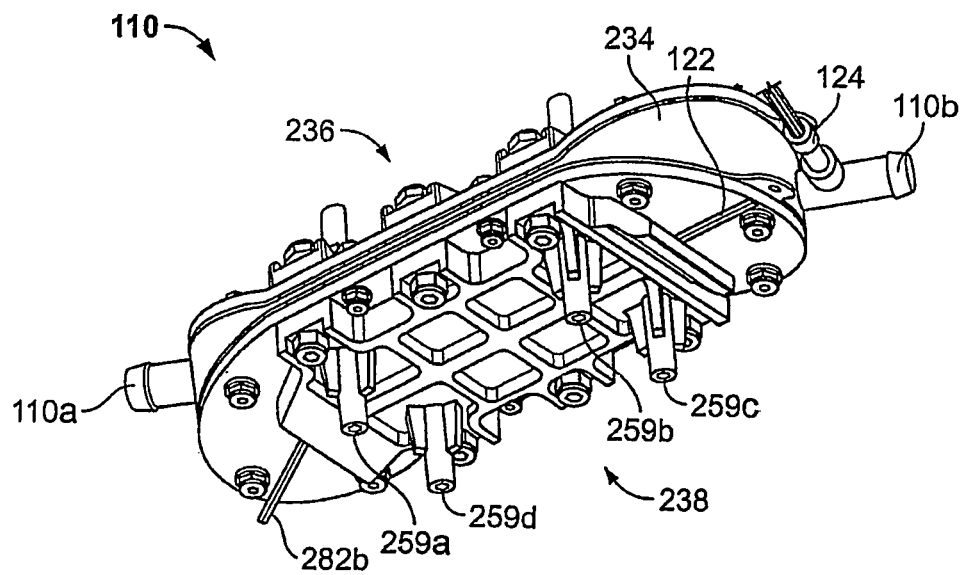
Figure 6C:
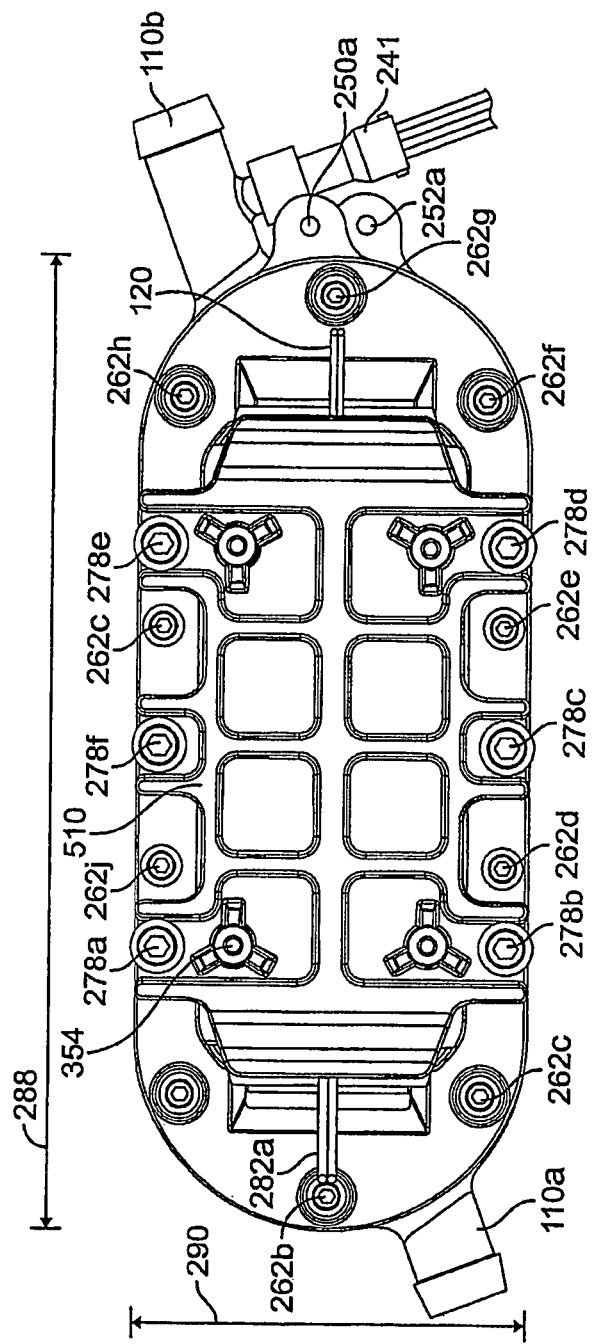

FIGS. 6A-6F depict various views of the perfusion fluid heater assembly 110 of FIG. 1. As shown in FIGS. 6A and 6B, the heater assembly 110 includes a housing 234 having an inlet 110a and an outlet 110b. As shown in both the longitudinal cross-sectional view of FIG. 6D and the lateral cross-sectional view of FIG. 6E, the heater assembly 110 includes a flow channel 240 extending between the inlet 110a and the outlet 110b. The heater assembly 110 may be conceptualized as having upper 236 and lower 238 symmetrical halves. Accordingly, only the upper half is shown in an exploded view in FIG. 6F.

Figure 6D:
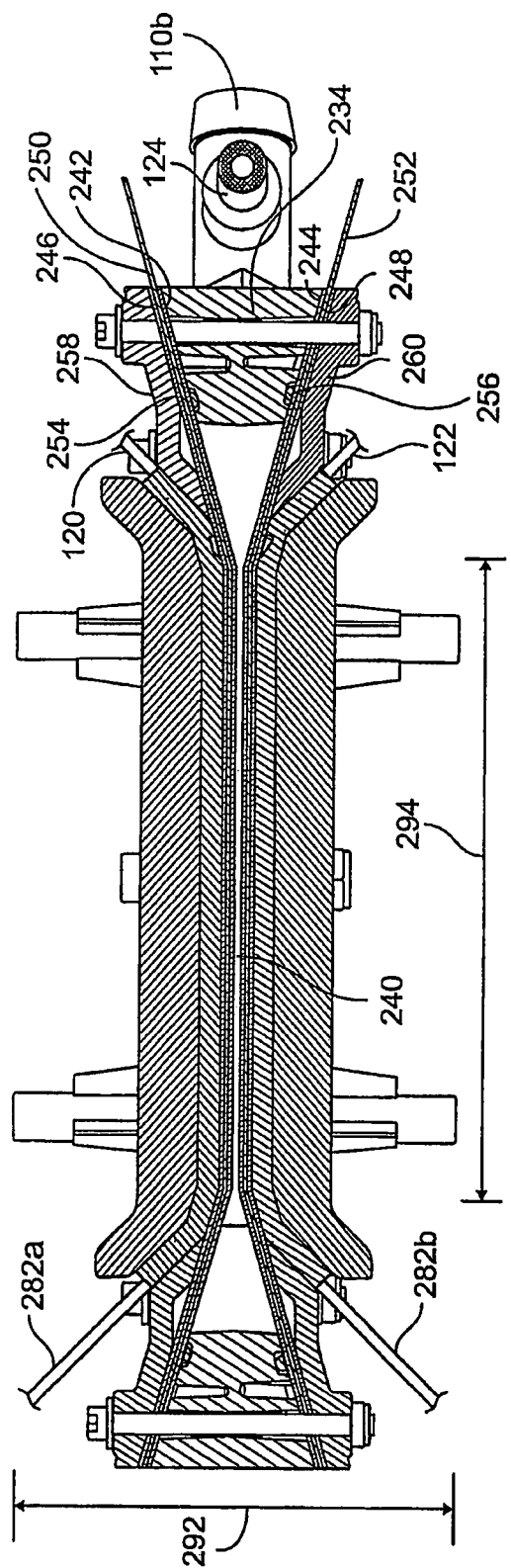
Figure 6E:
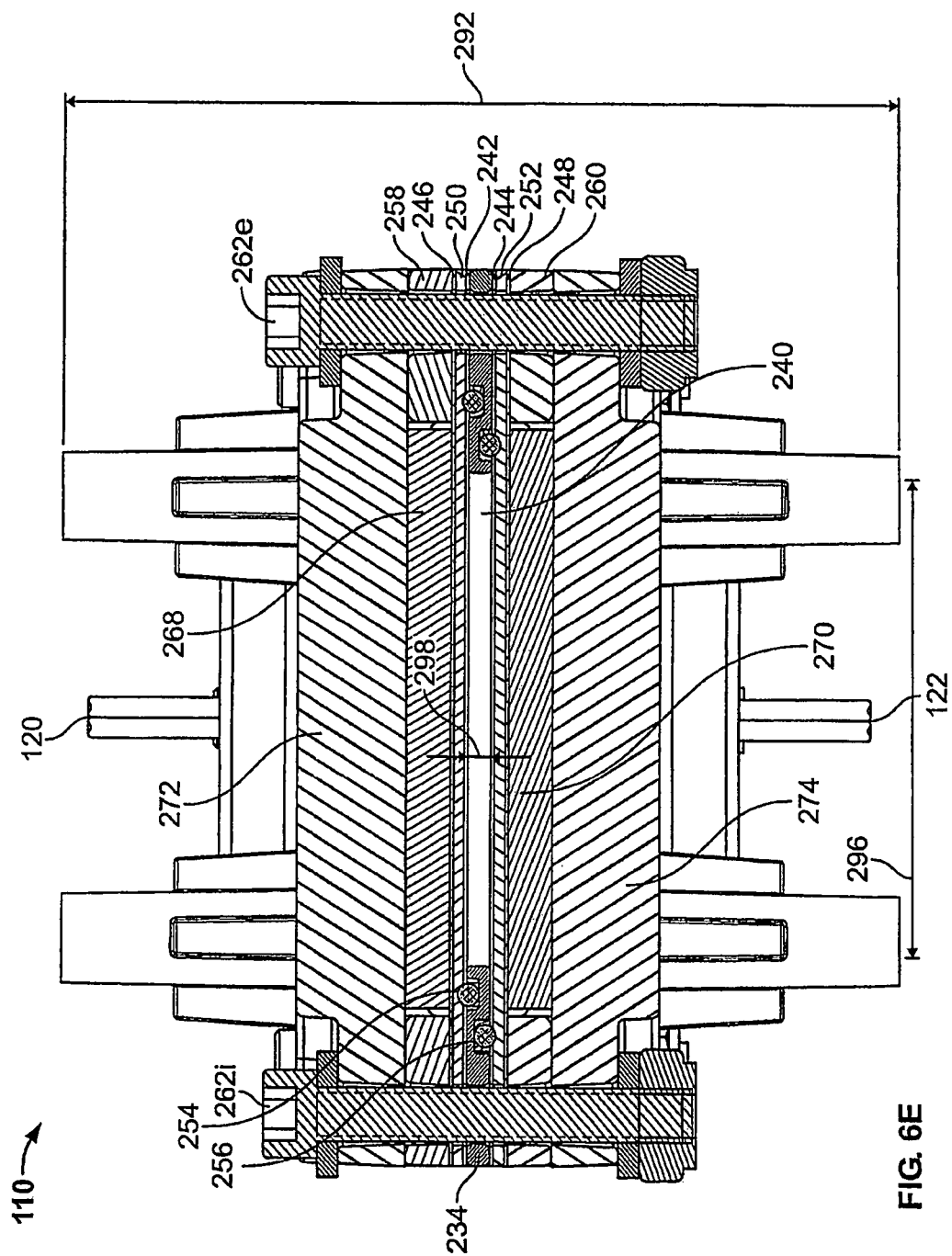
Figure 6F:
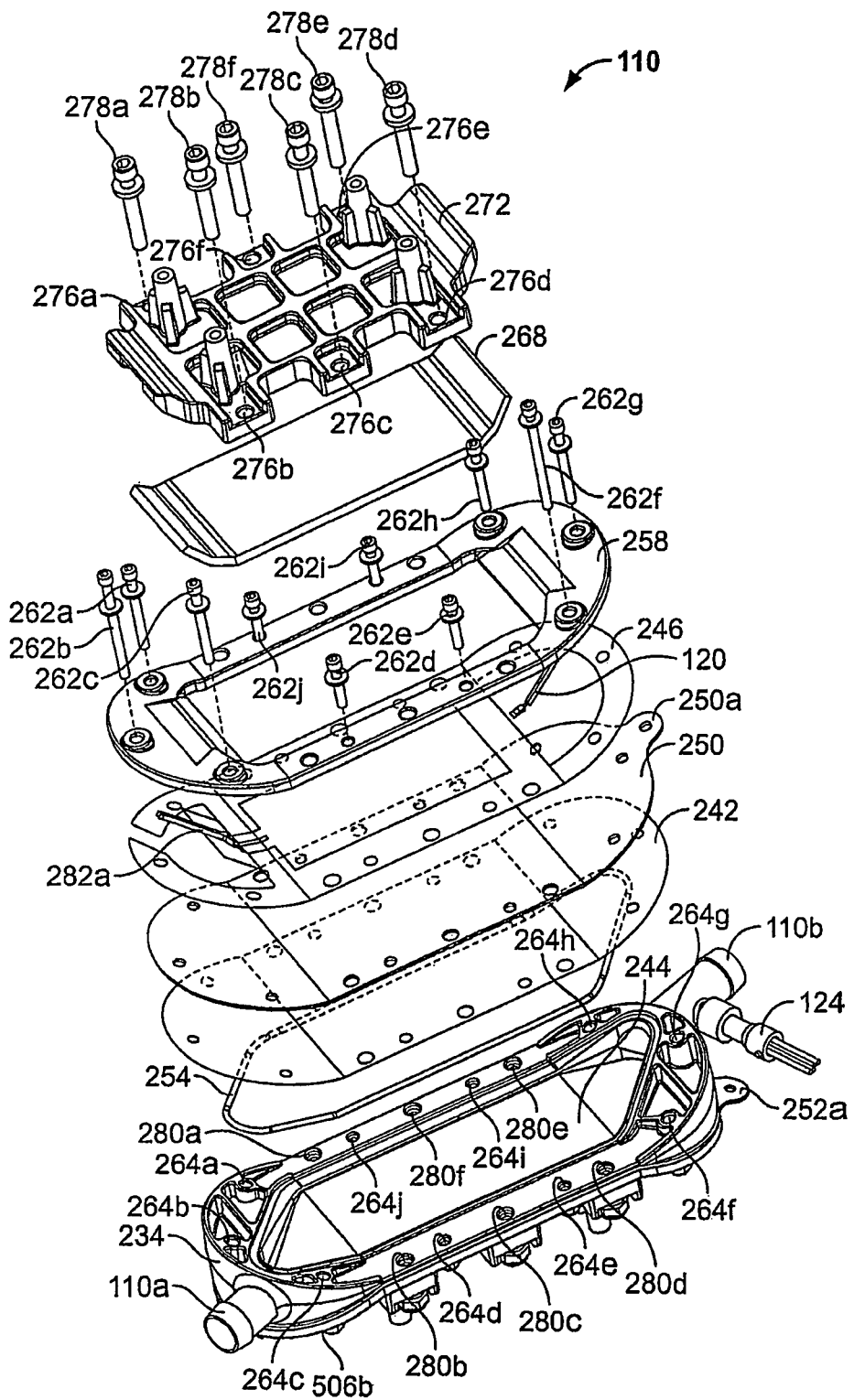

Referring now to FIGS. 6D-6F, the flow channel 240 is formed between first 242 and second 244 flow channel plates. The inlet 110a flows the perfusion fluid into the flow channel 240 and the outlet 110b flows the perfusion fluid out of the heater 110. The first 242 and second 244 flow channel plates have substantially bioinert perfusion fluid 108 contacting surfaces (which may contain a blood-product in certain embodiments) for providing direct contact with the perfusion fluid flowing through the channel 240. The fluid contacting surfaces may be formed from a treatment or coating on the plate or may be the plate surface itself. The heater assembly 110 includes first and second electric heaters 246 and 248, respectively. The first heater 246 is located adjacent to and couples heat to a first heater plate 250. The first heater plate 250, in turn, couples the heat to the first flow channel plate 242. Similarly, the second heater 248 is located adjacent to and couples heat to a second heater plate 252. The second heater plate 252 couples the heat to the second flow channel plate 244. According to the illustrative embodiment, the first 250 and second 252 heater plates are formed from a material, such as aluminum, that conducts and distributes heat from the first 246 and second 248 electric heaters, respectively, relatively uniformly. The uniform heat distribution of the heater plates 250 and 252 enables the flow channel plates to be formed from a bioinert material, such as titanium, reducing concern regarding its heat distribution characteristic.

Referring particularly to FIGS. 6E and 6F, the heater assembly 110 also includes O-rings 254 and 256 for fluid sealing respective flow channel plates 242 and 244 to the housing 234 to form the flow channel 240.

The heater assembly 110 further includes first assembly brackets 258 and 260. The assembly bracket 258 mounts on the top side 236 of the heater assembly 110 over a periphery of the electric heater 246 to sandwich the heater 246, the heater plate 250 and the flow channel plate 242 between the assembly bracket 258 and the housing 234. The bolts 262a-262j fit through corresponding through holes in the bracket 258, electric heater 246, heater plate 250 and flow channel plate 242, and thread into corresponding nuts 264a-264j to affix all of those components to the housing 234. The assembly bracket 260 mounts on the bottom side 238 of the heater assembly 110 in a similar fashion to affix the heater 248, the heater plate 252 and the flow channel plate 244 to the housing 234. A resilient pad 268 interfits within a periphery of the bracket 258. Similarly, a resilient pad 270 interfits within a periphery of the bracket 260. A bracket 272 fits over the pad 268. The bolts 278a-278f interfit through the holes 276a-276f, respectively, in the bracket 272 and thread into the nuts 280a-280f to compress the resilient pad 268 against the heater 246 to provide a more efficient heat transfer to the heater plate 250. The resilient pad 270 is compressed against the heater 248 in a similar fashion by the bracket 274.

As mentioned with respect to FIG. 1, and as also shown in FIG. 6A, the illustrative heater assembly 110 includes temperature sensors 120 and 122 and dual-sensor 124. The dual sensor 124 in practice includes a dual thermistor sensor for providing fault tolerance, measures the temperature of the perfusion fluid 108 exiting the heater assembly 110, and provides these temperatures to the controller 150. As described in further detail below with respect to the heating subsystem 149 of FIG. 13, the signals from the sensors 120, 122 and 124 may be employed in a feedback loop to control drive signals to the first 246 and/or second 248 heaters to control the temperature of the heaters 256 and 248. Additionally, to ensure that heater plates 250 and 252 and, therefore, the blood contacting surfaces 242 and 244 of the heater plates 250 and 252 do not reach a temperature that might damage the perfusion fluid, the illustrative heater assembly 110 also includes temperature sensors/lead wires 120 and 122 for monitoring the temperature of the heaters 246 and 248, respectively, and providing these temperatures to the controller 150. In practice, the sensors attached to sensors/lead wires 120 and 122 are RTD (resistance temperature device) based. As also discussed in further detail with respect to FIG. 13, the signals from the sensors attached to sensors/lead wires 120 and 122 may be employed in a feedback loop to further control the drive signals to the first 246 and/or second 248 heaters to limit the maximum temperature of the heater plates 250 and 252. As a fault protection, there are sensors for each of the heaters 246 and 248, so that if one should fail, the system can continue to operate with the temperature at the other sensor.

Figure 7:
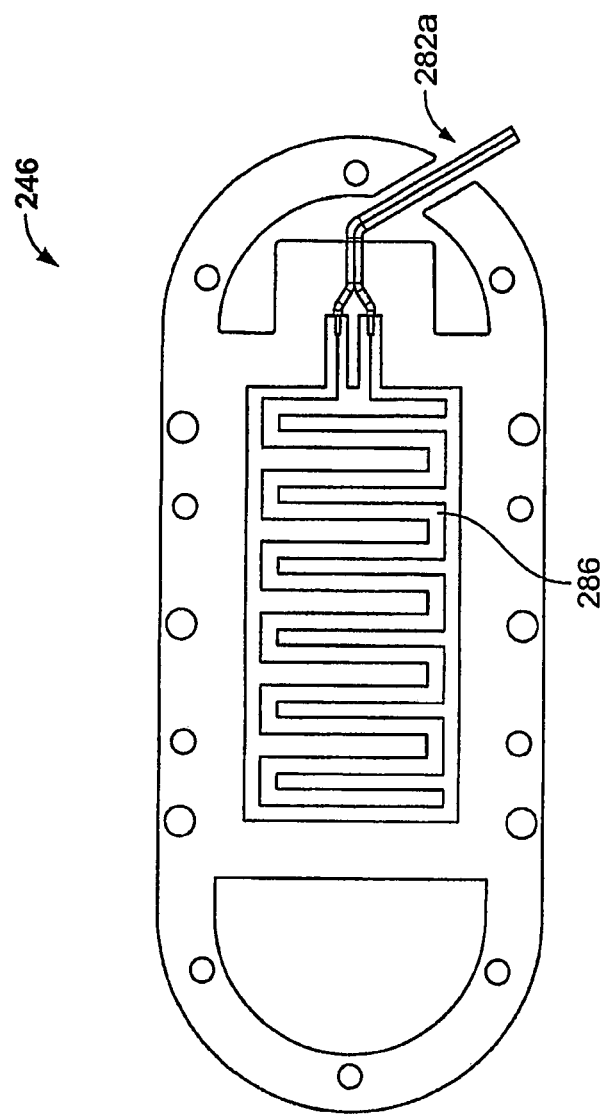
FIG. 7 shows a more detailed view of an exemplary resistive heater element of the type employed in the heater assembly of FIGS. 6A-6F.

As described in further detail below with respect to FIG. 13, the heater 246 of the heater assembly 110 receives from the controller 150 drive signals 281a and 281b (collectively 281) onto corresponding drive lead 282a. Similarly, the heater 248 receives from the controller 150 drive signals 283a and 283b (collectively 283) onto drive lead 282b. The drive signals 281 and 283 control the current to, and thus the heat generated by, the respective heaters 246 and 248. More particularly, as shown in FIG. 7, the drive leads 282a includes a high and a low pair, which connect across a resistive element 286 of the heater 246. The greater the current provided through the resistive element 286, the hotter the resistive element 286 gets. The heater 248 operates in the same fashion with regard to the drive lead 282b. According to the illustrative embodiments, the element 286 has a resistance of about 5 ohms. However, in other illustrative embodiments, the element may have a resistance of between about 3 ohms and about 10 ohms. As discussed in more detail below with regard to FIGS. 11 and 13, the heaters 246 and 248 may be controlled independently by the processor 150.

According to the illustrative embodiment, the heater assembly 110 housing components are formed from a molded plastic, for example, polycarbonate, and weighs less than about one pound. More particularly, the housing 234 and the brackets 258, 260, 272 and 274 are all formed from a molded plastic, for example, polycarbonate. According to another feature, the heater assembly is a single use disposable assembly.

In operation, the illustrative heater assembly 110 uses between about 1 Watt and about 200 Watts of power, and is sized and shaped to transition perfusion fluid 108 flowing through the channel 240 at a rate of between about 300 ml/min and about 5 L/min from a temperature of less than about 30° C. to a temperature of at least about 37° C. in less than about 30 minutes, less than about 25 minutes, less than about 20 minutes, less than about 15 minutes or even less than about 10 minutes, without substantially causing hemolysis of cells, or denaturing proteins or otherwise damaging any blood product portions of the perfusion fluid.

According to one feature, the heater assembly 110 includes housing components, such as the housing 234 and the brackets 258, 260, 272 and 274, that are formed from a polycarbonate and weighs less than about 5 lb. In other embodiments, the heater assembly may weigh less than about 4 lb, less than about 3 lb, less than about 2 lb, or even less than about 1 lb. In the illustrative embodiment, the heater assembly 110 has a length 288 of about 6.6 inches, not including the inlet 110a and outlet 110b ports, and a width 290 of about 2.7 inches. The heater assembly 110 has a height 292 of about 2.6 inches. The flow channel 240 of the heater assembly 110 has a nominal width 296 of about 1.5 inches, a nominal length 294 of about 3.5 inches, and a nominal height 298 of about 0.070 inches. The height 298 and width 296 are selected to provide for uniform heating of the perfusion fluid 108 as it passes through the channel 240. The height 298 and width 296 are also selected to provide a cross-sectional area within the channel 240 that is approximately equal to the inside cross-sectional area of fluid conduits that carry the perfusion fluid 108 into and/or away from the heater assembly 110. In one configuration, the height 298 and width 296 are selected to provide a cross-sectional area within the channel 240 that is approximately equal to the inside cross-sectional area of the inlet fluid conduit 792 (shown below with reference to FIG. 25C) and/or substantially equal to the inside cross-sectional area of the outlet fluid conduit 794 (shown below with reference to FIG. 24E).

Figure 20A:
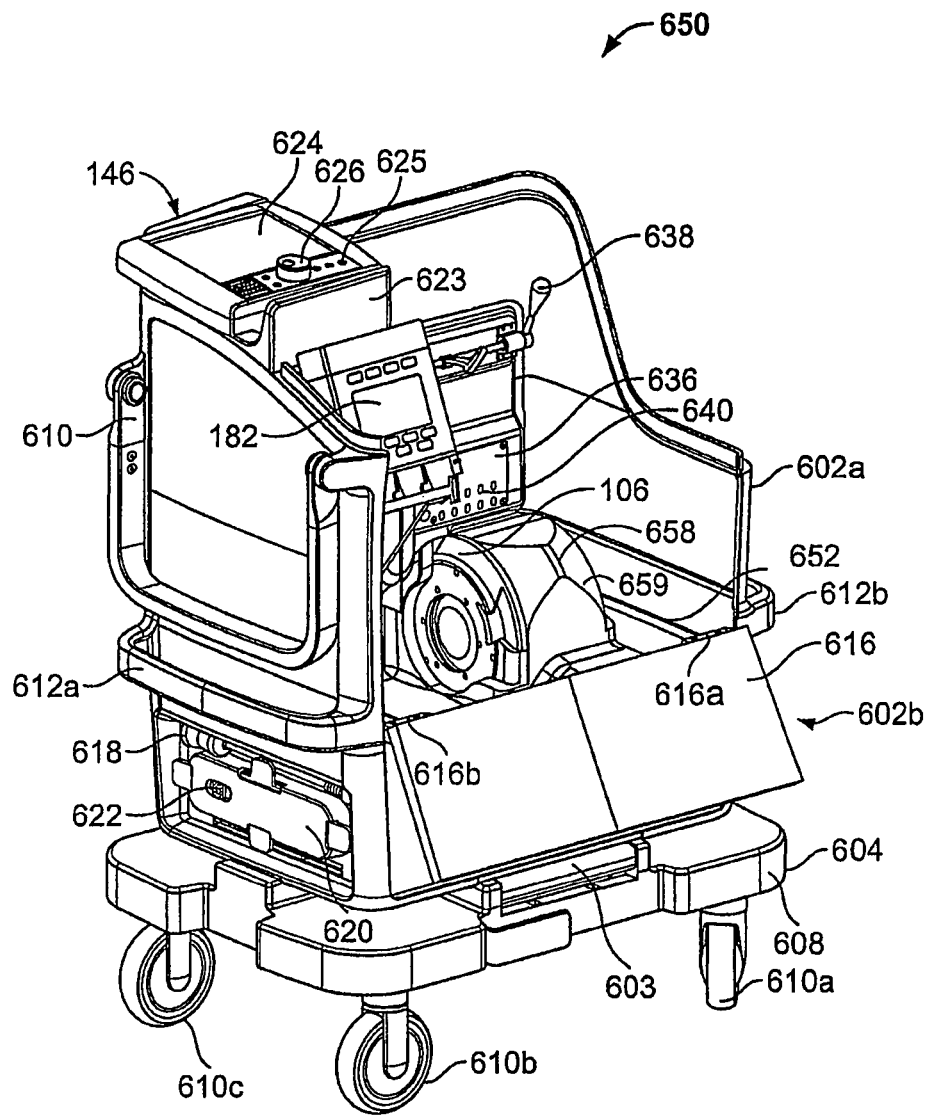
FIG. 20A is a front perspective view of the system of FIGS. 18A and 18B with the top removed, the front panel open and the single use disposable module removed according to an illustrative embodiment of the invention.

Projections 257a-257d and 259a-259d are included in the heater assembly 110 and are used to receive a heat-activated adhesive for binding the heating assembly to the multiple-use unit 650 (referenced in FIG. 20A).

Figure 8A:
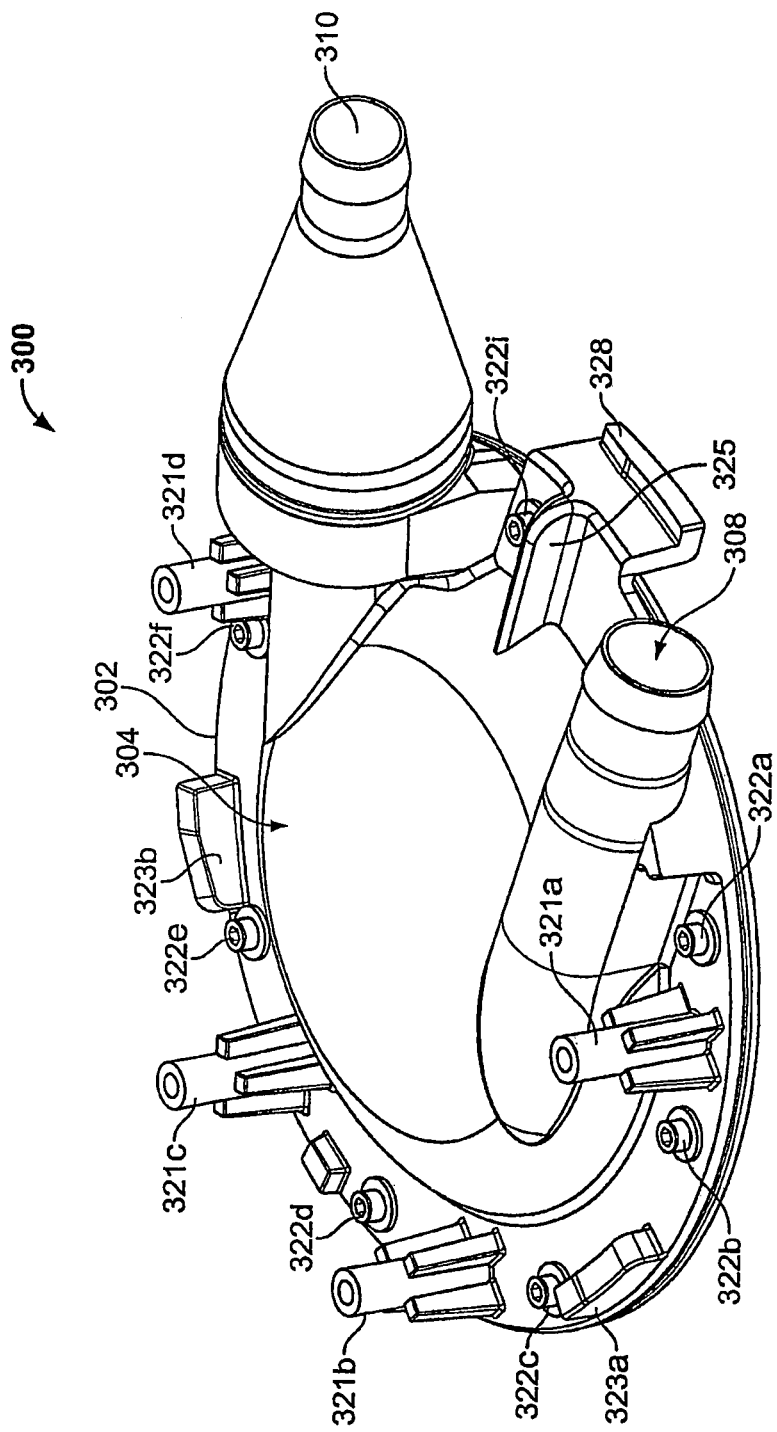
FIGS. 8A-8C show various views of a perfusion fluid pump interface assembly according to an illustrative embodiment of the invention.
Figure 8B:
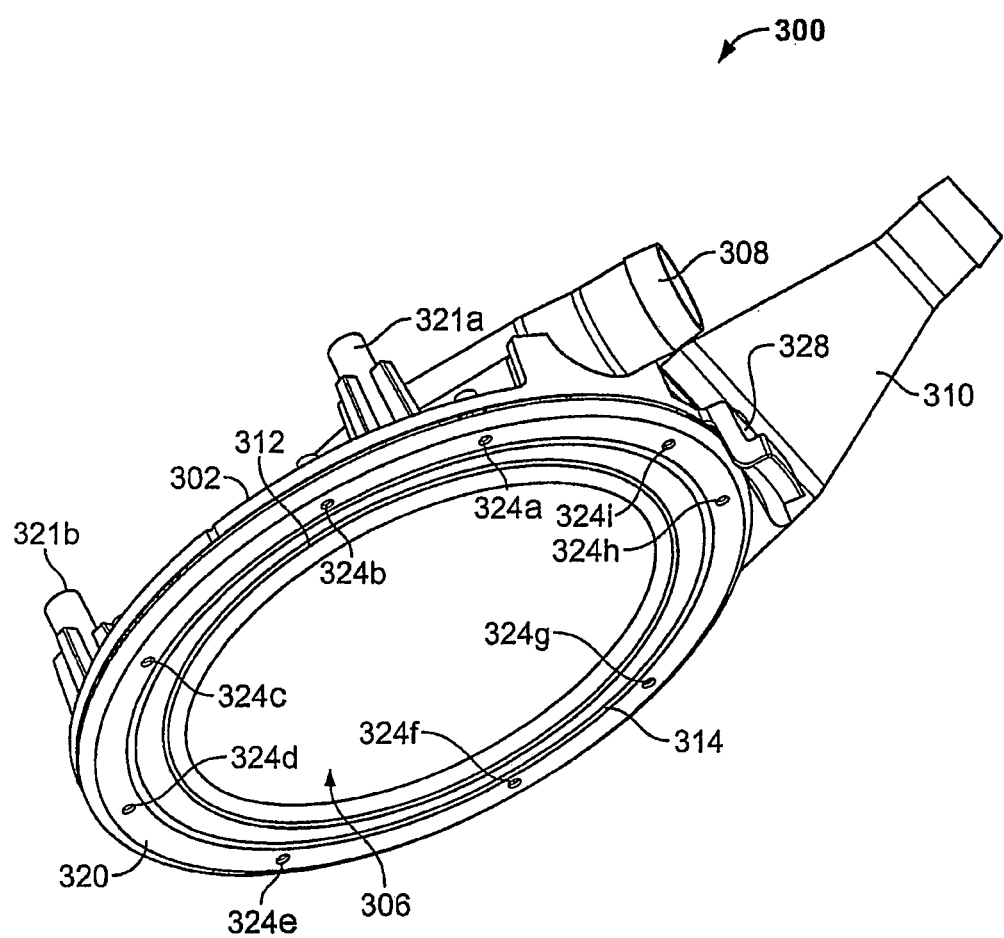
Figure 8C:
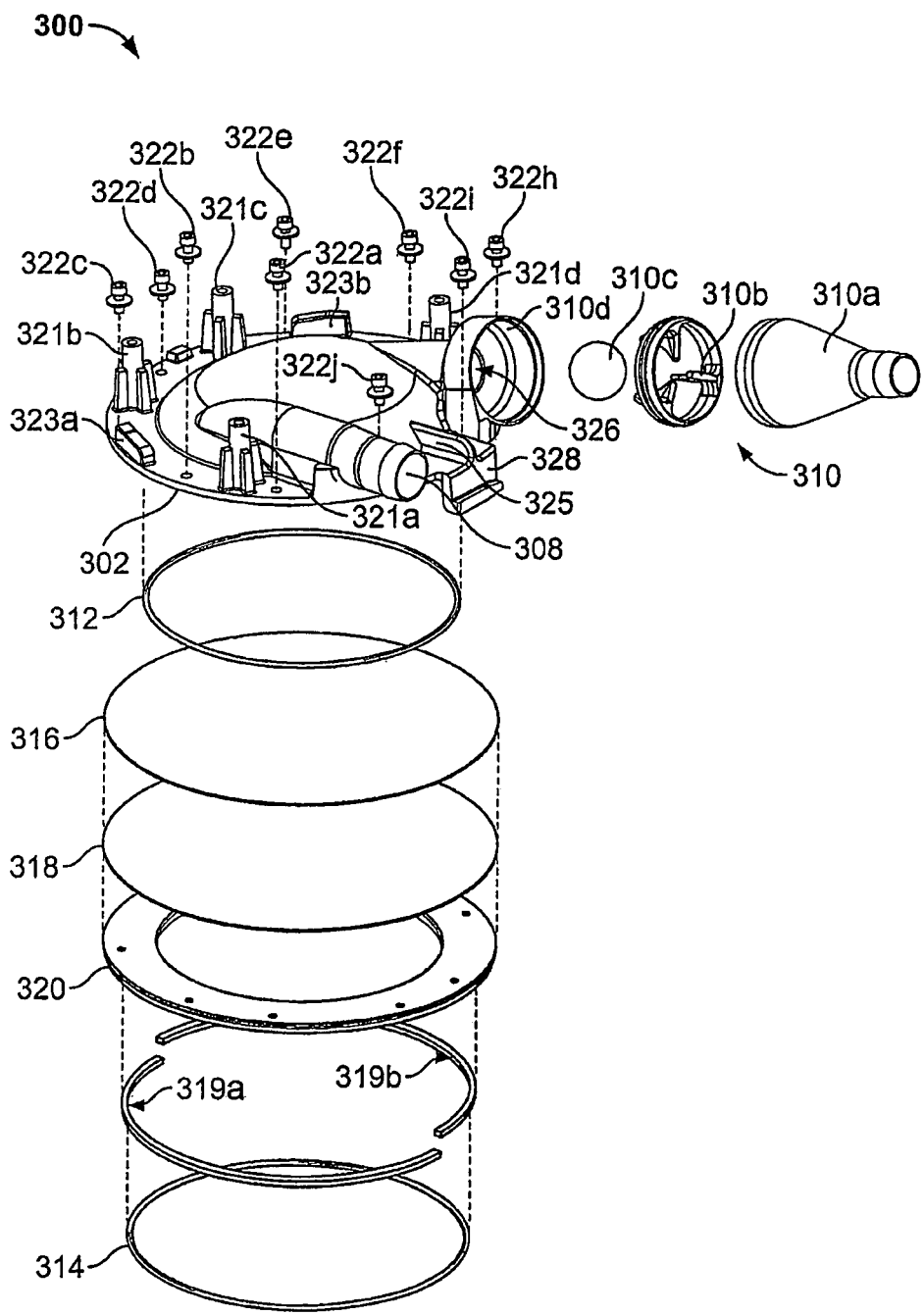
Figure 9:
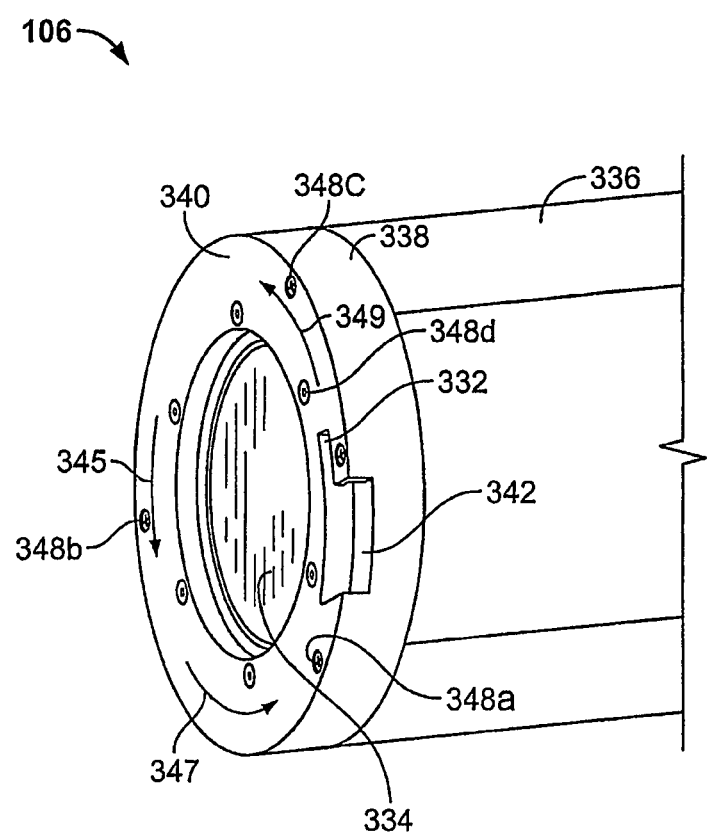
FIG. 9 shows a perspective view of a pump driver side of a perfusion fluid pump assembly of the type depicted in FIG. 1, along with a bracket for mounting with the perfusion pump interface assembly.
Figure 10:
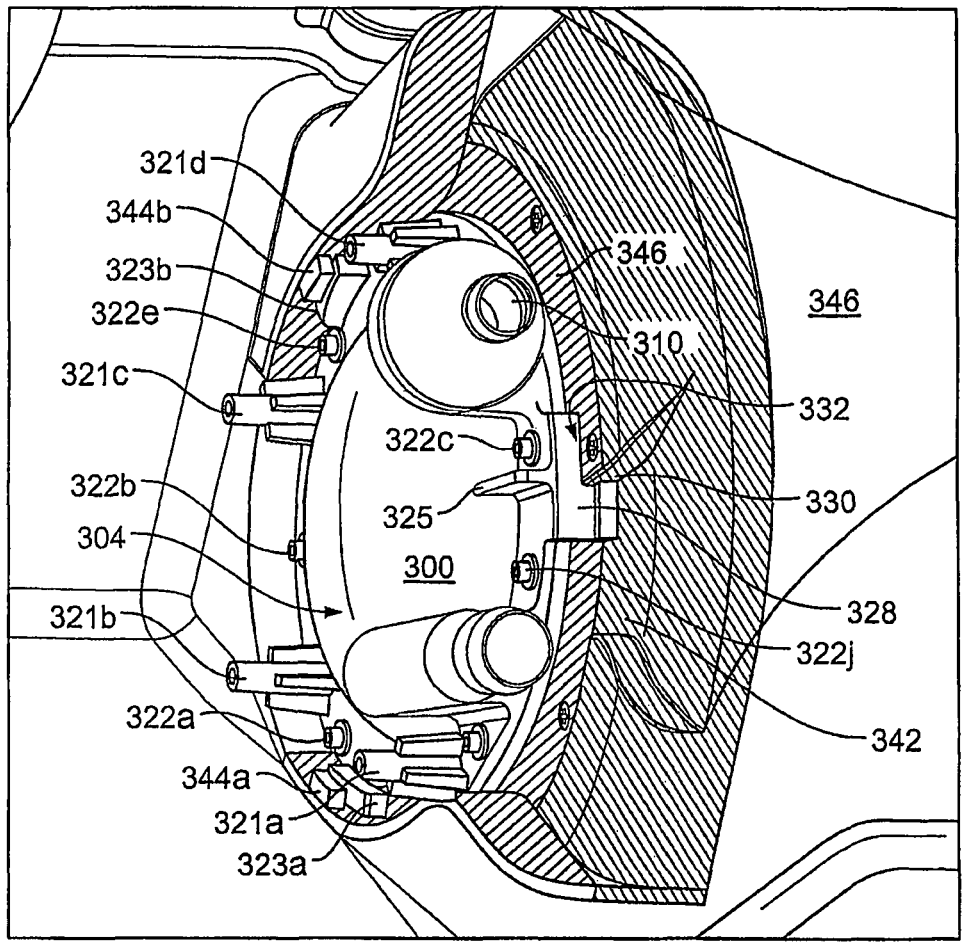
FIG. 10 shows a side view of the perfusion fluid pump interface assembly of FIGS. 8A-8C mated with the pump driver side of the perfusion fluid pump assembly of FIG. 9.

FIGS. 8A-8C show various views of a pump interface assembly 300 according to an illustrative embodiment of the invention. FIG. 9 shows a perspective view of a pump-driver end of the perfusion fluid pump assembly 106 of FIG. 1, and FIG. 10 shows the pump interface assembly 300 mated with the pump-driver end of the perfusion fluid pump assembly 106, according to an illustrative embodiment of the invention. Referring to FIGS. 8A-10, the pump interface assembly 300 includes a housing 302 having an outer side 304 and an inner side 306. The interface assembly 300 includes an inlet 308 and an outlet 310. As shown most clearly in the bottom view of FIG. 8B and the exploded view of FIG. 8C, the pump interface assembly 300 also includes inner 312 and outer 314 O-ring seals, two deformable membranes 316 and 318, a doughnut-shaped bracket 320, and half-rings 319a and 319b that fit between the o-ring 314 and the bracket 320. The half-rings 319a and 319b may be made of foam, plastic, or other suitable material.

The inner O-ring 312 fits into an annular track along a periphery of the inner side 306. The first deformable membrane 316 mounts over the inner O-ring 312 in fluid tight interconnection with the inner side 306 of the housing 302 to form a chamber between an interior side of the first deformable membrane 316 and the inner side 306 of the housing 302. A second deformable membrane 318 fits on top of the first deformable membrane 316 to provide fault tolerance in the event that the first deformable membrane 316 rips or tears. Illustratively, the deform able membranes 316 and 318 are formed from a thin polyurethane film (about 0.002 inches thick). However, any suitable material of any suitable thickness may be employed. Referring to FIGS. 8A and 8B, the bracket 320 mounts over the second deformable membrane 318 and the rings 319a and 319b and affixes to the housing 302 along a periphery of the inner side 306. Threaded fasteners 322a-322i attach the bracket 320 to the housing 302 by way of respective threaded apertures 324a-324i in the bracket 320. As shown in FIG. 8B, the outer O-ring 314 interfits into an annular groove in the bracket 320 for providing fluid tight seal with the pump assembly 106. Prior to inserting O-ring 314 into the annular groove in bracket 320, the half-rings 319a and 319b are placed in the groove. The O-ring 314 is then compressed and positioned within the annular groove in bracket 320. After being positioned within the annular groove, the O-ring 314 expands within the groove to secure itself and the half-rings 319a and 319b in place.

The pump interface assembly 300 also includes heat stake points 321a-321c, which project from its outer side 304. As described in further detail below with reference to FIGS. 21A-21C and 24A-24C, the points 321a-321c receive a hot glue to heat-stake the pump interface assembly 300 to a C-shaped bracket 656 of the single use disposable module chassis 635.

As shown in FIG. 8C, the fluid outlet 310 includes an outlet housing 310a, an outlet fitting 310b, a flow regulator ball 310c and an outlet port 310d. The ball 310c is sized to fit within the outlet port 310d but not to pass through an inner aperture 326 of the outlet 310. The fitting 310b is bonded to the outlet port 310d (e.g., via epoxy or another adhesive) to capture the ball 310c between the inner aperture 326 and the fitting 310b. The outlet housing 310a is similarly bonded onto the fitting 310b.

In operation, the pump interface assembly 300 is aligned to receive a pumping force from a pump driver 334 of the perfusion fluid pump assembly 106 and translate the pumping force to the perfusion fluid 108, thereby circulating the perfusion fluid 108 to the organ chamber assembly 104. According to the illustrative embodiment, the perfusion fluid pump assembly 106 includes a pulsatile pump having a driver 334 (described in further detail below with regard to FIG. 9), which contacts the membrane 318. The fluid inlet 308 draws perfusion fluid 108, for example, from the reservoir 160, and provides the fluid into the chamber formed between the inner membrane 316 and the inner side 306 of the housing 302 in response to the pump driver moving in a direction away from the deformable membranes 316 and 318, thus deforming the membranes 316 and 318 in the same direction. As the pump driver moves away from the deformable membranes 316 and 318, the pressure head of the fluid 108 inside the reservoir 160 causes the perfusion fluid 108 to flow from the reservoir 160 into the pump assembly 106. In this respect, the pump assembly 106, the inlet valve 191 and the reservoir 160 are oriented to provide a gravity feed of perfusion fluid 108 into the pump assembly 106. At the same time, the flow regulator ball 310c is drawn into the aperture 326 to prevent perfusion fluid 108 from also being drawn into the chamber through the outlet 310. It should be noted that the outlet valve 310 and the inlet valve 191 are one way valves in the illustrated embodiment, but in alternative embodiments the valves 310 and/or 191 are two-way valves. In response to the pump driver 334 moving in a direction toward the deformable membranes 316 and 318, the flow regulator ball 310c moves toward the fitting 310b to open the inner aperture 326, which enables the outlet 310 to expel perfusion fluid 108 out of the chamber formed between the inner side 306 of the housing 302 and the inner side of the deformable membrane 316. A separate one-way inlet valve 191, shown between the reservoir 160 and the inlet 308 in FIG. 1, stops any perfusion fluid from being expelled out of the inlet 308 and flowing back into the reservoir 160.

As discussed in further detail below with respect to FIGS. 18A-27B, in certain embodiments the organ care system 100 mechanically divides into a disposable single-use unit (shown at 634 in FIGS. 19A-19C and 24A-25C) and a non-disposable multi-use unit (shown at 650 in FIG. 20A). In such embodiments, the pump assembly 106 rigidly mounts to the multiple use module 650, and the pump interface assembly 300 rigidly mounts to the disposable single use module 634. The pump assembly 106 and the pump interface assembly 300 have corresponding interlocking connections, which mate together to form a fluid tight seal between the two assemblies 106 and 300.

More particularly, as shown in the perspective view of FIG. 9, the perfusion fluid pump assembly 106 includes a pump driver housing 338 having a top surface 340, and a pump driver 334 housed within a cylinder 336 of the housing 338 The pump driver housing 338 also includes a docking port 342, which includes a slot 332 sized and shaped for mating with a flange 328 projecting from the pump interface assembly 300. As shown in FIG. 10, the top surface 340 of the pump driver housing 338 mounts to a bracket 346 on the non-disposable multiple use module unit 650. The bracket 346 includes features 344a and 344b for abutting the tapered projections 323a and 323b, respectively, of the pump interface assembly 300. The bracket 346 also includes a cutout 330 sized and shaped for aligning with the docking port 342 and the slot 332 on the pump driver housing 338.

Operationally, the seal between the pump interface assembly 300 and the fluid pump assembly 106 is formed in two steps, illustrated with reference to FIGS. 9 and 110. In a first step, the flange 328 is positioned within the docking port 342, while the tapered projections 323a and 323b are positioned on the clockwise side next to corresponding features 344a and 344b on the bracket 346. In a second step, as shown by the arrows 345, 347 and 349 in FIG. 9, the pump interface assembly 300 and the fluid pump assembly 106 are rotated in opposite directions (e.g., rotating the pump interface assembly 300 in a counter clockwise direction while holding the pump assembly 106 fixed) to slide the flange 328 into the slot 332 of the docking port 342. At the same time, the tapered projections 323a and 323b slide under the bracket features 344a and 344b, respectively, engaging inner surfaces of the bracket features 344a and 344b with tapered outer surfaces of the tapered projections 323a and 323b to draw the inner side 306 of the pump interface assembly 300 toward the pump driver 334 and to interlock the flange 328 with the docking ports 342, and the tapered projections 323a and 323b with the bracket features 344a and 344b to form the fluid tight seal between the two assemblies 300 and 106.

Figure 11:
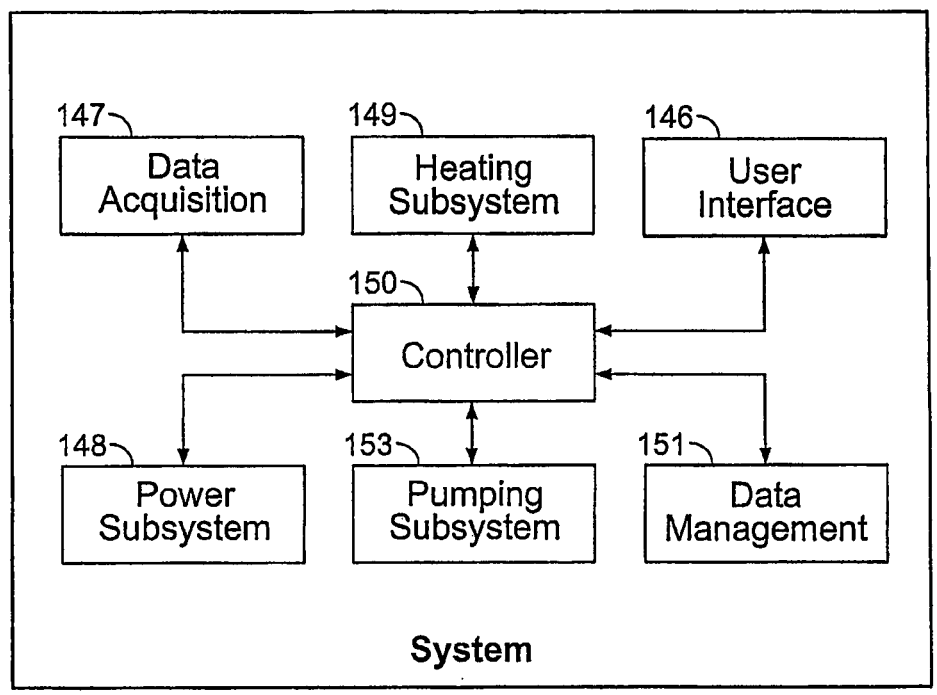
FIG. 11 depicts a block diagram of an illustrative control scheme for controlling operation of the organ care system of FIG. 1.

Having described the illustrative organ care system 100 from a system, operational and component point of view, illustrative control systems and methods for achieving operation of the system 100 are next discussed. More particularly, FIG. 11 depicts a block diagram of an illustrative control scheme for the system 100. As described above with reference to FIG. 1, the system 100 includes a controller 150 for controlling operation of the system 100. As shown, the controller 150 connects interoperationally with the following six subsystems: an operator interface 146 for assisting an operator in monitoring and controlling the system 100 and in monitoring the condition of the heart 102; a data acquisition subsystem 147 having various sensors for obtaining data relating to the heart 102 and to the system 100, and for conveying the data to the controller 150; a power management subsystem 148 for providing fault tolerant power to the system 100; a heating subsystem 149 for providing controlled energy to the heater 110 for warming the perfusion fluid 108; a data management subsystem 151 for storing and maintaining data relating to operation of the system 100 and with respect to the heart 102; and a pumping subsystem 153 for controlling the pumping of the perfusion fluid 108 through the system 100. It should be noted that although the system 100 is described conceptually with reference to a single controller 150, the control of the system 100 may be distributed in a plurality of controllers or processors. For example, any or all of the described subsystems may include a dedicated processor/controller. Optionally, the dedicated processors/controllers of the various subsystems may communicate with and via a central controller/processor.

FIGS. 12-17J illustrate the interoperation of the various subsystems of FIG. 11. Referring first to the block diagram of FIG. 12, the data acquisition subsystem 147 includes sensors for obtaining information pertaining to how the system 100 and the heart 102 is functioning, and for communicating that information to the controller 150 for processing and use by the system 100. As described with respect to FIG. 1, the sensors of subsystem 147 include, without limitation: temperature sensors 120, 122 and 124; pressure sensors 126, 128, and 130; flow rate sensors 134, 136 and 138; the oxygenation/hematocrit sensor 140; and electrodes 142 and 144. The data acquisition subsystem 147 also includes: a set of Hall sensors 388 and a shaft encoder 390 from the perfusion pump assembly 106; battery sensors 362a-362c for sensing whether the batteries 352a-352c, respectively, are sufficiently charged; an external power available sensor 354 for sensing whether external AC power is available; an operator interface module battery sensor 370 for sensing a state of charge of the operator interface module battery; and a gas pressure sensor 132 for sensing gas flow from the gas flow chamber 176. How the system 100 uses the information from the data acquisition subsystem 147 will now be described with regard to the heating 149, power management 148, pumping 153, data management 151, and operator interface 146 subsystems, shown in further detail in FIGS. 13-17J, respectively.

Figure 13:
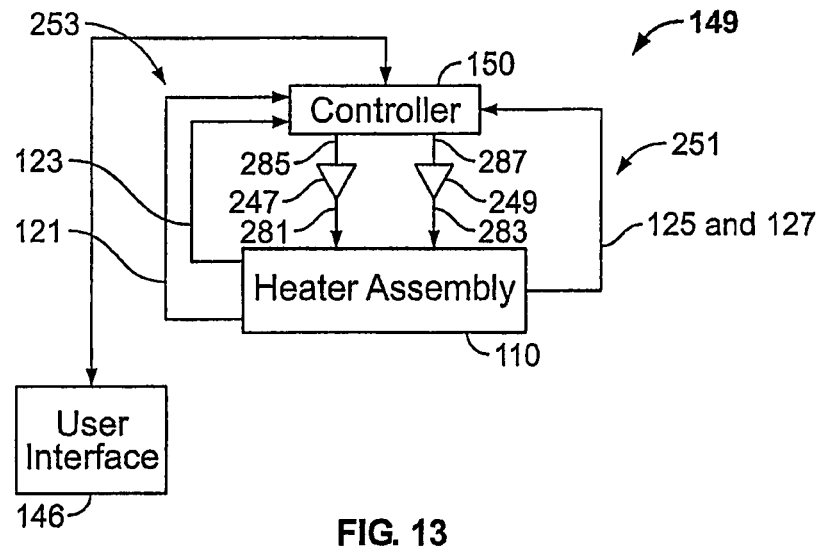
FIG. 13 is a block diagram of an exemplary heating control subsystem of the type that may be employed for maintaining perfusion fluid temperature in the illustrative organ care system of FIG. 1.

The heating subsystem 149 is depicted in the block diagram of FIG. 13. With continued reference also to FIG. 1, the heating subsystem 149 controls the temperature of the perfusion fluid 108 within the system 100 through a dual feedback loop approach. In the first loop 251 (the perfusion fluid temperature loop), the perfusion fluid temperature thermistor sensor 124 provides two (fault tolerant) signals 125 and 127 to the controller 150. The signals 125 and 127 are indicative of the temperature of the perfusion fluid 108 as it exits the heater assembly 110. The controller 150 regulates the drive signals 285 and 287 to the drivers 247 and 249, respectively. The drivers 247 and 249 convert corresponding digital level signals 285 and 287 from the controller 150 to heater drive signals 281 and 283, respectively, having sufficient current levels to drive the first 246 and second 248 heaters to heat the perfusion fluid 108 to within an operator selected temperature range. In response to the controller 150 detecting that the perfusion fluid temperatures 125 and 127 are below the operator-selected temperature range, it sets the drive signals 281 and 283 to the first 246 and second 248 heaters, respectively, to a sufficient level to continue to heat the perfusion fluid 108. Conversely, in response to the controller 150 detecting that the perfusion fluid temperatures 125 and 127 are above the operator-selected temperature range, it decreases the drive signals 281 and 283 to the first 246 and second 248 heaters, respectively. In response to detecting that the temperature of the perfusion fluid 108 is within the operator-selected temperature range, the controller 150 maintains the drive signals 281 and 283 at constant or substantially constant levels.

Preferably, the controller 150 varies the drive signals 281 and 283 in substantially the same manner. However, this need not be the case. For example, each heater 246 and 248 may respond differently to a particular current or voltage level drive signal. In such a case, the controller 150 may drive each heater 246 and 248 at a slightly different level to obtain the same temperature from each. According to one feature, the heaters 246 and 248 each have an associated calibration factor, which the controller 150 stores and employs when determining the level of a particular drive signal to provide to a particular heater to achieve a particular temperature result. In certain configurations, the controller 150 sets one of the thermistors in dual sensor 124 as the default thermistor, and will use the temperature reading from the default thermistor in instances where the thermistors give two different temperature readings. In certain configurations, where the temperature readings are within a pre-defined range, the controller 150 uses the higher of the two readings. The drivers 247 and 249 apply the heater drive signals 281 and 283 to corresponding drive leads 282a and 282b on the heater assembly 110.

In the second loop 253 (the heater temperature loop), the heater temperature sensors 120 and 122 provide signals 121 and 123, indicative of the temperatures of the heaters 246 and 248, respectively, to the controller 150. According to the illustrated embodiment, a temperature ceiling is established for the heaters 246 and 248 (e.g., by default or by operator selection), above which the temperatures of the heaters 246 and 248 are not allowed to rise. As the temperatures of the heaters 246 and 248 rise and approach the temperature ceiling, the sensors 121 and 123 indicate the same to the controller 150, which then lowers the drive signals 281 and 283 to the heaters 246 and 248 to reduce or stop the supply of power to the heaters 246 and 248. Thus, while a low temperature signal 125 or 127 from the perfusion fluid temperature sensor 124 can cause the controller 150 to increase power to the heaters 246 and 248, the heater temperature sensors 120 and 122 ensure that the heaters 246 and 248 are not driven to a degree that would cause their respective heater plates 250 and 252 to become hot enough to damage the perfusion fluid 108. According to various illustrative embodiments, the controller 150 is set to maintain the perfusion fluid temperature at between about 32° C. and about 37° C., or between about 34° C. and about 36° C. According to a further illustrative embodiment, the controller 150 is set to limit the maximum temperature of the heater plates 250 and 252 to less than about 38° C., 39° C., 40° C., 41° C., or 42° C.

As can be seen, the second loop 253 is configured to override the first loop 251, if necessary, such that temperature readings from temperature sensors 120 and 122 indicating that the heaters 246 and 248 are approaching the maximum allowable temperature override the effect of any low temperature signal from the perfusion fluid temperature sensor 124. In this respect, the subsystem 149 ensures that the temperature of the heater plates 250 and 252 do not rise above the maximum allowable temperature, even if the temperature of the perfusion fluid 108 has not reached the operator-selected temperature value. This override feature is particularly important during failure situations. For example, if the perfusion fluid temperature sensors 124 both fail, the second loop 253 stops the heater assembly 110 from overheating and damaging the perfusion fluid 108 by switching control exclusively to the heater temperature sensors 120 and 122 and dropping the temperature set point to a lower value. According to one feature, the controller 150 takes into account two time constants assigned to the delays associated with the temperature measurements from the heaters 246 and 248 and perfusion fluid 108 to optimize the dynamic response of the temperature controls.

Figure 14:
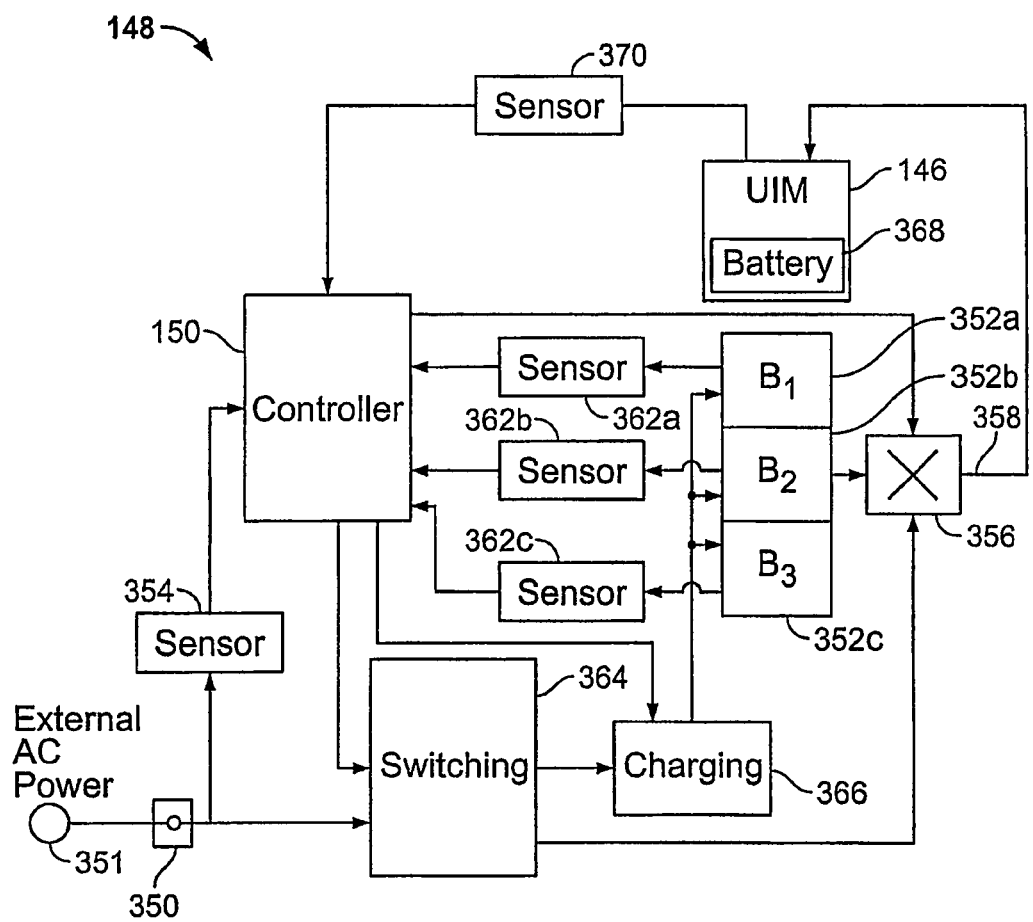
FIG. 14 is a block diagram of an exemplary power management subsystem of the type that may be employed in the illustrative organ care system of FIG. 1.

FIG. 14 depicts a block diagram of the power management system 148 for providing fault tolerant power to the system 100. As shown, the system 100 may be powered by one of four sources—by an external AC source 351 (e.g., 60 Hz, 120 VAC in North America or 50 Hz, 230 VAC in Europe) or by any of three independent batteries 352a-352c. The controller 150 receives data from an AC line voltage availability sensor 354, which indicates whether the AC voltage 351 is available for use by the system 100. In response to the controller 150 detecting that the AC voltage 351 is not available, the controller 150 signals the power switching circuitry 356 to provide system power high 358 from one of the batteries 352a-352c. The controller 150 determines from the battery charge sensors 362a-362c which of the available batteries 352a-352c is most fully charged, and then switches that battery into operation by way of the switching network 356.

Alternatively, in response to the controller 150 detecting that the external AC voltage 351 is available, it determines whether to use the available AC voltage 351 (e.g., subsequent to rectification) for providing system power 358 and for providing power to the user interface module 146, for charging one or more of the batteries 352a-352c, and/or for charging the internal battery 368 of user interface module 146, which also has its own internal charger and charging controller. To use the available AC voltage 351, the controller 150 draws the AC voltage 351 into the power supply 350 by signaling through the switching system 364. The power supply 350 receives the AC voltage 351 and converts it to a DC current for providing power to the system 100. The power supply 350 is universal and can handle any line frequencies or line voltages commonly used throughout the world. According to the illustrative embodiment, in response to a low battery indication from one or more of the battery sensors 362a-362c, the controller 150 also directs power via the switching network 364 and the charging circuit 366 to the appropriate battery. In response to the controller 150 receiving a low battery signal from the sensor 370, it also or alternatively directs a charging voltage 367 to the user interface battery 368. According to another feature, the power management subsystem 148 selects batteries to power the system 100 in order of least-charged first, preserving the most charged batteries. If the battery that is currently being used to power the system 100 is removed by the user, the power management subsystem 148 automatically switches over to the next least-charged battery to continue powering the system 100.

According to another feature, the power management subsystem 148 also employs a lock-out mechanism to prevent more than one of the batteries 352a-352c from being removed from the system 100 at a given time. If one battery is removed, the other two are mechanically locked into position within the system 100. In this respect, the system 148 provides a level of fault tolerance to help ensure that a source of power 358 is always available to the system 100.

Figure 16:
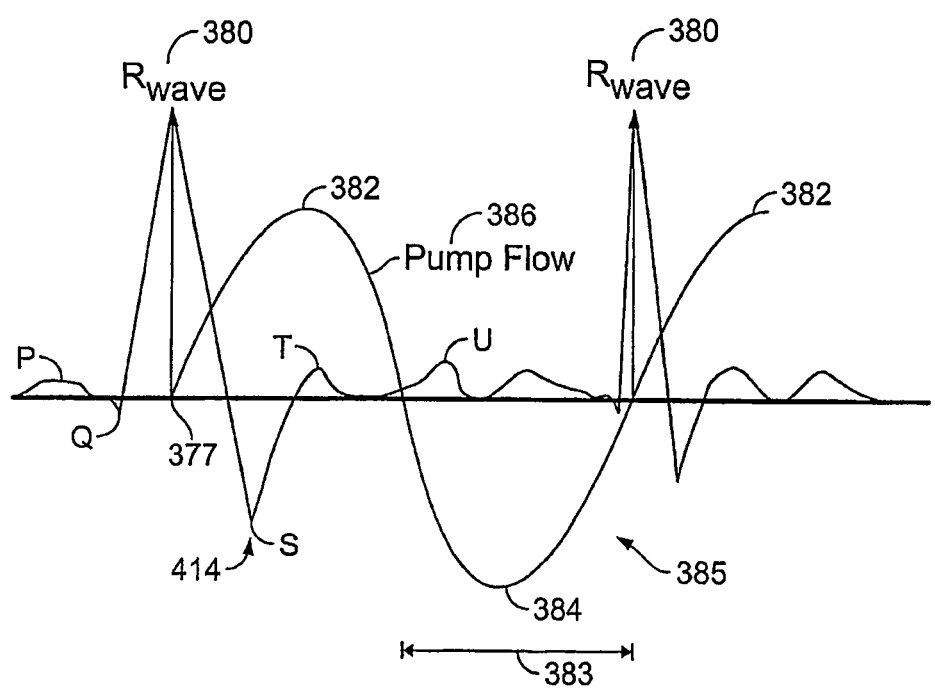
FIG. 16 is a graph depicting an r-wave with which the pumping control subsystem of FIG. 15 synchronizes according to an illustrative embodiment of the invention.

The pumping subsystem 153 of FIG. 11 will now be described in further detail with reference to FIGS. 15 and 16. More particularly, FIG. 15 is a conceptual block diagram depicting the illustrative pumping subsystem 153, and FIG. 16 shows an exemplary ECG 414 of a heart 102 synchronized with an exemplary wave 385 depicting pumping output by the subsystem 153. The ECG 414 shown in FIG. 16 has P, Q, R, S, T, and U peaks. The pumping subsystem 153 includes the perfusion fluid pump 106 interoperationally connected to the pump interface assembly 300, as described in more detail above with reference to FIGS. 8A-10. As shown in FIG. 15, the controller 150 operates the pumping subsystem 153 by sending a drive signal 339 to a brushless three-phase pump motor 360 using Hall Sensor feedback. The drive signal 339 causes the pump motor shaft 337 to rotate, thereby causing the pump screw 341 to move the pump driver 334 up and/or down. According to the illustrative embodiment, the drive signal 339 is controlled to change a rotational direction and rotational velocity of the motor shaft 337 to cause the pump driver 334 to move up and down cyclically. This cyclical motion pumps the perfusion fluid 108 through the system 100.

In operation, the controller 150 receives a first signal 387 from the Hall sensors 388 positioned integrally within the pump motor shaft 337 to indicate the position of the pump motor shaft 337 for purposes of commutating the motor winding currents. The controller 150 receives a second higher resolution signal 389 from a shaft encoder sensor 390 indicating a precise rotational position of the pump screw 341. From the current motor commutation phase position 387 and the current rotational position 389, the controller 150 calculates the appropriate drive signal 339 (both magnitude and polarity) to cause the necessary rotational change in the motor shaft 337 to cause the appropriate vertical position change in the pump screw 341 to achieve the desired pumping action. By varying the magnitude of the drive signal 339, the controller 150 can vary the pumping rate (i.e., how often the pumping cycle repeats) and by varying the rotational direction changes, the controller 150 can vary the pumping stroke volume (e.g., by varying how far the pump driver 334 moves during a cycle). Generally speaking, the cyclical pumping rate regulates the pulsatile rate at which the perfusion fluid 108 is provided to the heart 102, while (for a given rate) the pumping stroke regulates the volume of perfusion fluid 108 provided to the heart 102.

Both the rate and stroke volume affect the flow rate, and indirectly the pressure, of the perfusion fluid 108 to and from the heart 102. As mentioned with regard to FIG. 1, the system includes three flow rate sensors 134, 136 and 138, and three pressure sensors 126, 128 and 130. As shown in FIG. 15, the sensors 134, 136, and 138 provide corresponding flow rate signals 135, 137 and 139 to the controller 150. Similarly, the sensors 126, 128 and 130 provide corresponding pressure signals 129, 131 and 133 to the controller 150. The controller 150 employs all of these signals in feedback to ensure that the commands that it is providing to the perfusion pump 106 have the desired effect on the system 100. In some instances, and as discussed below in further detail with reference to FIGS. 17A-17J, the controller 150 may generate various alarms in response to a signal indicating that a particular flow rate or fluid pressure is outside an acceptable range. Additionally, employing multiple sensors enables the controller 150 to distinguish between a mechanical issue (e.g., a conduit blockage) with the system 100 and a biological issue with the heart 102.

According to one feature of the invention, the pumping system 153 may be configured to control the position of the pump driver 334 during each moment of the pumping cycle to allow for finely tuned pumping rate and volumetric profiles. This in turn enables the pumping system 153 to supply perfusion fluid 108 to the heart with any desired pulsatile pattern. According to one illustrative embodiment, the rotational position of the shaft 337 is sensed by the shaft encoder 390 and adjusted by the controller 150 at least about 100 increments per revolution. In another illustrative embodiment, the rotational position of the shaft 337 is sensed by the shaft encoder 390 and adjusted by the controller 150 at least about 1000 increments per revolution. According to a further illustrative embodiment, the rotational position of the shaft 337 is sensed by the shaft encoder 390 and adjusted by the controller 150 at least about 2000 increments per revolution. The vertical position of the pump screw 341 and thus the pump driver 334 is calibrated initially to a zero or a ground position, corresponding to a reference position of the pump screw 341.

According to the illustrative embodiment, the positional precision of the pumping subsystem 153 enables the controller 150 to precisely regulate the pumping of the perfusion fluid 108 through the heart 102. This process of synchronizing the pulsatile flow of the perfusion fluid to the heart's natural rate is referred to herein as "r-wave synchronization," which is described with continued reference to FIGS. 2, 15, and 16. A normally functioning heart has a two-phase pumping cycle—diastole and systole. During the diastolic phase, also known as the "resting phase," the heart's atria 157 and 152 contract, causing valves to open between the atria 157 and 152 and the ventricles 154 and 156 to allow blood to flow into and load the ventricles 154 and 156. During the systolic phase, the loaded ventricles eject the blood, and the atria 157 and 152 are opened and fill with blood. The cyclical expansion and contraction of the heart 102 during this process can be represented by graphing the heart's ventricular ECG wave form, shown at 414 in FIG. 16. FIG. 16 depicts the ECG waveform 414 synchronized with an exemplary wave 385 representative of a pumping output by the subsystem 153.

The pumping subsystem 153 is configured to provide the maximum output at a time that will result in delivery of fluid 108 to the heart 102 at the most beneficial time. In the illustrated embodiment, in retrograde mode, the pumping subsystem 153 is configured to pump fluid 108 toward the heart 102 so that the maximum pump output 382 occurs during the diastolic phase of the heart, which begins after the S peak shown in FIG. 16 and is when the left ventricle 156 has finished ejecting perfusion fluid 108 through the aorta 158. Timing the pump output in this manner allows the user to maximize the injection of perfusion fluid 108 through the aorta 158 and into the coronary sinus 155. The timed pumping is accomplished by starting the pumping at point 377 on wave 385, which is a point prior to point 382 and corresponds to the peak of the heart's r-wave pulse 380 and the middle of ventricular systole. The point 377 is selected to account for time-delay between the time a signal is provided from the controller 150 to start pumping the fluid and the time of actual delivery of the pumped fluid 108 to the heart 102. In another example, during normal flow mode where the left side of the heart fills and ejects perfusion fluid (as described in more detail with reference to FIG. 24A), the controller 150 synchronizes the pumping subsystem 153 to start pumping at a fixed period of time after the r-wave 380, so as to match the natural filling cycle of the left atrium 152. The synchronization may be adjusted and fine-tuned by the operator through a pre-programmed routine in the operating software on the system 100 and/or by manually operating the controls of the user interface display area 410, as described in more detail below in reference to FIGS. 17A-17J.

To achieve the synchronized pump output, the controller 150 predicts when the heart's r-wave pulses 380 will occur and causes the pump to pump at the appropriate time during the ECG 414. To make this prediction, the controller 150 measures the length various r-wave pulses 380 from the electrical signals 379 and 381 provided from the electrodes 142 and 144, respectively. From these pulses, the controller 150 tracks the time that elapses from one pulse 380 to the next, and uses this information to calculate a running average of the length of time separating two sequential r-wave pulses. From this information, the controller 150 projects the time of the next r-wave (and from the projection determines the time prior to or after that projected r-wave when the pumping should start to achieve optimal output delivery) by adding the average time separating two sequential r-wave pulses to the time of the previous r-wave 380. Based on this running average of separation time between r-waves, the controller 150 has the option to adjust the time of pump output in relation to subsequent r-waves, as reflected in the movement of wave 385 to the left or the right along the ECG 414 as signified by the arrow 383 in FIG. 16. Adjusting the wave 385 thus allows the user to adjust and customize the timing of output by the pump 106 so as to optimize the filling of the heart. In addition, the pump 106 may also be adjusted to increase or decrease the pump stroke volume to customize the volume of fluid 108 provided by the pump 106, and this may be done either in concert with or independent of the r-wave synchronization.

It should be noted that although the subsystem 153 particularly synchronizes with the r-wave cycle 385, this need not be the case. In alternative illustrative embodiments, the subsystem 153 may pump in synchronicity with any available characteristic of the heart, including fluid pressures into or out of a particular chamber or vessel. Also, the subsystem 153 may be programmed to pump in any arbitrary pattern, whether periodic or not.

Referring back to FIG. 11, the data management subsystem 151 receives and stores data and system information from the various other subsystems. The data and other information may be downloaded to a portable memory device and organized within a database, as desired by an operator. The stored data and information can be accessed by an operator and displayed through the operator interface subsystem 146.

Figure 17A:
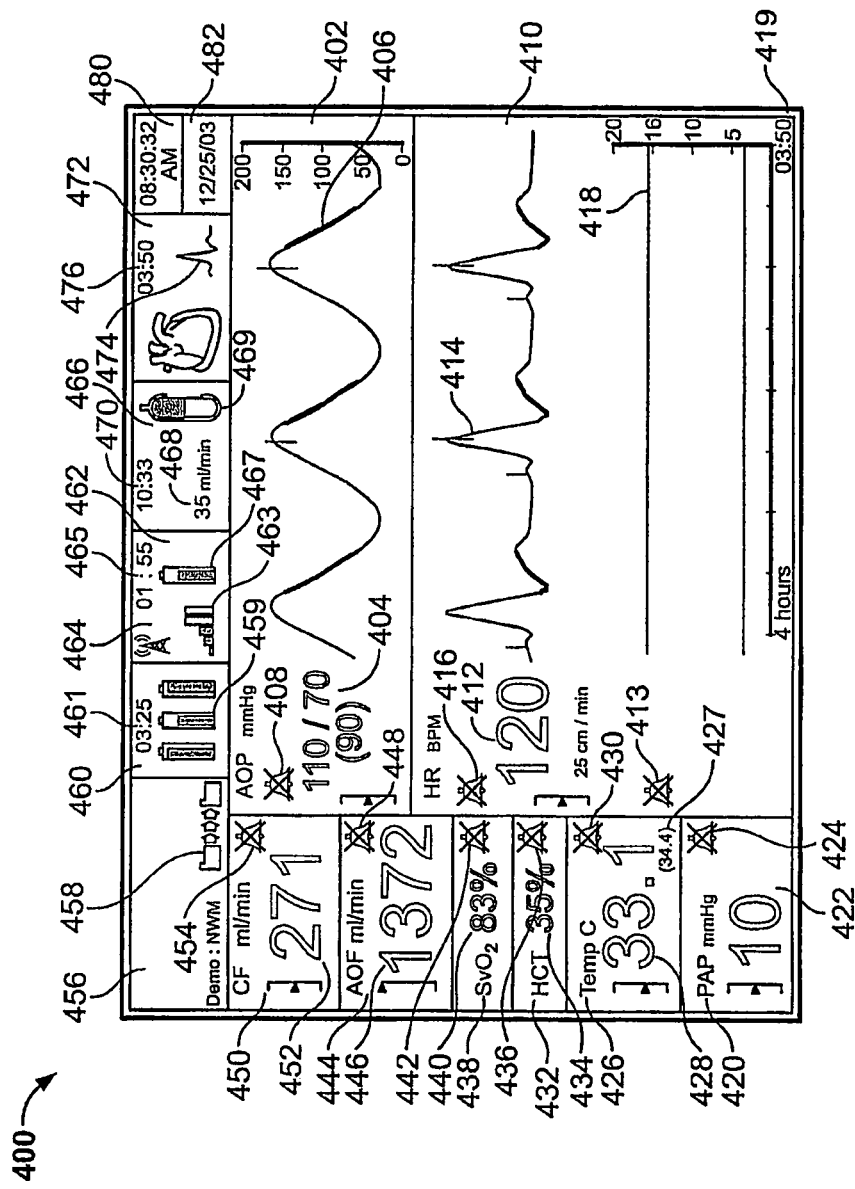
FIG. 17A-17J depict exemplary display screens of the type that may be employed with an operator interface according to an illustrative embodiment of the invention.

Turning now to the operator interface subsystem 146, FIGS. 17A-17J show various illustrative display screens of the operator interface subsystem 146. The display screens of FIGS. 17A-17J enable the operator to receive information from and provide commands to the system 100. FIG. 17A depicts a top level "home page" display screen 400 according to an illustrative embodiment of the invention. From the display screen 400 an operator can access all of the data available from the data acquisition subsystem 147, and can provide any desired commands to the controller 150. As described in more detail in reference to FIGS. 17B-17J, the display screen 400 of FIG. 17A also allows the operator to access more detailed display screens for obtaining information, providing commands and setting operator selectable parameters.

With continued reference to FIG. 1, the display screen 400 includes a display area 402, which shows a number of numerical and graphical indications pertaining to the operation of the system 100. In particular, the display area 402 includes a numerical reading of the aorta output pressure (AOP) 404 of the perfusion fluid 108 exiting the aorta interface 162 on the organ chamber assembly 104, a wave form depiction 406 of the aortic fluid pressure (AOP) 404, and an AOP alarm image 408 indicating whether the fluid pressure 404 is too high or too low (the alarm 408 is shown as "off" in FIG. 17A). The display screen 400 also includes a display area 410 having a numerical indication 412 of the rate at which the heart 102 is beating, an ECG 414 of the heart 102, a heart rate (HR) alarm image 416 indicating whether the HR 412 exceeds or falls below operator set thresholds, and a time log 418 indicating how long the system 100 has been running, including priming time (discussed in further detail below with reference to FIG. 29A). A numerical display 419 shows the amount of time for which the system 100 has been supporting the heart 102. The indicator alarm 413 indicates when an operator preset time limit is exceeded.

The display screen 400 includes a number of additional display areas 420, 424, 432, 438, 444, 450, 456, 460, 462, 466, 472, 480, and 482. The display area 420 shows a numerical reading of the pulmonary artery pressure (PAP) 422. The PAP 422 is an indication of the pressure of the perfusion fluid 108 flowing from the heart's pulmonary artery 164, as measured by the pressure sensor 130. The display area 420 also provides a PAP alarm indicator 424, which signals when the PAP 422 is outside an operator preset range. The display area 426 indicates the temperature (Temp) 428 of the perfusion fluid 108 as it exits the heater 110. The display area 426 also includes a Temp alarm indicator 430, which signals in response to the Temp 428 being outside of an operator preset range. The upper limit of the operator preset range is shown at 427. The display area 432 shows a numerical reading of the hematocrit (HCT) 434 of the perfusion fluid 108, and an HCT alarm indicator 436 for signaling the operator if the HCT 434 falls below an operator preset threshold. The display area 438 shows the oxygen saturation ($SvO_2$) 440 of the perfusion fluid 108. The display area 438 also includes a $SvO_2$ alarm 442 for indicating if the $SvO_2$ 440 of the perfusion fluid 108 falls below an operator preset threshold. The display area 444 indicates the aorta output flow rate (AOF) 446 of the perfusion fluid 108 as it flows out of the aorta 158. The AOF 446 is measured by the flow rate sensor 134. The AOF alarm 448 indicates whether the flow rate 446 falls outside of an operator preset range. The display area 450 shows the organ chamber flow rate (CF) 452. The CF 452 is an indication of the flow rate of the perfusion fluid 108 as it exits the organ chamber 104, as measured by the flow rate sensor 136. The display area 450 also includes a CF alarm 454, which signals in response to the CF 454 falling outside of an operator preset range. The display area 456 includes a graphic 458 for indicating when a file transfer to the memory card is occurring.

The display area 460 shows a graphical representation 459 of the degree to which each of the batteries 352a-352c (described above with reference to FIG. 14) is charged. The display area 460 also provides a numerical indication 461 of the amount of time remaining for which the batteries 352a-352c can continue to run the system 100 in a current mode of operation. The display area 462 identifies whether the operator interface module 146 is operating in a wireless 464 fashion, along with a graphical representation 463 of the strength of the wireless connection between the operator interface module 146 and the remainder of the system 100. The display area 462 also provides graphical indication 467 of the charge remaining in the operator interface module battery 368 (described above with reference to FIG. 14) and a numerical indication 465 of the amount of time remaining for which the operator interface module battery 368 can support it in a wireless mode of operation. The display area 466 indicates the flow rate 468 of oxygen from the gas flow chamber 176. It also provides a graphical indication 469 of how full an onboard oxygen tank is, and a numerical indication 470 of the amount of time remaining before the onboard oxygen tank runs out. The display area 472 shows the heart rate of the heart 102, and the amount of time 476 for which the heart 102 has been cannulated onto the system 100. This field is duplicative of the field 419 mentioned above. The display areas 480 and 482 show the current time and date, respectively, of operation of the system 100.

Figure 17B:
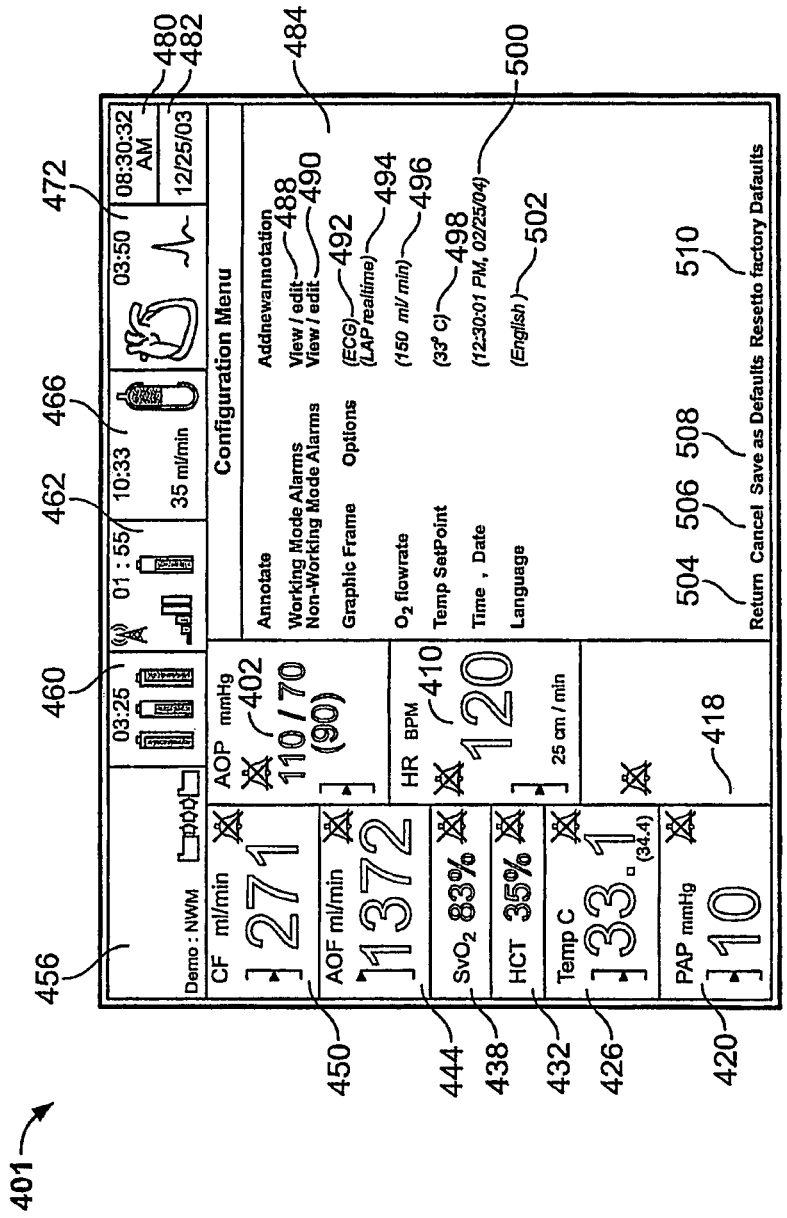
Figure 18A:
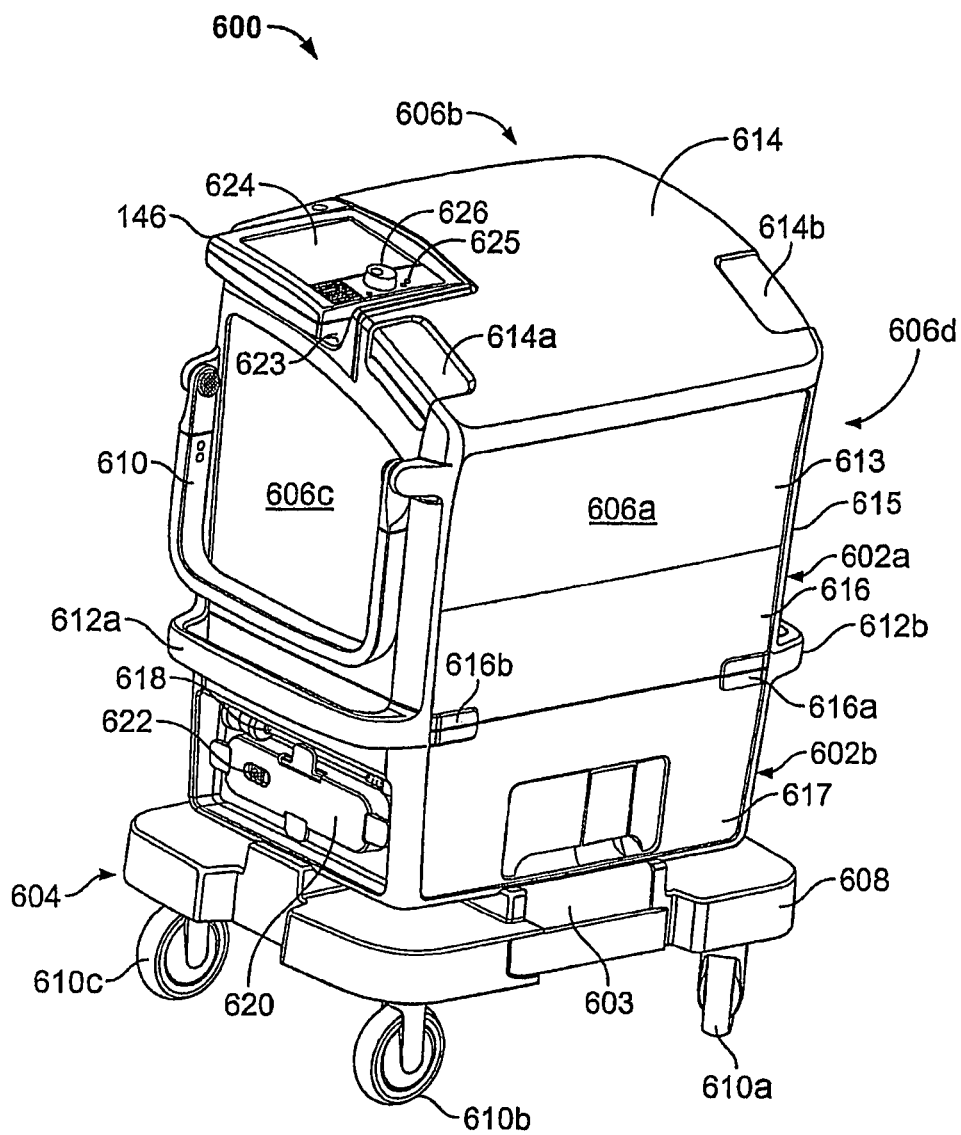
FIGS. 18A and 18B show an exemplary implementation of the system of FIG. 1 according to an illustrative embodiment of the invention.

Actuating a dial (or mouse, or other control device), such as the dial 626 shown in FIG. 18A, on the operator interface 146 opens a configuration menu 484, such as shown in the display screen 401 of FIG. 17B. As shown, accessing the configuration menu 484 covers the display areas 402 and 410 so they no longer show the graphical depictions of the pressure 406 and the heart rate 414, but continue to display critical alpha/numeric information. As also shown, all other display areas remain unchanged. This enables an operator to adjust operation of the system 100 while continuing to monitor critical information. According to one feature, the configuration menu 484 allows the operator to pre-program desired operational parameters for the system 100. Using the display screen 401, the operator can view/edit working and diastolic (or retrograde) mode alarms by selecting the fields 488 and 490, respectively. The operator can set particular ECG and LAP graphical options by selecting the fields 492 and 494. Additionally, the operator can set oxygen flow rate and perfusion fluid temperature by selecting the fields 496 and 498, respectively. Selecting the field 500 enables the operator to set the time and date, while selecting the field 502 enables the operator to select the language in which information is displayed. At the bottom of the display field 484, the operator has the option to return 504 to the display screen 400, cancel 506 any changes made to operational settings, save 508 the changes as new defaults, or reset 510 the operational settings to factory defaults.

Figure 17C:
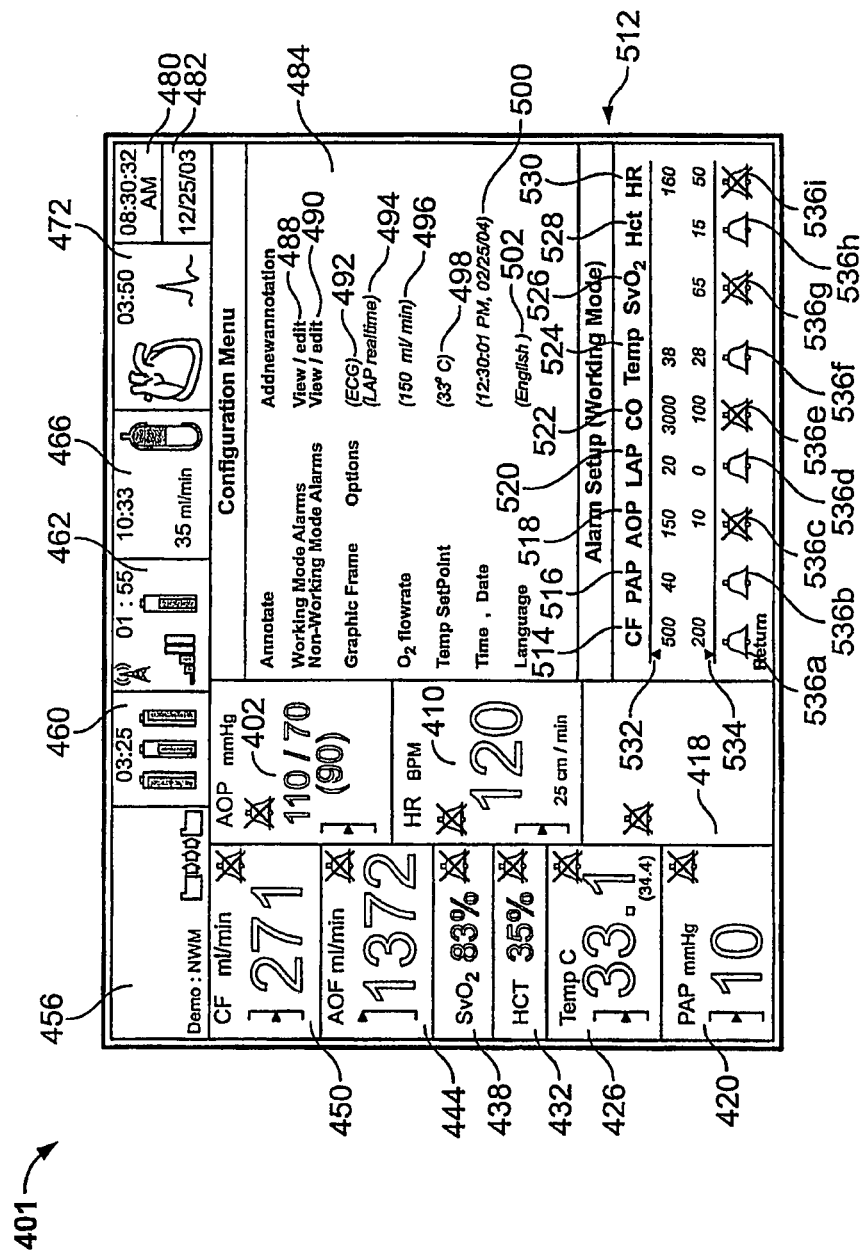
Figure 17D:
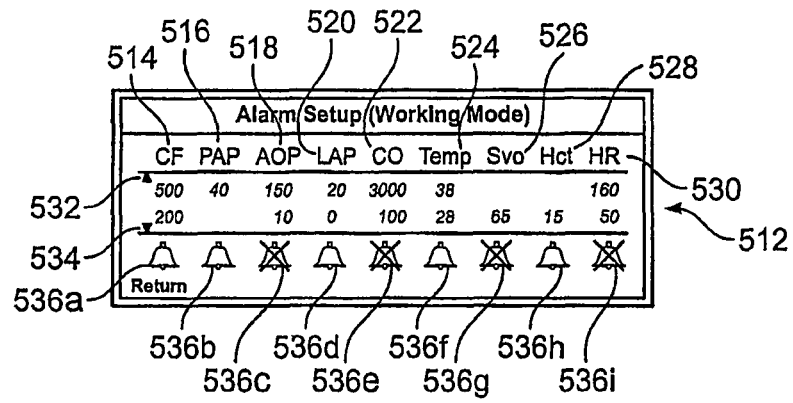

Referring to FIGS. 17C-17D, selecting the view/edit working mode alarms field 488 causes the working mode alarm dialog 512 of FIG. 17D to open within the display field 484 of FIG. 17C. The working mode dialog 512 displays the parameters associated with normal flow mode (described above with reference to FIGS. 1 and 3) and includes a field for setting numerical thresholds for each of the normal flow mode alarms. More specifically, the dialog 512 includes: CF alarm field 514; PAP alarm field 516; AOP alarm field 518; LAP alarm field 520; perfusion fluid Temp alarm field 524; $SvO_2$ alarm field 526; HCT alarm field 528; and HR alarm field 530. By selecting a particular alarm field and actuating the up 532 and/or down 534 arrows, a operator can adjust the acceptable upper and/or lower thresholds for each of the parameters associated with each of the alarms. The dialog 512 also includes alarm graphics 536a-536i, each of which being associated with a particular normal flow mode alarm. The operator can enable/disable any of the above normal flow mode alarms by selecting the associated alarm graphic 536a-536i. Any changes made using the dialog 512 are reflected in corresponding fields in the display screen 400 of FIG. 17A.

Figure 17E:
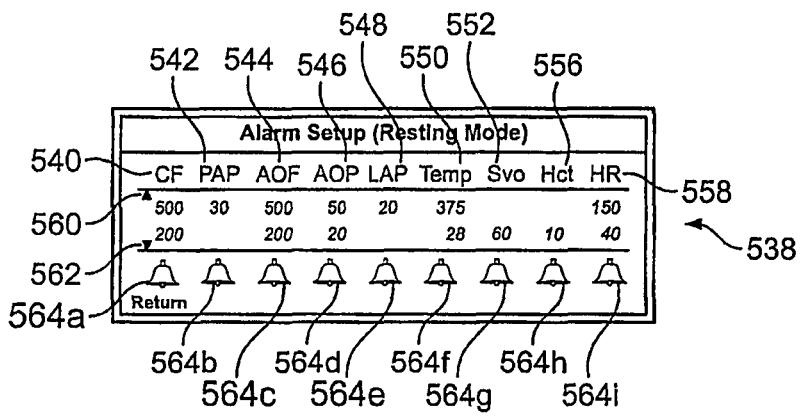
Figure 17F:
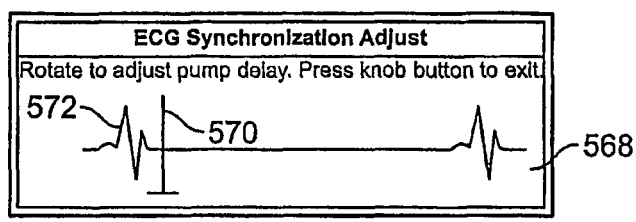
Figure 17G:
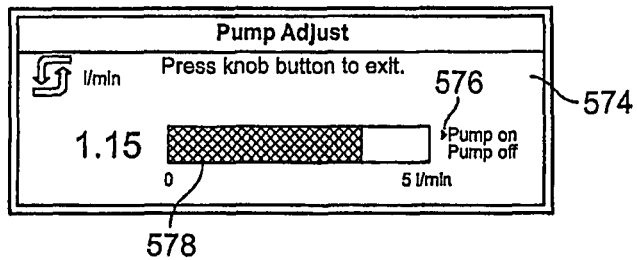
Figure 17H:
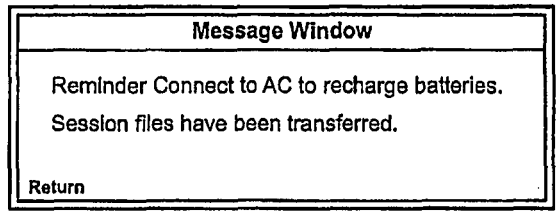
Figure 17I:
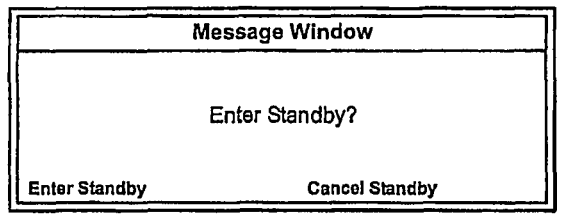
Figure 17J:
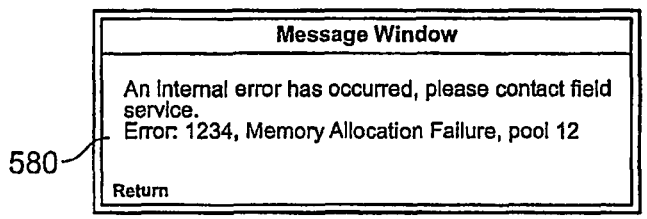

Referring to FIGS. 17A, 17B and 17E, selecting the view/edit non-working mode alarms field 490 causes the resting mode alarm dialog 538 of FIG. 17E to open within the display field 484 of FIG. 17C. The resting mode dialog 538 displays the parameters associated with retrograde flow mode (described above with reference to FIGS. 1 and 4) and includes a field for setting numerical thresholds for each of the retrograde flow mode alarms. According to the illustrative embodiment, the available alarms for the normal and retrograde flow modes are similar, but not necessarily the same. Additionally, even for those that are the same, the thresholds may differ. Accordingly, the invention enables the operator to select different alarms and/or different thresholds for each flow mode of operation. More specifically, the dialog 538 includes: CF alarm field 540; PAP alarm field 542; AOF alarm field 544; AOP alarm field 546; LAP alarm field 548; perfusion fluid Temp alarm field 550; $SvO_2$ alarm field 552; HCT alarm field 556; and HR alarm field 558. By selecting a particular alarm field and actuating the up 560 and/or down 562 arrows, an operator can adjust the acceptable numerical upper and/or lower thresholds for each of the parameters associated with each of the alarms. The dialog 538 also includes alarm graphics 564a-564i, each of which being associated with a particular normal flow mode alarm. The operator can enable/disable any of the above normal flow mode alarms by selecting the associated alarm graphic 564a-564i. As is the case of the dialog 512, any changes made using the dialog 538 are reflected in corresponding fields in the display screen 400 of FIG. 17A. In one implementation, the system 100 may be configured to automatically switch between sets of alarm limits for a given flow mode upon changing the flow mode.

Referring to FIGS. 17A, 17B, 17F and 17G, the operator interface 146 also provides graphical mechanisms for adjusting various parameters. For example, as noted above in reference to FIG. 16, one advantage of the user display area 402 is that it allows the operator to monitor (and adjust) the pumping of the subsystem 153. Display area 410 identifies the ECG waveform 414 of the heart 102, and display 402 shows in wave form 406 the pressure of fluid flowing through the aorta. In these two displays the operator can monitor the effect of the pumping profile on the heart's EGC 414, which allows the user to adjust the stroke volume of the pumping subsystem 153, to adjust the rate of the pumping subsystem 153 (and thus the flow-rate of the fluid 108 being pumped through the system 100), to manually impose, or adjust a time of, firing of the subsystem (e.g., by imposing a fixed delay between the r-wave 380 and the beginning of the pumping cycle), or to automatically program the pumping subsystem 153 to pump at a pre-determined time along the heart's ECG waveform 414, as needed to properly fill the heart according to whether the heart is being perfused in retrograde or normal mode. These pumping adjustments may be made by use of the various graphical frames of the operator interface 146. By way of example, in response to a operator selecting the ECG graphic frame option 492 located in the display field 484 of the display screen 401, the operator interface 146 displays the dialog 568 of FIG. 17F. The dialog 568 shows a graphical representation 572 of the ECG 414 along with a cursor 570. The position of the cursor 570 indicates the point at which the pumping subsystem 153 will initiate an output pumping stroke (i.e., the portion of the pumping cycle at which the pump motor 106 will push perfusion fluid 108 to the heart 102) relative to the ECG 414 of the heart 102. By rotating a mechanical knob 626 (shown in FIGS. 18A and 18B) on the operator interface 146, the operator moves the position of the cursor 570 to adjust when the pumping subsystem 153 will initiate the output pumping stroke relative to the r-wave pulse 380. As described above with regard to FIGS. 15 and 16, the pumping subsystem 153 receives an r-wave signal 380 from the ECG sensors 142 and 144. The pumping subsystem 153 uses the r-wave signal 380 along with the pumping adjustment information from the cursor 570 to synchronize perfusion fluid pumping with the beating of the heart 102. In another example, in response to the operator pressing the pump adjust button 625, the operator interface 146 displays the dialog 574 of FIG. 17G. From the dialog 574, the operator can select the pointer 576 and rotate the knob 626 to turn the pump motor 106 on and off. Additionally, the operator can select the bar graphic 578 and rotate the knob 626 to adjust the volume of fluid being pumped, which is displayed in liters/minute.

The operator interface 146 also provides a plurality of warning/reminder messages. By way of example, in FIG. 17H, the operator interface 146 displays a message to remind the operator to connect to AC power to recharge the batteries. This message appears, for example, in response to the controller 150 detecting an impending low battery condition. The operator interface 146 displays the message of FIG. 17I to confirm that the user wishes to enter standby mode and to remind the operator to insert a portable memory device, such as magnetic or optical disk, a portable disk drive, a flash memory card or other suitable memory device, to download and store information regarding a particular use of the system 100. The operator interface 146 displays the error messages, such as the error message of FIG. 17J, in response to an identifiable fault occurring. The error messages of FIG. 17J include, for example, error information 580 to aid a service technician in diagnosing and/or repairing the fault.

Figure 18B:
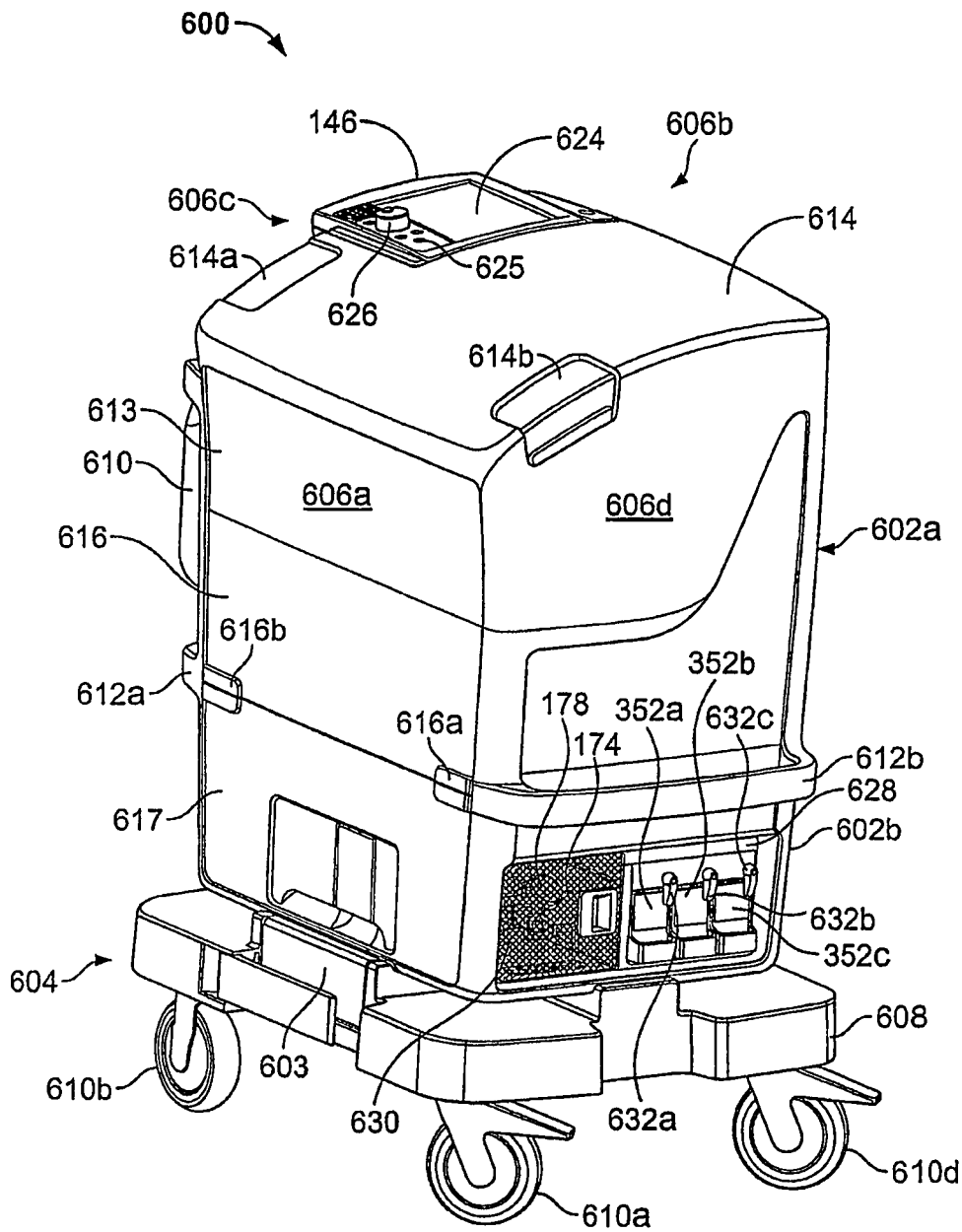

Having described an illustrative control systems and methods for achieving operation of the system 100, illustrative mechanical features of the system 100 will now be discussed, along with an illustrative division of components between the single use disposable module 634 and multiple use module 650 units. More particularly, FIGS. 18A-18B show a mechanical implementation 600 of the system of FIG. 1, according to an illustrative embodiment of the invention. As shown, the illustrative implementation 600 includes a housing 602 and a cart 604. The housing 602 conceptually divides into upper 602a and lower 602b housing sections, and includes front 606a, rear 606b, left 606c, and right 606d sides. The cart 604 includes a platform 608 and wheels 610a-610d for transporting the system 600 from place to place. A latch 603 secures the housing 602 to the cart 604. To further aid in portability, the system 600 also includes a handle 610 hinge mounted to the upper section 602a of the left side 606c of the housing 602, along with two rigidly mounted handles 612a and 612b mounted on the lower section 602b of the left 606c and right 606d sides of the housing 602.

The housing 602 further includes a removable top 614, and a front panel 615 having an upper panel 613, and a mid panel 616 hinged to a lower panel 617 by hinges 616a and 616b. The top 614 includes handles 614a and 614b for aiding with removal. In the illustrated embodiment, the upper panel 613 is screwed, bolted or otherwise adjoined to the top 614, such that removal of the top 614 also removes panel 613.

As shown in FIG. 18A, the system 600 includes an AC power cable 618, along with a frame 620 for securing the power cable 618, both located on the lower section 602b of the left side 606c of the housing 602. A software reset switch 622, also located on the lower section 602b of the left side 602c, enables an operator to restart the system software and electronics.

As shown in FIGS. 18A and 18B, the implementation 600 also includes the operator interface module 146, along with a cradle 623 for holding the operator interface module 146. The operator interface module 146 includes a display 624 for displaying information to an operator, for example, by way of the display screens of FIGS. 17A-17J. As mentioned above, the operator interface module 146 also includes a rotatable and depressible knob 626 for selecting between the various parameters and display screens of FIGS. 17A-17J. The knob 626 may also be used to set parameters for automatic control of the system 100, as well as to provide manual control over the operation of the system 100. For example, the knob 626 may be used to provide instructions to the controller 150 to increase perfusion fluid flow rates, gas flow rates, etc. As also discussed above with regard to FIGS. 1, 14 and 17A-17J, the operator interface module 146 includes its own battery 368 and may be removed from the cradle 623 and used in a wireless mode. While in the cradle 623, power connections enable the operator interface module 146 to be charged. As shown, the operator interface module also includes control buttons 625 for controlling the pump, silencing or disabling alarms, entering or exiting standby mode, entering or adjusting ECG synchronization mode, and starting the perfusion clock, which initiates the display of data obtained during organ care.

As shown in FIG. 18B, the illustrative implementation 600 also includes a battery compartment 628 and an oxygen tank bay 630, both located on the lower section 602b of the right side 606d of the housing 602. As shown, the battery compartment 628 houses the three system batteries 352a-352c, described above with regard to FIG. 14. According to one feature, the battery compartment 626 includes three battery locks 632a-632c. As described above with respect to FIG. 14, the battery locks 632a-632c interoperate mechanically so that only one of the three batteries 352a-352c may be removed at any given time.

The disposable module 634 and the multiple use unit 650 are constructed of material that is durable yet light-weight. In some illustrative embodiments, polycarbonate plastic is used to form one or more of the components of the units 634 and 650. To further reduce the weight, the chassis 635 and the multiple use module chassis 602 are formed from low weight materials such as, for example, carbon fiber epoxy composites, polycarbonate ABS-plastic blend, glass reinforced nylon, acetal, straight ABS, aluminum or magnesium. According to one illustrative embodiment, the weight of the entire system 600 is less than about 85 pounds, including the multiple use module, heart, batteries, gas tank, and priming, nutritional, preservative and perfusion fluids, and less than about 50 pounds, excluding such items. According to another illustrative embodiment, the weight of the disposable module 634 is less than about 12 pounds, excluding any solutions. According to a further illustrative embodiment, the multiple use module 650, excluding all fluids, batteries 352a-352c and oxygen supply 172, weighs less than about 50 pounds.

Figure 19A:
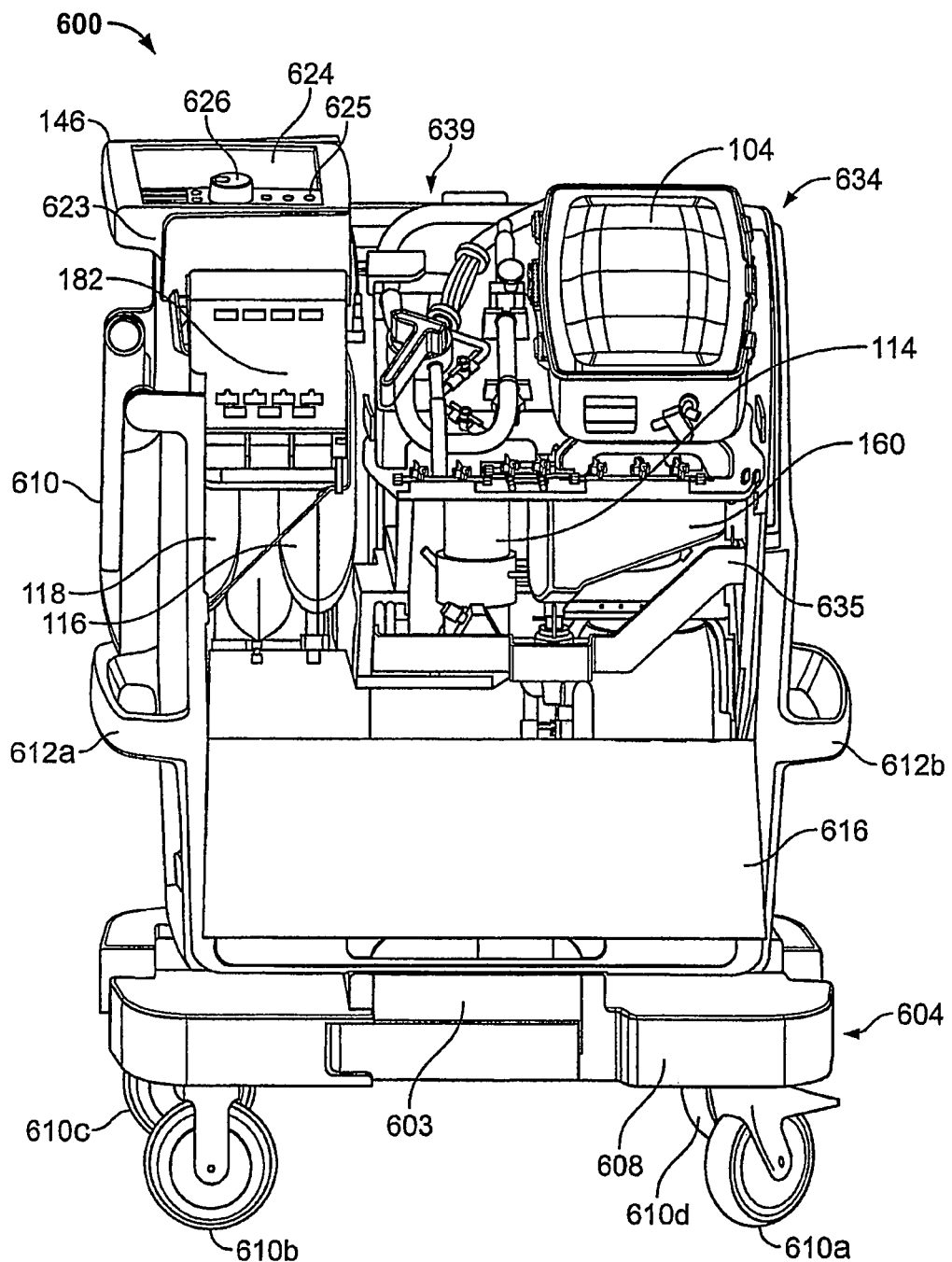
FIGS. 19A-19C show various views of the system of FIGS. 18A and 18B with its top off and front panel open according to an illustrative embodiment of the invention.
Figure 19B:
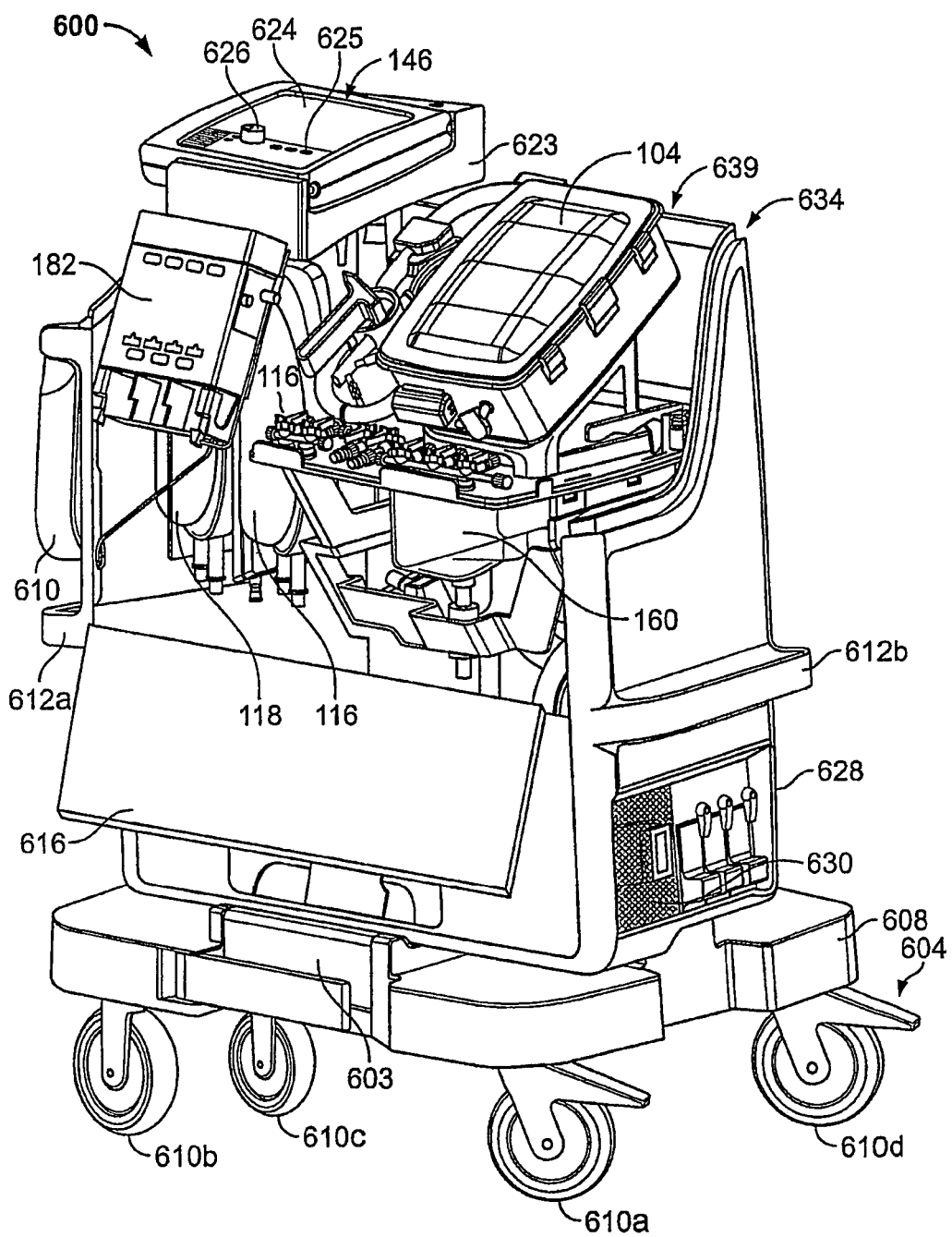
Figure 19C:
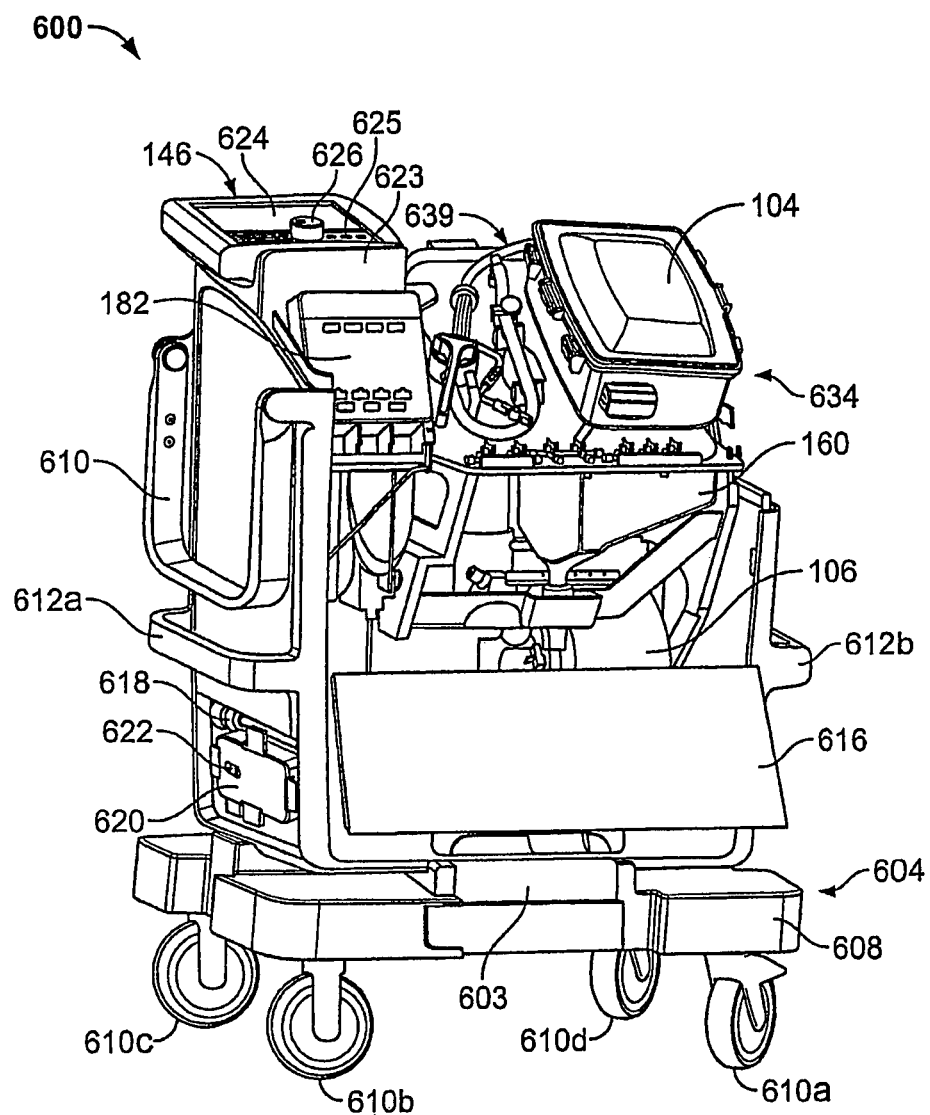

With continued reference to FIGS. 19A-19C, various views are shown of the implementation 600 of FIGS. 18A and 18B with the top 614 and upper front panel 613 removed and the front mid panel 616 open, according to an illustrative embodiment of the invention. With reference to FIGS. 19A-19C, the system 100 is structured as a single use disposable module 634 (shown and described in detail below with reference to FIGS. 24A-25C) and a multiple use module 650 (shown without the single use module in FIG. 20). As discussed in further detail below, according to one feature of the illustrative embodiment, all of the blood contacting components of the system 100 are included in the single use disposable module 634 so that after a use, the entire single use module 634 may be discarded, a new module 634 installed, and the system 100 available for use again within a very brief amount of time.

According to the illustrative embodiment, the single use module 634 includes a chassis 635 for supporting all of the components of the single use module 634. As described in more detail with regard to FIGS. 24A-25C, the components of the single use module 634 include the organ chamber assembly 104, described above in detail with respect to FIGS. 5A-5F, the perfusion fluid reservoir 160, the oxygenator 114, the perfusion fluid pump interface 300, and all of the various fluid flow conduits and peripheral monitoring components 633.

As shown in FIGS. 19A-20A, with the top 614 removed and the front panel 616 open, an operator has easy access to many of the components of the disposable 634 and multiple use 650 modules. For example, the operator may install, remove and view the levels of the nutrient 116 and preservative 118 supplies of the nutritional subsystem 115. The operator may also control operation of the nutrient 116 and preservative 118 infusion pump 182. The operator may also cannulate an organ, such as the heart 102, into the organ chamber assembly 104. As described in detail below with reference to FIGS. 21A-21C, this configuration also provides the operator with sufficient access to install and/or remove the single use module 634 to/from the multiple use module 650.

FIG. 20A shows a front perspective view of the multiple use module 650 with the single use module 634 removed. As shown, the multiple use module 650 includes: the cart 604; the lower section 602b of the housing 602, along with all of the components externally mounted to it, along with those contained therein (described in further detail below, with reference to FIGS. 21A-21C and 23A-23C); the upper section 602a of the housing 602 and all of the components externally mounted to it, including the top cover 614, the handles 610, 612a, and 612b, and the front panel 616; the operator interface module 146; and the perfusion fluid pump motor assembly 106. As described in detail below with reference to FIGS. 21A-21C, the multiple use module 650 also includes a bracket assembly 638 for receiving and locking into place the single use module 534.

Figure 22A:
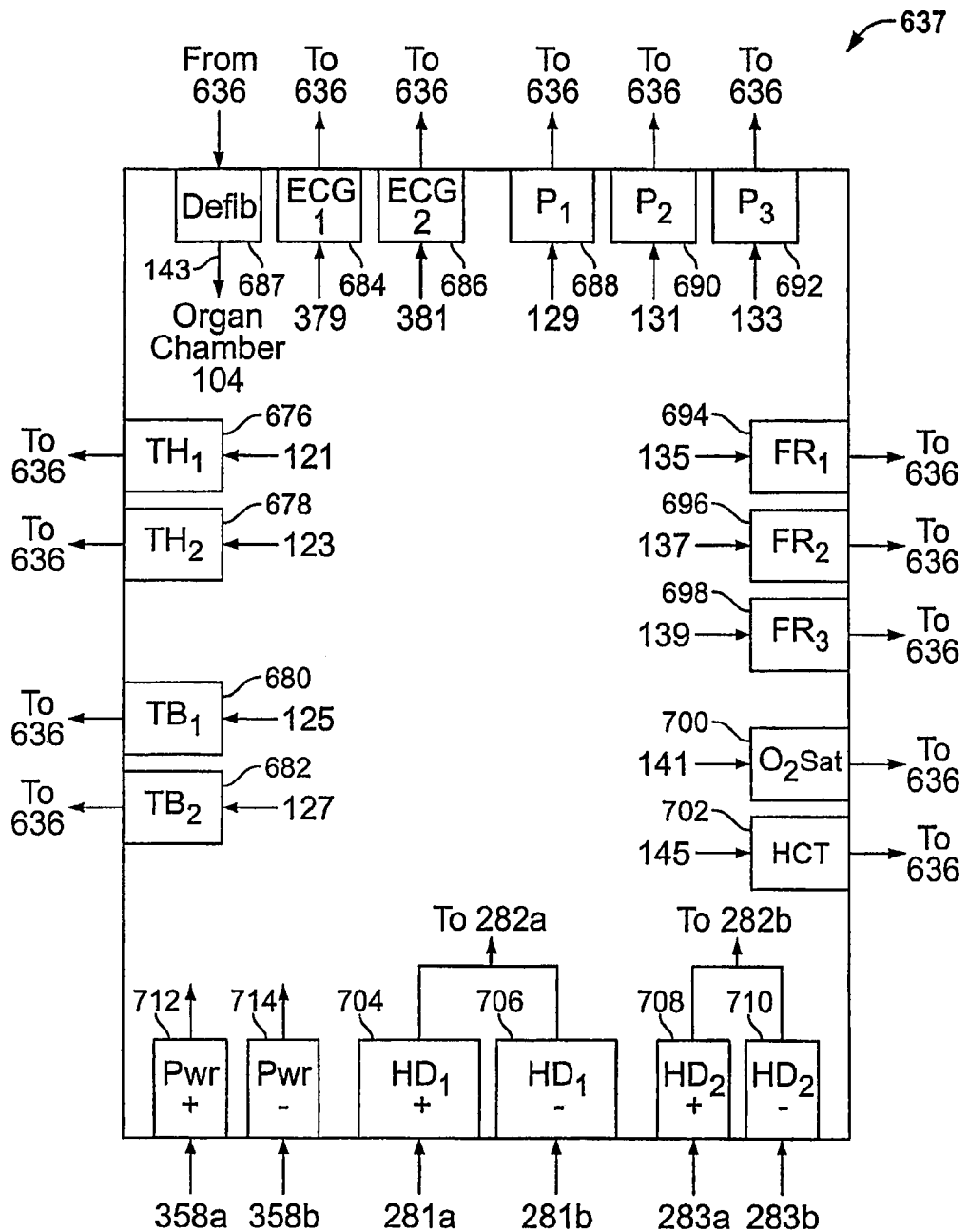
FIGS. 22A-22C show exemplary mechanisms for automatically making electro-optical interconnections between the single use disposable module and the multiple use module during the installation of FIGS. 21B and 21C.

As shown in FIG. 20A and described in further detail below with reference to FIGS. 22A-22C, the multiple use module 650 also includes a front-end interface circuit board 636 for interfacing with a front-end circuit board (shown in FIG. 24D at 637) of the disposable module 634. As also described in detail with reference to FIGS. 22A-22C, power and drive signal connections between the multiple use module 650 and the disposable module 634 are made by way of corresponding electromechanical connectors 640 and 647 on the front end interface circuit board 636 and the front end circuit board 637, respectively. By way of example, the front-end circuit board 637 receives power for the disposable module 634 from the front-end interface circuit board 636 via the electromechanical connectors 640 and 647. The front end circuit board 637 also receives drive signals for various components (e.g., the heater assembly 110, and the oxygenator 114) from the controller 150 via the front-end interface circuit board 636 and the electromechanical connectors 640 and 647. The front-end circuit board 637 and the front-end interface circuit board 636 exchange control and data signals (e.g., between the controller 150 and the disposable module 134) by way of optical connectors (shown in FIG. 22B at 648). As described in more detail with reference to FIGS. 22A-22F, the connector configuration employed between the front-end 637 and front-end interface 636 circuit boards ensures that critical power and data interconnections between the single and multiple use modules 634 and 650, respectively, continue to operate even during transport over rough terrain, such as may be experienced during organ transport.

As shown in FIG. 20A, according to another feature, the upper section 602a of the housing 602 includes a fluid tight basin 652, which is configured to capture any perfusion fluid 108 and/or nutritional 116 and/or preservative 118 solution that may inadvertently leak. The basin 652 also prevents any leaked fluid 108 or solution 116/118 from passing into the lower section 602b of the housing 602. In this way, the basin 652 shields the electronic components of the system 100 from any such leaked fluid 108 or solution 116/118. Shielded components include, for example, the power board 720 shown in and discussed in further detail below with reference to FIGS. 23C and 23D. The basin 652 includes a section 658, which extends over and shields the perfusion fluid pump 106 from any inadvertently leaked fluid. According to another feature, the basin 652 is sized to accommodate the entire volume of perfusion fluid 108 (including the maintenance solutions 116/118) contained within the system 100 at any particular time.

Figure 20B:
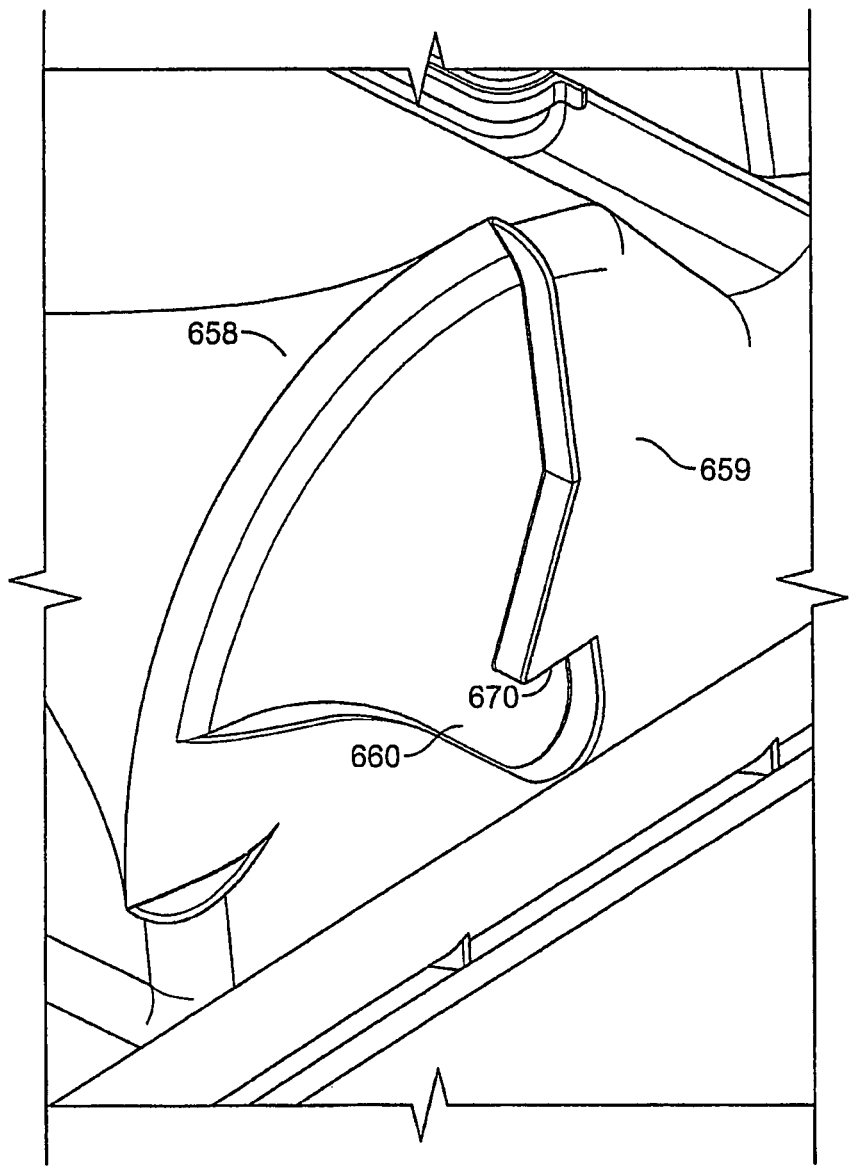
FIG. 20B is a side view of a slot formed in a basin of the multiple use module of FIG. 20A for engaging with a corresponding projection in the single use disposable module.

Referring also to FIG. 20B, according to a further feature of the illustrative embodiment, an outer side 659 of the pump covering portion 658 of the basin 652 includes a slot 660. As described in further detail below with reference to FIGS. 21A-21C and 24A, the slot 660 engages with a projection 662 on the single use module 634 during installation of the single use module 634 into the multiple use module 650.

Figure 21A:
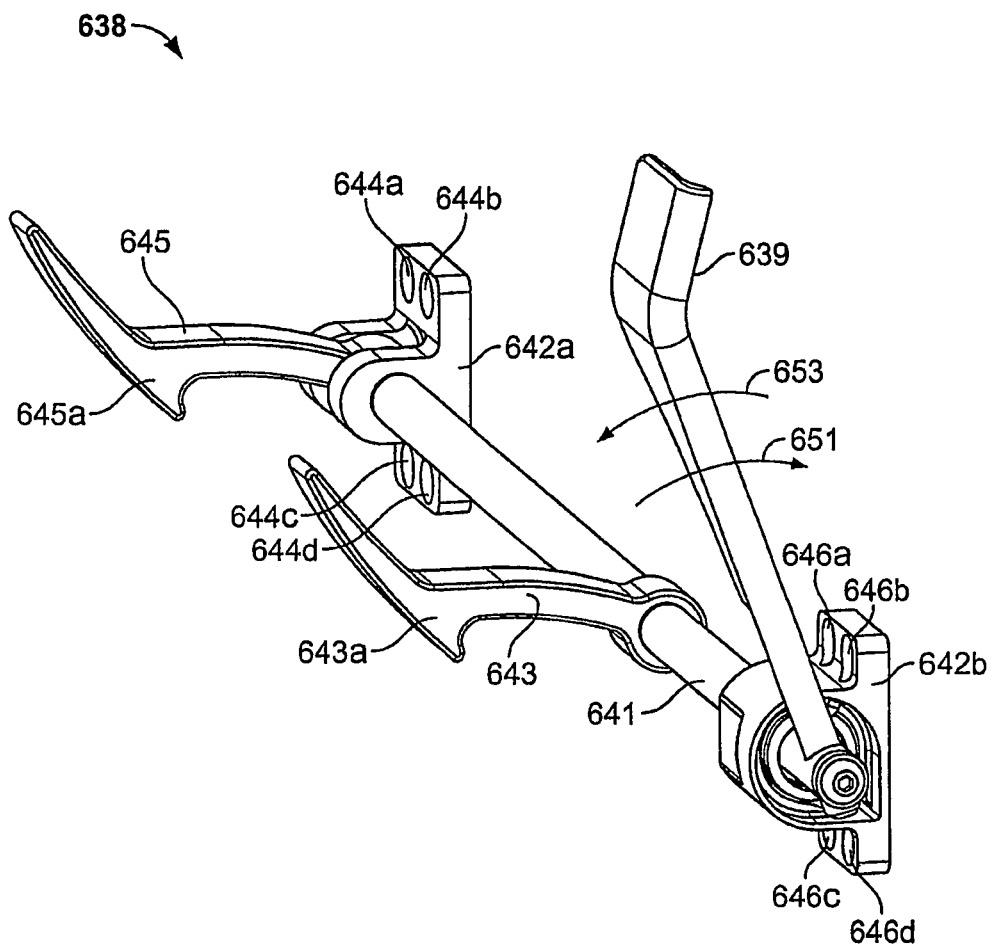
FIG. 21A shows a mounting bracket for receiving and locking into place the single use disposable module within the multiple use module of FIG. 20A.
Figure 21B:
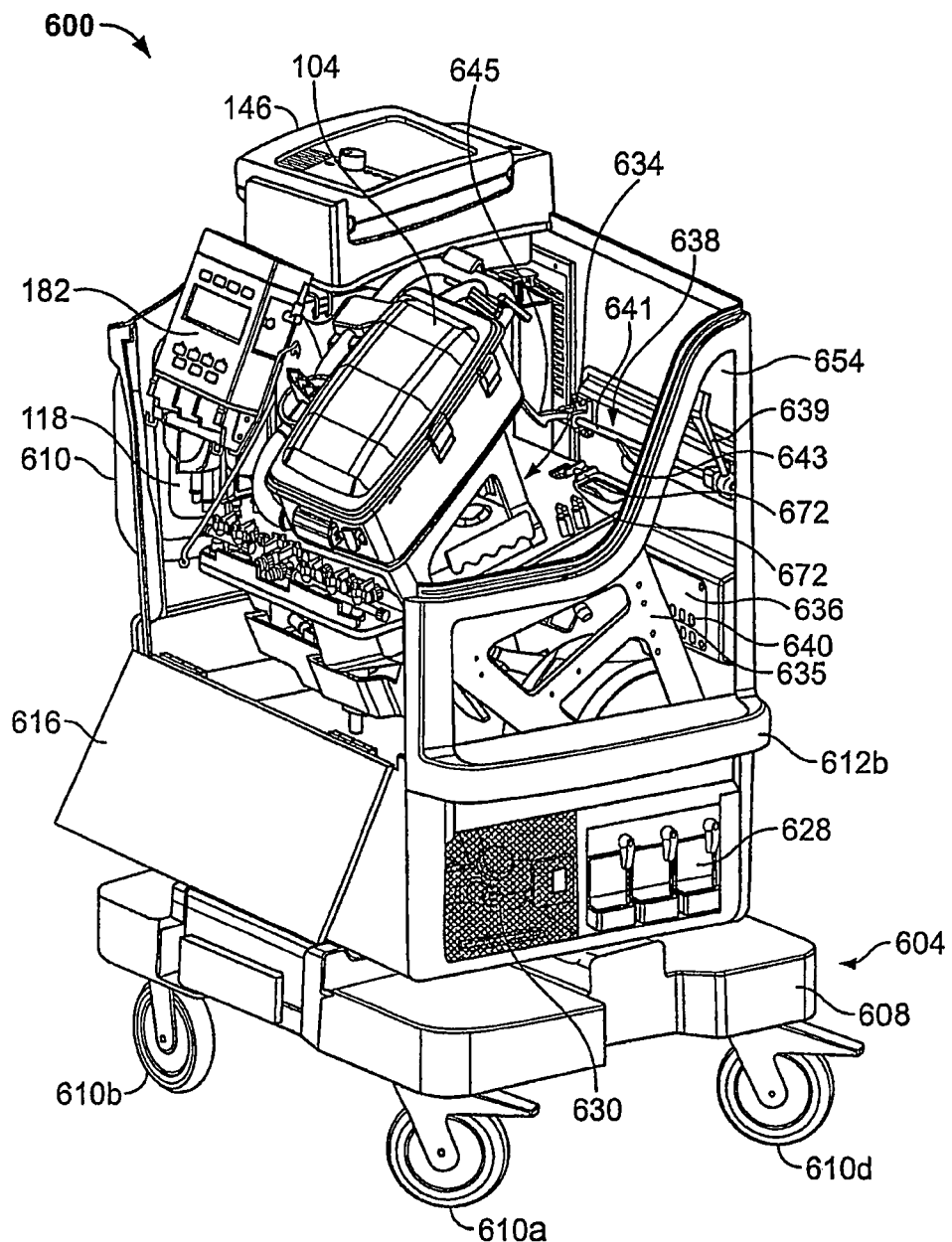
FIGS. 21B and 21C show installation of the single use disposable module into the multiple use module using the mounting bracket of FIG. 21A according to an illustrative embodiment of the invention.
Figure 21C:
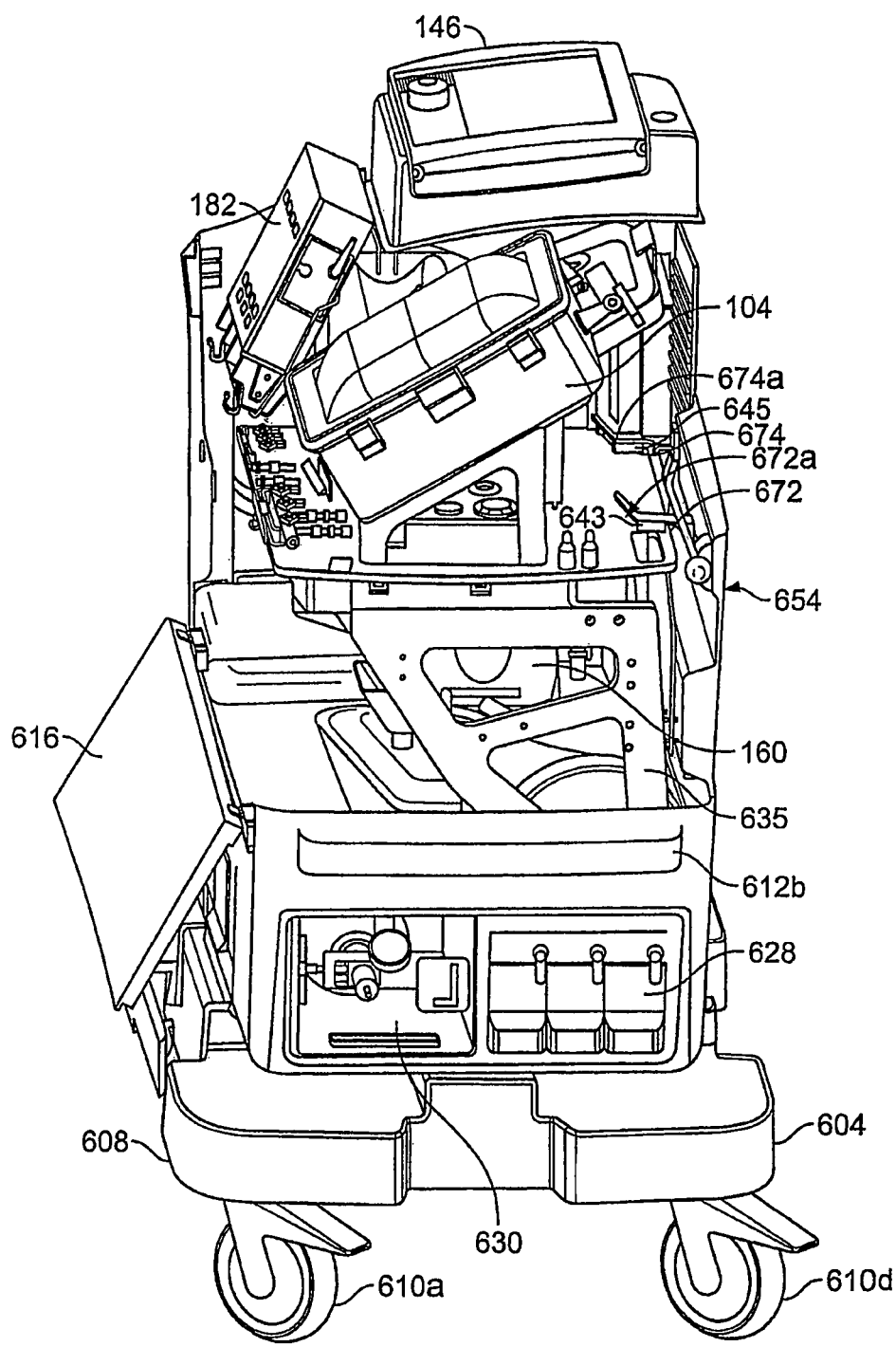

Turning now to the installation of the single use module 634 into the multiple use module 650, FIG. 21A shows a detailed view of the above-mentioned bracket assembly 638 located on the multiple use module 650 for receiving and locking into place the single use module 634. FIG. 21B shows a side perspective view of the single use module 634 being installed onto the bracket assembly 638 and into the multiple use module 650, and FIG. 21C shows a side view of the single use module 634 installed within the multiple use module 650. With reference to FIGS. 21A and 21B, the bracket assembly 638 includes two mounting brackets 642a and 642b, which mount to an internal side of a back panel 654 of the upper housing section 602a via mounting holes 644a-644d and 646a-646d, respectively. A cross bar 641 extends between and rotatably attaches to the mounting brackets 642a and 642b. Locking arms 643 and 645 are spaced apart along and radially extend from the cross bar 641. Each locking arm 643 and 645 includes a respective downward extending locking projection 643a and 645b. A lever 639 attaches to and extends radially upward from the cross bar 641. Actuating the lever 639 in the direction of the arrow 651 rotates the locking arms 643 and 645 toward the back 606b of the housing 602. Actuating the lever 639 in the direction of the arrow 653 rotates the locking arms 643 and 645 toward the front 606a of the housing 602.

Figure 24A:
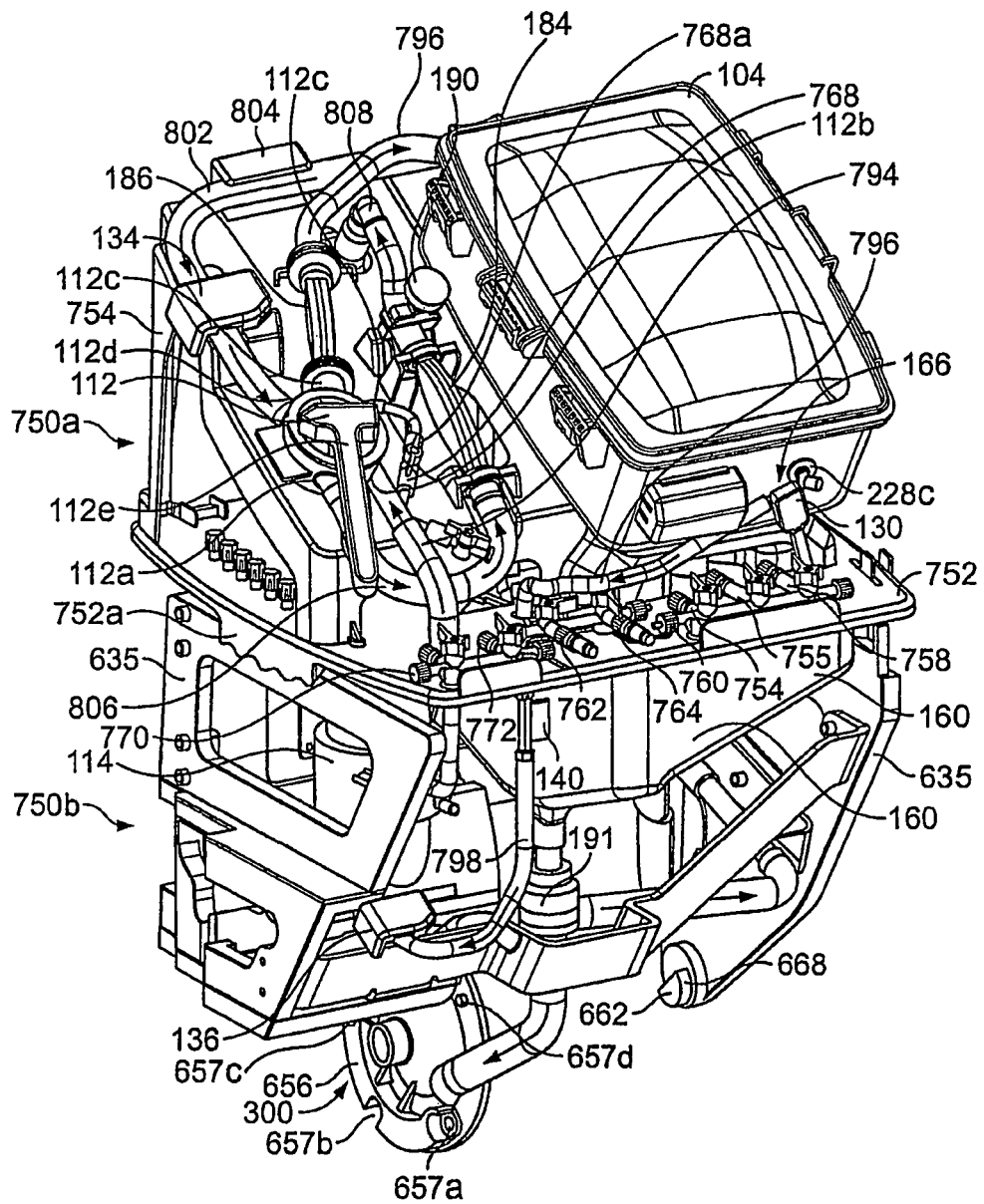
FIGS. 24A-24E show various top perspective views of a single use disposable module according to an illustrative embodiment of the invention.

As described above with respect to FIG. 10, the perfusion pump interface assembly 300 includes four projecting heat staking points 321a-321d. As shown in FIG. 24A, during assembly, the projections 321a-321d are aligned with corresponding apertures 657a-657d and heat staked through the apertures 657a-657d into the projections 321a-321d to rigidly mount the outer side 304 of the pump interface assembly 300 onto the C-shaped bracket 656 of the single use module chassis 635.

With reference to FIGS. 10, 20B, 21A, 21B and 24A, during installation, in a first step, the single use module 634 is lowered into the multiple use module 650 while tilting the single use module 634 forward (shown in FIG. 21B). This process slides the projection 662 of FIG. 24A into the slot 660 of FIG. 20B. As shown in FIG. 10, it also positions the flange 328 of the pump interface assembly 300 within the docking port 342 of the perfusion pump assembly 106, and the tapered projections 323a and 323b of the pump interface assembly 300 on the clockwise side of corresponding ones of the features 344a and 344b of the pump assembly bracket 346. In a second step, the single use module 634 is rotated backwards until locking arm cradles 672 and 674 of the single use module chassis 635 engage projections 643 and 645 of spring-loaded locking arm 638, forcing the projections 643 and 645 to rotate upward (direction 651), until locking projections 643a and 645a clear the height of the locking arm cradles 672 and 674, at which point the springs cause the locking arm 638 to rotate downward (direction 653), allowing locking projections 643a and 645a to releasably lock with locking arm cradles 672 and 674 of the disposable module chassis 635. This motion causes the curved surface of 668 of the disposable module chassis projection 662 of FIG. 24A to rotate and engage with a flat side 670 of the basin slot 660 of FIG. 20B. Lever 639 can be used to rotate the locking arm 638 upwards (direction 651) to release the single use module 635.

As shown in FIG. 10, this motion also causes the pump interface assembly 300 to rotate in a counterclockwise direction relative to the pump assembly 106 to slide the flange 328 into the slot 332 of the docking port 342, and at the same time, to slide the tapered projections 323a and 323b under the respective bracket features 344a and 344b. As the tapered projections 323a and 323b slide under the respective bracket features 344a and 344b, the inner surfaces of the bracket features 344a and 344b engage with the tapered outer surfaces of the tapered projections 323a and 323b to draw the inner side 306 of the pump interface assembly 300 toward the pump driver 334 to form the fluid tight seal between the pump interface assembly 300 and the pump assembly 106. The lever 639 may lock in place to hold the disposable module 634 securely within the multiple use module 650.

As mentioned briefly above with reference to FIG. 20A, interlocking the single use module 374 into the multiple use module 650 forms both electrical and optical interconnections between the front end interface circuit board 636 on the multiple use module 650 and the front end circuit board 637 on the single use module 634. The electrical and optical connections enable the multiple use module 650 to power, control and collect information from the single module 634. FIG. 22A is a conceptual drawing showing various optical couplers and electromechanical connectors on the front end circuit board 637 of the single-use disposable module 634 used to communicate with corresponding optical couplers and electromechanical connectors on the front end interface circuit board 636 of the multiple use module 650. Since this correspondence is one for one, the various optical couplers and electromechanical connectors are described only with reference to the front end circuit board 637, rather than also depicting the front end circuit board 650.

According to the illustrative embodiment, the front end circuit board 637 receives signals from the front end interface circuit board 636 via both optical couplers and electromechanical connectors. For example, the front end circuit board 637 receives power 358 (also shown in FIG. 14) from the front end interface circuit board 636 via the electromechanical connectors 712 and 714. The front end circuit board 637 the power to the components of the single use module 634, such as the various sensors and transducers of the single use module 634. Optionally, the front end circuit board 637 converts the power to suitable levels prior to distribution. The front end interface circuit board 636 also provides the heater drive signals 281a and 281b of FIG. 13 to the applicable connections 282a on the heater 246 of FIG. 6E via the electromechanical connectors 704 and 706. Similarly, the electromechanical connectors 708 and 710 couple the heater drive signals 283a and 283b of FIG. 13 to the applicable connections in 282b of the heater 248. The front-end circuit board 637 may receive a defibrillation command from the front end interface circuit board 636 via the electromechanical connector 687. In response, the front end circuit board 637 generates the defibrillation signal 143 having suitable current and voltage levels, and as shown in FIG. 5E, couples the signal 143 to the organ chamber assembly 104 via the electrical interface connections 235*a*-235*b*.

In another illustrative embodiment, the defibrillation command can be provided from an external source (not shown), rather than through the circuit board 636. As an example, and with reference to FIG. 5E and FIG. 1, an external defibrillation device can be plugged into the electrical coupler 613 shown in FIG. 24E, which is connected to the electrical interface connections 235*a*-235*b*. The external defibrillation device sends a defibrillation signal 143 through the coupler 613 and the interface connections 235*a* and 235*b* to electrodes 142 and 144. The electrodes 142 and 144 then deliver the signal 143 to the heart 102. This alternative embodiment allows the user to provide defibrillation (and pacing) without passing the signal 143 through the circuit boards 618, 636, and 637. An exemplary external defibrillation device may include the Zoll M-Series Portable Defibrillator.

According to the illustrative embodiment, the front end circuit board 637 receives signals from temperature, pressure, fluid flow-rate, oxygentation/hematocrit and ECG sensors, amplifies the signals, converts the signals to a digital format and provides them to the front-end interface circuit board 636 by way of optical couplers. For example, the front end circuit board 637 provides the temperature signal 121 from the sensor 120 on the heater plate 250 (shown in FIGS. 6A and 13) to the front end interface circuit board 636 by way of the optical coupler 676. Similarly, the front end circuit board 637 provides the temperature signal 123 from the sensor 122 on the heater plate 252 (shown in FIGS. 6A and 13) to the front end interface circuit board 636 by way of the optical coupler 678. The front end circuit board 637 also provides the perfusion fluid temperature signals 125 and 127 from the thermistor sensor 124 (shown in FIGS. 6A and 13) to the front end interface circuit board 636 via respective optical couplers 680 and 682. Perfusion fluid pressure signals 129, 131 and 133 are provided from respective pressure transducers 126, 128 and 130 to the front end interface circuit board 636 via respective optical couplers 688, 690 and 692. The front end circuit board 637 also provides perfusion fluid flow rate signals 135, 137 and 139 from respective flow rate sensors 134, 136 and 138 to the front end interface circuit board 636 by way of respective optical couplers 694, 696 and 698. Additionally, the front end circuit board 637 provides the oxygen saturation 141 and hematocrit 145 signals from the oxygen saturation sensor 140 to the front end interface circuit board 636 by way of respective optical couplers 700 and 702.

In other illustrative embodiments, one or more of the foregoing sensors are wired directly to the main system board 718 (described below with reference to FIG. 23D) for processing and analysis, thus by-passing the front-end interface board 636 and front-end board 637 altogether. Such embodiments may be desirable where the user prefers to re-use one or more of the sensors prior to disposal. In one such example, the flow rate sensors 134, 136 and 138 and the oxygen and hematocrit sensor 140 are electrically coupled directly to the system main board 718 through electrical coupler 611 shown in FIG. 23C, thus by-passing any connection with the circuit boards 636 and 637.

As described above with respect to FIGS. 11-16, the controller 150 employs the signals provided to the front end interface circuit board 636, along with other signals, to transmit data and otherwise control operation of the system 100. As described with respect to FIGS. 17A-17J, the controller 150 also displays sensor information, and may display to the operator various alarms relating to the sensor information by way of the operator interface module 146.

Figure 22B:
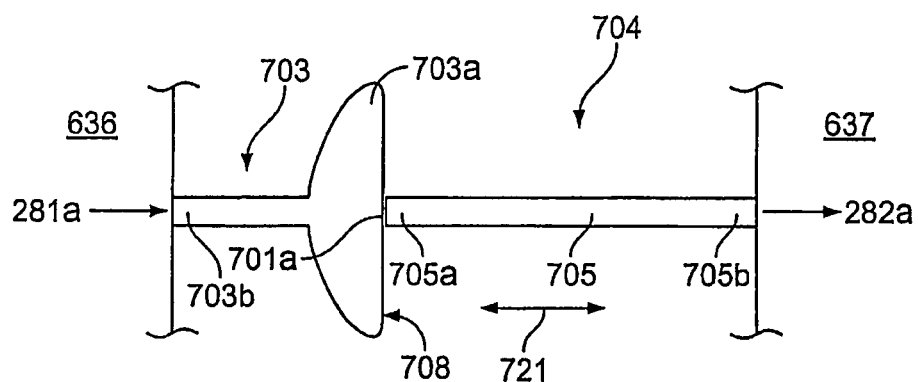
Figure 22C:
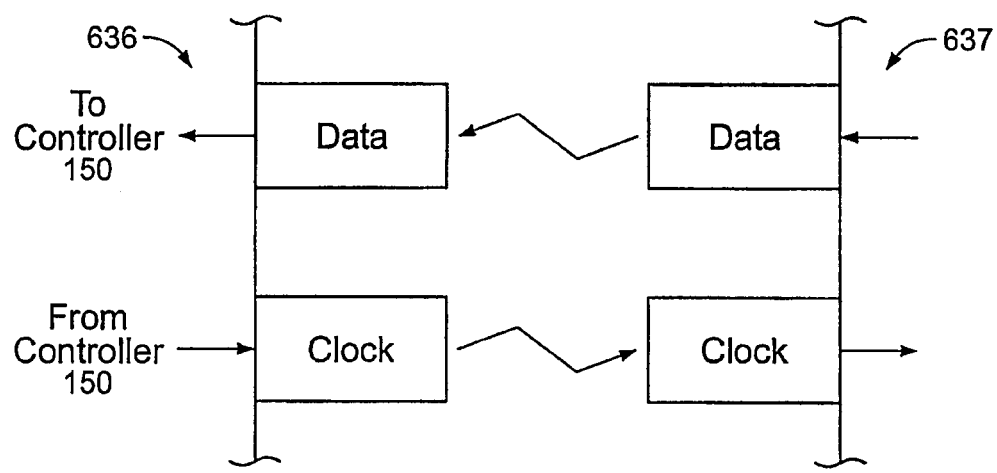

FIG. 22B illustrates the operation of an exemplary electromechanical connector pair of the type employed for the electrical interconnections between the circuit boards 636 and 637. Similarly, FIG. 22C illustrates the operation of an optical coupler pair of the type employed for the optically coupled interconnections between the circuit boards 636 and 637. One advantage of both the electrical connectors and optical couplers employed is that they ensure connection integrity, even when the system 100 is being transported over rough terrain, for example, such as being wheeled along a tarmac at an airport, being transported in an aircraft during bad weather conditions, or being transported in an ambulance over rough roadways. Additionally, the optical couplers electrically isolate the temperature, pressure and ECG sensors from the rest of the system 100, which prevents a defibrillation signal from damaging the system 100. The power for the front end board 637 is isolated in a DC power supply located on the front end interface board 636.

As shown in FIG. 22B, the electromechanical connectors, such as the connector 704, include a portion, such as the portion 703, located on the front end interface circuit board 636 and a portion, such as the portion 705, located on the front end circuit board 637. The portion 703 includes an enlarged head 703*a* mounted on a substantially straight and rigid stem 703*b*. The head 703 includes an outwardly facing substantially flat surface 708. The portion 705 includes a substantially straight and rigid pin 705 including an end 705*a* for contacting the surface 708 and a spring-loaded end 705*b*. Pin 705 can move axially in and out as shown by the directional arrow 721 while still maintaining electrical contact with the surface 708 of the enlarged head 703*a*. This feature enables the single use module 634 to maintain electrical contact with the multiple use module 650 even when experiencing mechanical disturbances associated with transport over rough terrain. An advantage of the flat surface 708 is that it allows for easy cleaning of the interior surface of the multiple use module 650. According to the illustrative embodiment, the system 100 employs a connector for the electrical interconnection between the single use disposable 634 and multiple use 650 modules. An exemplary connector is part no. 101342 made by Interconnect Devices. However, any suitable connector may be used.

Optical couplers, such as the optical couplers 684 and 687 of the front end circuit board 637, are used and include corresponding counterparts, such as the optical couplers 683 and 685 of the front end interface circuit board 636. The optical transmitters and optical receiver portions of the optical couplers may be located on either circuit board 636 or 637. For example, in the case of the ECG signal 379, the optical transmitter 684 is located on the circuit board 637 for receiving the electrical signal 379 and optically coupling it to the optical receiver 683 on the circuit board 636. In the case where the defibrillator signal is transmitted through the circuit boards 636 and 637 (rather than directly to the main board 718), the optical transmitter 685 on the circuit board 636 optically couples the signal to the optical receiver 687 on the circuit board 637.

As in the case of the electromechanical connectors employed, allowable tolerance in the optical alignment between the optical transmitters and corresponding optical receivers enables the circuit boards 636 and 637 to remain in optical communication even during transport over rough terrain. According to the illustrative embodiment, the system 100 uses optical couplers made under part nos. SFH485P and/or SFH203PFA by Osram. However, any suitable coupler may be used.

The couplers and connectors facilitate the transmission of data within the system 100. The front-end interface circuit board 636 and the front-end board 637 transmit data pertaining to the system 100 in a paced fashion. As shown in FIG. 22C, circuit board 636 transmits to the front-end board 637 a clock signal that is synchronized to the clock on the controller 150. The front-end circuit board 637 receives this clock signal and uses it to synchronize its transmission of system data (such as temperatures, pressures, ECG, r-wave detection, or other desired information) with the clock cycle of the controller 150. This data is digitized by a processor on the front-end circuit board 637 according to the clock signal and a pre-set sequence of data type and source address (i.e. type and location of the sensor providing the data). The front-end interface circuit board 636 receives the data from the front-end board 637 and transmits the data set to the main board 618 for use by the controller 150 in evaluation, display, and system control, as described above with reference to FIGS. 11, 12 and 14. Additional optical couplers can be added between the multiple use module and single use module for transmission of control data from the multiple use module to the single use module, such data including heater control signals or pump control signals.

Figure 23A:
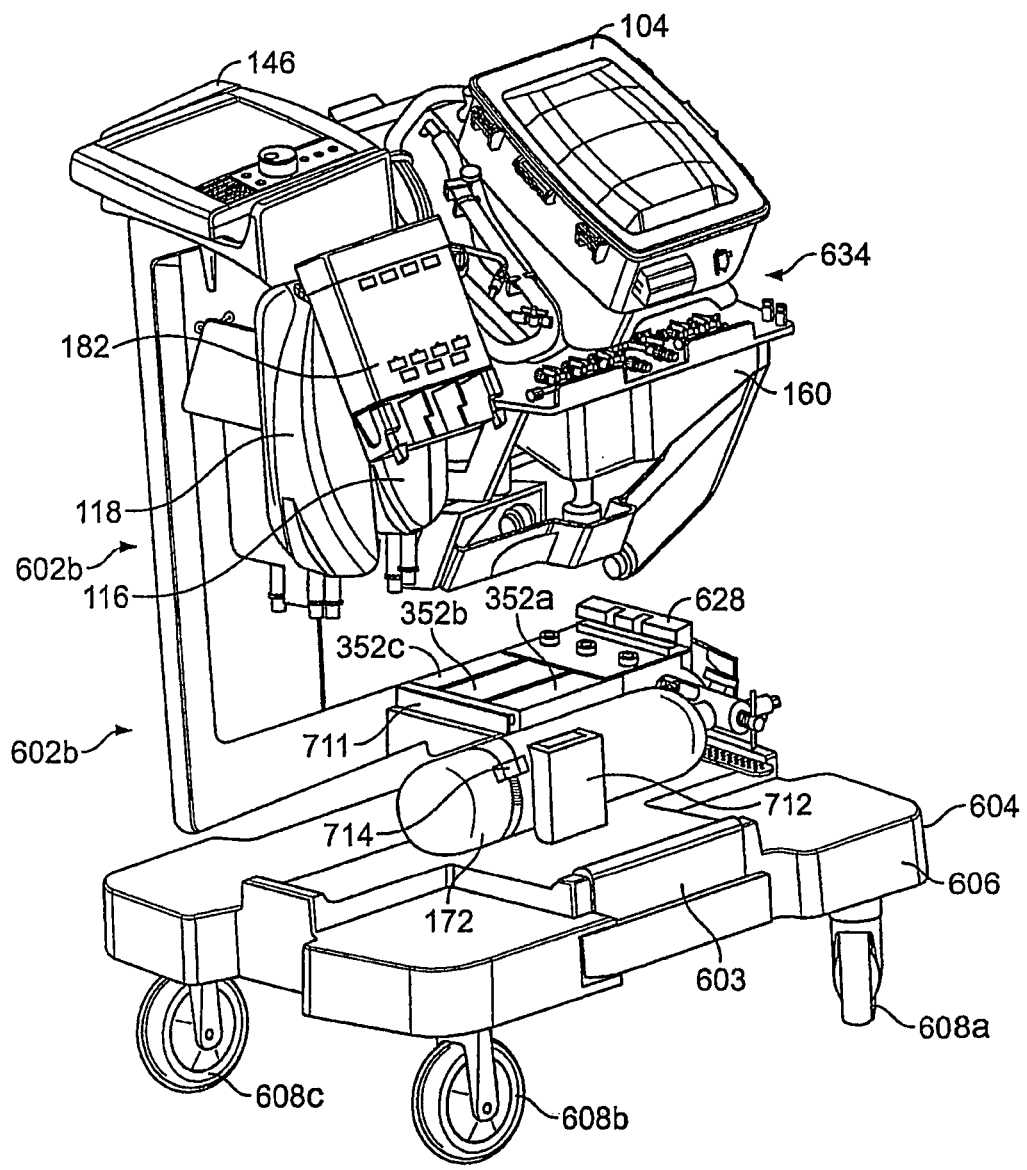
FIGS. 23A-23C show various views of the system of FIGS. 18A and 18B with all of the external walls removed according to an illustrative embodiment of the invention.
Figure 23B:
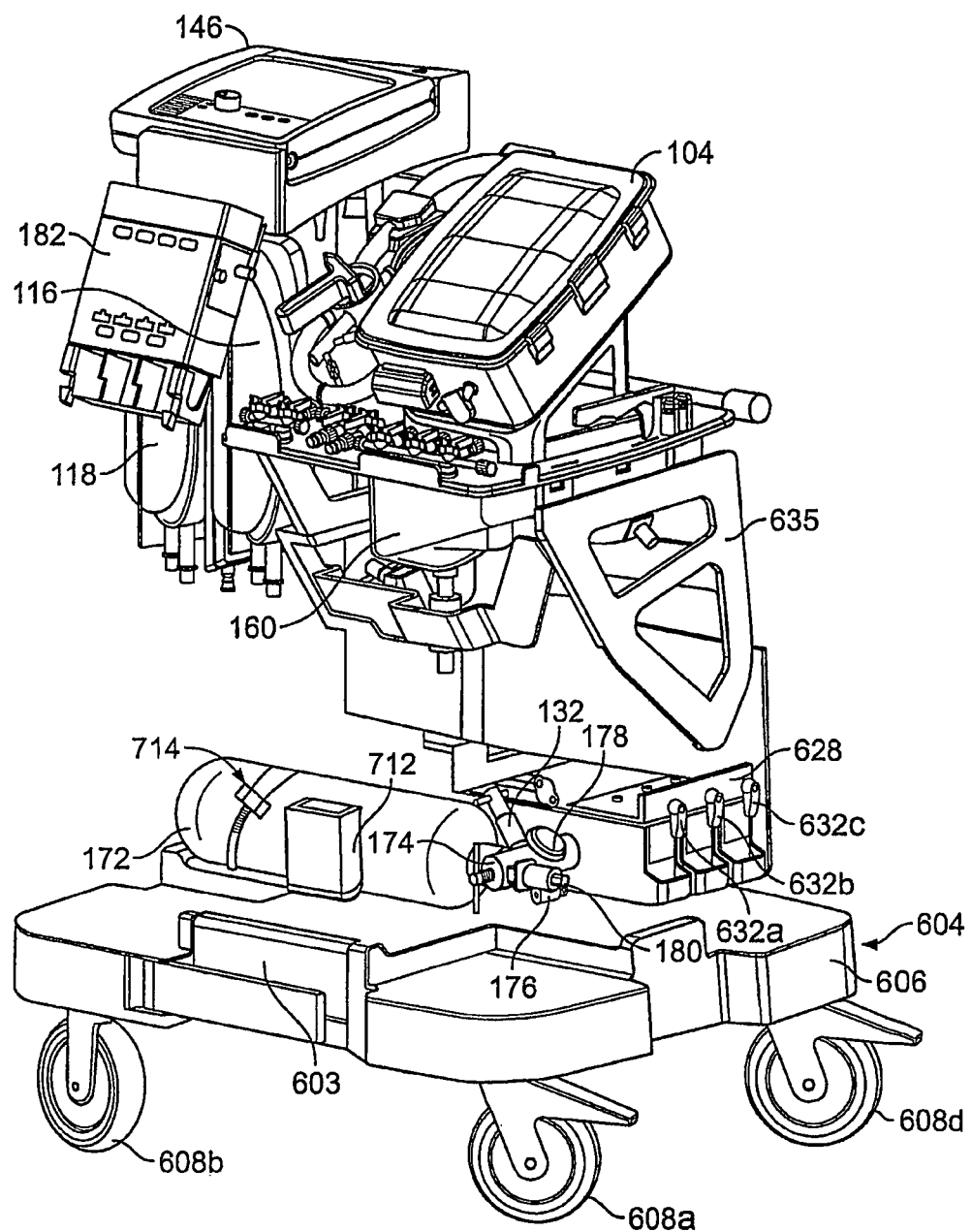

Having described the mechanical, electrical and optical interconnections between the single use module 634 and the multiple use module 650, additional components of the multiple use module 650 will now be discussed with respect to FIGS. 23A-23D, followed by a description of the mechanical arrangement of the components of the single use module 634 with respect to FIGS. 24A-28C. As shown in FIGS. 23A-23D, with the walls of the housing 602 removed, in addition to those components previously discussed, the multiple use module 650 includes an on-board gas supply 172, located in the lower section 602b of the housing 602. The gas supply 172 is depicted in FIGS. 23A-23D as a tank, positioned within the gas tank bay 630 by a support structure 712, which abuts the tank 172. Optionally, the gas supply 172 may be further secured within the gas tank bay 630 by a strap and buckle assembly 714 or other suitable mechanism. With particular reference to FIG. 23B and as described above with reference to FIG. 1, the gas supply 172 provides gas to the system 100 through the gas regulator 174 and the gas flow chamber 176. The gas pressure sensor 132 measures the gas pressure in the gas supply 172, and the gas pressure gauge 178 provides a visual indication of the fullness of the gas supply 172. Additionally, an electrical connection between the controller 150 and the gas flow chamber 176 enables the controller 150 to regulate automatically the gas flow into the oxygenator 114.

Figure 23C:
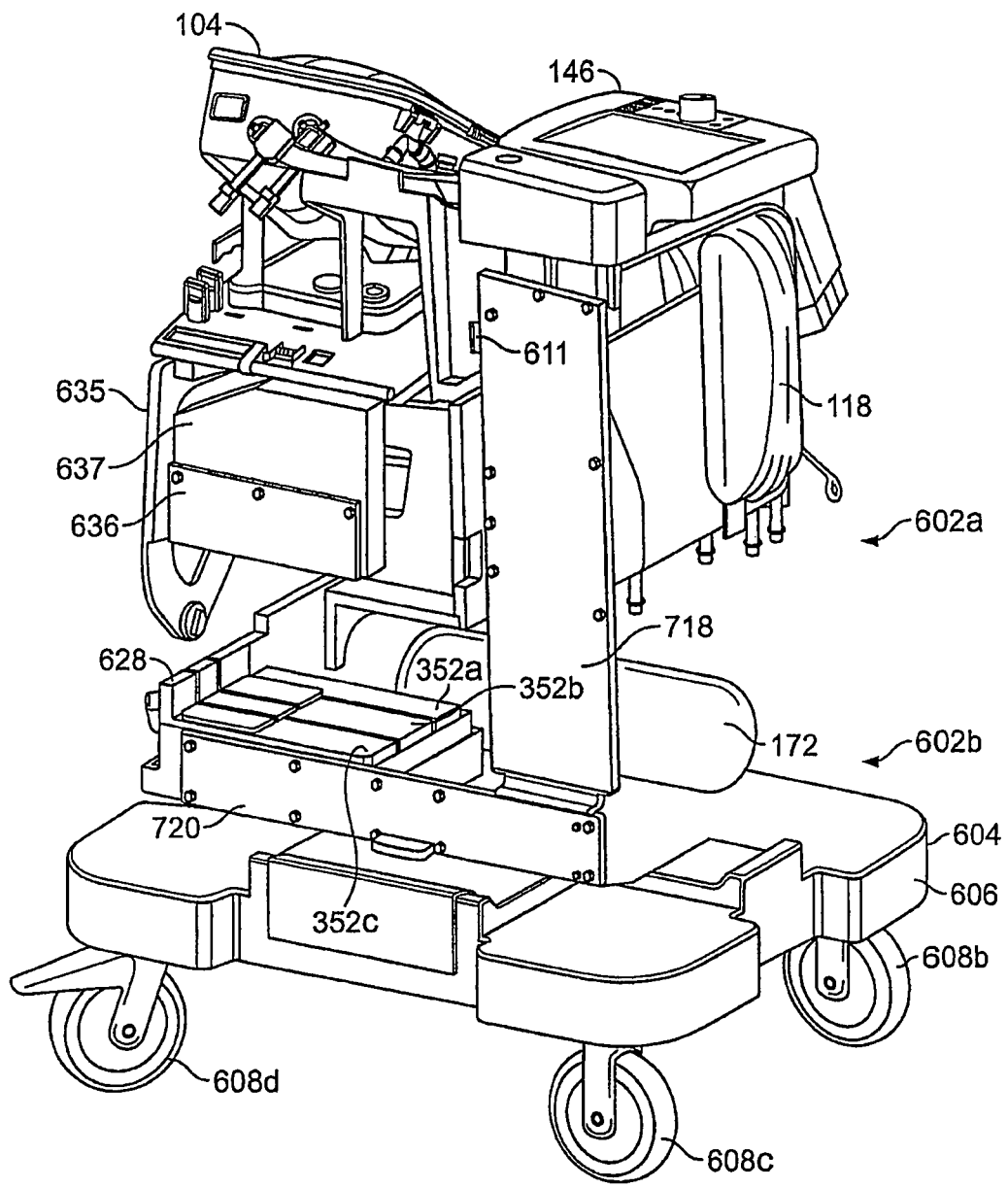

As shown most clearly in FIG. 23C, the battery bay 628 houses the batteries 352a-352c. As noted above with reference to FIG. 14, a lock-out mechanism is used to prevent more than one of the batteries 352a-352c from being removed from the battery bay 628 at a given time while the system 100 is operating.

Figure 23D:
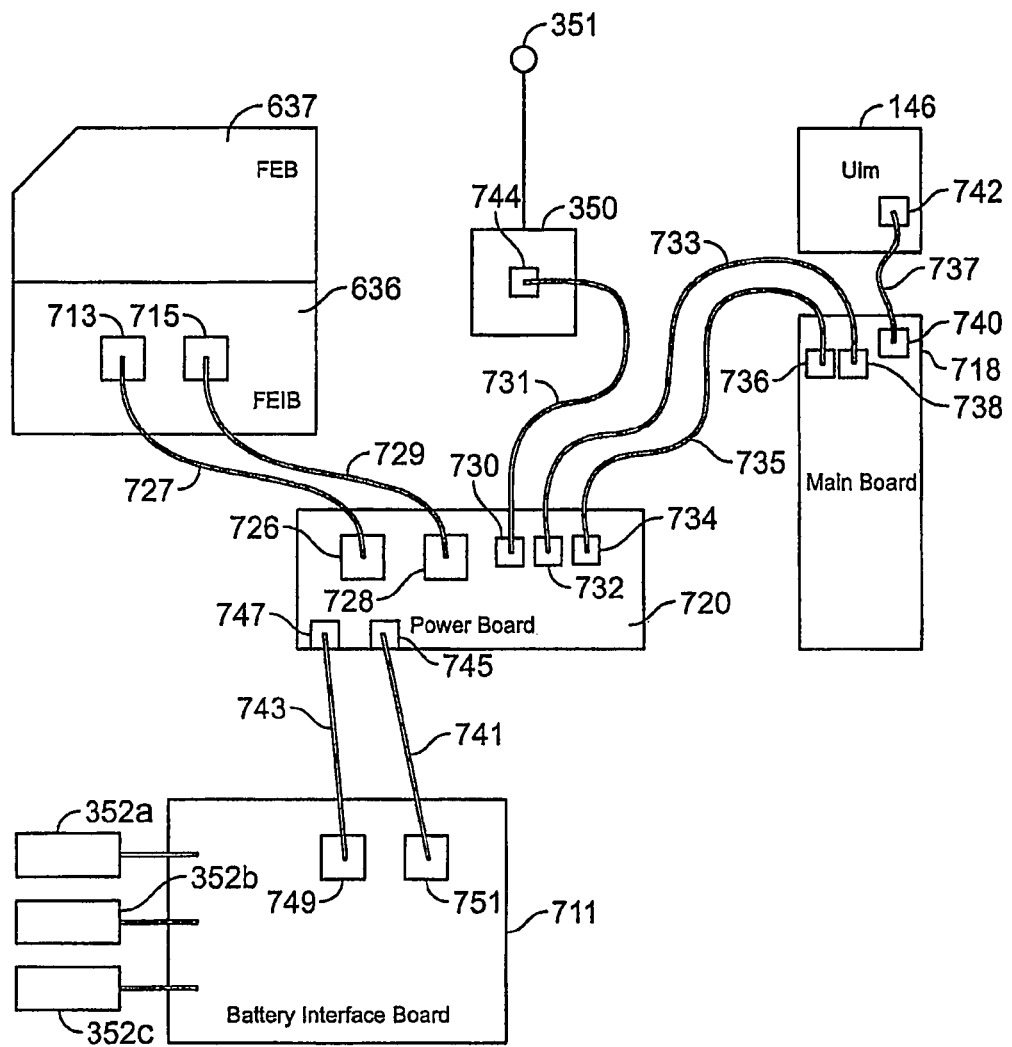
FIG. 23D is a conceptual diagram showing interconnections between the circuit boards of FIGS. 23A-23C according to an illustrative embodiment of the invention.

As discussed above, the system 100 includes a plurality of interconnected circuit boards for facilitating power distribution and data transmission to, from and within the system 100. Particularly, as discussed above with reference to FIGS. 22A-22E and as shown in FIG. 23C, the multiple use module 650 includes a front end interface circuit board 636, which optically and electromechanically couples to the front end circuit board 637 of the single use module 650. As also shown in FIG. 23C, the system 100 further includes a main board 718, a power circuit board 720, and a battery interface board 711 located on the multiple use module 650. The main board 718 is configured to allow the system 100 to be fault tolerant, in that if a fault arises in the operation of a given circuit board (as shown in FIG. 23D), the main board 718 saves pumping and heating parameters in non-volatile memory. When the system 100 reboots, it can re-capture and continue to perform according to such parameters.

Referring to the conceptual drawing of FIG. 23D, cabling 731 brings power (such as AC power 351) from a power source 350 to the power circuit board 720 by way of connectors 744 and 730. The power supply 350 converts the AC power to DC power and distributes the DC power as described above with reference to the power subsystem of FIG. 14. Referring also to FIGS. 14 and 22A, the power circuit board 720 couples DC power and a data signal 358 via respective cables 727 and 729 from the connectors 726 and 728 to corresponding connectors 713 and 715 on the front end interface circuit board 636. Cable 729 carries both power and a data signal to the front end interface board 636. Cable 727 carries power to the heater 110 via the front-end interface board 636. The connectors 713 and 715 interfit with corresponding connectors 712 and 714 (described above with respect to FIG. 22A) on the front end circuit board 637 on the single use module 634 to provide power to the single use module 634.

As shown in FIG. 23D, the power circuit board 720 also provides DC power 358 and a data signal from the connectors 732 and 734, respectively, on the power circuit board 720 to corresponding connectors 736 and 738 on the main circuit board 718 by way of the cables 733 and 735. Referring also to FIGS. 14 and 19A, the cable 737 couples DC power 358 and a data signal from a connector 740 on the main circuit board 718 to the operator interface module 146 by way of a connector 742 on the operator interface module cradle 623. The power circuit board 720 also provides DC power 358 and a data signal from connectors 745 and 747 via cables 741 and 743 to connectors 749 and 751 on a battery interface board 711. Cable 741 carries the DC power signal and cable 743 carries the data signal. Battery interface board 711 distributes DC power and data to batteries 352a, 352b and 352c. Batteries 352a, 352b and 352c contain electronic circuits that allow them to communicate with each other to monitor the respective charges, as described above in reference to FIG. 14, so that the controller 150 can monitor and control the charging and discharging of the batteries 352a-352c.

According to some illustrative embodiments, the controller 150 is located on the main circuit board 718 and performs all control and processing required by the system 100. However, in other illustrative embodiments, the controller 150 is distributed, locating some processing functionality on the front end interface circuit board 636, some on the power circuit board 720, and/or some in the operator interface module 146. Suitable cabling is provided between the various circuit boards, depending on whether and the degree to which the controller 150 is distributed within the system 100.

As described above with reference to FIGS. 19A-19C and 23A-23C, the system 100 mechanically divides into the single use disposable module 634 and the multiple use module 650. As also described above, according to the illustrative embodiment, the single use module 634 includes all or substantially all of the perfusion fluid 108 contacting elements/assemblies of the system 100, along with various peripheral components, flow conduits, sensors and support electronics for operating the blood contacting components. As discussed above with reference to FIGS. 22A and 23D, according to the illustrative embodiment, the module 634 does not include a processor, instead relying on the controller 150, which may, for example, be distributed between the front end interface circuit board 636, the power circuit board 720, the operator interface module 146, and the main circuit board 718, for control. However, in other illustrative embodiments, the single use module 634 may include its own controller/processor, for example, on the front end circuit board 637.

Referring to FIGS. 24A-28C, the single use module 634 will next be described in terms of the components included therein. After that, exemplary forward and retrograde flow modes are traced through the described components.

Figure 24B:
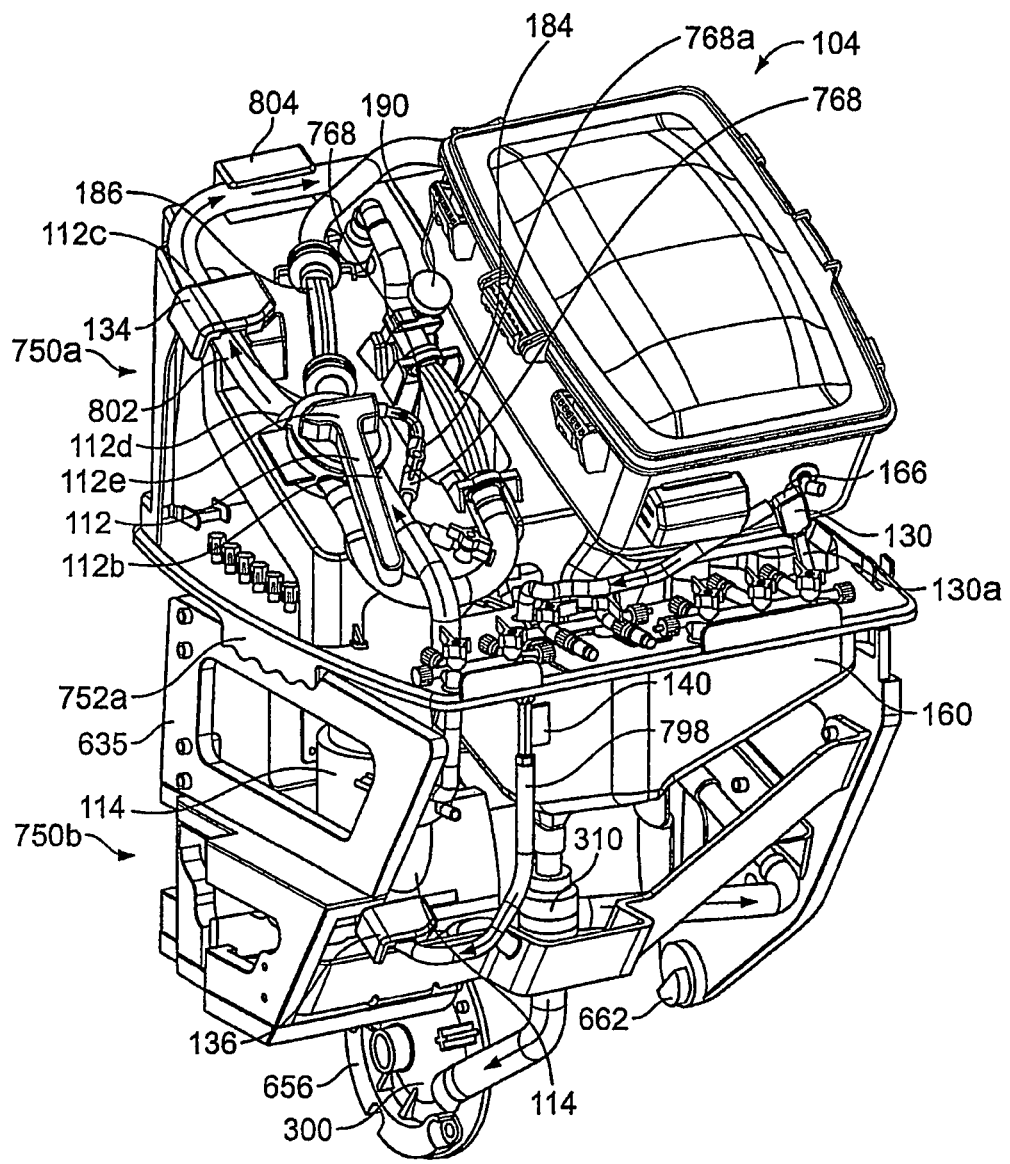
Figure 24C:
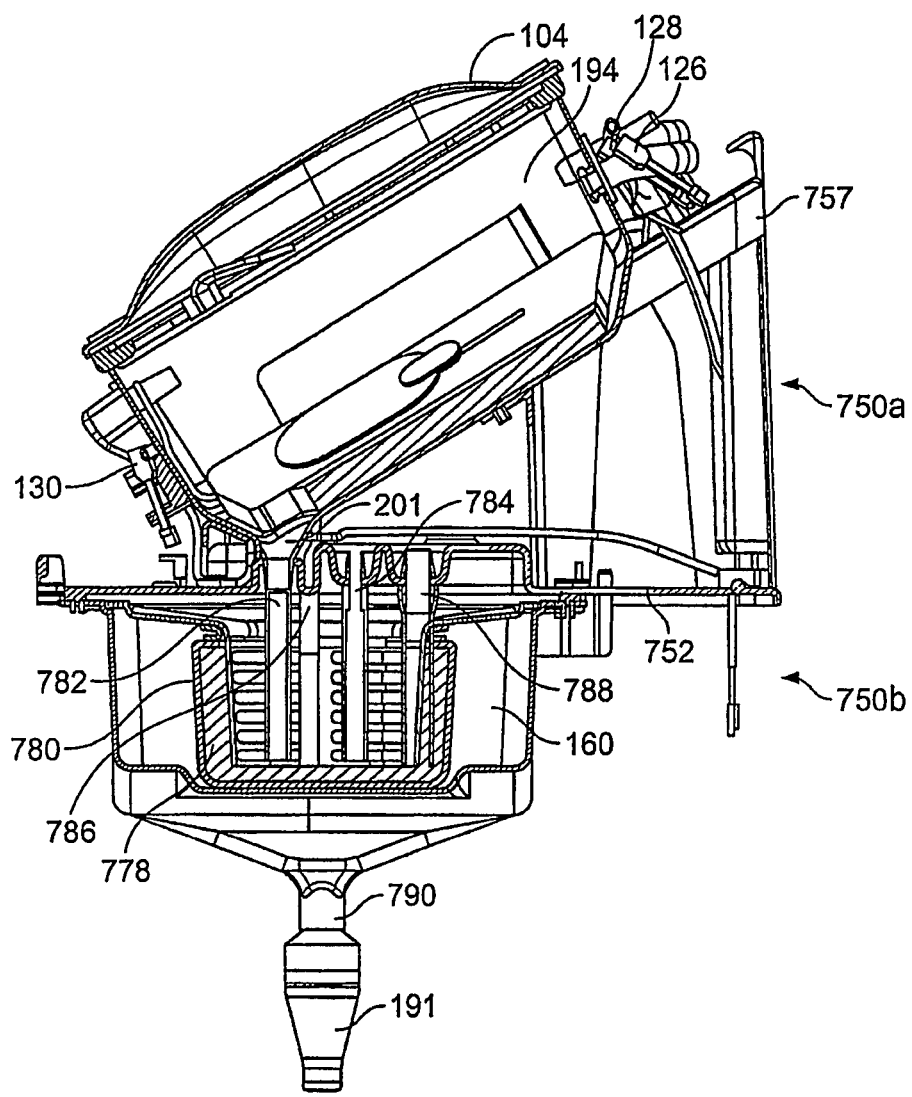
Figure 24D:
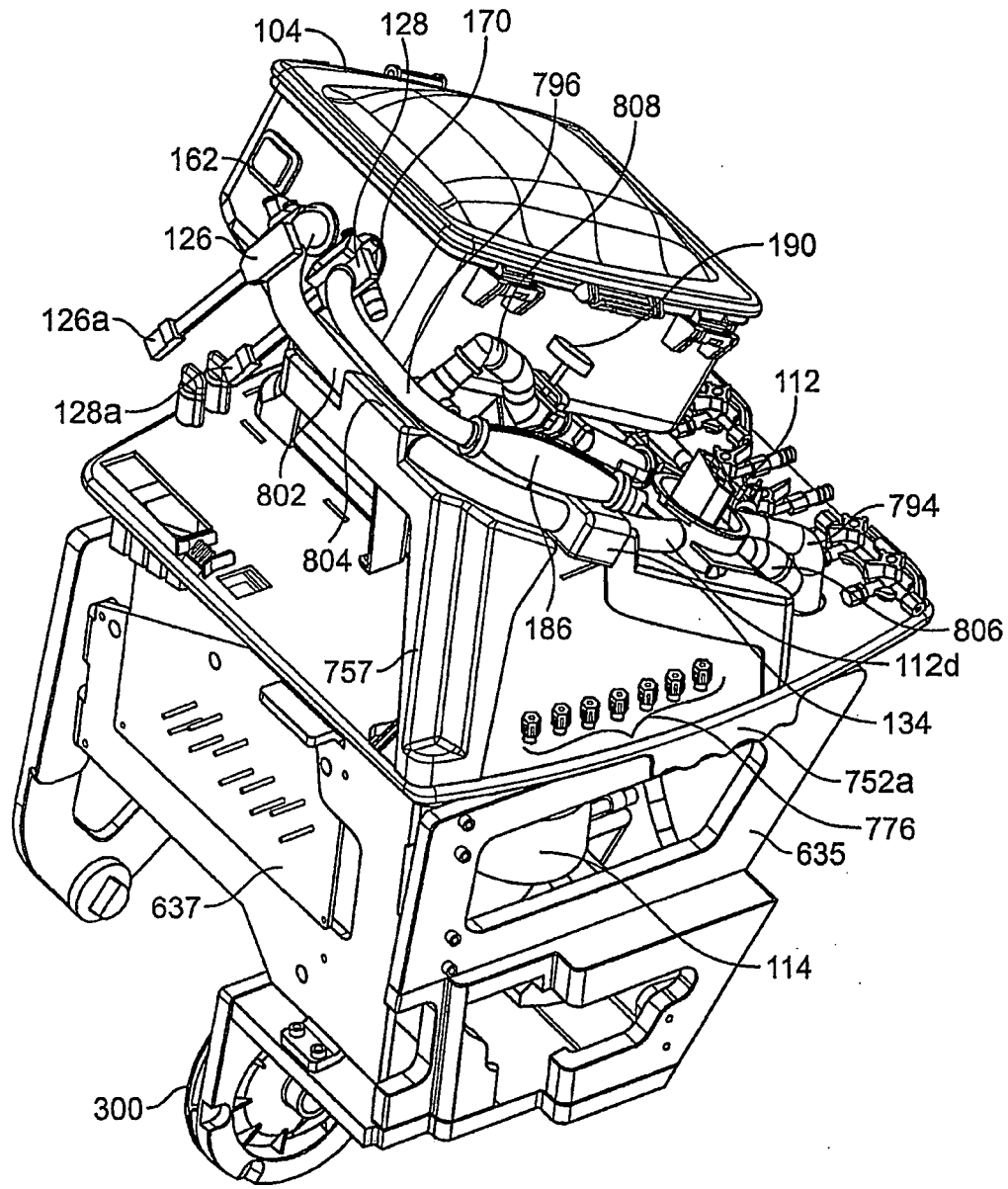
Figure 25A:
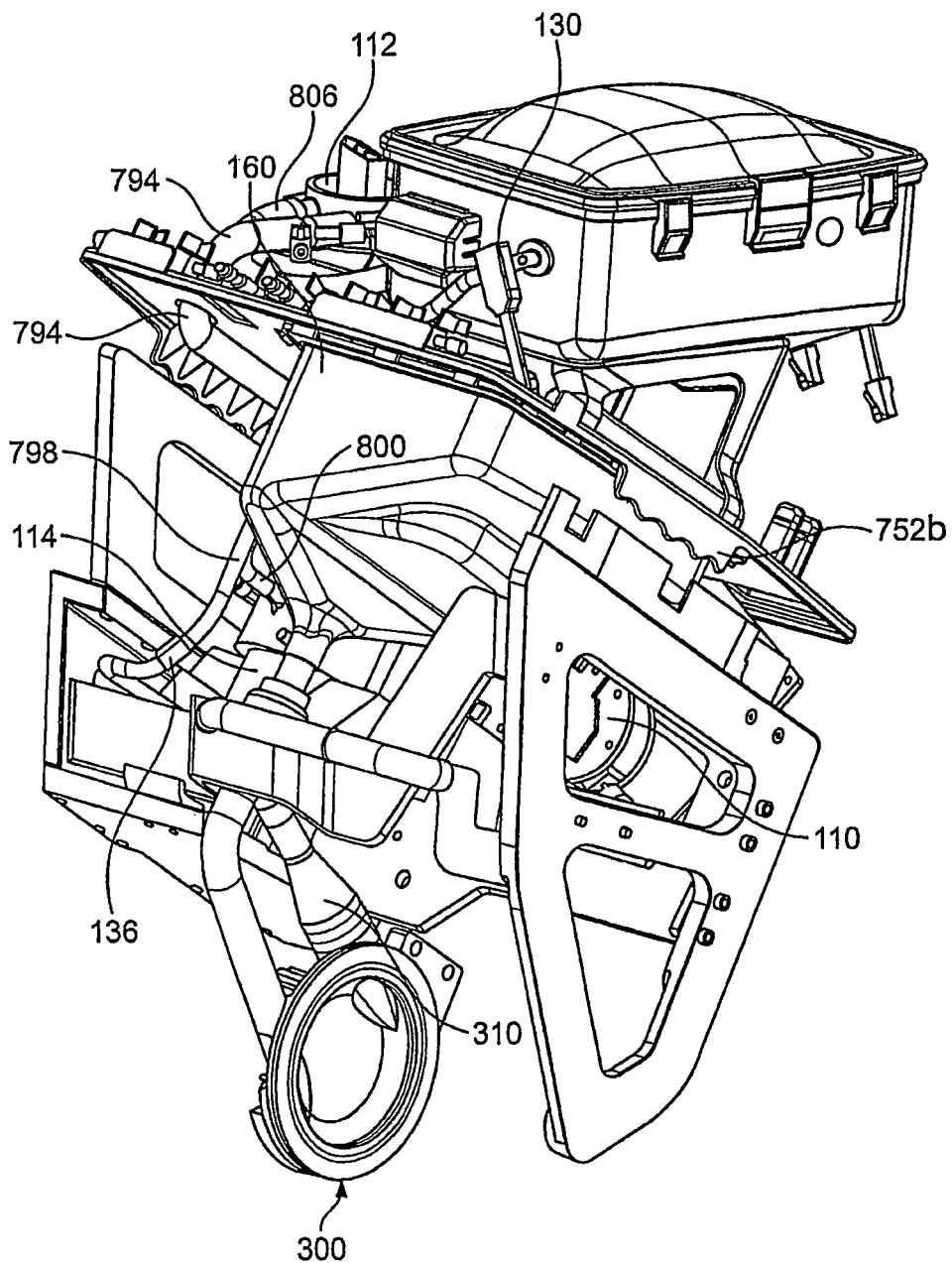
FIGS. 25A-25C show various bottom perspective views of the illustrative single use disposable module of FIGS. 24A-24D.
Figure 25B:
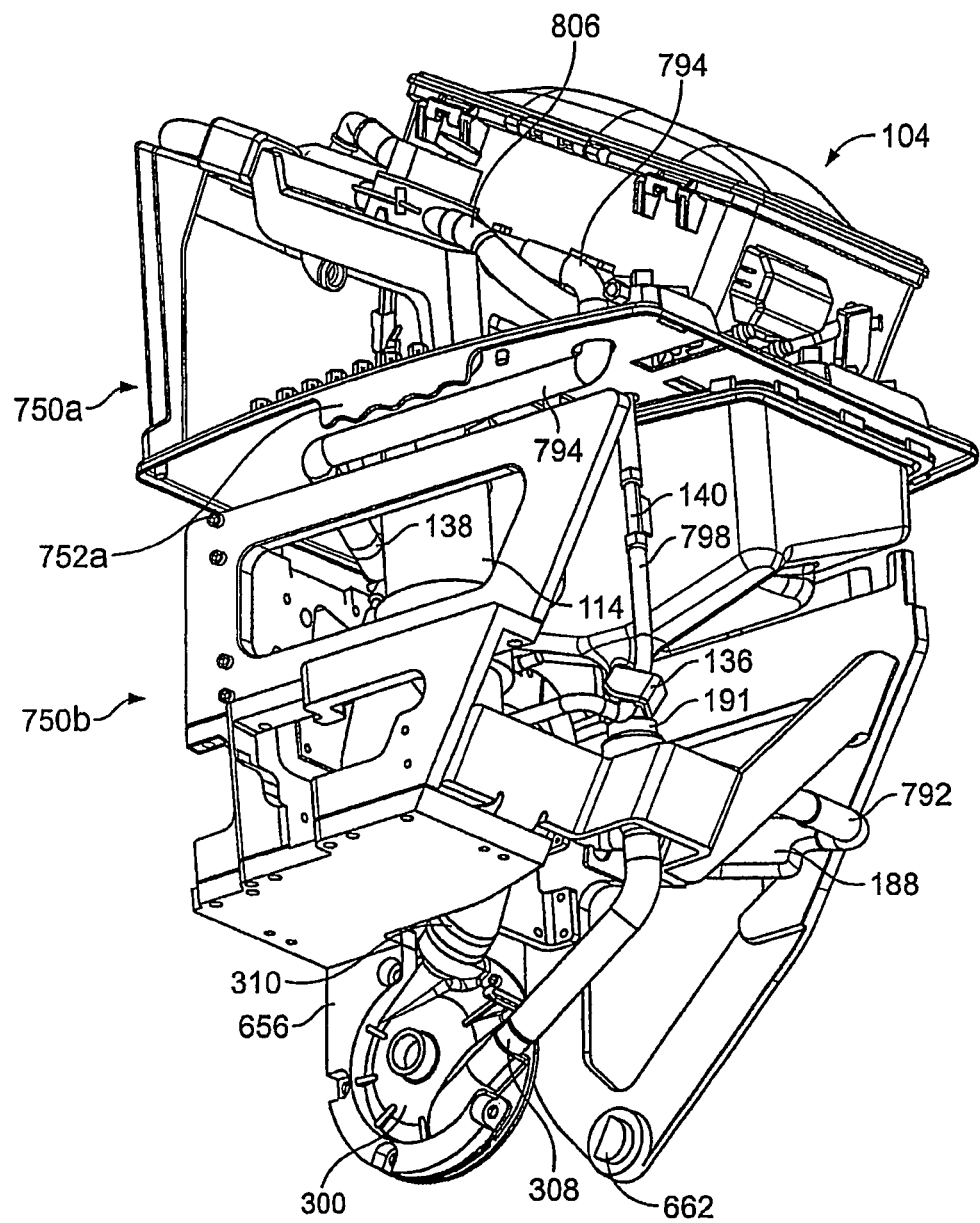
Figure 25C:
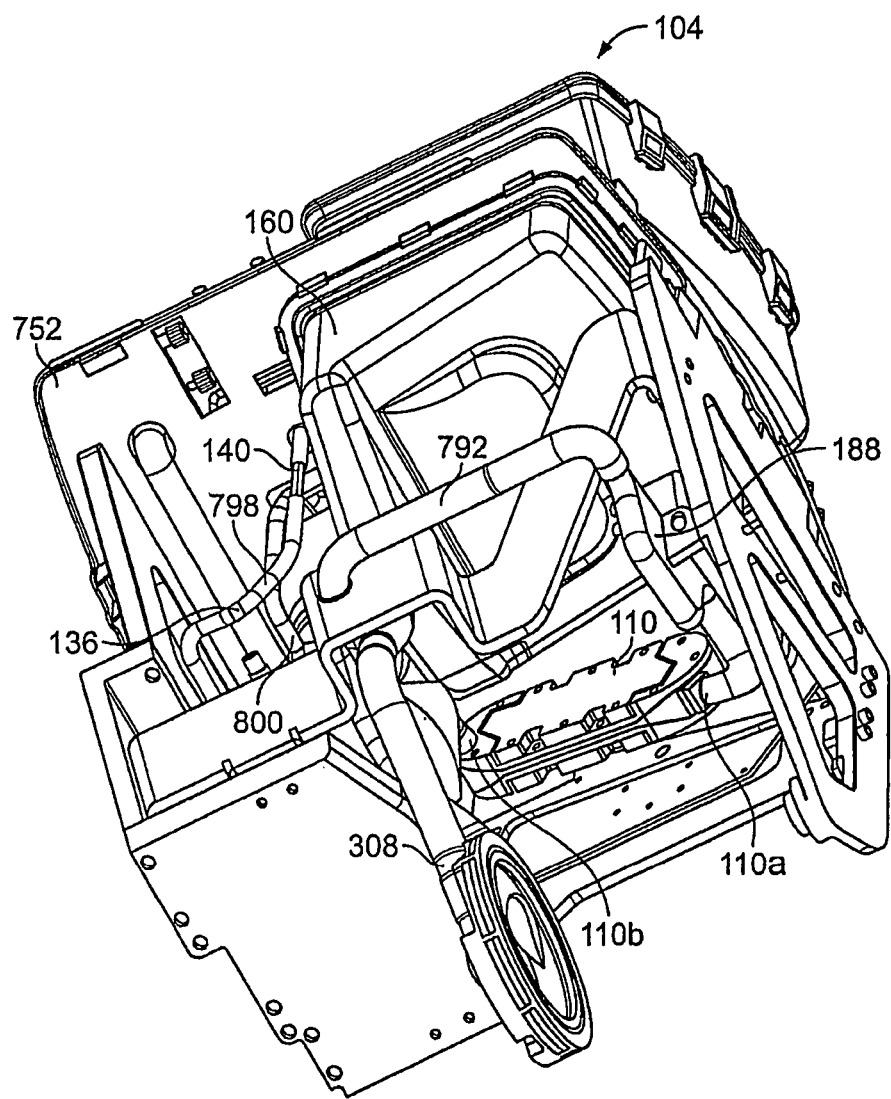

Referring first to FIG. 24A, the disposable module 634 includes a chassis 635 having upper 750a and lower 750b sections. The upper section 750a includes a platform 752 for supporting various components. The lower section 750b supports the platform 752 and includes structures for pivotably connecting with the multiple use module 650. More particularly, the lower chassis section 750b includes the C-shaped mount 656 for rigidly mounting the perfusion fluid pump interface assembly 300, and the projection 662 for sliding into and snap fitting with the slot 660 of FIG. 20B. The lower chassis section 750b also provides structures for mounting the oxygenator 114. As shown in FIGS. 25A and 25C, the lower section 750b further includes structures for mounting the heater assembly 110. Additionally, the reservoir 160 mounts to the underside of the platform 725 and extends into the lower chassis section 750b. Various sensors, such as the $O_2$ saturation and hematocrit sensor 140 (shown in FIG. 24A and described in detail below with reference to FIGS. 28A-28C), the flow rate sensor 136 (shown in FIG. 24A), the flow rate sensor 138 (shown in FIG. 25B), are located within and/or mount to the lower chassis section 750b. The flow pressure compliance chamber 188 (shown in FIG. 25B) is also located in the lower chassis section 750b. As shown in FIG. 24D, the lower chassis section 750b also mounts the front end circuit board 637. Conduits located in the lower chassis section 750b are described in further detail below with reference to the normal and retrograde flow paths through the single use module 634.

Referring to FIGS. 24A-25C, and as mentioned above, the upper chassis section 750a includes the platform 752. The platform 752 includes handles 752a and 752b formed therein to assist in installing and removing the single use module 634 from the multiple use module 650. Alternatively, such handles can be located on the platform 757 to allow for easier accessibility during installation of the single use module into the multiple use module. As shown most clearly in FIG. 24C, an angled platform 757 mounts onto the platform 752. The organ chamber assembly 104 mounts to the angled platform 757. According to the illustrative embodiment, with the single use module 634 installed within the multiple use module 650, the platform 757 is angled at about 10° to about 80° relative to horizontal, to provide an optimal angle of operation for the heart 102 when placed within the organ chamber assembly 104. In some illustrative embodiments, the platform 757 is angled at about 20° to about 60°, or about 30° to about 50° relative to horizontal. The flow mode selector valve 112, the flow rate sensor 134, and the perfusion fluid flow pressure compliance chambers 184 and 186 also mount onto the angled platform 757.

Figure 24E:
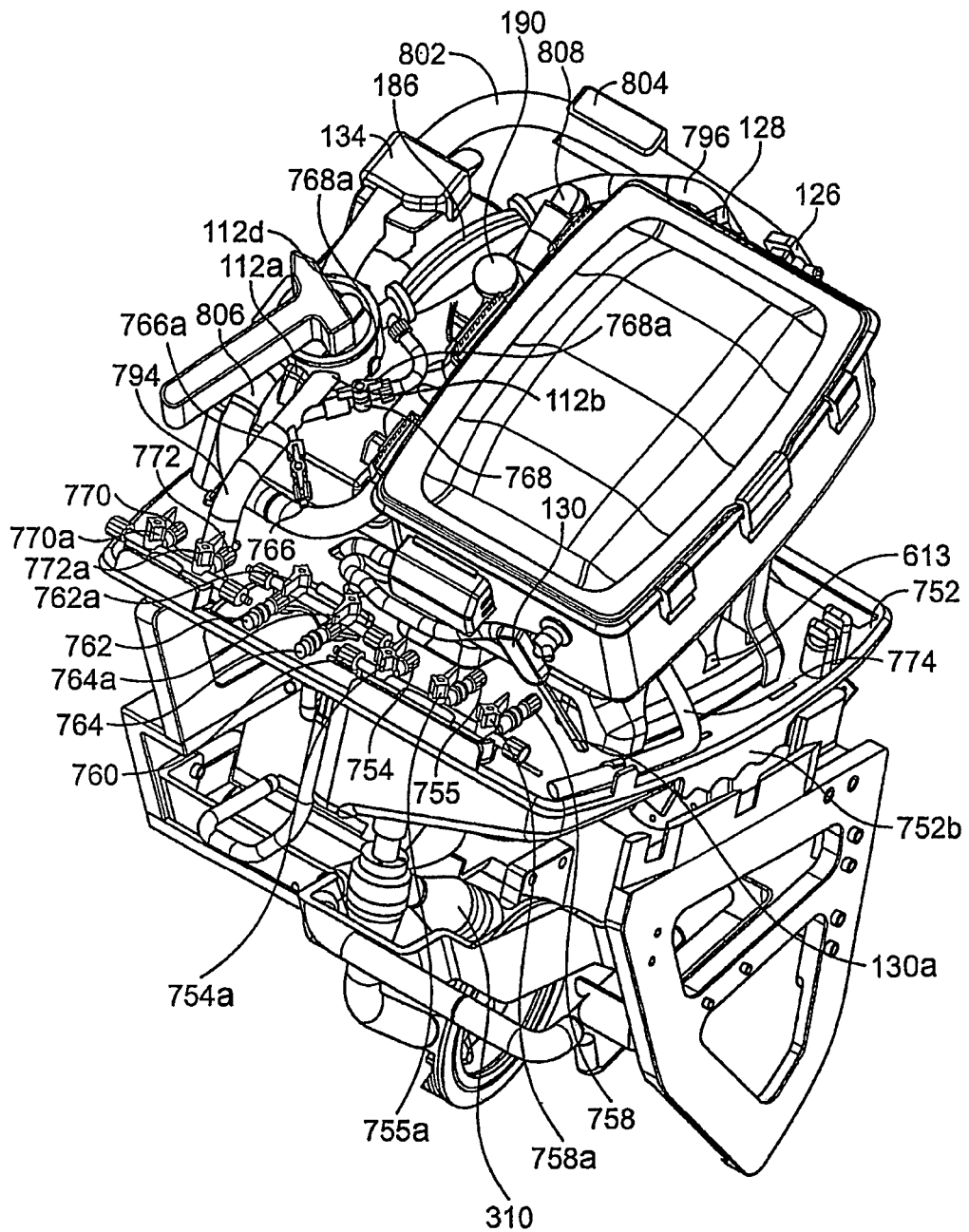

Referring to FIG. 24E, several fluid ports mount to the platform 752. For example, a fluid sampling port 754 enables an operator to sample the flow into and/or out of the aorta 158 via the cannulation interface 162 on the organ chamber assembly 104. A fluid sampling port 755 enables the operator to sample the flow into the left atrium 152 via the interface 170 on the organ chamber assembly 104. Additionally, a fluid port 758 enables the operator to sample the coronary flow out of the pulmonary artery 164 via the pulmonary artery interface 166 on the organ chamber 104. According to the illustrative embodiment, the operator turns the a respective valve 754a, 755a or 758a to obtain flow from the sampling ports 754, 755 and 758. Flow from the particular port selected is provided at a single common outlet 764. According to one feature, only flow from the left most port selected is provided at the outlet 764. By way of example, if the operator opens both ports 755 and 758, only flow from port 755 is provided at the outlet 764. In this way, system 100 reduces the likelihood of an operator mixing samples from multiple ports.

The single use module 634 also includes a general injection port 762, operable with the valve 762a, for enabling the operator to inject medication into the perfusion fluid 108, for example, via the reservoir 160. Both the sampling 764 and injection 762 ports mount to the platform 752. Also located on the upper chassis section 750a is an infusion port 766, operable with the valve 766a, for flowing the nutritional 116 and preservative 118 fluids into the perfusion fluid 108. The upper chassis section 750a also includes a tube 774 for loading the exsanguinated blood from the donor into the reservoir 160. As shown in FIG. 24D, the single use module 634 also includes non-vented caps 776 for replacing vented caps on selected fluid ports that are used while running a sterilization gas through the single use module 634 during sterilization. Preferably, such sterilization takes place prior to packaging the single use module 634 for sale.

The upper chassis section 750a also includes the flow clamp 190 for regulating back pressure applied to the left atrium 152 when the heart 102 is cannulated and operating in normal flow mode in the organ chamber assembly 104. The upper chassis section 750a further includes a trickle valve 768. The trickle valve 768 may be opened and closed with the handle 768a to regulate a small fluid flow to the left atrium 152 to moisten the left atrium 152 during retrograde flow mode. The upper chassis section 750a also includes ports 770 for infusion of additional solutions and 772 for purging the oxygenator 114, operable with respective valves 770a and 772a.

As shown most clearly in FIGS. 24A and 24D, the upper chassis section 750 further includes the flow pressure probes 126, 128 and 130. As described above with reference to FIG. 1, the probe 126 measures the pressure of the perfusion fluid 108 flowing into/out of the aorta 158. The probe 128 measures the pressure of the perfusion fluid 108 flowing into the left atrium 152 through the pulmonary vein 168. The probe 130 measures the pressure of the perfusion fluid 108 flowing out of the pulmonary artery 164. Each probe includes a respective connector 126a, 128a and 130a (shown shortened for clarity) for coupling a respective signal 129, 131, and 133 to the front end circuit board 637.

Referring particularly to the single use module 654 cross-sectional side view of FIG. 24C, the reservoir 160 includes several components. More specifically, the reservoir 160 includes four inlets: 782, 784, 786 and 788. The inlet 782 transfers perfusion fluid 108 from the drain 201 of the organ chamber 194 into the reservoir 160. The inlet 784 receives exsanguinated blood from the tube 774. The inlet 786 receives oxygenated perfusion fluid 108 from the oxygenator 114, and the inlet 788 receives perfusion fluid 108 out of the aorta 158 via the back pressure clamp 190. The reservoir 160 also has an outlet 790, which provides the perfusion fluid to the one way inlet valve 191. The reservoir 160 further includes a defoamer 778 and a filter 780. The defoamer 778 removes bubbles out of the perfusion fluid 108 as it enters the reservoir 160. According to the illustrative embodiment, the defoamer is made of porous polyurethane foam with an anti-foam coating. The filter 780 is a polyester felt, which filters debris, blood particles, emboli, and air bubbles out of the perfusion fluid as it enters the reservoir 160.

As mentioned above in the summary, the $O_2$ saturation and hematocrit sensor 140 employed in the single use module 634 includes important advantages over prior art approaches. FIGS. 28A-28C depict an illustrative embodiment of the $O_2$ saturation and hematocrit sensor 140 of the invention. As shown in FIG. 28A, the sensor 140 includes an in-line cuvette shaped section of tube 812 connected to the conduit 798, which has at least one optically clear window through which an infrared sensor can provide infrared light. Exemplary sensors used in the in-line cuvette-shaped tube 812 are those made by Datamed, BL0P4. As shown in the cross-sectional view of FIG. 28B, the cuvette 812 is a one-piece molded part having connectors 801a and 801b. The connectors 801a and 801b are configured to adjoin to connecting receptacles 803a and 803b, respectively, of conduit ends 798a and 798b. This interconnection between cuvette 812 and conduit ends 798a and 798b is configured so as to provide a substantially constant cross-sectional flow area inside conduit 798 and cuvette 812. The configuration thereby reduces, and in some embodiments substantially removes, discontinuities at the interfaces 814a and 814b between the cuvette 812 and the conduit 798. Reduction/removal of the discontinuities enables the blood based perfusion fluid 108 to flow through the cuvette with reduced lysing of red blood cells and reduced turbulence, which enables a more accurate reading of perfusion fluid oxygen levels. This also reduces damage to the perfusion fluid 108 by the system 100, which ultimately reduces damage done to the heart 102 while being perfused by the system 100.

According to the illustrative embodiment, the cuvette 812 is formed from a light transmissive material, such as any suitable light transmissive glass or polymer. As shown in FIG. 28A, the sensor 140 also includes an optical transceiver 816 for directing light waves at perfusion fluid 108 passing through the cuvette 812 and for measuring light transmission and/or light reflectance to determine the amount of oxygen in the perfusion fluid 108. As illustrated in FIG. 28C, in some embodiments a light transmitter is located on one side of the cuvette 812 and a detector for measuring light transmission through the perfusion fluid 108 is located on an opposite side of the cuvette 812. FIG. 28C depicts a top cross-sectional view of the cuvette 812 and the transceiver 816. The transceiver 816 fits around cuvette 812 such that transceiver interior flat surfaces 811 and 813 mate against cuvette flat surfaces 821 and 823, respectively, while the interior convex surface 815 of transceiver 816 mates with the cuvette 812 convex surface 819. In operation, when uv light is transmitted from the transceiver 816, it travels from flat surface 811 through the fluid 108 inside cuvette 812, and is received by flat surface 813. The flat surface 813 may be configured with a detector for measuring the light transmission through the fluid 108.

Figure 26A:
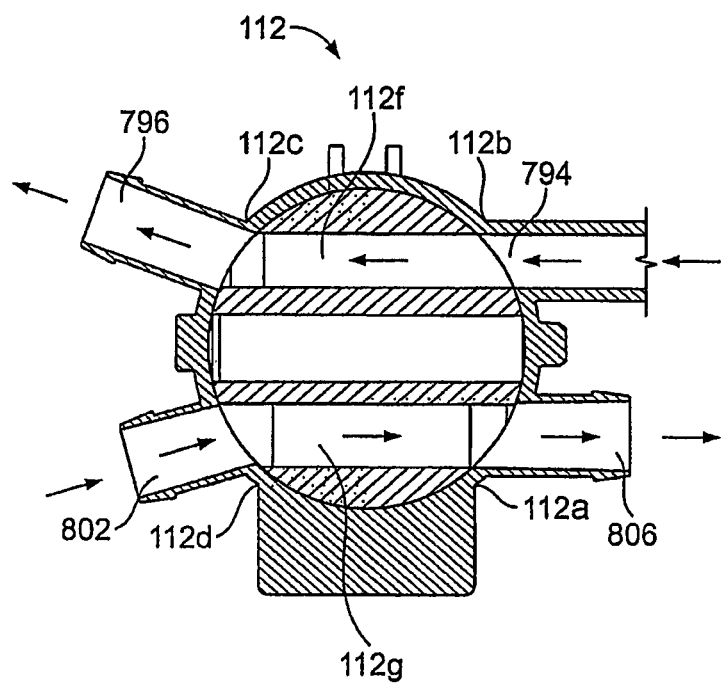
FIGS. 26A and 26B depict the operation of a flow mode selector valve according to an illustrative embodiment of the invention.
Figure 26B:
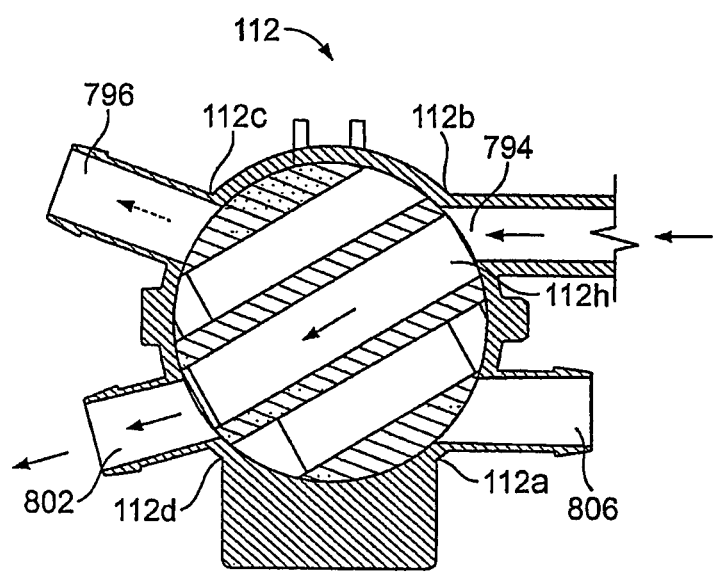

The fluid flow path through the single use module 634 in both normal and retrograde flow modes will now be described with reference to FIGS. 24A-24D and FIG. 25A. As described above with reference to FIGS. 1-4, the system 100 can maintain the heart 102 in two modes of operation; a normal flow mode, shown in FIG. 3, and a retrograde flow mode shown in FIG. 4. As mentioned above with regard to FIG. 1, to change between normal and retrograde flow modes, the system 100 provides the flow mode selector valve 112, shown in detail in FIGS. 26A and 26B. To operate in normal flow mode, the operator sets the flow mode selector valve handle 112e to the position indicated in FIG. 24A. This has the effect of aligning the flow paths through the selector valve 112 as shown in FIG. 26A. Specifically, in normal flow mode, fluid can flow into port 112b, through the flow channel 112f and out the port 112c. Additionally, fluid can flow into port 112d, through the flow channel 112g and out the port 112a. To operate in retrograde flow mode, the operator sets the flow mode selector valve handle 112e to the position indicated in FIG. 24B. This has the effect of aligning the flow paths through the selector valve 112 as shown in FIG. 26B. Specifically, in retrograde flow mode, fluid can flow into port 112b, through the flow channel 112h and out the port 112d.

Referring to FIG. 24A, in normal flow mode, the reservoir 160 provides the perfusion fluid 108 to the one way inlet valve 191 of the perfusion pump interface assembly 300. Referring to FIG. 25A, the perfusion pump 106 pumps the perfusion fluid 108 out the outlet valve 310. Referring to FIG. 25C, the perfusion fluid 108 then flows through the conduit 792 and the compliance chamber 188 and into the inlet 110a of the heater assembly 110. The heater assembly 110 heats the perfusion fluid 108 and then flows it out the heater outlet 110b. Referring to FIG. 24A, the heated perfusion fluid 108 flows from the heater outlet 110b in the lower chassis section 750b through the chassis plate 752 and into the port 112b of the mode select valve 112 via the conduit 794. Referring also to FIG. 24D, the perfusion fluid 108 flows out the mode valve port 112c, through the compliance chamber 186, the conduit 796, and the pressure sensor 128 into the pulmonary vein cannulation interface 170 on the organ chamber assembly 104.

Referring to FIG. 24A, in normal flow mode, the heart 102 pumps the perfusion fluid 108 out the pulmonary artery 164 through the pulmonary artery interface 166 and the pressure sensor 130. The conduit 796 then flows the perfusion fluid 108 from the pulmonary artery interface 166 through the plate 752 and through the $O_2$ saturation and hematocrit sensor 140. Referring also to FIGS. 25A and 25C, the conduit 798 then flows the perfusion fluid 108 from the sensor 140 through the flow-rate sensor 136 into the oxygenator 114. The conduit 800 flows the perfusion fluid 108 from the oxygenator 114 back into the reservoir 160 by way of the reservoir inlet 786.

Referring to FIGS. 24A, 24D and 24E, in normal flow mode, the heart 102 also pumps the perfusion fluid 108 out of the aorta 158 through the aorta interface 162 and the pressure sensor 126. The conduit 802 flows the perfusion fluid 108 from the pressure sensor 126 through the flow rate sensor 134 and back into the port 112d on the flow mode selector valve 112. A clamp 804 holds the conduit 802 in place. A conduit 806 flows the perfusion fluid 108 out the port 112a from the flow mode selector valve 112 through the compliance chamber 184 and the back pressure adjustment clamp 190. As mentioned above, the clamp 190 may be adjusted to restrict flow through the conduit 806 to adjust the back pressure seen by the aorta 158 during normal flow mode to more realistically simulate normal physiologic conditions. The compliance chamber 184, which can expand and contract as perfusion fluid 108 is pumped into and out of it, interoperates with the clamp 190 to dampen flow pressure spikes to further improve simulation of near-normal physiologic conditions. The after-load clamp 190 is configured to closely emulate systemic vascular resistance of the human body which affects aortic pressure, left atrial pressure, and coronary flow. A conduit 808 returns the perfusion fluid 108 into the reservoir 160 by way of the reservoir inlet 788.

In retrograde flow mode, the flow mode selector valve 112 is positioned as shown in FIG. 24B. Referring to FIG. 24B, the reservoir 160 provides the perfusion fluid 108 to the inlet valve 191. As shown in FIG. 25A, the perfusion pump 106 pumps the perfusion fluid 108 out the outlet valve 310. As shown in FIG. 25C, the perfusion fluid 108 then flows through the conduit 792 and the compliance chamber 188 and into the inlet 110a of the heater assembly 110. The heater assembly 110 heats the perfusion fluid 108 and then flows it out the heater outlet 110b. Referring to FIG. 24B, the heated perfusion fluid 108 flows from the heater outlet 110b in the lower chassis section 750b through the chassis plate 752 and into the input 112b of the mode select valve 112 via the conduit 794. Referring also to FIG. 24D, the perfusion fluid 108 flows out the mode valve outlet 112d, into the conduit 802, through the flow rate sensor 134, the pressure sensor 126 and into the aorta 158 via the aorta interface 162. The perfusion fluid 108 then flows through the coronary sinus 155 and the rest of the coronary vasculature.

Referring to FIG. 24B, in retrograde flow mode, the heart 102 pumps the perfusion fluid 108 out of the pulmonary artery 164 and through the pulmonary artery interface 166 and the pressure sensor 130. The conduit 796 then flows the perfusion fluid from the pulmonary artery interface 166 through the plate 752 and into the $O_2$ saturation and hematocrit sensor 140. Referring also to FIGS. 25A and 25C, the conduit 798 then flows the perfusion fluid 108 from the sensor 140 through the flow rate sensor 136 into the oxygenator 114. The conduit 800 flows the perfusion fluid 108 from the oxygenator 114 back into the reservoir 160 by way of the reservoir inlet 786. In retrograde flow mode, substantially no perfusion fluid is pumped into or out of the left atrium 152 via the pulmonary vein 168 and the pulmonary vein interface 170, with the exception of a small amount of perfusion fluid diverted by the trickle valve 768 from the conduit 794 around the flow mode selector valve 112 into the compliance chamber 186. As mentioned above, the trickle flow provides sufficient perfusion fluid 108 to keep the left atrium 152 moistened during retrograde flow.

As described above, the illustrative embodiment of the system 100 has one or more sensors or probes for measuring fluid flow and pressure. The probes and/or sensors may be obtained from standard commercial sources. The flow rate sensors 134, 136 and 138 are conventional, ultrasonic flow sensors, such as those available from Transonic Systems Inc., Ithaca, N.Y. The fluid pressure probes 126, 128 and 130 may be conventional, strain gauge pressure sensors available from MSI or G.E. Thermometrics. Alternatively, a pre-calibrated pressure transducer chip can be embedded into organ chamber connectors and wired to a data collection site such as the front end board 637.

Figure 29A:
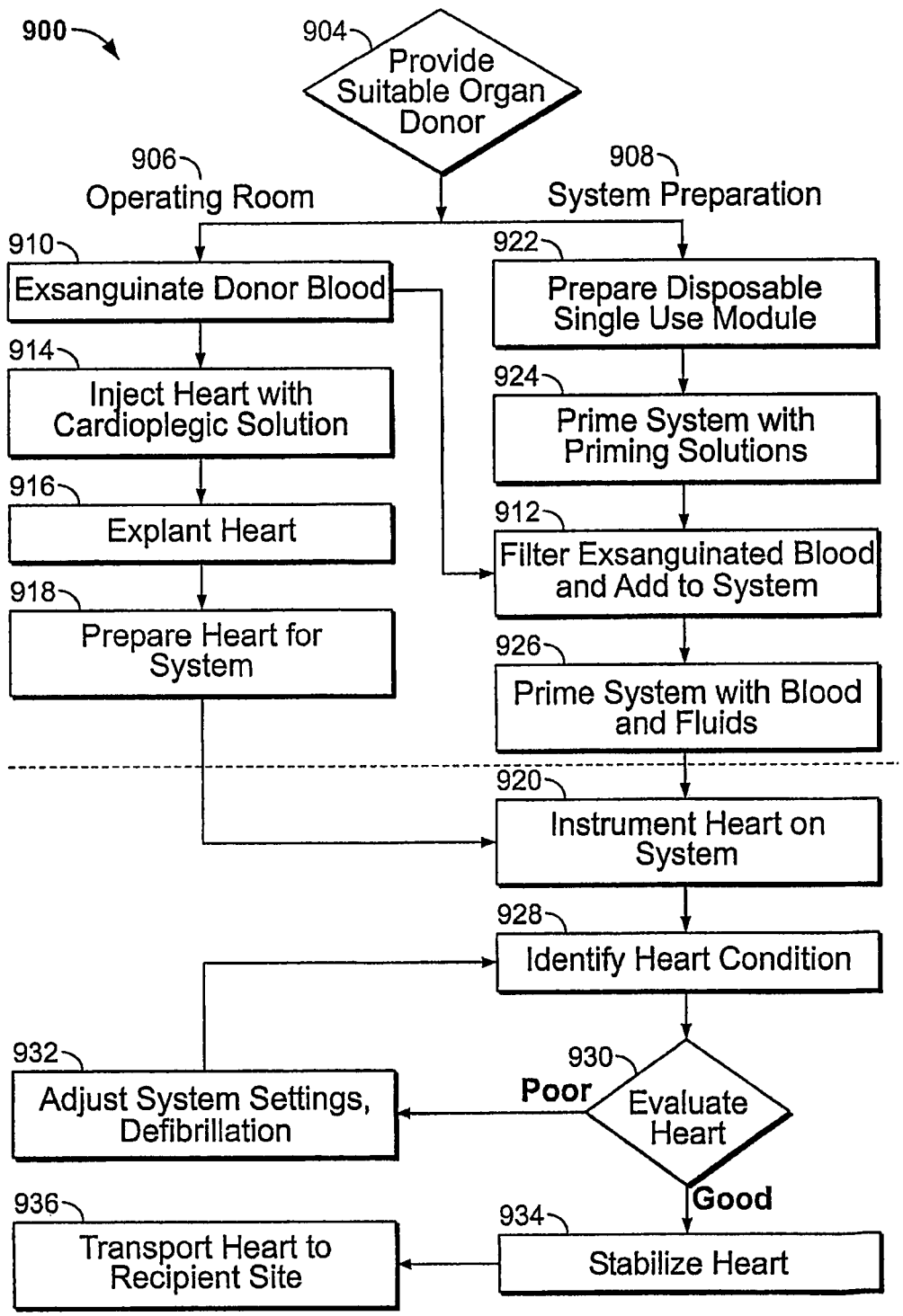
FIG. 29A is a flow diagram depicting a donor-side process for removing an organ from a donor and placing it into the organ care system of FIG. 1 according to an illustrative embodiment of the invention.
Figure 29B:
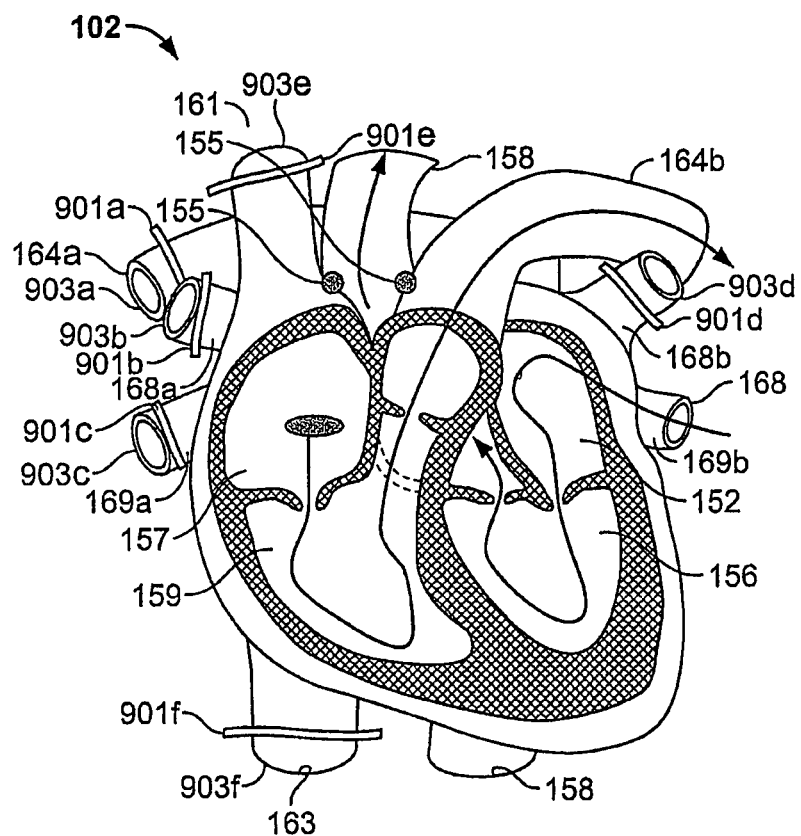
FIG. 29B is a diagram depicting a harvested heart with suture and cannulation sites according to an illustrative embodiment of the invention.
Figure 30:
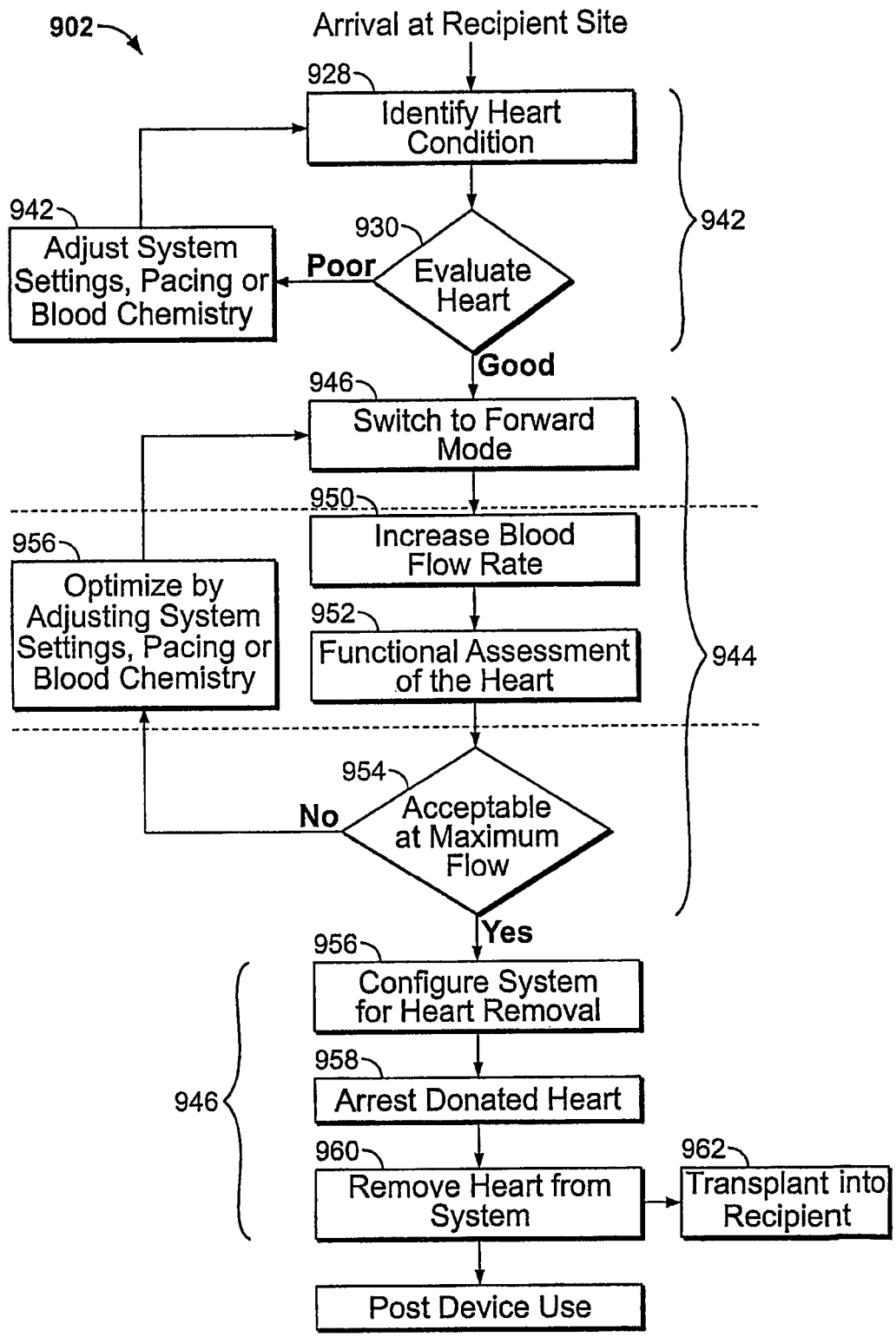
FIG. 30 is a flow diagram depicting a recipient-side process for removing an organ from the organ care system of FIG. 1 and transplanting it into a recipient according to an illustrative embodiment of the invention.

Having described the electrical and mechanical components and functionality of illustrative embodiments of the system 100 and certain modes of operation thereof, the system 100 will next be described with reference to the illustrative organ harvest and transplant procedures of FIGS. 29A and 29B. More particularly, FIG. 29A is a flow diagram 900 depicting exemplary methodologies for harvesting the donor heart 102 and cannulating it into the system 100 at a donor location. FIG. 29B depicts particular points of care for handling the heart 102 in preparation for cannulation, and FIG. 30 is a flow diagram 902 of exemplary methodologies for removing the donor organ 102 from the system 100 and transplanting it into a patient at a recipient site.

As shown in FIG. 29A, the process of obtaining and preparing the heart 102 for cannulation and transport begins by providing a suitable organ donor 904. The organ donor is brought to a donor location, whereupon the process of receiving and preparing the donor heart 102 for cannulation and transport proceeds down two intersecting pathways 906 and 908. The pathway 906 principally involves preparing the donor heart 102 for transplant, while the pathway 908 principally involves preparing the system 100 to receive the donor heart 102 and then transporting the heart 102 via system 100 to the recipient site.

With particular reference to FIG. 29A, the first pathway 906 includes exsanguinating the donor 910, arresting the donor heart 914, explanting the heart 916, and preparing the heart 102 for cannulation 918 into the system 100. In particular, in the exsanguination step 910, the donor's blood is removed and set aside so it can be used to perfuse the heart 102 during preservation on the system 100. This step is performed by inserting a catheter into either the arterial or venous vasculature of the donor to allow the donor's blood to flow out of the donor and be collected into a blood collection bag. The donor's blood is allowed to flow out until the necessary amount of blood is collected, typically 1.0-2.5 liters, whereupon the catheter is removed. The blood extracted through exsanguination is then filtered and added to a fluid reservoir 160 of the system 100 in preparation for use with the system 100. Alternatively, the blood can be exsanguinated from the donor and filtered for leukocytes and platelets in a single step that uses an apparatus having a filter integrated with the cannula and blood collection bag. An example of such a filter is a Pall BC2B filter. After the donor's blood is exsanguinated, the donor heart 102 is injected in step 914 with a cardioplegic solution to temporarily halt beating in preparation for harvesting the heart 102.

After the heart 102 is arrested, the heart 102 is explanted 916 from the donor and prepared 918 for loading onto the system 100. In general, the steps of explanting the heart 916 and preparing for loading 918 involve severing the connections between the vasculature of the heart 102 and the interior chest cavity of the donor, suturing various of the severed connections, then lifting the heart 102 from the chest cavity.

More particularly, as shown in FIG. 29B, the right and left pulmonary arteries 164a and 164b are severed, and the right pulmonary artery 164a is tied-off by a surgical thread 901a or other suitable mechanism. The tying prevents fluid from flowing through the severed end 903a of the left pulmonary artery 164a. As described above with reference to FIGS. 24A-24B, the left pulmonary artery 164b remains unsutured to allow it to be cannulated to the organ chamber assembly 104, thereby allowing perfusion fluid 108 to flow through the left pulmonary artery 164b, through the pulmonary artery cannulation interface 170, and back to the reservoir 160. The left pulmonary veins 168b and 169b and the right pulmonary veins 168a and 169a are also severed, and all except a single pulmonary vein 169b are tied off with surgical thread 901b, 901c, and 901d, respectively. This prevents fluid from flowing through the severed ends 903b and 903c of the right pulmonary veins 168a and 169a, or through the severed end 903d of the left pulmonary vein 168b, but allows the untied pulmonary vein to be cannulated to the organ chamber assembly 104 through the pulmonary vein interface 170. As described above with reference to FIGS. 24A-24B, this arrangement allows the perfusion fluid 108 to flow through the right pulmonary artery 164b, through the pulmonary artery interface 166, and back to the oxygenator 114. Alternatively, blood can be expelled from the right ventricle via cannulating the pulmonary arterial trunk. The pulmonary arterial trunk is not shown but includes the segment of pulmonary artery 164 between the branches 164a and 164b of the pulmonary artery 164 and the right ventricle 159. The superior vena cava 161 is also severed and, once the heart is connected to the system 100 and begins beating, is tied with thread 901e to prevent fluid from flowing through its end 903e. The inferior vena cava 163 is similarly severed and tied with thread 901f or oversewn to prevent fluid from flowing through its end 903f.

The aorta 158 is also severed (in the illustrated embodiment at a point downstream from the coronary sinus 155) but is not tied off, allowing it to be cannulated to the organ chamber assembly 104. In one embodiment, the aorta 158 is cannulated to an aortic connector, which can be easily attached to the aorta interface 170.

With continued reference to the flow chart of FIG. 29A, after the heart vasculature is severed and appropriately tied, the heart 102 is then loaded onto the system 100 by inserting it into the organ chamber assembly 104 and cannulating the aorta 158, left pulmonary artery 164b, and a pulmonary vein 169b to the appropriate points in the organ chamber assembly 104.

Often, hearts obtained from donors who have also donated their lungs are missing part or all of the left atrium 152. In this situation, the heart 102 can still be instrumented and perfused in the retrograde mode by cannulating the aorta 158 and either the right pulmonary artery 164a or pulmonary artery trunk (not shown, but described above), and allowing any remaining left atrium 152 portion to remain open during the preservation period.

With continued reference to FIG. 29A, during the preparation of the heart via path 906, the system 100 is prepared through the steps of path 908 so it is primed and waiting to receive the heart 102 for cannulation and transport as soon as the heart 102 is prepared. By quickly transferring the heart 102 from the donor to the system 100, and subsequently perfusing the heart 102 with the perfusion fluid 108, a medical operator can minimize the amount of time the heart 102 is deprived of oxygen and other nutrients, and thus reduce ischemia and other ill effects that arise during current organ care techniques. In certain embodiments, the amount of time between infusing the heart 102 with cardioplegic solution and beginning flow of the perfusion fluid 108 through the heart 102 via the system 100 is less than about 15 minutes. In other illustrative embodiments, the between-time is less than about 1 hour, less than about 1 hour, less than about 2 hours, or even less than about 3 hours. Similarly, the time between transplanting the heart into an organ care system 100 and bringing the heart 102 to a near physiological temperature (e.g., between about 34° C. and about 37° C.) occurs within a brief period of time so as to reduce ischemia within the heart tissues. In some illustrative embodiments, the period of time is less than about 5 minutes, while in other applications it may be less than about 1 hour, less than about 1 hour, less than about 2 hours, or even less than about 3 hours. According to some illustrative embodiments, the heart can be transferred directly from the donor to the system 100, without the use of cardioplegia, and in such applications the time to beginning the flow of warm perfusion fluid 108 and/or time to the heart reaching near physiologic temperature is similarly less than about 5 minutes, less than about ½ hour, less than about 1 hour, less than about 2 hours, or even less than about 3 hours. In one implementation, the donor heart is not arrested prior to removal from the donor, and is instrumented onto the system 100 while the heart 102 is still beating.

As shown in FIG. 29A, the system 100 is prepared in pathway 908 through a series of steps, which include preparing the single use module 634 (step 922), priming the system 100 with priming solution (step 924), filtering the blood from the donor and adding it to the system 100 reservoir 160 (step 912), and connecting the heart 102 into the system 100 (step 904). In particular, the step 922 of preparing the single use module 634 includes assembling the disposable single use module 634. Suitable assemblies are shown, for example, in FIGS. 24A-24D, FIGS. 25A-25C, and FIG. 26. After the module 634 is assembled, or provided in the appropriate assembly, it is then inserted into multiple use module 650 through the process described above with reference to FIGS. 21A-21C.

In step 924, the loaded system 100 is primed with priming solution, as described in more particular detail below with reference to Table 1. According to one feature, to aid in priming, the system 100 provides an organ bypass conduit 810 shown installed into the organ chamber assembly 104 in FIG. 27A. As depicted, the bypass conduit includes three segments 810a-810c. Segment 810a attaches to the pulmonary artery cannulation interface 170. The segment 810b attaches to the aorta cannulation interface 810b, and the segment 810c attaches to the pulmonary vein cannulation interface 166. Using the bypass conduit 810 so attached/cannulated into the organ chamber assembly 104, an operator can cause the system 100 to circulate the perfusion fluid 108 through all of the paths used during actual operation. This enables the system 100 to be thoroughly tested and primed prior to cannulating the heart 102 into place.

In the next step 912, blood from the donor is filtered and added to the reservoir 160. The filtering process helps reduce the inflammatory process through the complete or partial removal of leukocytes and platelets. Additionally, the donor blood is mixed with one or more nutritional 116 and/or preservative 118 solutions to form the perfusion fluid 108. In step 926, the system 100 is primed with the perfusion fluid 108 by pumping it through the system 100 in the retrograde flow mode, as described above in reference to FIG. 24B, and with the bypass conduit 810 in place. As the perfusion fluid 108 circulates through the system 100 in priming step 926, it is warmed to the desired temperature as it passes through heater assembly 110. The desired temperature range and heating applications are described above in reference to FIGS. 6A through 6E, and in respect to FIG. 13. In step 920, after the system 100 is primed with the perfusion fluid 108, the bypass conduit 810 is removed, and the heart 102 is instrumented, as described above and shown in FIG. 27B, onto the system 100.

After the heart 102 is instrumented onto the system 100, the pump 104 is activated and the flow mode valve 112 is positioned in retrograde flow mode (described above with reference to FIGS. 1 and 4) to pump the perfusion fluid 108 in retrograde flow mode through the aorta into the vasculature of the heart 102. The pumping of the warm, oxygen and nutrient enriched perfusion fluid 108 through the heart 102 allows the heart 102 to function ex vivo in a near normal physiologic state. In particular, the warm perfusion fluid 108 warms the heart 102 as it perfuses through it, which may cause the heart 102 to resume beating in its natural fashion. In some instances, it is desirable to assist the heart 102 in resuming its beating, which may be done by providing hand massage or a defibrillation signal 143 (shown in FIG. 22E) to the heart 102. This may be done as described above with reference to the organ chamber assembly of FIGS. 5A-5F and operator interface 146 of FIGS. 17A-17J.

Figure 27A:
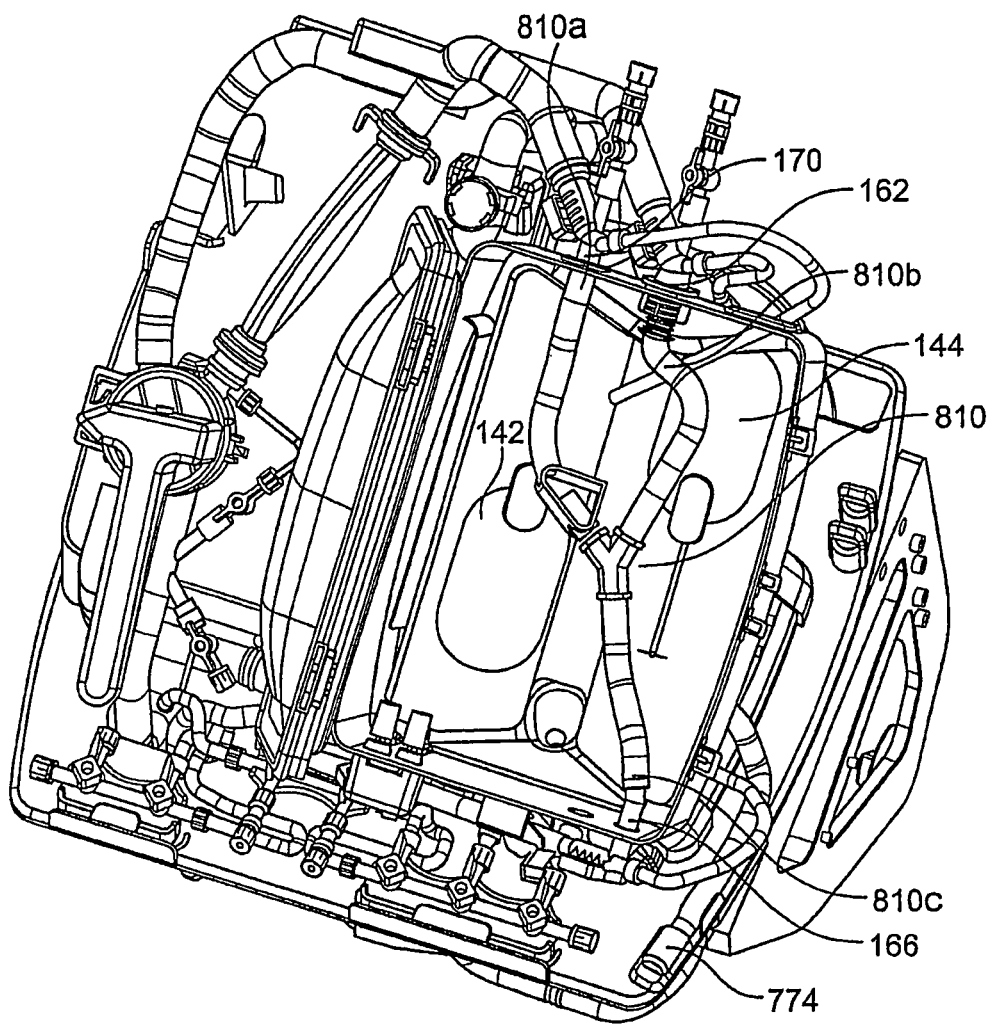
FIGS. 27A and 27B show various top views of the single use disposable module of FIGS. 19A-19C with the top off of illustrative organ chamber.
Figure 27B:
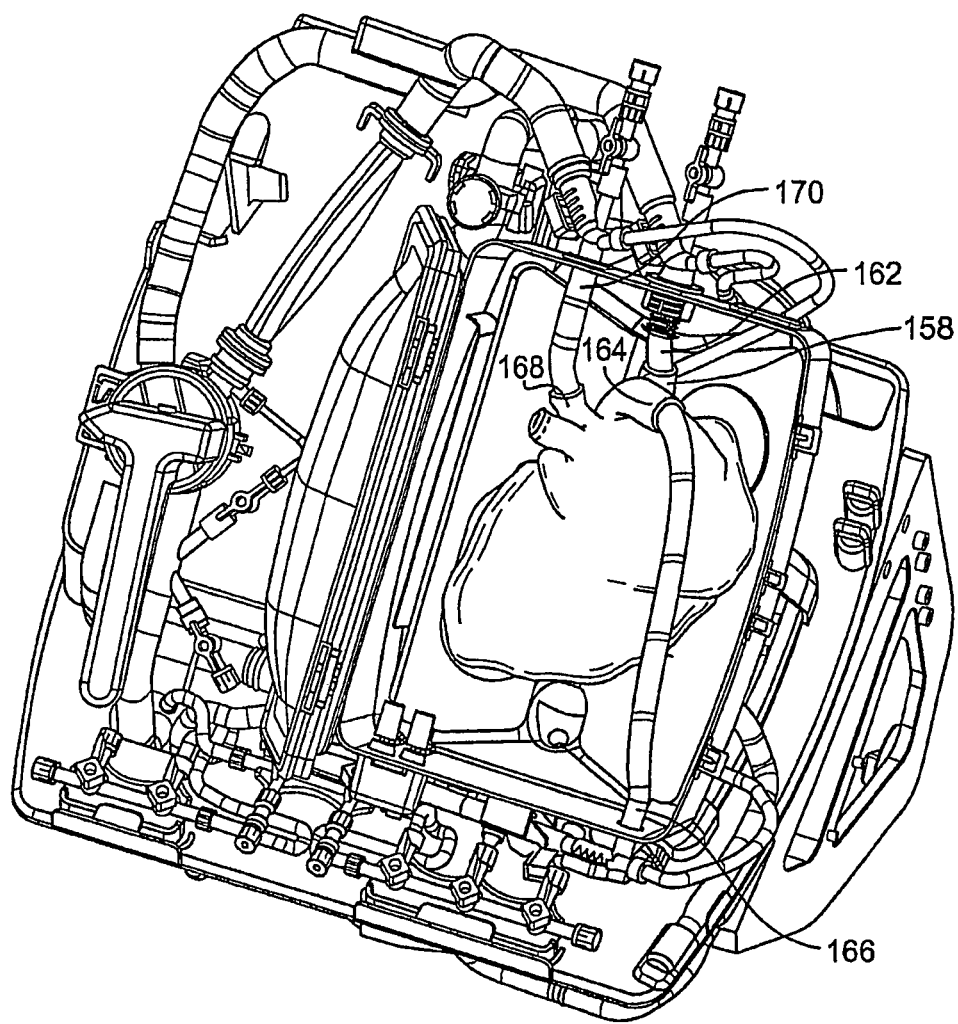

After the heart is instrumented onto the system 100 at step 920, subsequent steps 928 and 930 allow the operator to test the heart 102 and the system 100, and to evaluate their respective conditions. Illustratively, step 928 involves evaluating ECG signals 379 and 381 from the sensors 142 and 144 (positioned as shown in FIG. 27A), respectively, as well as hematocrit 145 and oxygen saturation 141 levels of the perfusion fluid 108 from the sensor 140. As further described in reference to FIG. 12 and FIGS. 17A-17I, the operator can also monitor the fluid flows, pressures, and temperatures of the system 100 while the heart 102 is cannulated. As described above with reference to FIGS. 5E and 5F, the testing step 928 may also include having the operator touch/examine the heart 102 by lifting an outer lid 196 of the organ chamber 104 and touching/examining the heart 102 indirectly through the flexible membrane 198b. During the evaluation step 930, based on the data and other information obtained during testing 928, the operator determines whether and how to adjust the system 100 properties (e.g., fluid flows, pressures, and temperatures), and whether to provide additional defibrillation, or other needed modes of treatment to the heart 102. The operator makes any such adjustments in step 932, then repeats steps 928 and 930 to re-test and re-evaluate the heart 102 and the system 100. In certain embodiments, the operator may also opt to perform surgical, therapeutic or other procedures on the heart 102 during the adjustment step 932. For example, the operator can conduct an evaluation of the physiological fitness of the heart, such as for example, performing an ultrasound or other imaging test, performing an echocardiogram or diagnostic test on the heart, measuring arterial blood gas levels and other evaluative tests.

In another application, during or after step 932, the system 100 allows a medical operator to evaluate the organ for compatibility with an intended recipient after explantation but prior to implantation into the donor. For example, the operator can perform a Human Leukocyte Antigen (HLA) matching test on the organ while the organ is cannulated to the system 100. Such tests may require 12 hours or longer and are performed to ensure compatibility of the organ with the intended recipient. The preservation of an organ using the system 100 described above may allow for preservation times in excess of the time needed to complete an HLA match, potentially resulting in improved post-transplant outcomes. In the HLA matching test example, the HLA test can be performed on the heart while a preservation solution is pumping into the heart.

According to a further illustrative embodiment, after the heart is functioning as determined by the step 932, the operator can perform surgery on the heart or provide therapeutic or other treatment, such as immunosuppressive treatments, chemotherapy, genetic testing and therapies, or irradiation therapy. Because the system 100 allows the heart 102 to be perfused under near physiological temperature, fluid flow rate, and oxygen saturation levels, the heart 102 can be maintained after the adjustment step 932 for a long period of time (e.g., for a period of at least 3 days or more, greater than at least 1 week, at least 3 weeks, or a month or more) to allow for repeated evaluation and treatment.

According to the illustrative embodiment, the testing 928, evaluation 930 and adjustment 932 steps may be conducted with the system 100 operating in retrograde flow mode, or may be conducted with the system 100 operating in normal flow mode. In normal flow mode, the operator can test the function of the heart 102 under normal or near normal physiologic blood flow conditions. Based on the evaluation 930, the settings of the system 100 may be adjusted in step 932, if necessary, to modify the flow, heating and/or other characteristics to stabilize the heart 102 in step 934 in preparation for transport to the recipient site in step 936. After the heart 102 and the system 100 is tested and evaluated to ensure appropriate performance, the system 100 with the loaded heart 102 is transported to the recipient site at step 936.

Referring now to FIG. 30, the first phase 942 of the transplant process involves repeating the testing 928 and evaluation 930 steps undertaken just prior to leaving the donor site 936. If the function and characteristics of the heart 102 are not acceptable, the system 100 can be adjusted 942 as appropriate, for example, to provide appropriate fluid oxygenation or nutritional levels, or to increase or decrease the appropriate fluid temperature. As noted above, surgical and/or other therapeutic/remedial procedures may be performed on the heart 102, along with the testing 928 and evaluation 930. According to the illustrative embodiment, testing at the recipient site may be performed in retrograde flow mode, normal flow mode, or a combination of both.

At step 946, after testing is complete, the system 100 is placed in normal/forward flow mode. In certain embodiments, this step 946 is not initiated until the left atrium 152 and pulmonary vein 164 are cannulated, there is adequate operating volume in the system, the heart exhibits stable electrical activity, the ABG and electrolytes are within acceptable ranges, SvO2 is >80%, and blood temperature is between about 34° C. and about 36° C. The step 946 is may be accomplished by slowing and/or stopping the retrograde pumping of the system 100, then restarting the pumping in forward mode. In certain embodiments, prior to restarting in forward mode, the user opens the aortic sampling port 754a, releases the pressure control clamp 190 by turning it counterclockwise, then increases the flow rate of pump 106 to about 1.0 L/min, sets the flow control valve 112 to normal/forward flow, and increases the flow rate of pump 106 to about 2.0 L/min to allow the blood 102 to displace air in the perfusate lines (e.g., 802) of the system 100 and pass through the left side of the heart 102 and down the reservoir return line 808. The user then closes the aortic sampling port 754a.

The flow rate of the perfusion fluid 108 emitted from the pump 106 is then increased at step 950 to a level of the clinician's choosing (typically between about 1 L/min to about 5 L/min) to approximate the physiologic flow rate provided by the heart 102 while functioning in normal beating mode. The heart 102 and the system 100 are again tested at step 952 in a similar fashion to that described above with respect to steps 928 and 930. The clinician may also choose to perform any other tests or evaluations on the heart, for example echocardiogram, electrolyte measurements, cardiac enzyme measurements, metabolyte measurements, intravascular ultrasound evaluation, pressure-volume loop evaluation, and Millar pressure evaluation.

In the third phase 946 at the recipient site, the heart 102 is prepared for implantation into the recipient. This phase includes the step 956 of powering down the pump 106 to stop the flow of perfusion fluid 108. Next, in step 958, the heart 102 is arrested, for example by injecting it with cardioplegic solution in a similar fashion to what is done in step 914 at the donor site. In step 960, the heart 102 is de-cannulated and removed from the organ chamber assembly 106. In step 962, the heart 102 is transplanted into the recipient patient by first removing the sutures 901a-901f, then inserting the heart 102 into the recipient's chest cavity, and suturing the various heart vesicles (e.g., 158, 164a, 164b, 168a, 168b, 169a, 169b, and 903a-903f) to their appropriate mating vesicles within the recipient.

While external devices and methods have been described to defibrillate the heart, deliver pacing signals to the heart, and perform blood chemistry analyses from samples taken from the perfusion fluid, it may also be beneficial to integrate these features into the portable system. Such features include defibrillation, pacing, diagnostic ECG sensing, and blood chemistry analyses.

As described above, the system 100 employs a priming solution, and also employs a perfusion fluid 108 that combines a nutritional supplement 116 solution and a preservative solution 118 with a blood product or synthetic blood product to form the perfusion fluid 108. The priming, supplement 116, and preservative 118 solutions are described next.

According to certain embodiments, solutions with particular solutes and concentrations are selected and proportioned to enable the organ to function at physiologic or near physiologic conditions. For example, such conditions include maintaining organ function at or near a physiological temperature and/or preserving an organ in a state that permits normal cellular metabolism, such as protein synthesis. Exemplary solutions for perfusing a heart are disclosed in U.S. Provisional Application Ser. No. 60/793,472 and are incorporated by reference herein.

Figure 31:
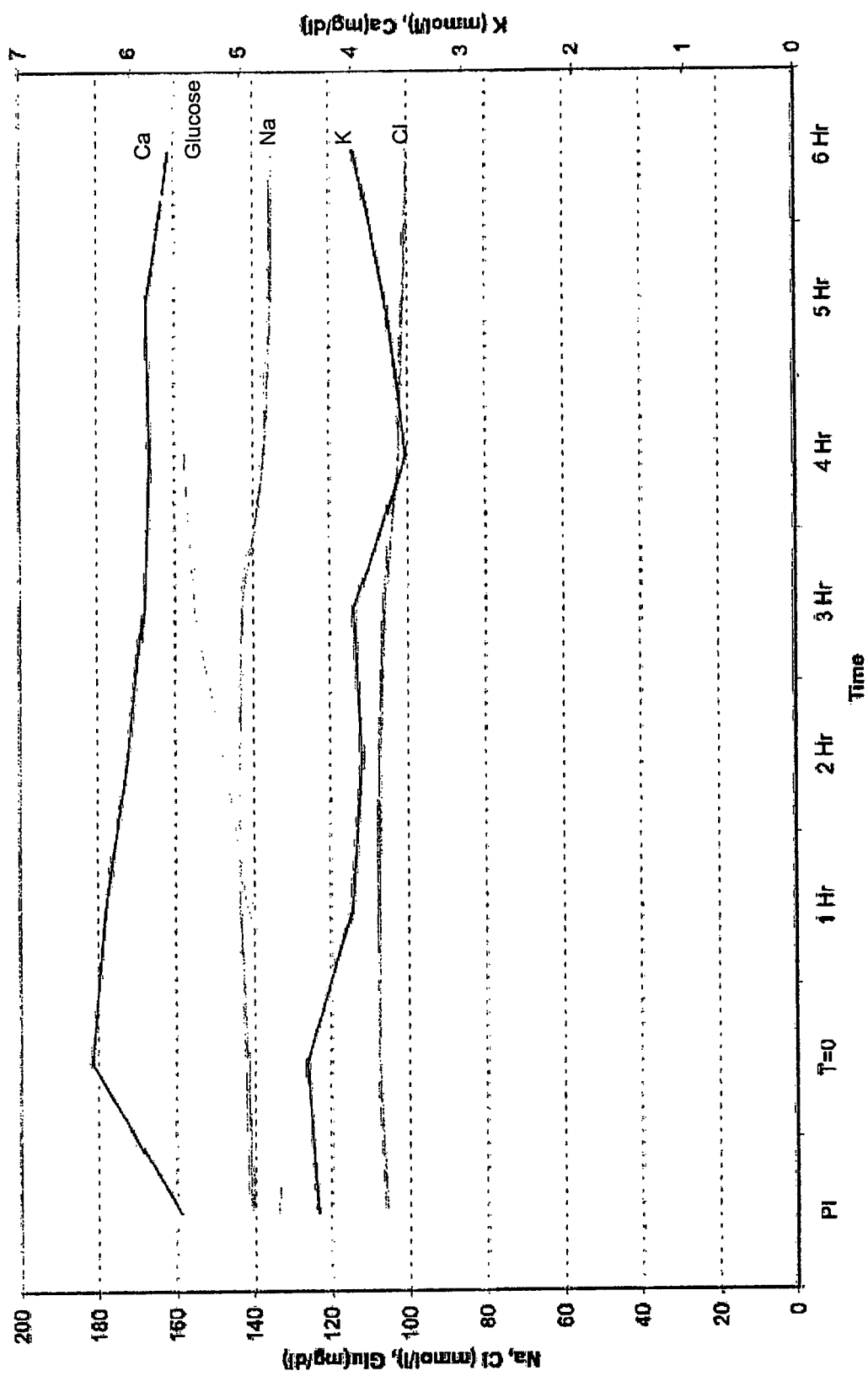
FIG. 31 depicts a chart demonstrating electrolyte stability for an organ under going perfusion in forward mode according to an embodiment of the invention.
Figure 32:
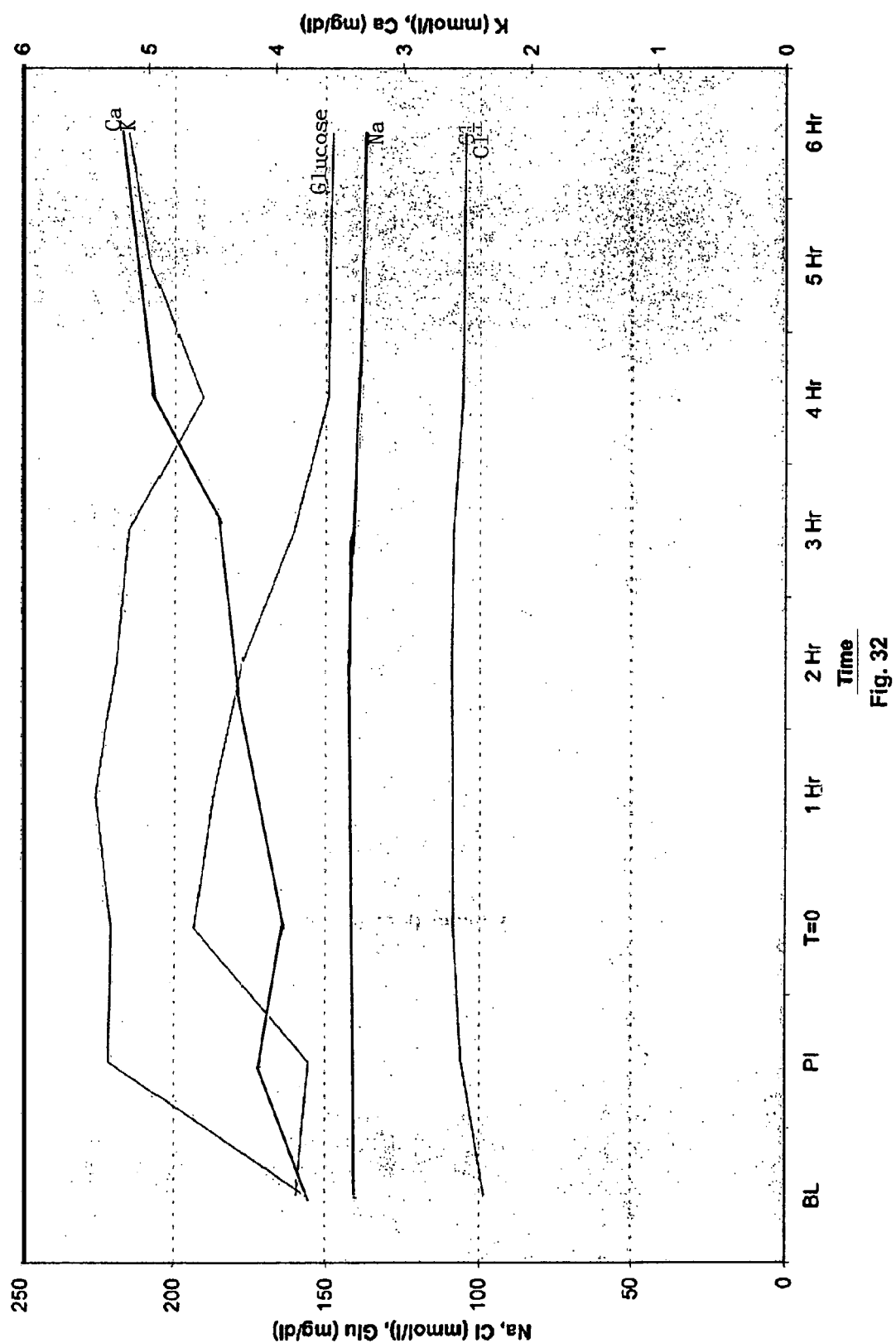
FIG. 32 depicts a chart demonstrating electrolyte stability for an organ under going perfusion in retrograde mode according to another an embodiment of the invention.
Figure 33:
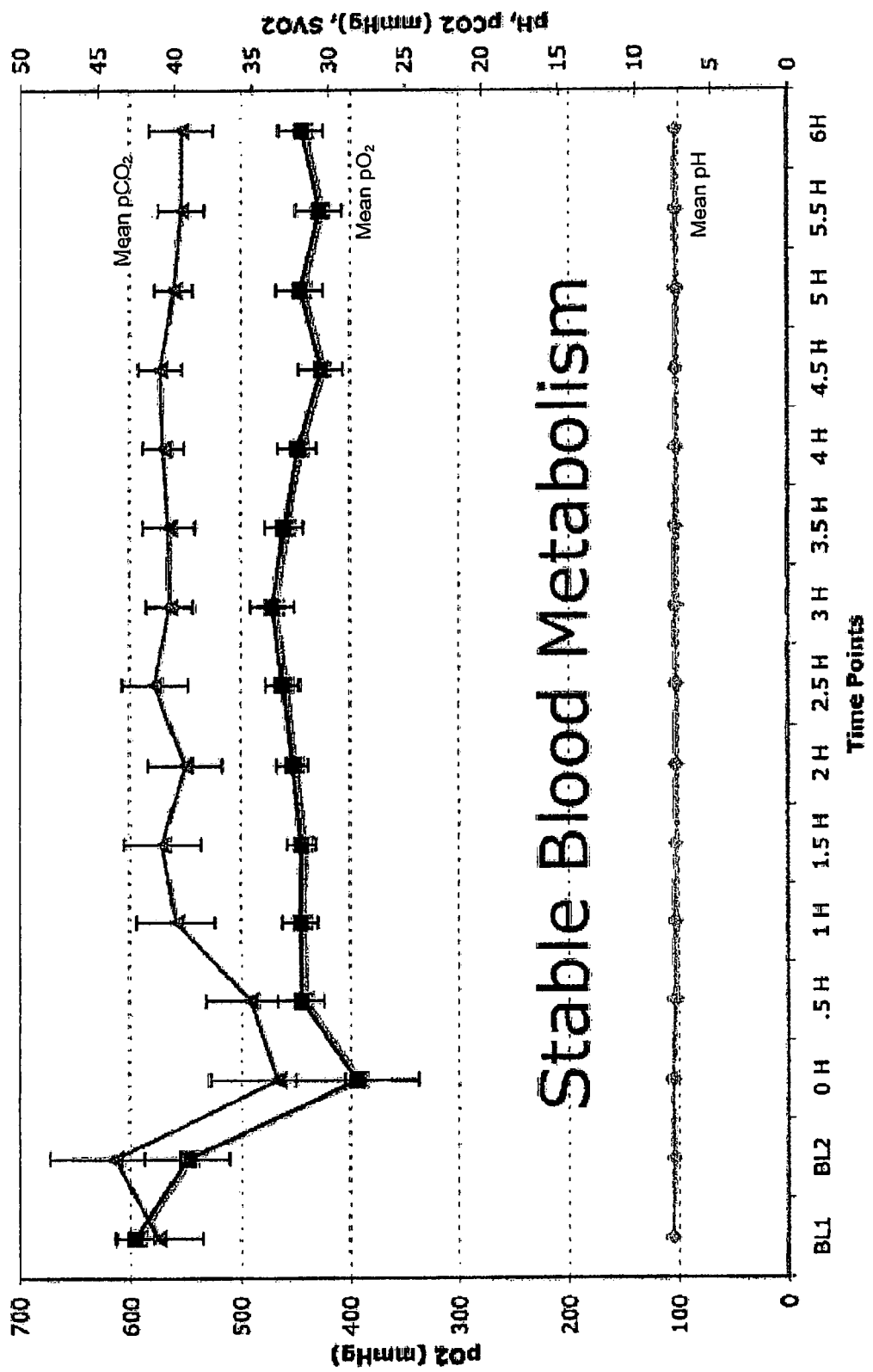
FIG. 33 depicts a chart demonstrating the arterial blood gas profile for an organ under going perfusion according to an embodiment of the invention.

Certain experimental data are available to describe certain embodiments of solutions described herein and their use in heart perfusion and are set forth in FIGS. 31-33. FIG. 31 depicts a chart demonstrating electrolyte stability for a heart under going perfusion in forward mode according to an embodiment of the system 100. In the embodiment associated with FIG. 31, the organ is a heart 102 wherein perfusion is conducted in forward mode (as described above) by pumping perfusion fluid 108 containing solution 116/118 to the let atria 152 and out of the aorta 158. The rate of perfusion is approximately 30 mL/hr. As can be seen from FIG. 31, the levels of various electrolytes: sodium, potassium, calcium, and chloride ions, as well as dissolved glucose, remain at stable levels throughout the course of perfusion, from before the organ is cannulated to the perfusion system 100 to six hours after cannulation within the system 100.

FIG. 32 depicts a chart demonstrating electrolyte stability for an organ under going retrograde perfusion according to another embodiment of the system 100. In the embodiment associated with FIG. 32, the organ is a heart wherein perfusion occurs by pumping the perfusion fluid 108 containing the solution 116/118 into the aorta 158 and through the coronary sinus 155. The rate of perfusion is approximately 30 mL/hr. As can be seen from FIG. 32, the levels of various electrolytes: sodium, potassium, calcium, and chloride ions, as well as dissolved glucose, remain at stable levels throughout the course of perfusion, from before the organ is cannulated to the perfusion system 100 to six hours after cannulation. FIG. 32 also demonstrates that the levels of the electrolytes and glucose remain at levels similar to those for the base line (BL) normal physiological state for the organ.

FIG. 33 depicts a chart demonstrating the arterial blood gas profile for an organ under going perfusion according to another embodiment of the invention. As can be seen from FIG. 33, the levels of various blood gasses: carbon dioxide and oxygen, and pH remain at stable levels throughout the six hour course of perfusion. FIG. 33 also demonstrates that the levels of carbon dioxide, oxygen, and pH remain at levels similar to those for two base line (BL) measurements for the normal physiological state for the organ. FIGS. 31-33 demonstrate the ability of the present systems and methods to maintain an organ under stable physiological or near physiological conditions.

The systems and methods described above for use in perfusing a heart ex vivo may also be adapted for the maintenance of one or more lungs in an ex vivo environment. In general, an exemplary system adapted for ex vivo lung maintenance includes a perfusion circuit that can circulate warm blood or other perfusion fluid through the lungs, and one or more gas sources for ventilating and supplying necessary oxygen, carbon dioxide and nitrogen to the lungs. An exemplary perfusion circuit includes a pump to circulate the perfusion fluid and one or more cannulation or other interfaces for connecting the lungs within the perfusion circuit. Similar to the system 100, the lung maintenance system may also include other features such as a gas exchange device (e.g., an oxygenator, or a ventilator), a fluid heater to allow the user to control the temperature of the perfusion fluid, and fluid pumping and heating process control systems. Nutritional sources may also be provided to replenish carbohydrates, electrolytes and other components of the perfusion fluid that are consumed during system operation.

An exemplary system for lung maintenance will next be described, along with a description of lung anatomical features that impact how the lungs are harvested and connected into the system. Exemplary techniques are then described for maintaining lungs ex vivo and for evaluating lungs to ascertain their functionality and suitability for transplantation. An exemplary embodiment of the system and components thereof are then described in further detail.

Figure 34:
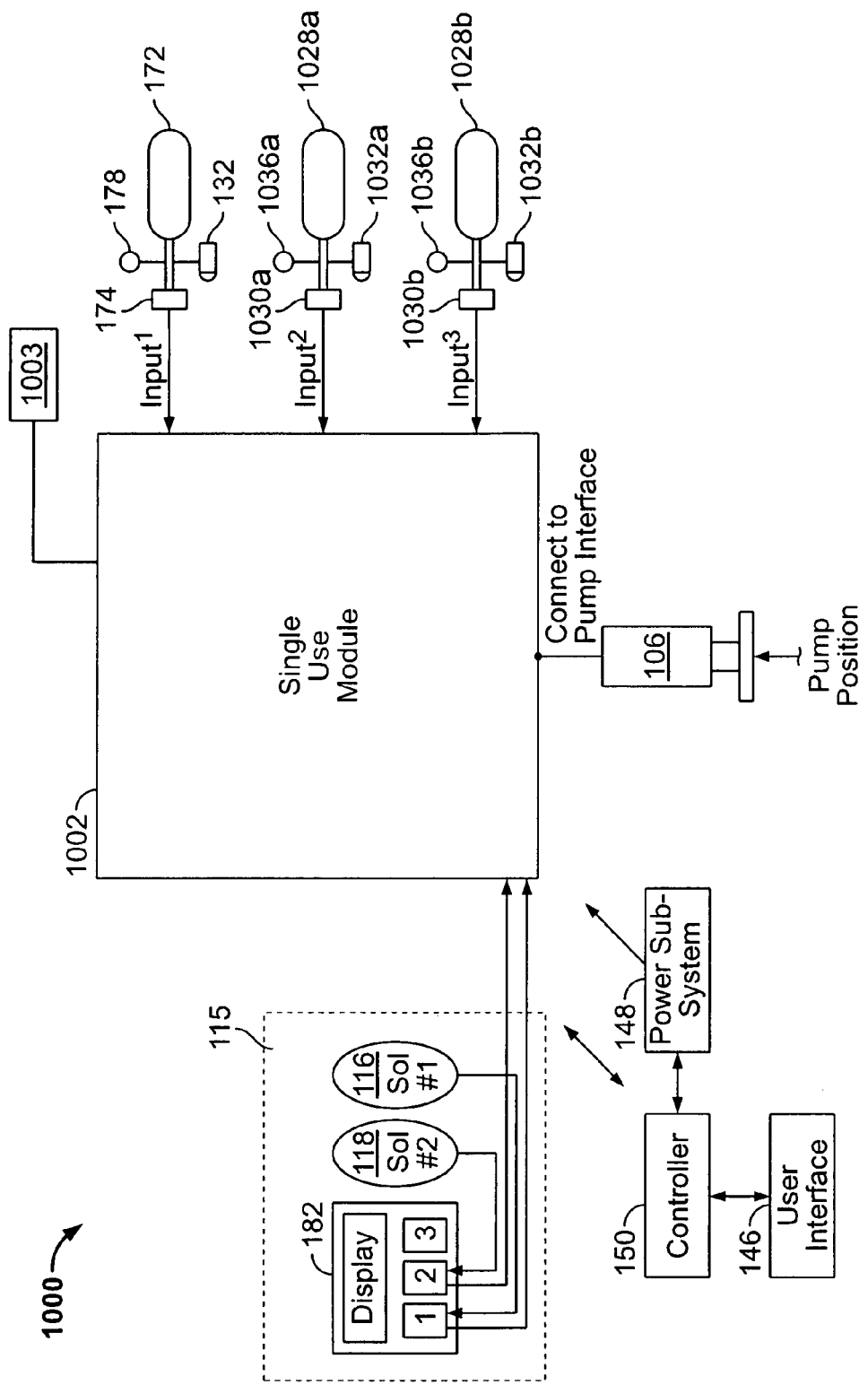
FIG. 34 is a schematic diagram of a portable lung care system with a disposable module configured according to an illustrative embodiment of the invention.
Figure 41:
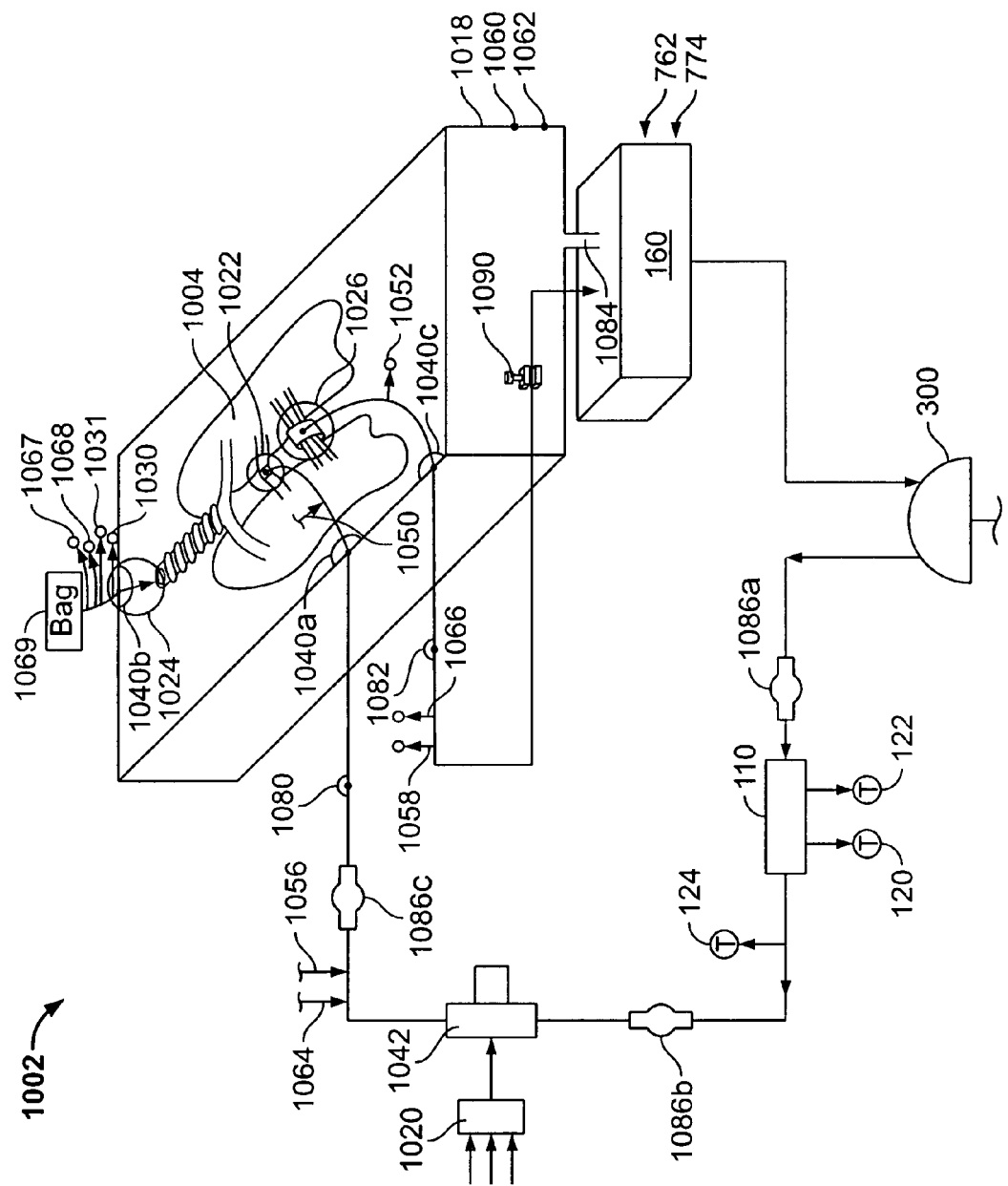
FIG. 41 shows an embodiment of the disposable module configured to preserve the harvested lungs of FIG. 35A.
Figure 42:
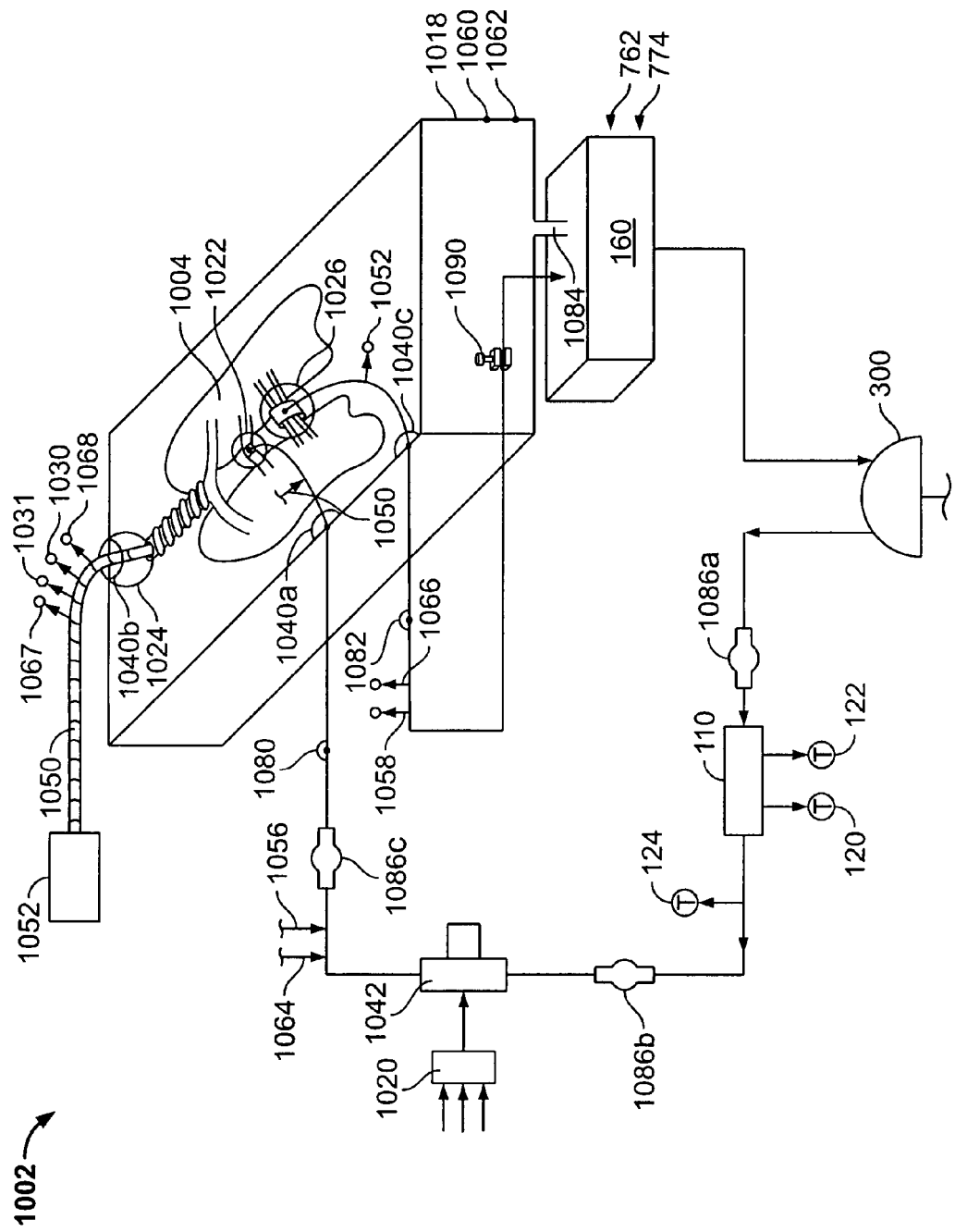
FIG. 42 shows another embodiment of the disposable module configured to preserve the harvested lungs of FIG. 35A.
Figure 43:
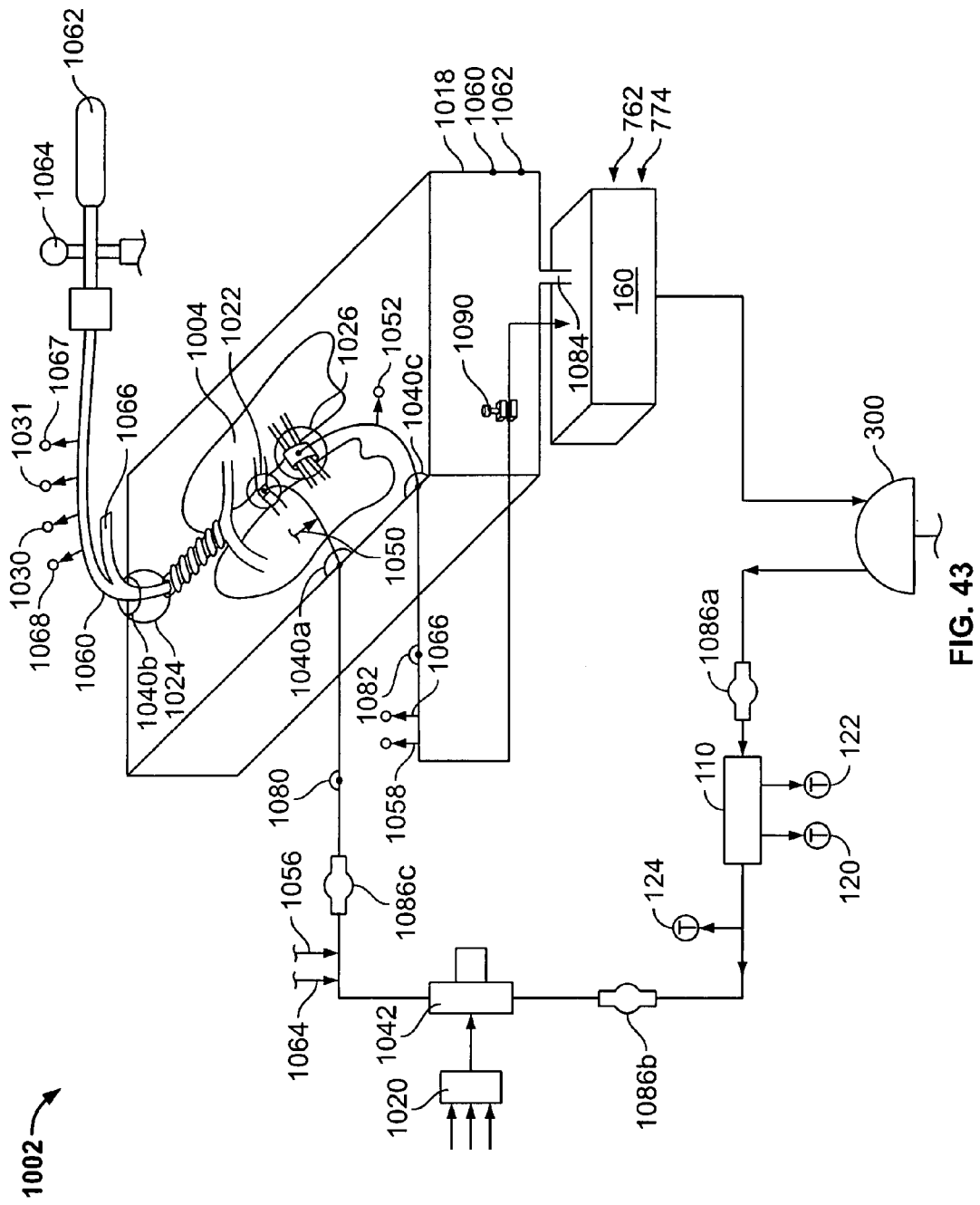
FIG. 43 shows yet another embodiment of the disposable module configured to preserve the harvested lungs of FIG. 35A.
Figure 44:
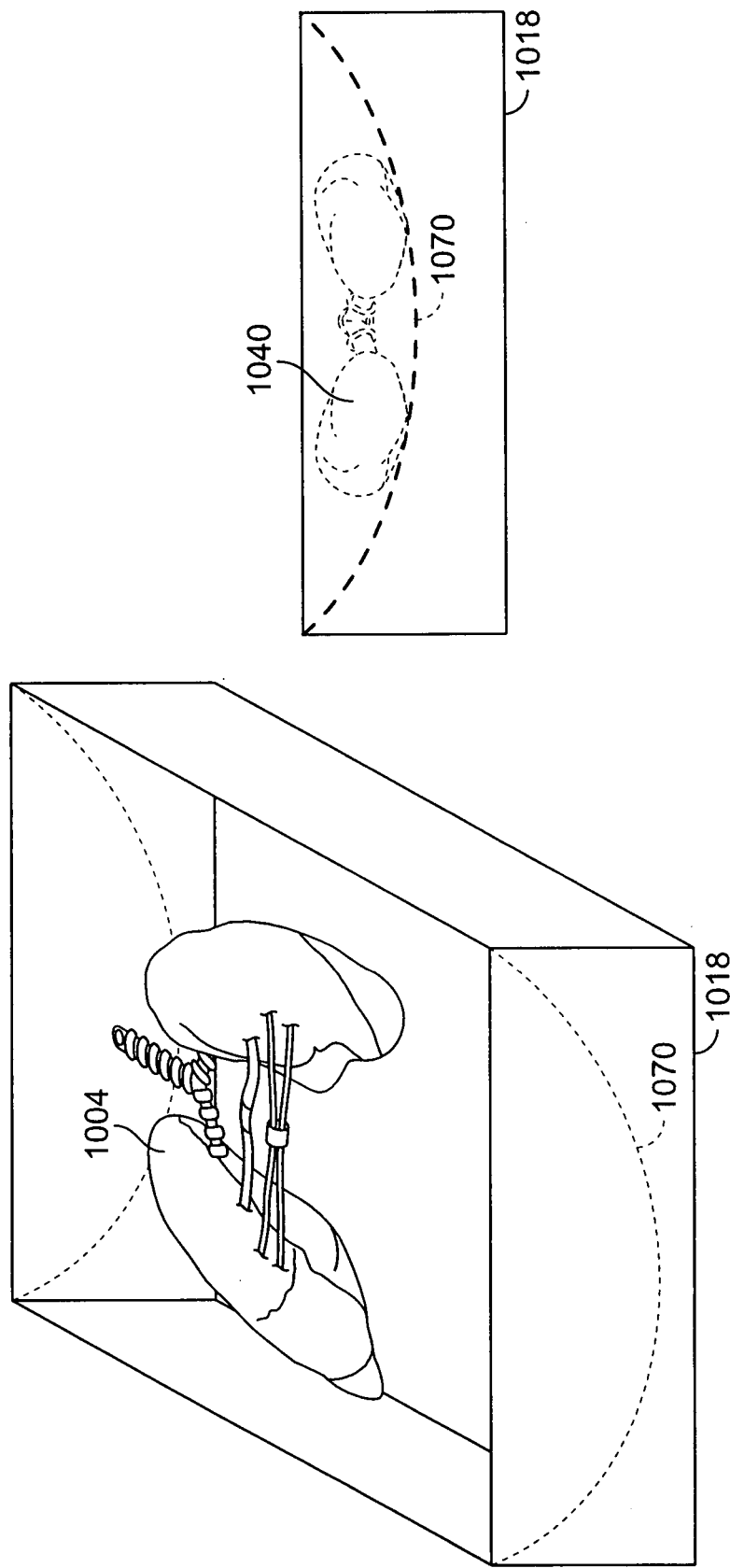
FIG. 44 depicts a top view and a profile view of an exemplary lung chamber assembly employed in the illustrative single use disposable module of FIGS. 41-43.

In certain embodiments, a lung maintenance system is configured in a portable module similar to the heart system described above, with both single-use and multiple use components that allow for optimal costs of production and system re-use. FIG. 34 depicts a schematic diagram of an exemplary portable lung care system 1000. The illustrated system 1000 includes a disposable single use module 1002, similar to the single use module 634, and designed to inter-fit within the system 1000 for containing at least one lung during ex vivo maintenance and for regulating gas composition and flow of the perfusion fluid 108 (not shown) to and from the harvested organ. More particularly, as shown in FIGS. 41-43, the disposable module 1002 includes a lung chamber assembly 1018, wherein at least one lung 1004 is instrumented via a pulmonary artery interface 1022, a pulmonary vein interface 1026, and a tracheal interface 1024. The disposable module 1002 also includes a fluid reservoir 160 for containing the circulating perfusion fluid 108, a perfusion pump interface 300, a heater assembly 110, and a plurality of fluid flow conduits and peripheral monitoring components. The single use module 1002 is described in further operational detail below with reference to FIGS. 34 and 41-43. The system 1000 also includes a perfusion fluid pump 106, a nutritional subsystem 115, a power subsystem 148, an operator interface 146, a ventilation source 1003 (e.g., a ventilator/respirator or a breathing circuit including a bag), a controller 150 and a multiple use module 650 (not shown), similar to those described above. In addition, the system 1000 includes one or more gas sources connected to the single use module 1002, each having an ability to control pressure and flow rate of the gases. The exemplary system 1000 also includes a gas exchange device, which in certain embodiments is an oxygenator 114, for receiving and mixing gases from the one or more gas sources.

Figure 35A:
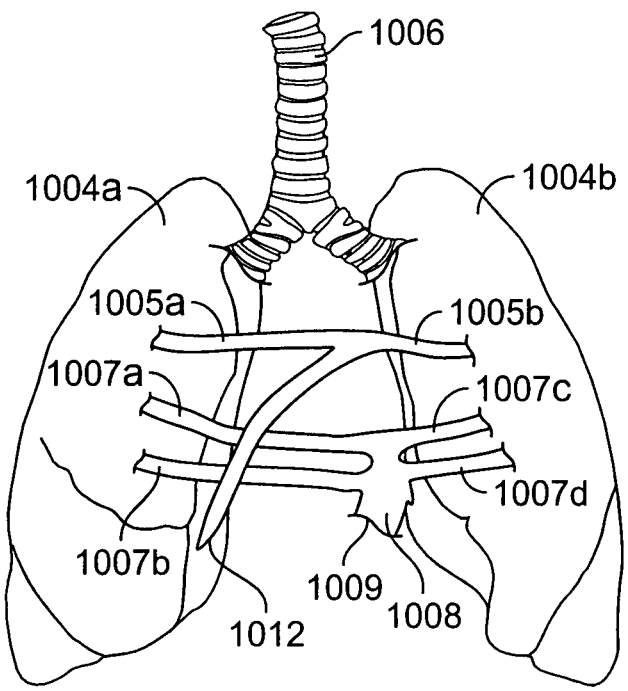
FIG. 35A is a diagram depicting a pair of harvested lungs.
Figure 36:
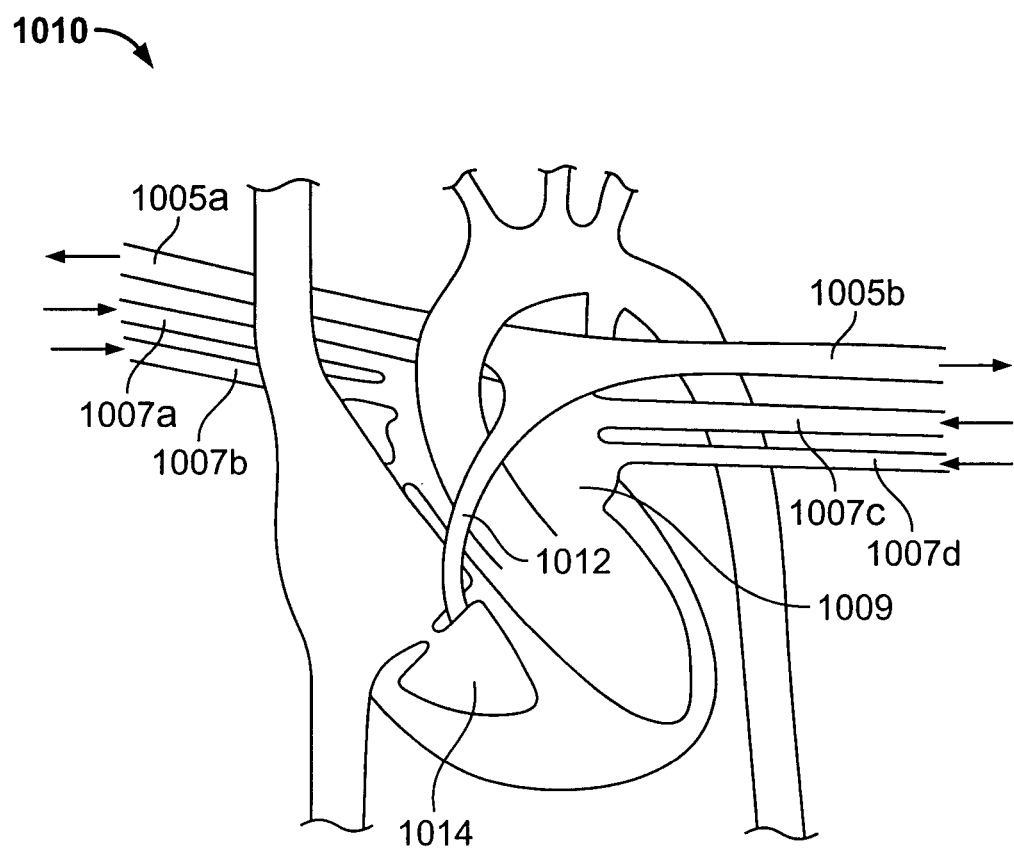
FIG. 36 is a diagram depicting a portion of a body's pulmonary circuit from which at least one lung may be harvested.

FIG. 35A depicts a pair of explanted lungs 1004 that can be connected into the system 1000 for extended ex vivo maintenance. The explanted lungs 1004 are excised from a donor along with a portion of the donor's pulmonary circuitry 1010, as illustrated in FIG. 36. In particular, the harvested lungs 1004 are excised from the donor by cutting across the donor's left atrium 1009, which allows for the explantation of a plurality of pulmonary veins 1007 that connect respective lungs 1004 to the piece of excised left atrial tissue, known as a left atrial cuff 1008. The pulmonary veins 1007 are four in number, two from each lung, and include a right inferior vein 1007*a*, a right superior vein 1007*b*, a left inferior vein 1007*c* and a left superior vein 1007*d*. In an alternative embodiment, multiple pieces of left atrial tissue are excised from a donor, each connecting one or more pulmonary veins 1007 to a single aggregation of the left atrial cuff. Excision is also made at the donor's main pulmonary artery 1012, beginning at the base of the donor's right ventricle 1014, to which both the donor's right pulmonary artery 1005*a* and left pulmonary artery 1005*b* are confluently attached. Optionally, the explanted lungs 1004 also include the donor's trachea 1006 through which air is transported into both of the lungs 1004.

Figure 35B:
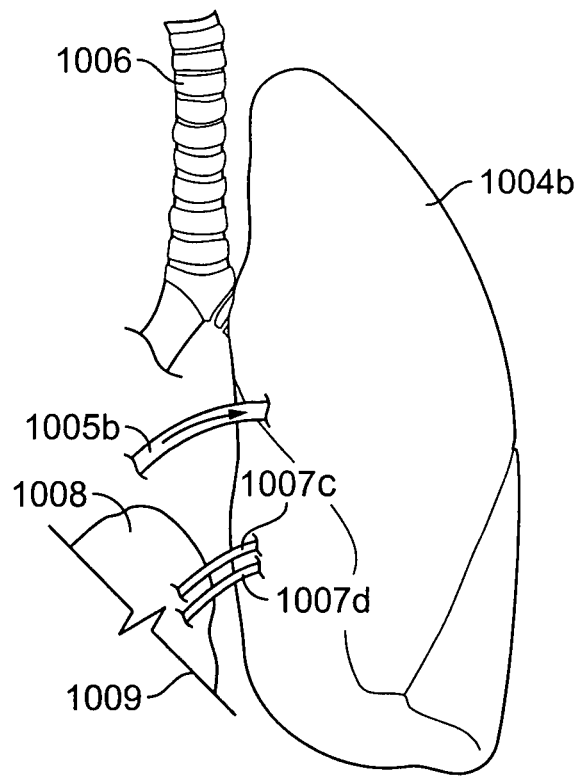
FIG. 35B is a diagram depicting a single harvested lung.

FIG. 35B sets forth a close-up view of a single lung 1004 that is explanted for use in the system 1000. The depicted left lung 1004b is excised from a donor by cutting across the donor's left atrium 1009, as described above, which allows for the explanation of the left superior 1007c and inferior veins 1007d that are joined at the excised left atrial cuff 1008. The explanted lung 1004b may also include the donor's left pulmonary artery 1005b and, optionally, the donor's trachea 1006.

After explantation, lungs 1004 are placed in an ex vivo perfusion system in which they are perfused during transport to a donor site, and in which they can be evaluated to ascertain their functionality and suitability for transplantation.

More particularly, the system 1000 of FIG. 34 is adapted to maintain the explanted lungs 1004 in two modes of operation—a maintenance mode and an evaluation mode. The maintenance mode is used by the system 1000 to preserve the lungs 1004 ex vivo for an extended period of time. In general, in the maintenance mode, the system 1000 circulates the perfusion fluid 108 into the lungs 1004 through the pulmonary artery interface 1022 and away from the lungs 1004 through the pulmonary vein interface 1026. The system 1000 also ventilates the lungs 1004 through the tracheal interface 1024 during perfusion. Ventilation occurs mechanically by delivering a gas through the tracheal interface 1024 in breaths that include periodic inspiration and expiration, in a manner that approximates the normal mechanical function of a lung in-vivo. In an alternative embodiment, periodic inspiration and expiration is obtained in a protective ventilation fashion, whereby the breaths are triggered by a critical opening pressure and a critical closing pressure to achieve a PEEP of about 8 to about 10 $cmH_2O$ and a tidal volume of about 5 to about 7 ml/kg indicating the volume of gas flowing into the lungs with each breath. The breathing rate of the lung may be selected by the operator. In certain implementations, the system 1000 provides 12 or fewer breaths per minute; in certain implementations the system provides 6 breaths per minute. The number of breaths per minute is determined by the operator through the controller 150, which sends one or more electrical signals to a valve in the tracheal conduit, which opens and allows gas from the gas mixture to flow through the tracheal interface 1024 and into the lung. Ventilation can be done by lung ventilators for example, VentiPAC Model 200D or PneuPac.

Figure 37:
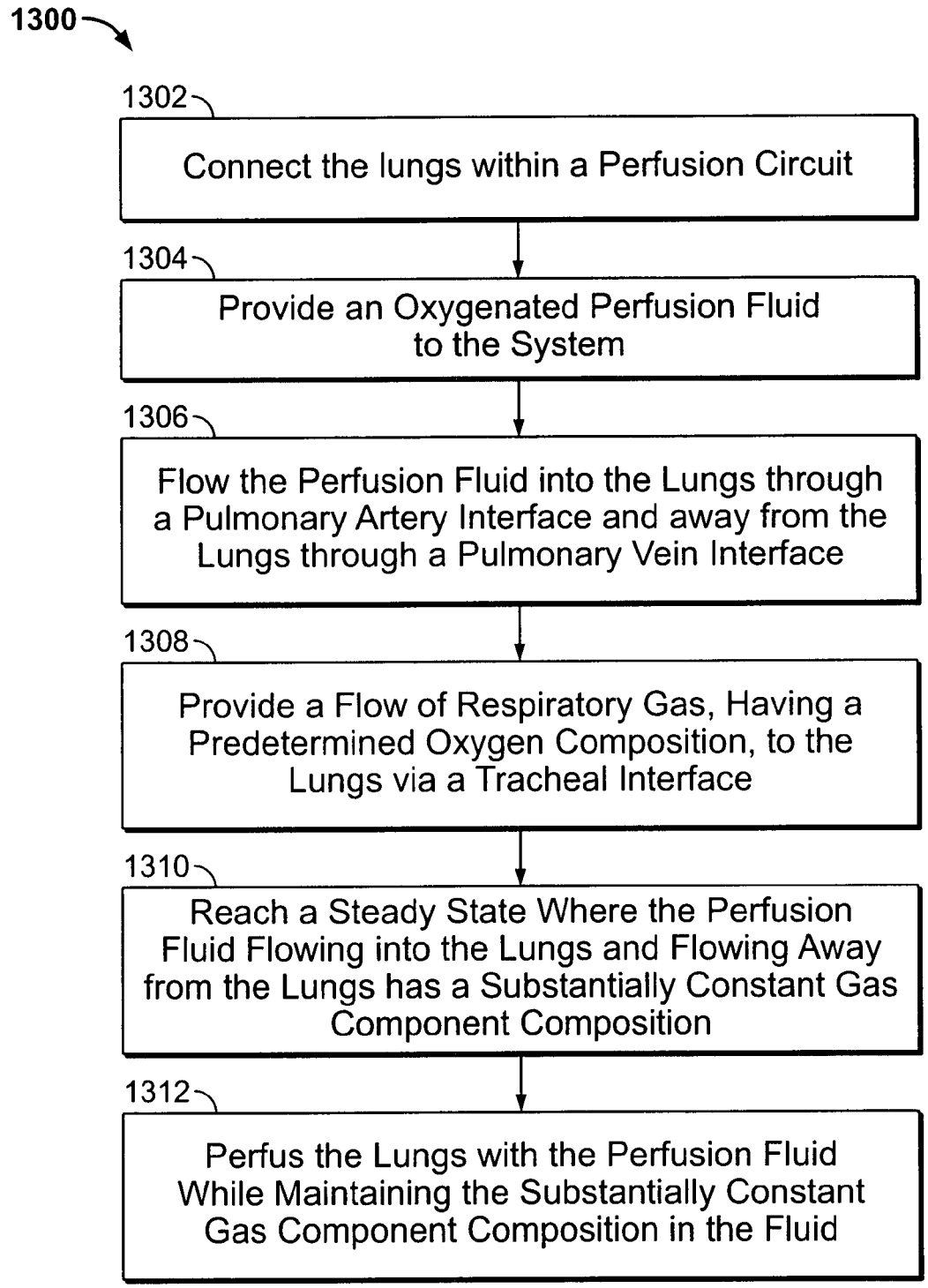
FIG. 37 is a flow diagram depicting an exemplary process for implementing a maintenance mode of operation within the lung care system of FIG. 34.
Figure 38:
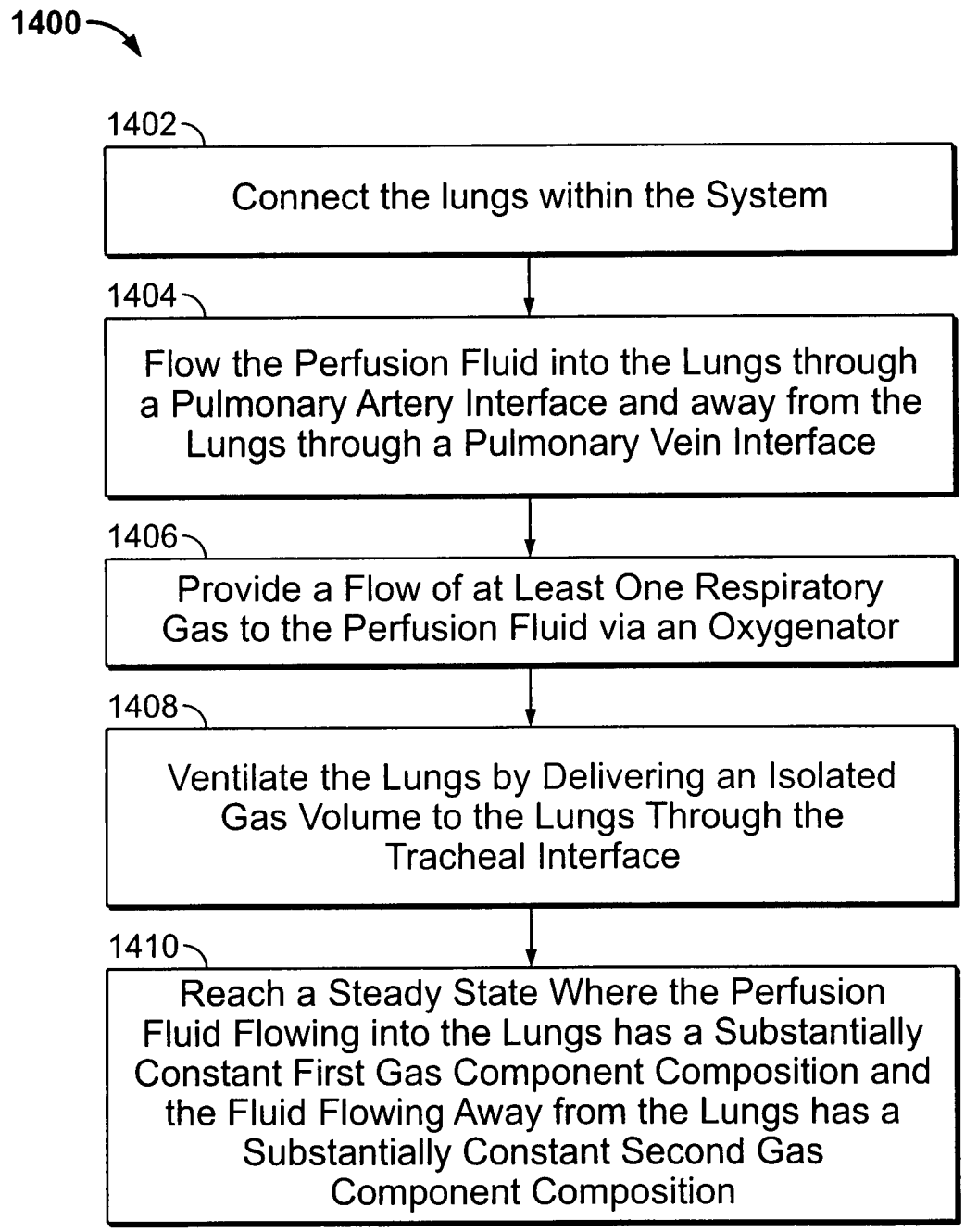
FIG. 38 is a flow diagram depicting another exemplary process for implementing a maintenance mode of operation within the lung care system of FIG. 34.

In addition, the system 1000 supplies a flow of a respiratory gas, having a pre-determined composition of gas components, to the lungs 1004 for use in respiration by the lungs 1004 during perfusion. Upon reaching a steady state of the system 1000, the perfusion fluid 108 flowing into the lungs 1004 includes a substantially constant composition of gas components, and the perfusion fluid 108 flowing away from the lungs 1004 also includes a substantially constant composition of gas components. As used herein, a substantially constant composition of a component in a fluid is achieved at equilibrium, which occurs when the quantity of the component in the fluid varies over time by an amount less than about 5%, less than about 3%, or less than about 1% at a given sampling location within the system. In this respect, the perfusion fluid 108 used to perfuse the lungs 1004 includes equilibrium compositions of gas components. This mode of operation provides the amount of gas that needs to be supplied to the lungs 1004 for sustaining their viability during extended periods of ex vivo maintenance and economizes the transportation of the explanted lungs 1004 to the donor location. As illustrated in FIGS. 37 and 38, the maintenance mode may be implemented using two different approaches, both of which yield the steady state condition in the perfusion fluid 108 as described above. In addition, FIG. 39 provides exemplary steady-state measurements of gas components in the perfusion fluid 108 obtained during one of the two maintenance mode approaches.

The maintenance mode is implemented in two exemplary approaches—a tracheal oxygen delivery approach, and an isolated tracheal volume re-breathing approach. FIG. 37 depicts a flow diagram 1300 of the steps involved in the tracheal oxygen delivery approach of the maintenance mode. At step 1302, the explanted lungs 1004 are instrumented within a perfusion circuit of the system 1000. At step 1304, the explanted lungs 1004 are perfused by a perfusion fluid 108 that is oxygenated to a desired level prior to initiating the perfusion of the lungs 1004. Optionally, the perfusion fluid 108 may be brought to a high level of oxygen prior to initiating the perfusion of the lungs 1004 so that an initial high level of oxygen is delivered to the explanted lungs 1004. During perfusion of the lungs 1004, the oxygenated perfusion fluid 108 flows into the explanted lungs 1004 via the pulmonary artery interface 1022 and flows away from the lungs 1004 via the pulmonary vein interface 1026 (step 1306). The explanted lungs 1004 are ventilated through the tracheal interface 1024 by a gas mixture that contains a pre-determined composition of gas components for organ respiration (step 1308).

Ventilation is performed in this approach by flowing the ventilation/respiratory gas into the tracheal interface 1024 in periodic breaths containing a pre-determined volume and pressure of gas. Each breath includes a compression stage where the gas is delivered into the lung in a desired volume, followed by decompressing or relaxing of the lungs 1004 (and allowing the lungs 1004 to expel gas in an unaided manner) so that the lungs 1004 exhale the gas through the tracheal interface 1024 in a volume approximately equal to the compression volume. An outlet valve on the tracheal interface 1024 may be used to ensure a minimum PEEP is maintained by preventing the pressure falling below a user-determined value.

In certain embodiments, the respiratory gas mixture includes about 10% to about 20% oxygen, about 2% to about 8% carbon dioxide, and the balance is nitrogen. In certain embodiments, the gas mixture includes about 14% oxygen, about 5% carbon dioxide, and the balance is nitrogen. The oxygen component in the ventilation/respiratory gas provided through the tracheal interface 1024 enters alveoli of the lungs 1004 and exchanges with carbon dioxide from the perfusion fluid 108 flowing into the lungs 1004. The perfusion fluid 108 that enters the lungs 1004 is oxygenated as a result of this exchange and then flows into the vasculature of the lung, where oxygen is consumed and carbon dioxide produced. The lungs 1004 may consume oxygen in an amount less than the amount of oxygen provided in the tracheal breaths. The carbon dioxide produced by the lungs 1004 passes into the perfusion fluid 108, then into the alveoli and is excreted from the lungs 1004 via exhaled breaths through an outlet valve in the tracheal interface 1024. The outlet valve is provided across the tracheal interface 1024 to allow the exhaled breaths to be expelled from the system 1000 and is described below with reference to FIG. 43.

In the tracheal oxygen delivery approach, the composition of the ventilation/respiratory gas is pre-determined by the operator so as to establish gas component equilibrium in the system. In other words, oxygen supplied to the lungs 1004 through the tracheal interface 1024 is consumed in the lungs 1004 and resulting carbon dioxide is expelled through the tracheal interface 1024 without altering the gas composition in the perfusion fluid 108 entering or exiting the lung. In equilibrium by this delivery approach, the perfusion fluid 108 flowing into the lungs 1004 and flowing away from the lungs 1004 have substantially the same composition of oxygen and carbon dioxide, as indicated at step 1310. Moreover, at step 1312, the lungs 1004 are perfused over an extended period of time while maintaining fluid and gas equilibrium in the lung.

FIG. 38 depicts a flow diagram 1400 of the steps involved in the second implementation of the maintenance mode. Similar to the first mode, at step 1402, the explanted lungs 1004 are instrumented within the lung care system 1000. At step 1404, the instrumented lungs 1004 are perfused with a perfusion fluid 108 that flows into the lungs 1004 via the pulmonary artery interface 1022 and flows away from the lungs 1004 via the pulmonary vein interface 1026. In addition, one or more respiratory gas mixtures, each containing a pre-determined composition of gas components, are supplied to the perfusion fluid 108 via a gas exchange device (e.g., oxygenator) 1042 of the system 1000 (step 1406). More specifically, a first gas source supplied to the oxygenator 1042 includes a gas composition of about 11% to about 14% oxygen and about 3% to about 7% carbon dioxide, and the balance is nitrogen. In certain instances, the first gas source includes about 12% oxygen and about 5% carbon dioxide, and the balance is nitrogen. Other gases may be used, for example nitric oxide (for endothelial protection and vasodilation) and carbon monoxide (to provide anti-apoptototic effects).

At step 1408, the lungs 1004 are also ventilated with an isolated gas volume delivered through the tracheal interface 1024. The isolated gas volume is provided in a configuration that prevents it from communicating or otherwise interfacing with other fluids except in the lung alveoli. In this approach, the gas components in the isolated gas volume are able to reach a substantially constant composition by exchanging with the gas components from the perfusion fluid 108 pumped into the lungs 1004 via the pulmonary artery interface 1022 (step 1408). This gas exchange takes place across the alveolar membrane of the lungs 1004. Exhaled carbon dioxide component produced from the exchange is then carried away from the lungs 1004 via the circulating perfusion fluid 108. This carbon dioxide component is substantially removed from the perfusion fluid 108 by the gas exchange device 1042.

Upon reaching equilibrium, as indicated in step 1410, oxygen and carbon dioxide in the perfusion fluid 108 flowing into the lungs 1004 have a substantially constant first composition, and oxygen and carbon dioxide in the perfusion fluid 108 flowing away from the lungs 1004 have a substantially constant second composition. However, unlike in the tracheal oxygen delivery mode, in the isolated tracheal volume mode the first composition of oxygen and carbon dioxide components in the perfusion fluid 108 flowing into the lungs 1004 may differ from the second composition of the gas components in the perfusion fluid 108 flowing away from the lungs 1004. In preferred embodiments of this approach, such first and second compositions differ by amounts substantially equivalent to the quantity of oxygen consumed by the lungs 1004 and the quantity of carbon dioxide produced by the lungs 1004 during metabolism.

In certain embodiments, the oxygen composition in the perfusion fluid 108 is maintained during perfusion at a steady-state partial pressure or oxygen saturation that is greater in the perfusion fluid 108 flowing into the lungs 1004 than in the perfusion fluid 108 flowing away from the lungs 1004. In certain embodiments, the carbon dioxide component is maintained during perfusion at a steady state partial pressure that is lower in the perfusion fluid 108 flowing into the lungs 1004 than in the perfusion fluid 108 flowing out of the lungs 1004. This approach of implementing the maintenance mode is also referred to as an isolated tracheal volume re-breathing approach, wherein oxygen supplied to the perfusion fluid 108 through the oxygenator 1042 is consumed in the lungs 1004 and resulting carbon dioxide is carried away from the lungs 1004 by the perfusion fluid 108 and removed through the oxygenator 1042.

Ventilation is performed in the second mode with breaths that occur approximately as frequent as those provided in the first mode. However, ventilation in the second mode occurs by first compressing the isolated gas volume, thereby flowing the gas from the isolated volume and into the tracheal interface 1024, and then allowing the lungs to relax and expirate gas, in an unaided manner, from the lung alveoli to fill the isolated volume.

In the maintenance mode, the system 1000 pumps the perfusion fluid 108 to the lungs 1004 at a rate of about 500 to about 5000 ml/min. This mode of operation may help reduce damage to the lungs 1004 during extended periods of ex vivo maintenance. Thus, according to one feature of the invention, the lungs 1004 are transported to a donor site in the maintenance mode. Additionally, the functional tests performed during the evaluation mode, described below, can also be conducted during the maintenance mode to evaluate various lung capabilities. In certain instances, recruitment of the lungs 1004 may be performed in the maintenance mode. For example, a suction force may be applied to the lungs 1004 via the tracheal interface 1024 to clear the lungs 1004 of fluid or alveoli debris. Collapsed alveoli in the lungs 1004 may be inflated by causing the lungs 1004 to inhale breaths that are of variable volume, such as sigh breathing which causes the lungs 1004 to inhale a first breath having a volume that is larger than the volumes of at least two next breaths using, for example, a ventilator or a breathing circuit including a bag.

Having described the two different approaches of implementing a maintenance mode of operation with respect to FIGS. 37 and 38, exemplary measurements of gas components in the perfusion fluid 108 flowing into and away from a pair of lungs 1004 equilibrium is described next for an isolated tracheal volume re-breathing approach. In particular, as shown in FIG. 39, data in column 4000 provides steady-state measurements of gas components in the perfusion fluid 108 flowing into the explanted lungs 1004 through the pulmonary artery interface 1022. Data in column 4002 provides steady-state measurements of gas components in the perfusion fluid 108 flowing away from the explanted lungs 1004 through the pulmonary vein interface 1026. The data in FIG. 39 was obtained using a blood gas analyzer, such as Radiometer ABL800 FLEX, to analyze samples of perfusion fluid 108 taken during the isolated tracheal volume re-breathing approach. Briefly referring to the lung maintenance system 1000 of FIGS. 41-43, a first sample of the perfusion fluid 108 was taken at port 1080 on the arterial fluid flow. This fluid sample was analyzed by the blood gas analyzer to generate the data in column 4000. For the sake of measurement accuracy, the radiometer was recalibrated after performing each analysis on a fluid sample. A second sample of the perfusion fluid 108 was taken at port 1082 and was analyzed by the blood gas analyzer to generate the data in column 4002. The two sets of measurements were spaced apart in time because of the recalibration requirement.

In general, during the maintenance mode, the perfusion fluid 108 flowing into and away from the lungs 1004 are maintained at a relatively similar gas component composition. For instance, the partial pressure 4000a of carbon dioxide in the arterial fluid flow (43.8 mmHg) is only slightly lower than the partial pressure 4002a of carbon dioxide in the venous fluid flow (44.6 mmHg), and the partial pressure 4000b of oxygen in the arterial fluid flow (84.5 mmHg) is only slightly higher than the partial pressure 4002b of oxygen in the venous fluid flow (83.9 mmHg). These differences in the partial pressures can be attributable to imprecision in the measuring system, lung metabolism, or interactions with the oxygenator 1042.

Figure 40:
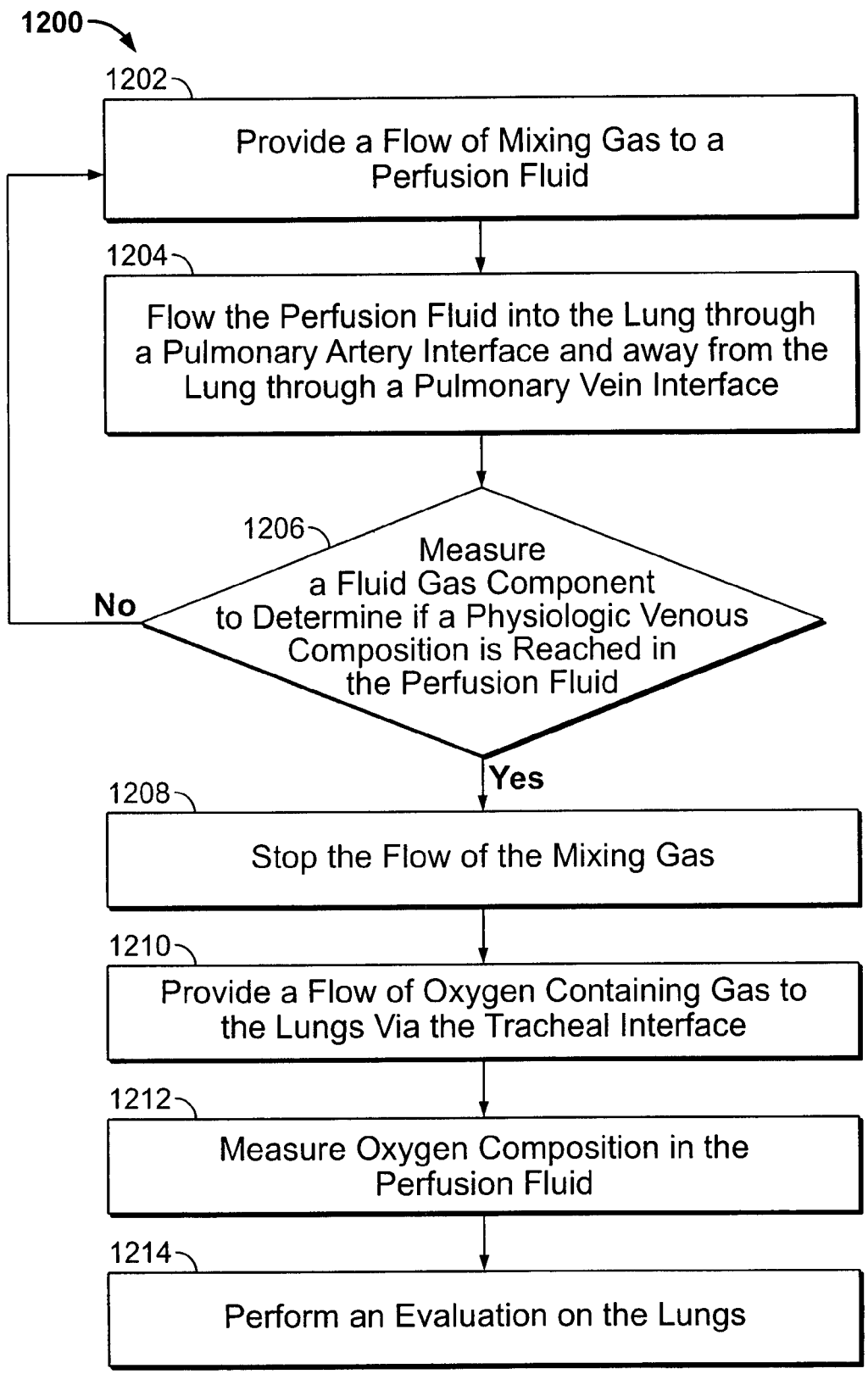
FIG. 40 is a flow diagram depicting an exemplary process for implementing an evaluation mode of operation within the lung care system of FIG. 34.

In certain embodiments, the composition of gas components in the perfusion fluid 108 is chosen to provide steady-state partial pressures of the gas components within the circulating fluid in a range between a body's physiologic arterial blood gas composition and physiologic venous blood gas composition. For example, as shown in FIG. 39, the composition of the oxygen component in the perfusion fluid 108 is at a partial pressure that is greater than a composition of the oxygen component in physiologic venous blood and less than a composition of the oxygen component in physiologic arterial blood. More specifically, this partial pressure of the oxygen component in the perfusion fluid 108 may be between about 75 mmHg to about 100 mmHg, between about 80 mmHg to about 90 mmHg, or between about 83 mmHg to about 85 mmHg. In addition, as shown in FIG. 40, the composition of the carbon dioxide component in the perfusion fluid 108 is at a partial pressure that is less than a composition of the carbon dioxide component in physiologic venous blood and greater than a composition of the carbon dioxide component in physiologic arterial blood. More specifically, this partial pressure of the carbon dioxide component in the perfusion fluid 108 may be between about 40 mmHg to about 50 mmHg or between about 42 mmHg to about 48 mmHg.

Having discussed the maintenance mode in detail with respect to FIGS. 37-39, the evaluation mode is explained next. Techniques for evaluating the lungs 1004 to ascertain their functionality and suitability for transplantation will also be described.

In particular, FIG. 40 provides a flow diagram 1200 illustrating the steps involved in implementing the evaluation mode. As depicted, the system 1000 perfuses the explanted lungs 1004 with a perfusion fluid 108. The perfusion fluid 108 is made to be similar in partial pressures of blood gases to a body's physiologic venous blood. This venous gas composition in the perfusion fluid 108 may be achieved by mixing one or more gases, having a combined composition of carbon dioxide and low or no oxygen, with the perfusion fluid 108 (step 1204), until a desired venous composition is reached (1206), at which point the gases may optionally be stopped from being supplied to the perfusion fluid 108 (step 1208). In one embodiment, the gases include about 5% carbon dioxide and about 95% nitrogen. The perfusion fluid 108 is adapted to flow into the lungs 1004 through the pulmonary artery interface 1022 and flow away from the lungs 1004 through the pulmonary vein interface 1026. As indicated at step 1210, the explanted lungs 1004 may be ventilated by an oxygen-containing gas that is flowed into the tracheal interface 1024 from a suitable ventilation source, such as from a ventilator/respirator. This gas may comprise about 100% oxygen, about less than 100% oxygen, less than about 75% oxygen, less than about 50% oxygen or less than about 25% oxygen. In certain embodiments, this gas may be the same composition as ambient air.

The evaluation mode is useful, for example, for performing tests to evaluate the gas-transfer capacity of the lungs 1004 by determining the partial pressure or oxygen saturation of the perfusion fluid 108 both before and after it flows through the lungs 1004. To perform this test in the evaluation mode, as shown at steps 1212 and 1214, the system 1000 monitors the blood gas composition of the perfusion fluid 108 after ventilation begins by taking sample measurements of oxygen saturation or partial pressure of oxygen in the perfusion fluid 108 flowing into the lungs 1004 via the pulmonary artery interface 1022 and flowing away from the lungs 1004 via the pulmonary vein interface 1026. The resulting pulmonary artery and pulmonary vein oxygen saturation or partial pressure oxygen measurements are then compared with each other to identify a maximum difference that is representative of the gas-transfer capacity of the lungs 1004. In a second approach to evaluating the gas-transfer capacity of the lungs, the oxygen saturation or partial pressure of oxygen in the perfusion fluid flowing into the lungs 1004 is taken before ventilation begins. At a pre-determined time period after ventilation begins, another measurement of oxygen saturation or partial pressure of oxygen in the perfusion fluid flowing away from the lungs 1004 is taken and is compared with the first measurement to evaluate the gas-transfer capacity of the lungs 1004. The operator determines whether this capacity is sufficient and decides to carry out the transplant, or not. In addition, other functional tests on the lungs 1004 may be performed, such as diagnostic bronchoscopy, visual evaluation and biopsy, both prior and subsequent to transportation of the lungs 1004 to a donor location.

Exemplary functional tests performed on the lungs 1004 during the evaluation mode include tests that assess the gas exchange functionality of the lungs 1004, which may be conducted using blood gas analysis of fluid samples taken from both the arterial-side (e.g., through port 1080) and venous-side (e.g., through port 1082) of fluid flow in the perfusion circuit. Tests can be conducted to assess pulmonary circulation of the perfusion fluid 108 through the lungs. This may involve the calculation of pulmonary vascular resistance (PVR) which is a measure of the ability of the lungs 1004 to resist fluid flow. Details regarding the PVR value calculation are provided below with respect to FIG. 52. In addition, alterations in the PVR value may be monitored in response to an infusion of nitric oxide into the perfusion fluid 108 to detect any reversibility of pulmonary hypertension. Pulmonary angiography on the lungs 1004 may also be performed. In certain implementations, assessment of the bronchial tree is conducted using bronchoscopy along with other analysis applications such as inspecting the airways, collecting bronchial washings for cytological or microbiological studies or obtaining multiple biopsies. In certain implementations, image studies are performed on the lungs 1004 using, for example, x-rays, CTs, or nuclear studies such as perfusion or ventilation scans. These imaging devices may be external to or onboard the organ care system 1000. In certain instances, viability studies are conducted on parenchymal or bronchial tissue of the lungs 1004 using techniques such as biopsies or measurements of tissue levels of AMP, ADP and ATP. Additionally, assessments may be performed such as assessing the severity of ischemia reperfusion injury in the instrumented lungs 1004 by measuring levels of indicator agents, such as conjugated dienes or lactate, in the perfusion fluid 108. Moreover, a lung permeability test may be perform on the explanted lungs to determine if the lungs are injured or otherwise comprised. This test includes injecting an agent, such as a dye, into the perfusion fluid and, after a time period of perfusion, visually inspecting the lungs. If the agent is visually detectable in the endo-bronchial tree of the lungs or in the alveoli, then the lungs are injured because they are permeable to the injected substance. Further assessments include using biomarkers based on proteomic or genomic approaches to predict organ graft rejection or development of bronchiolitis obliterans syndrome (BOS) in a potential organ recipient. In certain instances, one or more of the above-mentioned tests can be performed on the lungs 1004 during a maintenance mode of operation.

Having described the exemplary processes for implementing the maintenance mode and the evaluation mode, along with techniques for evaluating lungs 1004 to ascertain their functionality and suitability for transplantation, features of the lung care system 1000 will be described next in further detail with respect to these two modes of operation. In particular, instrumentation of the lungs 1004 within the system 1000 is described in further detail. Then a generalized approach for operating the system is described, followed by a discussion of specific system features that are tailored to each mode of operation.

FIGS. 41-43 illustrate a pair of explanted lungs 1004, such as the explanted lungs 1004 of FIG. 35a, cannulated within an embodiment of the disposable single-use module 1002. In particular, the module 1002 includes a lung chamber assembly 1018 that contains the explanted lungs 1004 connected to the assembly 1018 from at least one of the pulmonary artery interface 1022, the pulmonary vein interface 1026, and the tracheal interface 1024. The lungs 1004 may lay prone or supine in the lung chamber assembly 1018. With brief reference to FIG. 35A, the pulmonary artery interface 1022 includes a cannulation of the lungs 1004 at or near the main pulmonary artery 1012. The tracheal interface 1024 may include a cannulation of the lungs 1004 at or near the trachea 1006. In optional embodiments, where the trachea 1006 is not excised with the lungs 1004, the tracheal interface 1024 may include a conduit that is directly placed in a bronchial branch of each lung 1004, and the lungs 1004 are vented by such conduit. The pulmonary vein interface 1026 may include cannulation to the lungs 1004 at the excised left atrial cuff 1008 where at least one of the pulmonary veins 1007 of the two lungs 1004 is attached. However, in certain embodiments, the excised left atrial cuff 1008 remains un-cannulated. Specific details regarding the pulmonary vein interface 1026 are discussed below in the context of exemplary operational processes and with reference to FIGS. 48-51. The module 1002 also includes the reservoir 160 for holding the perfusion fluid 108 and an oxygenator 1042 that provides at least one appropriate gas mixture to the perfusion fluid 108.

Referring again to FIGS. 34 and 41-43, in an illustrative embodiment of a general operational process, the perfusion fluid 108 is prepared for use within the module 1002 (and, ultimately, within the system 1000) by being loaded into the reservoir 160 via portal 774 and, optionally, is treated with therapeutics via portal 762. The loaded perfusion fluid 108 is subsequently pumped from the reservoir 160 to the heater assembly 110 and warmed to a near physiologic temperature. In this illustrated embodiment, this pumping action is provided by an alignment of the pump interface assembly 300 with the pump driver 334 of the multiple use module 650 which is described above with reference to FIG. 8C. The pump interface assembly 300 receives a pumping force from the pump driver 334 and translates the pumping force to the perfusion fluid 108, thereby circulating the perfusion fluid 108 to the lung chamber assembly 1018. However, any fluid pump may be used to flow the perfusion fluid 108 in the perfusion circuit. The heat assembly 110 includes temperature sensors 120 and 122 and dual-sensor 124 that provide temperature measurement of the perfusion fluid 108. A plurality of compliance chambers, such as compliance chambers 1086a-c, may be included in the system 1000. They are essentially small inline fluid accumulators with flexible, resilient walls designed to simulate the human body's vascular compliance by aiding the system 1000 to more accurately mimic blood flow in the human body. In particular, compliance chamber 1086a is located at an outlet of the perfusion fluid pump 300, compliance chamber 1086b is located at an outlet of the heater assembly 110, and compliance chamber 1086c is located at an outlet of the oxygenator 1042. Any one of these compliance chambers 1086a-c may be used individually or a plurality of compliance chambers may be used in any combination.

The perfusion fluid 108 from the heater assembly 110 is then pumped to the gas exchange device 1042. Depending on the flow mode selected as well as the type of implementation chosen for executing the selected flow mode, one or more mixing gases, each having a pre-determined gas composition, may be automatically or manually supplied to the perfusion fluid 108 through the gas exchange device (e.g., an oxygenator) 1042. In certain embodiments, the flow mode type selection is made using a mode selector switch 1020 located on the system 1000 between the gas supplies and the oxygenator 1042. The mode selector switch 1020 may be operated manually as well as by the controller 150. In certain embodiments, the order of the oxygenator 1042 and the heater assembly 110 along the illustrated perfusion circuit is switched.

Depending on the mode switch 1020 selected, the oxygenator 1042 receives one or more mixing gases, from respective gas sources through gas regulators 174, 1030a and 103b and gas flow chambers 172, 1028a and 1028b. The gas sources may be external to or onboard the system 1000. Gas pressure gauges, such as gauges 178, 1036a and 1036b, provide visual indication of the level of gas in the respective gas supplies 172, 1028a and 1028b. Transducers 132, 1032a and 1032b provide similar information to the controller 150. The controller is able to regulate automatically the gas flow from each gas source into the oxygenator 1042 in dependence, for example, on the perfusion fluid oxygen content measured at oxygenation/hematocrit sensor 1064, much like the sensor 140 described above. This sensor also provides a signal indicative of a hematocrit measurement of the perfusion fluid 108. Subsequent to the mixing of the selected gases with the perfusion fluid 108, the perfusion fluid 108 is pumped towards the lungs 1004 through the pulmonary artery interface 1022. In one exemplary embodiment, a mixing gas supplied to the oxygenator 1042 from a gas flow chamber is pre-mixed to include a desired gas composition for infusion into the perfusion fluid 108. One or more additional gas sources each containing, for example, a high level of oxygen, carbon dioxide or hydrogen, may be additionally supplied to the oxygenator 1042 from other gas flow chambers to modulate the composition of the mixing gas in the perfusion fluid 108. In another embodiment, gases having different compositions are controllably released from the appropriate gas chambers to the oxygenator 1042 at rates and volumes that allow the desired gas mixture composition to be obtained in the perfusion fluid 108. However, for certain perfusion modes, the oxygenator 1042 is not activated.

In certain practices, a flow rate sensor 1056, much like the flow rate sensor 134, is positioned along the arterial fluid flow from the oxygenator 1042 to the pulmonary artery interface 1022 to measure a flow rate of the fluid 108. A pressure sensor 1050, much like the pressure sensor 126 described above, is also positioned along the arterial fluid flow to measure the pressure of the perfusion fluid 108. This pressure sensor 1050 may be on an edge of the lung chamber assembly 1018 or inside of the assembly 1018 and as close as possible to a site of pulmonary artery cannulation. In certain embodiments, a port 1080 is provided for allowing an operator to extract samples of the perfusion fluid 108 along the arterial flow for further offline analysis.

The perfusion fluid 108 is then pumped into the lung chamber assembly 1018 and the lungs 1004 cannulated therein via the pulmonary artery interface 1022. The pulmonary artery interface 1022 includes cannulation to the main pulmonary artery 1005 through an aperture 1040a located on the lung chamber assembly 1018. The lungs 1004 may be ventilated with a gas mixture via the trachea interface 1024 that includes cannulation to the trachea 1006 (or a substitute conduit not shown) via an aperture 1040b located on the lung chamber assembly 1018. Alternatively, cannulation may be made to a portion of a trachea 1006 intact on the explanted lungs 1004. FIGS. 41-43 illustrate various approaches of ventilating the lungs 1004 through the tracheal interface 1024. These approaches are mode-specific for the maintenance mode approaches described above and as described below in further operational detail. In certain embodiments, the controller 150 is able to regulate a composition of gas components supplied to the lungs 1004 via the tracheal interface 1024 based on fractional inspired $O_2$ ($FiO_2$) concentration measurements and fractional expired $CO_2$ concentration measurements obtained at $FiO_2$ meter 1030 and $FiCO_2$ meter 1031, respectively. A flow rate sensor 1067 may also be used to measure the rate at which the lungs 1004 are ventilated via the tracheal interface 1024. A pressure sensor 1068 may be used to measure the pressure of the gas supplied to the lungs 1004 via the tracheal interface 1024. In certain embodiments, electrode sensors 1060 and 1062 are coupled to the lung chamber assembly 1018 to measure the weight and elasticity, respectively, of the explanted lungs 1004.

The perfusion fluid 108 is pumped out of the lung chamber assembly 1018 via the pulmonary vein interface 1026 that includes, in certain embodiments, a cannulation to the pulmonary veins 1007 through an aperture 1040c located on the lung chamber assembly 1018. In other embodiments, the pulmonary veins 1007 remain un-cannulated. In general, the pulmonary vein interface 1026 establishes a return path of the perfusion fluid 108 from the pulmonary veins 1007 to the reservoir 160 for continued circulation through the perfusion circuit. In addition, a fluid passageway 1084 is provided that connects the lung chamber assembly to the reservoir 160. Along a path of fluid flow from the pulmonary vein interface 1026 to the reservoir 160, one or more sensors can be positioned to provide measurements such as fluid flow rate via flow rate sensor 1058, fluid pressure via pressure sensor 1052, and fluid oxygenation and hematocrit via sensor 1066. The pressure sensor 1052 may be on an edge of the lung chamber assembly 1018 or inside of the assembly 1018 and as close as possible to the site of pulmonary vein cannulation. In certain embodiments, a port 1082 is provided for allowing the operator to extract samples of the perfusion fluid 108 along the venous flow. In certain embodiments, a flow clamp 1090, much like flow clamp 190 described above, is positioned along the path of fluid flow from the pulmonary vein interface 1026 to the reservoir 160 for regulating a back pressure applied to the pulmonary veins 1007 when the lungs 1004 are instrumented in the lung chamber assembly 1018.

Having described a generalized process for operating the system 1000, the system 1000 is next described in further detail with reference to individual modes. These modes include the evaluation mode and the maintenance mode, the latter of which can be implemented using the tracheal oxygen delivery approach or the isolated tracheal volume re-breathing approach, as described above with reference to FIGS. 37 and 38.

FIGS. 41 and 42 illustrate various embodiments of the single-used module 1002 configured for use with the isolated tracheal re-breathing approach. In particular, the first gas source, including a gas composition of about 3% to about 7% carbon dioxide, about 11% to about 14% oxygen, and the balance being nitrogen, is supplied to the gas exchange device (i.e., an oxygenator) 1042 for circulation through the perfusion system 1000. During perfusion, the perfusion fluid 108 is pumped into the lungs 1004 through the pulmonary artery interface 1022 and pumped away from the lungs 1004 through the pulmonary vein interface 1026. In addition, an isolated gas volume is delivered to the lungs 1004 during perfusion via the tracheal interface 1024 to ventilate the lungs 1004, as described above in FIG. 38. In one embodiment depicted in FIG. 41, the isolated gas volume is provided by a flexible bag 1069 that may contract and expand with each breath of the lungs 1004 during ex vivo care. In one embodiment depicted in FIG. 42, the constant gas volume is provided by a hose 1050 connected to a gas source 1052 such as a gas tank or a ventilator. The hose 1050 is appropriately configured to allow the lungs 1004 to inspire a constant gas volume during perfusion. In yet another embodiment, a specialized ventilator may be used to supply the constant gas volume to the lungs 1004.

FIG. 43 illustrates an embodiment of the single-use module 1002 configured for use with the tracheal oxygen delivery approach described above with reference to FIG. 37. The perfusion fluid 108 is oxygenated to a desired gas component level prior to perfusing the lungs 1004. This may be achieved by circulating the perfusion fluid 108 through the system 1000 before lung instrumentation and supplying the fluid 108 with an appropriate gas mixture through, for example, the oxygenator 1042. After the perfusion fluid 108 reaches a desired gas component level, the oxygenator 1042 is deactivated to stop the delivery of respiratory gas to the perfusion fluid 108. The oxygenated perfusion fluid 108 is subsequently stored in the reservoir 160 before organ perfusion begins.

During perfusion, the perfusion fluid 108 is pumped from the reservoir 160 to the heater assembly 110 and warmed to a near physiologic temperature before being supplied to the lungs 1004 in the lung chamber assembly via the pulmonary artery interface 1022. In the embodiment of FIG. 43, the lungs 1004 are ventilated with a continuous supply of a gas mixture from an external gas source through an inlet valve 1060 of the tracheal interface 1024. As described above, in one implementation the gas mixture includes a composition of about 14% oxygen, about 5% carbon dioxide, and the balance is nitrogen. The gas source may be a gas chamber 1062, such as gas chambers 172, 1028a and 1028b of FIG. 34, housed external to or onboard the system 1000. A gas pressure gauge 1064, such as gauges 178, 1036a and 1036b of FIG. 34, provide visual indication of the pressure of gas in the chamber 1062. During perfusion, the oxygen component in the gas mixture inhaled by the lungs 1004 through the inlet valve 1060 exchanges with the carbon dioxide component in the perfusion fluid 108 across the alveoli of the lungs 1004, and the carbon dioxide component is subsequently expelled from the alveoli in an exhaled breath via an outlet valve 1066 of the tracheal interface 1024. Both the inlet 1060 and the outlet 1066 valves are configured to prevent substantial mixing of gas components between the gas mixture flowing through each valve. The perfusion fluid 108 flows out of the lung chamber assembly 1018 via the pulmonary vein interface 1026.

Having described the system 1000 in relation to the maintenance mode, the system 1000 is next discussed with respect to the evaluation mode. As mentioned above, the perfusion fluid 108 in the reservoir 160 is allowed to reach a predetermined gas composition before tests are performed on the lungs 1004 to evaluate, for example, their gas-transfer capability. The pre-determined gas composition may be, for example, a physiologic venous blood-gas composition. This venous blood-gas composition in the perfusion fluid 108 may be achieved by applying a low-oxygen or oxygen-free gas mixture to the perfusion fluid 108 through the oxygenator 1042 after the perfusion fluid 108 flows out of the reservoir 160. Exemplary low-oxygen or oxygen-free gas mixtures include a mixture having about 4% to about 11% carbon dioxide, about 0% to about 8% oxygen, and the balance is nitrogen, a mixture having about 5% carbon dioxide, about 0% oxygen and the balance is nitrogen, and a mixture having about 5% carbon dioxide, about 5% oxygen, and the balance is nitrogen. The resulting perfusion fluid 108 is optionally passed through the heater assembly 110, pumped into the lungs 1004 via the pulmonary artery interface 1022, and flows away from the lungs 1004 via the pulmonary vein interface 1026, thereafter returning to the reservoir 160 for subsequent return through the circuit. In this manner, the perfusion fluid 108 is circulated in the system 1000 until a venous blood gas composition is reached in the perfusion fluid 108 flowing into and flowing away from the lungs 1004. After the perfusion fluid 108 reaches the desired venous gas composition, the oxygenator 1042 may be deactivated to stop the flow of low-oxygen or no-oxygen gas mixture to the perfusion fluid 108. The lungs 1004 are then ventilated with an oxygen-containing gas from an external source via the tracheal interface 1024. The gas-transfer capability of the lungs 1004 may thus be determined by monitoring the oxygen saturation or partial pressure of oxygen on the venous and arterial flows of the perfusion fluid 108 after ventilation begins.

Thus far, an exemplary system 1000 for lung maintenance has been described, along with a description of lung anatomical features that impact how the lungs 1004 are harvested and connected into the system 1000. In addition, exemplary techniques have been described for maintaining lungs 1004 ex vivo during a maintenance mode of operation. Exemplary techniques have also been described for evaluating lungs 1004 to ascertain their functionality and suitability for transplantation during the evaluation mode. Moreover, exemplary features of the system 1000 have been described in detail in relation to the various modes. Next, additional exemplary features of the system 1000 are discussed, including the lung chamber assembly 1018, the pulmonary vein interface 1026, system controls, and data acquisition and display modules. An exemplary transplantation procedure is then described, along with a description of exemplary solutions that are used in the perfusion circuit to care for the lungs 1004.

Various embodiments of the lung chamber assembly 1018 are described with reference to FIGS. 44-47. As depicted, the lung chamber assembly 1018 may be rectangular in shape to house a pair of explanted lungs 1004. Alternatively, the lung chamber assembly 1018 may be triangular in shape to accommodate a single explanted lung 1004. With brief reference to FIGS. 41-43, the lung chamber assembly 1018 includes apertures 1040a-1040c adapted to receive the pulmonary artery interface 1022, the trachea interface 1024 and the pulmonary vein interface 1026. Overall, the structure and material composition of the lung chamber assembly 1018 closely resembles the organ chamber assembly 104 for the containment of a heart described above and depicted in FIGS. 5A-5F, but expanded to a size sufficient to house a pair of lungs 1004. Particularly, the explanted lungs 1004 may be contained in either a soft or hard shell casing in the lung chamber assembly 1018. In certain embodiments, the assembly 1018 lies flat. In other embodiments, the assembly 1018 is tilted at an adjustable angle such that the explanted lungs 1004 lie at the same angle therein.

Figure 45:
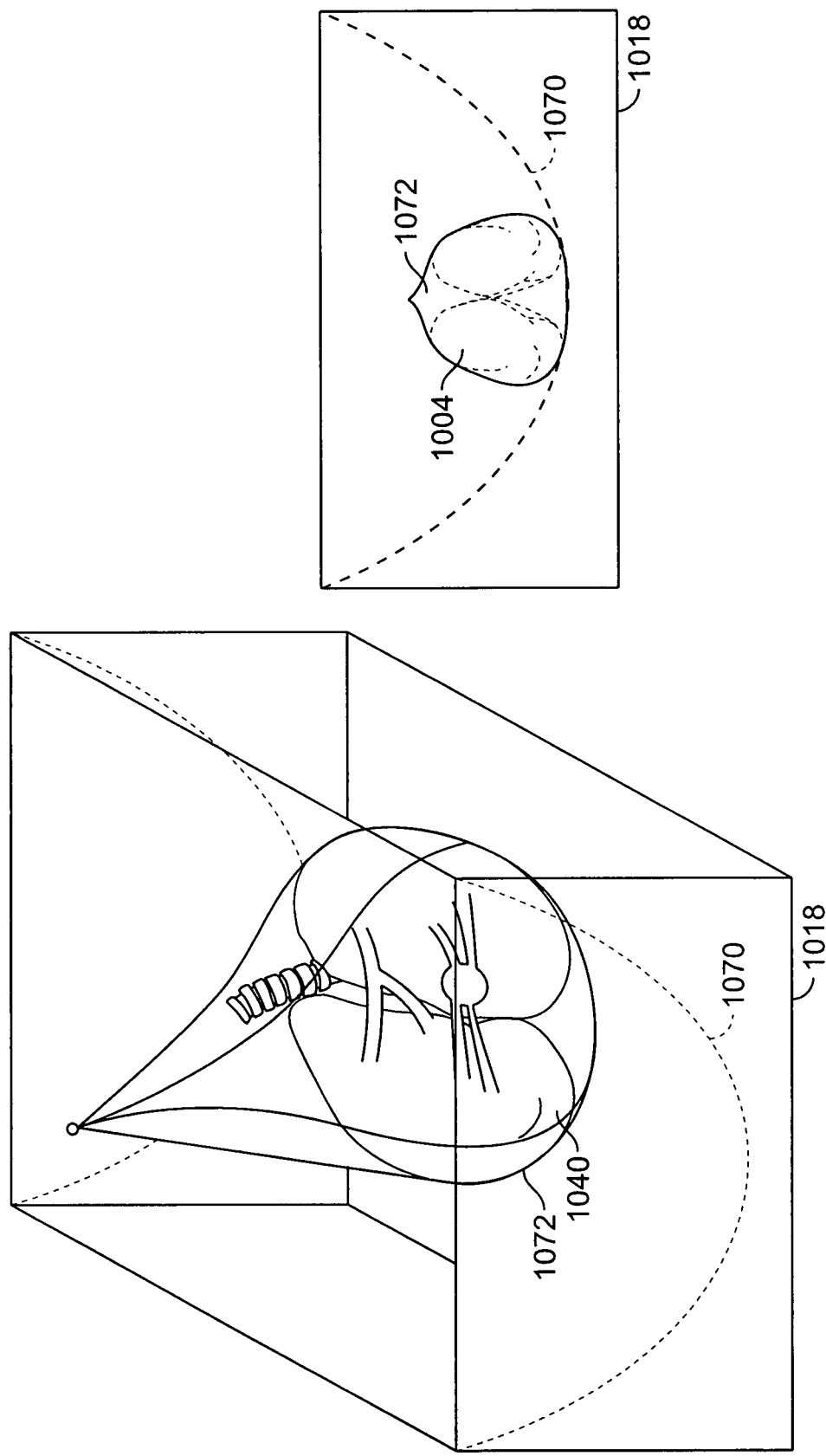
FIG. 45 depicts a top view and a profile view of another exemplary lung chamber assembly employed in the illustrative single use disposable module of FIGS. 41-43.

The shell casing of the lung chamber assembly 1018 may include a suspension mechanism to provide support and stability to the lungs 1004. Exemplary suspension mechanisms are depicted in FIGS. 44-47. In one illustrative embodiment of the lung chamber assembly 1018 shown in FIG. 44, a flexible membrane (e.g., a netting, fabric, cloth or other suitably flexible material) is used to suspend the explanted lungs 1004 in the lung chamber assembly 1018 so as to minimize contact between a surface of the lungs 1004 and one or more inner walls of the lung chamber assembly 1018. The membrane contacts a large portion of the surface of the lung to support the lung's weight in a manner that distributes the weight across the membrane, thereby reducing the pressure on any particular region of the lungs 1004 and avoiding alveolar damage. The flexible membrane 1070 in the depicted embodiment is a netting structure. The netting structure 1070 may be meshed or porous and may substantially prevent alveoli in at least a portion of the lungs 1004 from collapsing while being held in the assembly 1018 for ex vivo maintenance. In an alternative embodiment of the lung chamber assembly 1018 as illustrated in FIG. 45, the lungs 1004 may be additionally or alternatively contained in a second netting 1072 that suspends the lungs 1004 from a top cover of or other structures within the assembly 1018. This second netting 1072 simulates the effects a ribcage has on the lungs 1004 by preventing the lungs 1004 from over expanding during respiration while maintaining their physiologic shape. The second netting 1072 may be constructed from the same material as the first netting 1070 or may be constructed from a substantially different material.

Figure 47:
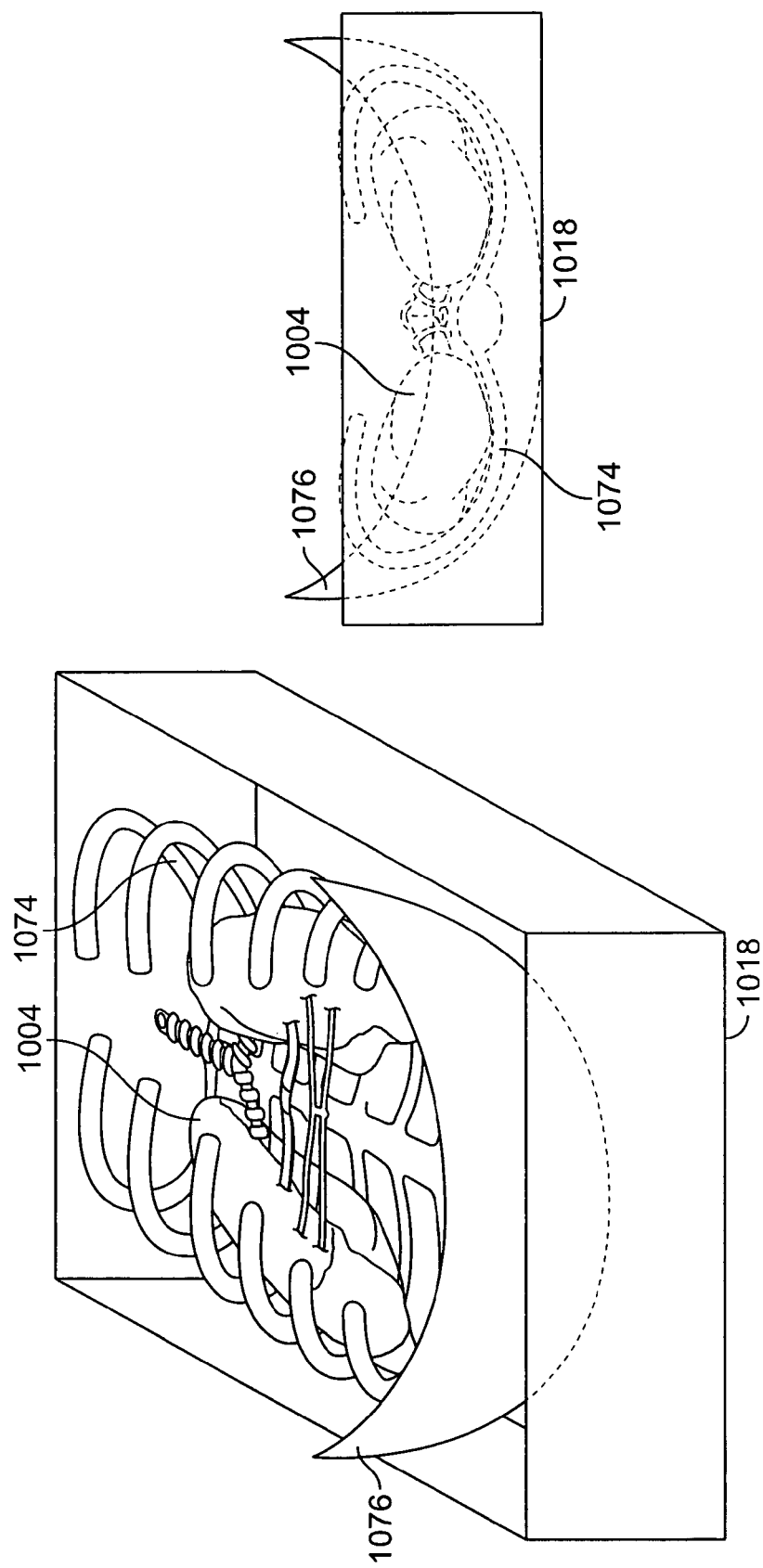
FIG. 47 depicts a top view and a profile view of yet another exemplary lung chamber assembly employed in the illustrative single use disposable module of FIGS. 41-43.

In certain embodiments, there is a support structure for the lungs that simulates the interior of the chest cavity, supporting the lungs on anterior and posterior sides, and helping the lungs to maintain their physiologic shape. For example, in an illustrative embodiment of the lung chamber assembly 1018 as shown in FIG. 46, a ribcage-shaped housing 1074 is used to hold the explanted lungs 1004 in the lung chamber assembly 1018. This ribcage-shaped housing 1074, constructed from a flexible material, simulates the shape and movement of a real ribcage. In certain implementations as depicted in FIG. 47, a feature 1076 similar to a body's diaphragm is coupled to the ribcage-shaped housing 1074 (refer to the ribcage cut away in FIG. 47 for better view) by extending across a bottom portion of the housing 1074. This diaphragm 1076 may also be constructed from a flexible material so that it may contract and relax with each respiration of the lungs 1004.

Having described specific features of the lung chamber assembly 1018, exemplary features of the pulmonary vein interface 1026 are described next with reference to FIGS. 48-51. More specifically, FIGS. 48-51 illustrate various embodiments of connecting the pulmonary veins 1007 in the system 1000 at the pulmonary vein interface 1026 as illustrated above with reference to FIGS. 41-43. In certain embodiments the veins 1007 are cannulated at the interface 1026. However, the pulmonary veins 1007 may remain uncannulated, such that fluid flowing away from the pulmonary veins 1007 freely drains into the lung chamber assembly 1018 and returns to the reservoir 160 through passageway 1084, as depicted in the system of FIGS. 41-43.

Figure 48A:
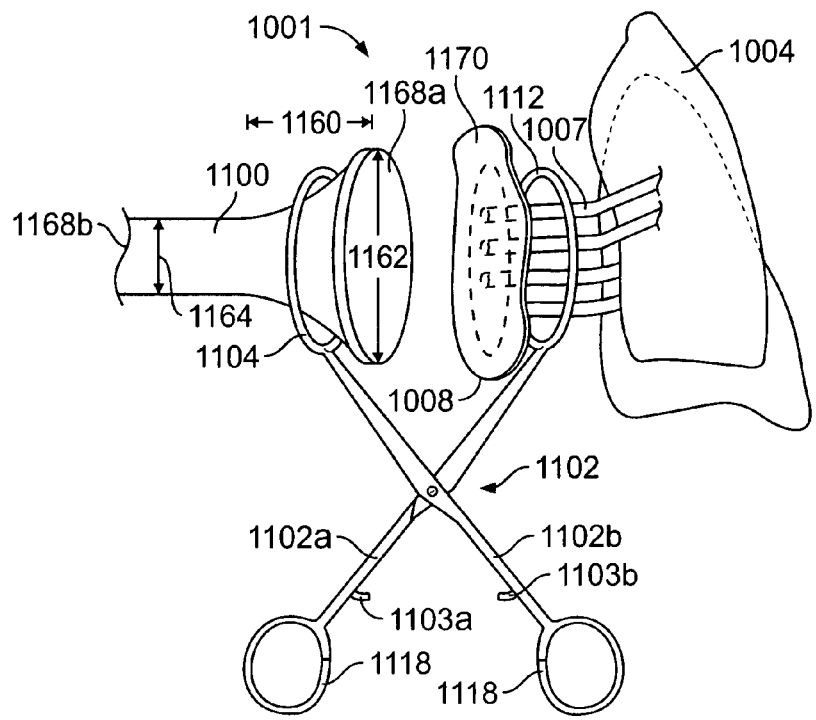
FIG. 48A and FIG. 48B show various views of an exemplary connector device used for cannulating the pair of harvested lungs of FIG. 35A.

FIGS. 48A*a* and 48B depict an exemplary apparatus for cannulation at the pulmonary vein interface 1026 of FIGS. 41-43. As illustrated, the cannulation device 1001 includes a funnel-shaped cannula 1100 having proximal 1168*a* and distal 1168*b* ends and a connector device 1102 having legs 1102*a* and 1102*b*. Using the connector device 1102, an operator mates the cannula 1100 with the donor's excised left atrial cuff 1008 having all of the donor's pulmonary veins 1007 confluently attached. As the donor's pulmonary veins 1007 also attach to the donor's lungs 1004, the mating of the cannula 1100 with the cuff 1008 secures such cuff 1008, veins 1007 and lungs 1004 within the system 1000.

Figure 48B:
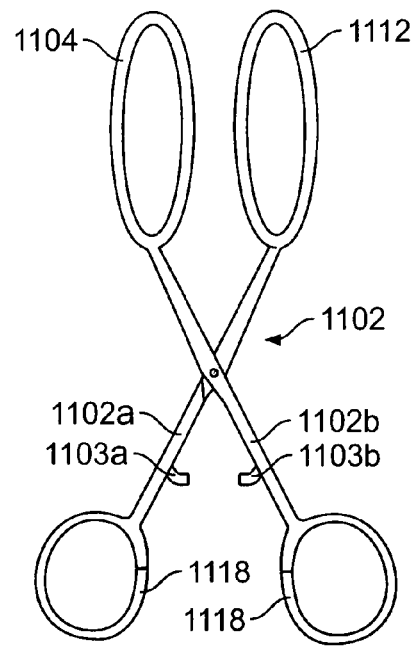

As illustrated in FIG. 48B, the connector device 1102 includes connection surfaces 1104 and 1112 that are used to form the mating interface between the cuff 1008 and the cannula 1100. As shown, the surfaces 1104 and 1112 are each configured as a ring with a hollow center and attached to respective legs 1102a and 1102b. The ring 1104 is larger than a cross-section 1164 of the distal end 1168b of the cannula 1100 but smaller than a cross-section 1162 of the proximal end 1168a of the cannula 1100 so that the ring 1104 can be secured behind the funneled portion 1160 of the cannula 1100. In addition, the ring 1112 is configured to be small enough in comparison to the size of the left atrial cuff 1008 such that the cuff 1008 cannot easily be pulled out of the ring 1112 after the cuff 1008 has been pushed through the ring 1112.

When operating the cannulation device 1001 according to the illustrative embodiment, the ring 1104 is inserted on the distal end 1168b of the cannula 1100 and slides through the length of the cannula 1100 until the ring 1104 abuts and optionally tightly encircles a section of the cannula 1100. The excised left atrial cuff 1008 is then pushed through the ring 1112, leaving a portion 1170 of the cuff 1008 extending beyond the perimeter of the ring 1112. An operator then compresses the handles 1118 of the connector device 1102 until the left atrial cuff 1008 mates with the funneled opening at the proximal end 1168a of the cannula 1100 so that locking mechanism 1103a and 1103b engage each other to keep the connector device 1102 secured. The cannula 1100 is suitably configured such that the funnel portion 1160 of the cannula 1100 is able to receive and engage the left atrial cuff 1008. In certain embodiments, the cannula 1100 is malleable to allow it to be bent as needed to secure the lungs 1004 and inter-fit with the system 1000. A cannula 1100 is malleable, in general, if it is able to bend but maintain a generally consistent cross-sectional diameter regardless of how severely it is bent. In certain embodiments, appropriately sized cannulas and connector devices are provided to accommodate excised left atrial cuff of various sizes.

After engaging the cuff 1008, the legs 1102a and 1102b are locked in place by the locking mechanism 1103a and 1103b or other suitable mechanisms to hold the connector device 1102 at the compressed position.

Figure 49A:
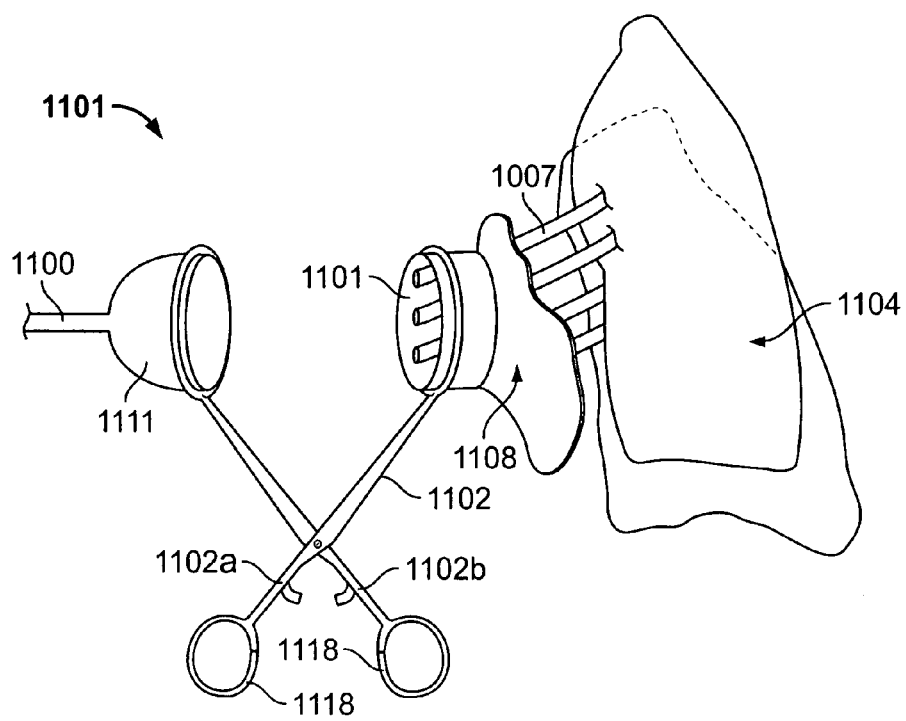
FIG. 49A and FIG. 49B show various views of another exemplary connector device used for cannulating the pair of harvested lungs of FIG. 35A.
Figure 49B:
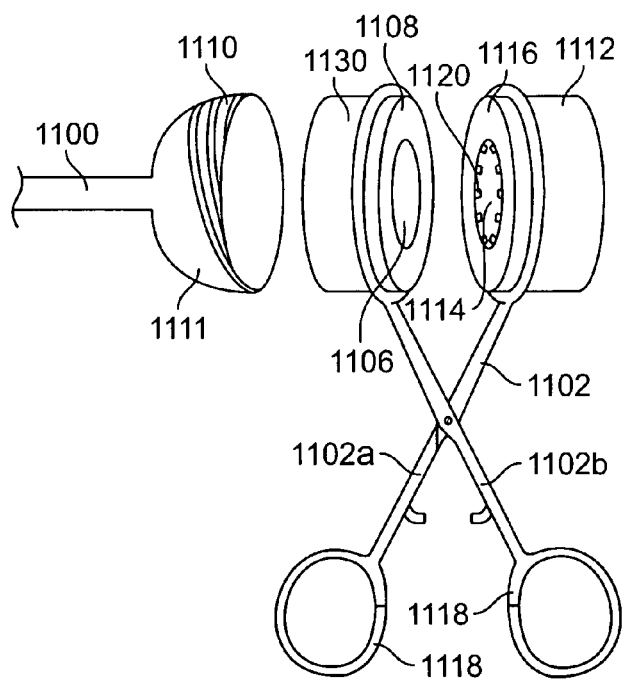

FIGS. 49A and 49B depict another embodiment of the apparatus for cannulation at the pulmonary vein interface 1026. This apparatus is also designed for use with a single piece of excised left atrial cuff having all four of the donor's pulmonary veins 1007 confluently attached. As shown in FIG. 49A, the connector device 1102 includes a first connection surface 1130 configured as a ring with a first inner peripheral surface 1106 and a first outer O-ring seal 1108. The first inner peripheral surface 1106 includes threads (not shown) that interlock with the outwardly extending grooves 1110 projecting from the funnel-shaped cannula's outer peripheral surface 1111. Consequently, the cannula 1100 is coaxially coupled to the ring 1130. The connector device 1102 also includes a second connection surface 1112 configured as a ring with a second inner peripheral surface 1114 and a second outer O-ring seal 1116. In one embodiment as depicted in FIG. 49B, projections 1120 are regularly spaced around the circumference of the inner peripheral surface 1114 to firmly engage a portion 1101 of the left atrial cuff 1008 to the ring 1112 when the cuff 1008 is pushed through the ring 1112. Other suitable mechanisms may be used to provide the same tissue-securing function. It is noted that the size of the second O-ring seal 1116 may be small enough in comparison to the size of the left atrial cuff 1008 such that the portion 1101 of the cuff 1008 securely rests within the O-ring seal 1116. In turn, the cannula 1100 and the first O-ring seal 1108 are accordingly configured such that when the first 1108 and second 1116 O-ring seals mate, a fluid tight seal is formed around the cannula 1100 and the portion 1101 of the left atrial cuff 1008. In certain embodiments, appropriately sized cannulas and connector devices are provided to accommodate excised left atrial cuff of various sizes.

When operating the cannulation device 1001, the ring 1130 is screwed to the outer peripheral surface 1111 of the cannula 1100 via the grooves 1110 until tight. A portion 1101 of the excised left atrial cuff 1008 is then pushed through the second inner peripheral surface 1114 of the second ring 1112 until the portion 1101 is securely fitted within the seal 1116. An operator then pushes together the handles 1118 of the connector device 1102 until the first 1108 and second 1116 O-ring seals mate to provide a seal around the cannula 1100 and the left atrial cuff 1008. The legs 1102a and 1102b are then locked in place by a locking pin (not shown) or other suitable mechanisms such as the locking mechanism 1103a and 1103b of FIG. 48. In certain embodiments, to break the seal around the cannula 1100 and the left atrial cuff 1008, the operator releases the locking pin (not shown) followed by pulling apart the handles 1118 of the connector device 1102 until the first 1108 and second 116 O-ring seals separate.

Figure 50A:
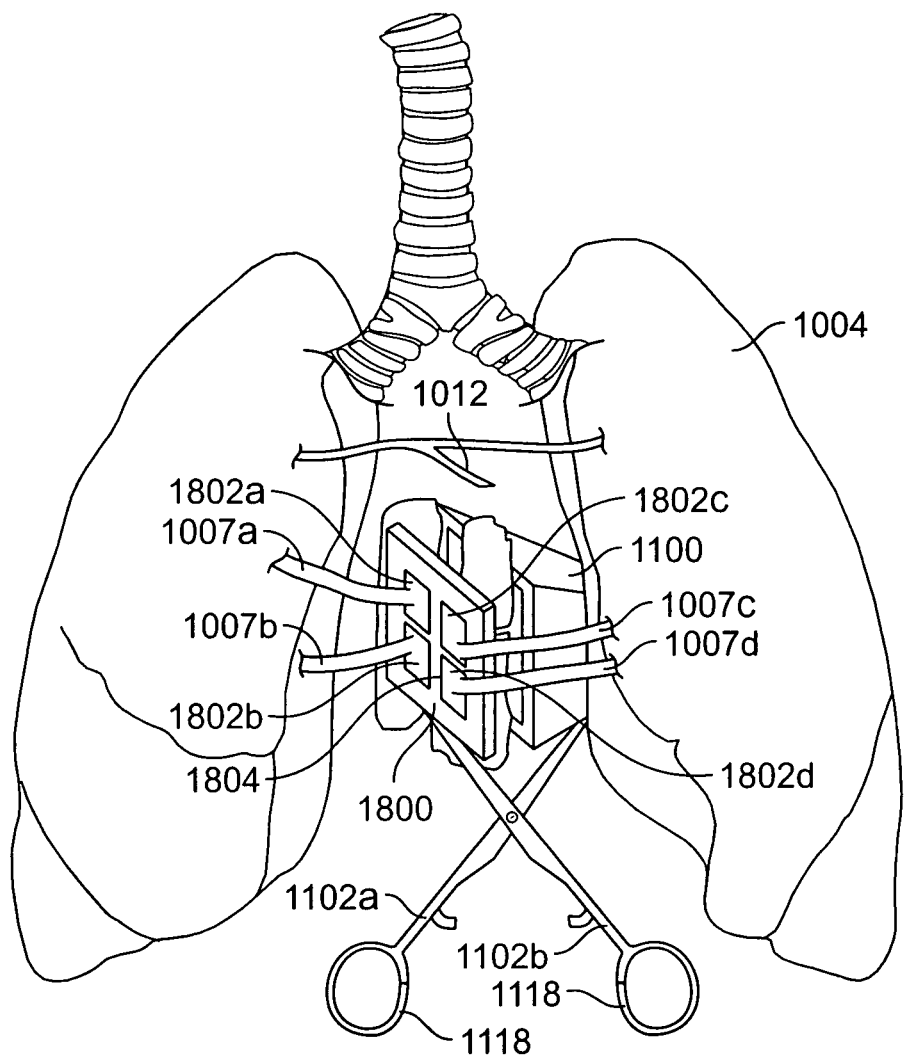
FIG. 50A and FIG. 50B show various views of yet another exemplary connector device used for cannulating the pair of harvested lungs of FIG. 35A.
Figure 50B:
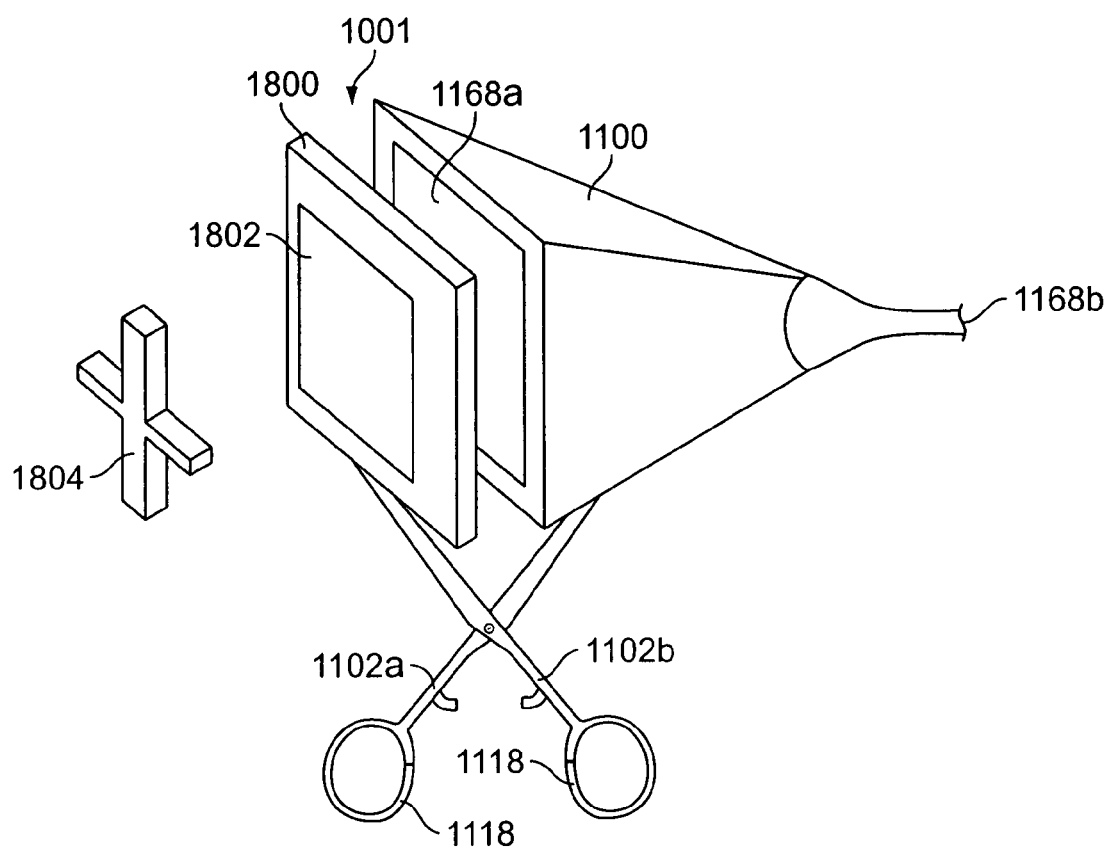

FIGS. 50A and 50B depict yet another embodiment of the apparatus for cannulation at the pulmonary vein interface 1026. This apparatus is designed for use with the donor's left atrial cuff 1008 that is attached to the four pulmonary veins 1007 of the donor. As illustrated 50B, the cannulation device 1001 includes a funnel-shaped cannula 1100 having a proximal end 1168a, a connection surface 1800, a stopper 1804, and legs 1102a and 1102b attached to the cannula 1100 and the connection surface 1800, respectively.

In certain embodiments, the proximal end 1168a of the cannula 1100 and the connection surface 1800 are configured to form a mating surface when the handles 1118 of the cannulation device 1001 are in a compressed position and the stopper 1804 inter-fits within a center perforation 1802 of the connection surface 1800. More specifically, the connection surface 1800 is configured as a square structure having a square perforation 1802 etched through a center portion of the connection surface 1800. The stopper 1804 is adapted to inter-fit within the square perforation 1802 such that the square perforation 1802 is divided into four smaller square perforations 1802a-d. A cross-section of the proximal end 1168a of the cannula 1100 is also square in shape and is similarly sized as a cross-section of the connection surface 1800. In addition, the size of each the smaller square perforations 1802a-d is small enough in comparison to the size of the left atrial cuff 1008 that the cuff 1008 cannot easily be pulled out of the perforations 1802a-d after the cuff 1008 has been pushed through the large perforation 1802 and secured into place by the stopper 1804.

When operating the cannulation device 1001 according to the illustrative embodiment, the excised left atrial cuff 1008 is pushed through the large center perforation 1802 of the connection surface 1800, leaving a portion of the cuff 1008 extending beyond a perimeter of the perforation 1802. An operator then inter-fits the stopper 1804 into the center perforation 1802 to secure the cuff 1800 to the connection surface 1800. The operator then compresses the handles 1118 of the cannulation device 1001 until the left atrial cuff 1008 mates with the funneled opening at the proximal end 1168a of the cannula 1100. The cannula 1100 is suitably configured such that it is able to receive and engage all the left atrial cuff 1008 secured to the connection surface 1800. In certain embodiments, the cannula 100 is malleable to allow it to be bent as needed to further secure the lungs 1004 and inter-fit with the system 1000.

After engaging all the left atrial cuff 1008 to the cannula 1100, the legs 1102a and 1102b are locked in place by a locking pin (not shown) or other suitable mechanisms to hold the connector device 1102 at the compressed position.

Referring again to FIGS. 48-50B, in certain instances, a cross-section of a proximal opening 1168a of a cannula 1100 may be larger in size than a cross-section of the left atrial cuff 1008 cannulated to the cannula 1100. This configuration allows a portion of the perfusion fluid 108 flowing through the pulmonary veins 1007 to drain into the lung chamber assembly 1018 instead of flowing into the cannula 1100. In certain instances, the mating interface between the cannula 1100 and the left atrial cuff 1008 is configured to be semi-sealable so that at least a portion of the perfusion fluid 108 flowing from the pulmonary veins 1007 to the cannula 1100 is able to leak into the lung chamber assembly 1018. In certain instances, the cannula 1100 is situated in the lung chamber assembly 1018 in a relatively upright position in relation the left atrial cuff 1008 such that the perfusion fluid 108 flows in an upward direction from the left atrial cuff 1008 to the cannula 1100. Due to the semi-sealable mating interface formed between the cannula 1100 and the left atrial cuff 1008, a portion of the perfusion fluid 108 is adapted to seep out of the mating interface and drain into the lung chamber assembly 1018. A back pressure is subsequently created by the perfusion fluid 108 in the cannula 1100. In one example, this back pressure is created by a column of perfusion fluid 108 in the cannula 1100 that is between about 1 cm to about 3 cm high.

Figure 51A:
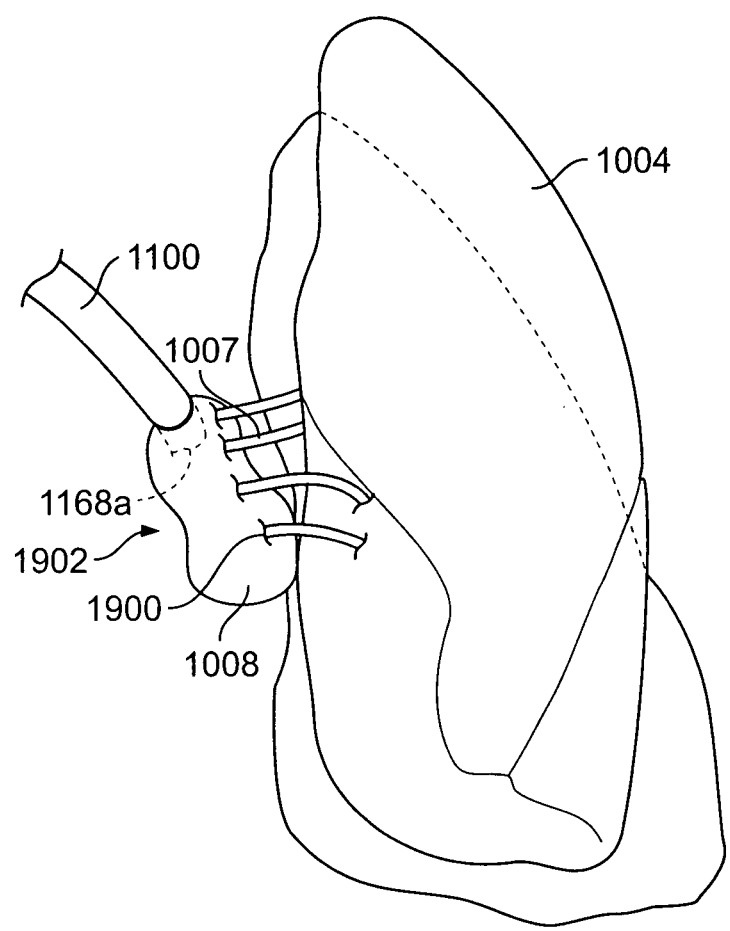
FIG. 51A depicts an illustrative arrangement for cannulating the pair of harvested lungs of FIG. 35A.

FIG. 51A illustrates another embodiment of connection (e.g., by cannulation) at the pulmonary vein interface 1026. An excised left atrial cuff 1008, having one or more pulmonary veins 1007 attached thereto, is folded upon itself and sealed at a seam 1900 to form a pocket interface 1902. In particular, the left atrial cuff 1008 is folded in a manner such that the pulmonary veins 1007 are fluidly connected to a void interior region defined by the pocket interface 1902. In addition, a proximal end 1168a of a cannula 1100 is sealed within the pocket 1902 such that that the proximal opening 1168a of the cannula 1100 is also fluidly connected to the void region of the pocket interface 1902. This two-way connection between the pulmonary veins 1007 and the cannula 1100 via the pocket interface 1902 is adapted to conduct the perfusion fluid 108 away from the lungs 1004 during perfusion. The pocket interface 1902 may be surgically sewn or stapled together. In certain embodiments, the pocket interface 1902 is relatively leak proof so that almost all of the fluid 108 flowing through the pulmonary veins 1007 are conducted to the proximal opening 1168a of the cannula 1100. In certain embodiments, the pocket interface 1902 is designed to allow a certain amount of the fluid 108 to drain into the lung chamber assembly 1018 instead of flowing into the cannula 1100. This leaked-through fluid 108 may be returned to the reservoir 160 via the passageway 1084 that connects the lung chamber assembly 1018 to the reservoir 160.

Figure 51B:
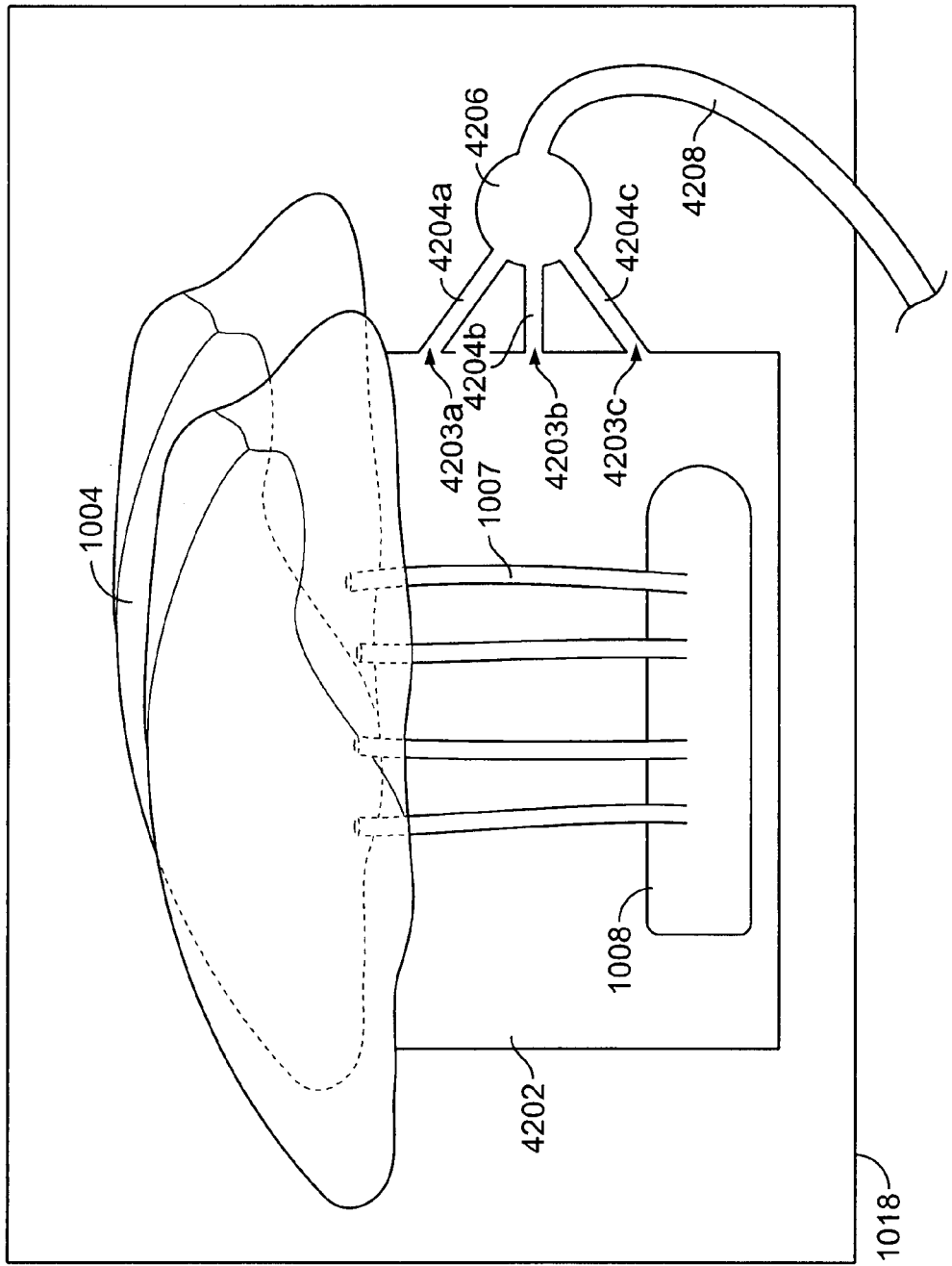
FIG. 51B depicts an exemplary cup-shaped interface according to an embodiment of the invention.

FIG. 51B illustrates yet another embodiment of connection (e.g., by cannulation) at the pulmonary vein interface 1026. An excised left atrial cuff 1008 is lowered into a cup-shaped interface 4202 from a top opening 4210 (not shown) of the cup-shaped interface 4202 that is located inside of the lung chamber assembly 1018. In an exemplary embodiment, a size of the top opening 4210 is less than the size of the explanted lungs 1004, but is small enough to allow the left atrial cuff 1008 to be lowered comfortably into the interface 4202. The cup-shaped interface 4202 also includes openings 4203a-c situated at varying heights along a sidewall of the interface 4202 and in fluid communication with a selector valve 4206 via conduits 4204a-c, respectively. The selector valve 4206 is additionally coupled to an outlet conduit 4208 that is adapted to conduct perfusion fluid 108 away from the lung chamber assembly 1018 and into the reservoir 160. In certain instances, the selector valve 4206 is manually or electromechanically controlled by controller 150 and/or user interface 146 to perform selective and controlled dispensing of the perfusion fluid 108 from the cup-shaped interface 4202 through a selected one of the openings 4203a-c and into the outlet conduit 4208. Hence, the selector valve 4206 may be used to maintain a desired level of perfusion fluid 108 in the cup-shaped interface 4202. In operation, as perfusion fluid 108 exits from the pulmonary veins 1007 via the left atrial cuff 1008, it collects into the cup-shaped interface 4204 until the height of the perfusion fluid 108 within the interface 4202 reaches one of the openings 4203a-c as set by the selector valve 4206. The fluid 108 then exists the cup-shaped interface 4202 via the selected opening, flows through the corresponding conduit, enters the selector valve 4206 and ported away from the lung chamber assembly 1018 via the outlet conduit 4208. Hence, the perfusion fluid 108 is able to fill the cup-shaped interface 4202 to a height where the selected one of the openings 4203a-c is located in order to create a desired level of back pressure on the pulmonary veins 1007.

Having described specific features of the lung chamber assembly 1018 and exemplary processes for cannulation at the pulmonary vein interface 1026, details regarding the data acquisition and display modules of the system 1000 are described next.

Figure 12:
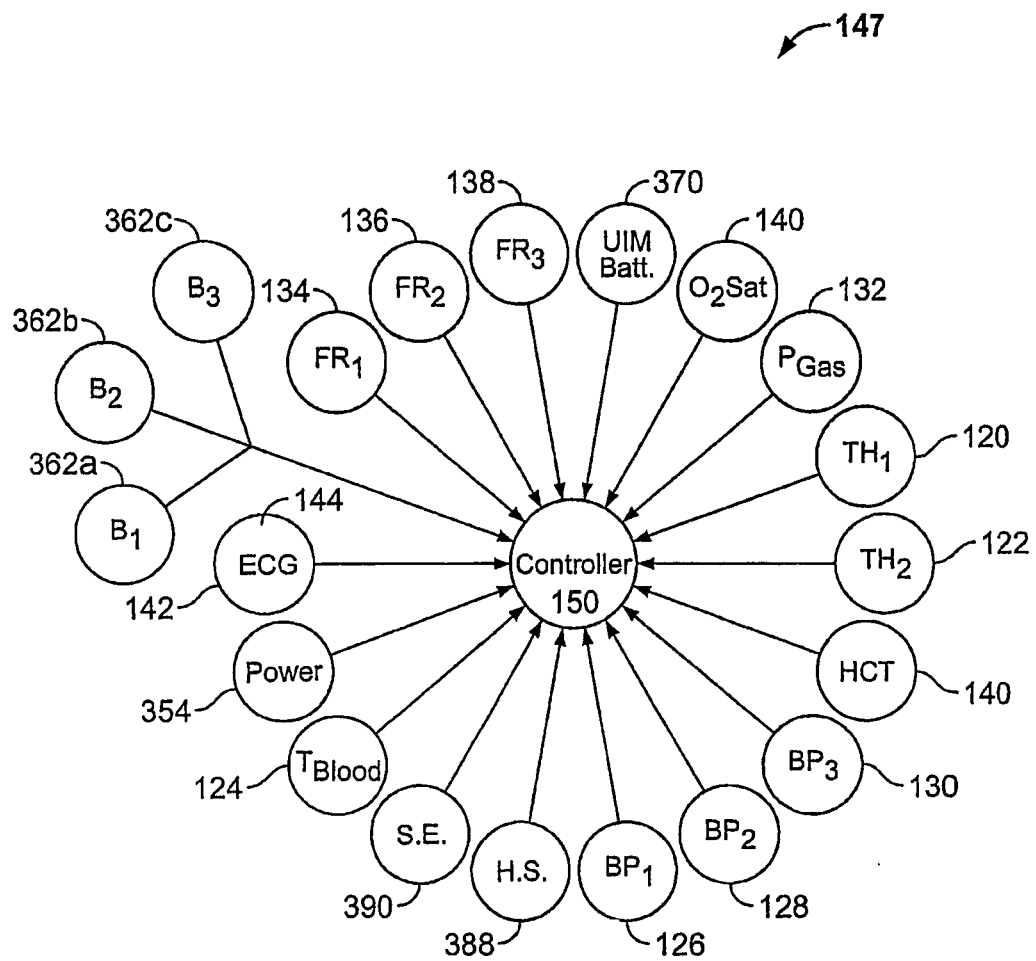
FIG. 12 is a block diagram of an exemplary data acquisition subsystem of the type that may be employed with an the illustrative organ care system of FIG. 1.

In one aspect, the illustrative control system scheme depicted in the block diagram of FIG. 11 is used for operating the system 1000 to care for the explanted lungs 1004. Each subsystem depicted in the functional blocks of FIG. 11 is particularly configured to maintain the lungs 1004 in an optimally viable state at or near physiologic conditions. More specifically, the data acquisition subsystem 147, as illustrated in the block diagram of FIG. 12, is modified to include sensors for obtaining information pertaining to the function of system 1000 and the lungs 1004, and for communicating the information to the controller 150 for processing and use by the system 1000. As described above with reference to FIGS. 41-43, the sensors used in the system 1000 include pressure sensors 1050, 1052 and 1068, flow rate sensors 1056, 1058 and 1067, oxygen/hematocrit sensors 1064 and 1066, $FiO_2$ and $FiCO_2$ concentration meters 1030 and 1031, weight sensor 1060, and elasticity sensor 1062. Some of the sensors utilized by the system 100 may also be utilized by the system 1000. These sensors include the temperature sensors 120, 122 and 124, the set of Hall sensors 388 and shaft encoder sensor 390 from the perfusion pump assembly 106, the battery sensors 352a-352c, the external power available sensor 354 and the operator interface module battery sensor 370.

Figure 52:
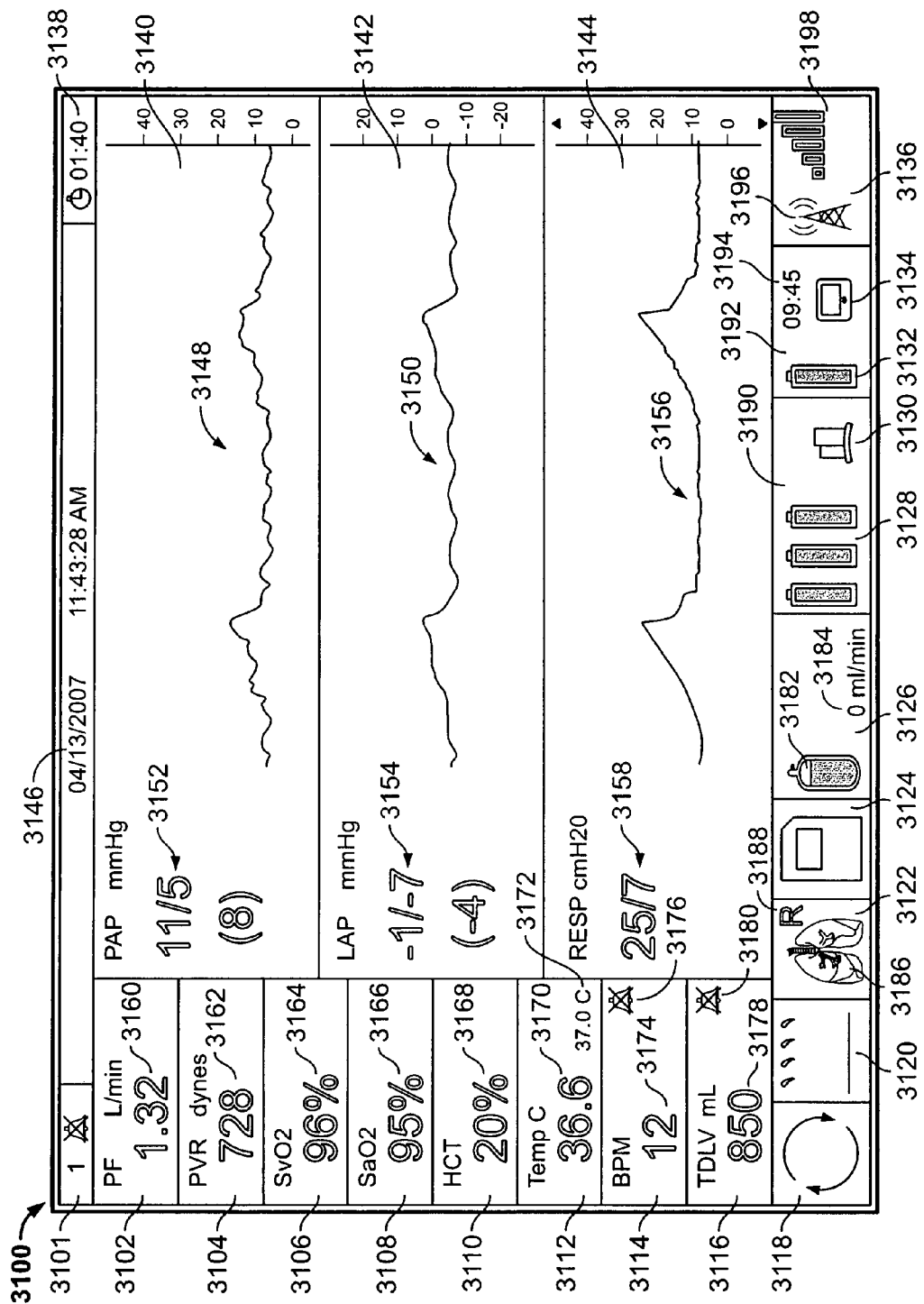
FIG. 52 depicts an illustrative screen for real-time displaying and plotting of data collected from the lung care system of FIG. 34.

The information obtained by the various sensors in the data acquisition subsystem 147 is transmitted to the controller 150 and displayed via the operator interface subsystem 146. The operator interface subsystem 146 includes a display screen 3100, as depicted in FIG. 52, that shows a number of numerical and graphical indications pertaining to the care of lungs 1004. In particular, the display screen 3100 includes a display area 3140 showing a waveform depiction 3148 of the pulmonary arterial pressure (PAP). The display area 3140 also includes a numerical display 3152 of a PAP reading, as measured by the pressure sensor 1050. Display area 3142 of the display screen 3100 shows a waveform depiction 3150 of the left atrial or pulmonary venous pressure (LAP) and a reading 3154 of the LAP, as measured by the pressure sensor 1052. Display area 3144 includes a waveform depiction 3156 of the respiration-ventilation pressure through the tracheal interface 1024 (RESP) and a reading 3158 of the RESP, as measured by the pressure sensor 1068. In certain embodiments, the displayed PAP, LAP and RESP values are instantaneous readings. In certain embodiments, the PAP and LAP values are displayed as an average, a mean or a minimum of instantaneous readings collected over a time period that is less than 30 seconds, less than 20 seconds, or less than 10 seconds. In certain embodiments, the RESP value is displayed as an average or a minimum of instantaneous readings collected over a time period that is less than 30 seconds, less than 20 seconds, or less than 10 seconds. In addition, the waveforms 3148, 3150, and 3156 are displayed on a real-time basis or a periodic basis with each batch of data collected.

The display screen 3100 further includes a number of additional display areas 3102, 3104, 3106, 3108, 3110, 3112, 3114, and 3116. The display area 3102 shows a numerical reading 3160 of the pulmonary flow (PF) of the perfusion fluid 108 into the lungs 1004 via the pulmonary artery interface 1022, as measured by the flow rate sensor 1056. The display area 3104 shows a numerical value 3162 representative of pulmonary vascular resistance (PVR). The PVR value 3162 indicates the amount of resistance the lungs 1004 exert to a flow of the perfusion fluid 108 and is calculated by subtracting a LAP value, such as the LAP reading 3154, from a PAP value, such as the PAP reading 3152, divided by a PF value, such as the PF reading 3160 and applying a unit conversion factor. In general, a lower PVR value 3162 is preferable because it indicates a less restricted flow of the perfusion fluid 108 through the vasculature of the lungs 1004. In certain embodiments, favorable values of the PVR is in a range between about 200 dynes to about 400 dynes. The display area 3106 shows the venous oxygen saturation (SvO$_2$) 3164 of the perfusion fluid 108, as measured from the oxygen/hemacorit sensor 1066. Similarly, the display area 3108 shows the arterial oxygen saturation (SaO$_2$) 3166 of the perfusion fluid 108, as measured from the oxygen/hemacorit sensor 1064. In certain embodiments, the display areas 3106 and 3108 additionally include a SvO$_2$ alarm and a SaO$_2$ alarm, respectively, for signaling the operator if each oxygen saturation value falls below an operator preset threshold. Such alarm may be implemented for any parameter measured, calculated or displayed. The display area 3110 includes a numerical reading 3168 of the hematocrit (HCT) of the perfusion fluid 108 and, optionally, an HCT alarm indicator for signaling the operator if the HCT 3168 falls below an operator preset threshold. The display area 3112 indicates the temperature (Temp) 3170 of the perfusion fluid 108 as it flows away from the heater assembly 110. The display area 3112 may also include a Temp alarm indicator which signals in response to the Temp 3170 being outside of an operator preset range. A temperature set point 3172 selected by the operator is also shown in the display area 3112. The display area 3114 shows a numerical reading 3174 of the ventilation rate measured as breaths per minute (BPM) of a gas delivered to the lungs 1004 via the tracheal interface 1024. A BPM reading may be ascertained from a flow sensor, communicated from a respirator, or obtained from a pressure sensor, such as pressure sensor 1068. The BPM value 3174 may be measured at the flow rate sensor 1067. In addition, the display area 3114 includes a BPM alarm indicator 3176 signaling if the BPM value 3174 is outside of an operator preset range. The display area 3116 includes a numerical display 3178 of tidal volume (TDLV) of a gas flow into the lungs 1004 with each breath of the lungs 1004 and a TDLV alarm indicator 3180 signaling if the TDLV value 3178 is outside of an operator preset range.

The display screen 3100 further includes a circulatory pump indicator 3118 showing a status of the system's circulatory pump, a perfusion fluid warmer indicator 3120 showing a status of the perfusion fluid heater assembly 110, and an SD card indicator 3124 showing whether an SD card is used to store data collected during organ perfusion. A display area 3126 is provided that includes a gas tank image 3182 graphically indicating a remaining gas volume in a gas supply connected to the system 1000. The display area 3126 also includes one or more numerical displays 3184 indicating a flow rate of the gas in the gas supply along with the time remaining for which the gas is delivered to the lungs 1004 during perfusion. This remaining time may be calculated based on the remaining gas volume and the gas flow rate. Display area 3122 shows an organ type indicator 3186 that indicates which organ is being perfused and an organ mode indicator 3188 that indicates what mode of operation is being used to perfuse the organ. For example, an "R" is used to indicate a maintenance mode of operation. Display area 3190 shows a graphical representation 3128 of the degree to which each of the batteries 352a-352c of the multi-use module 650 is charged. Battery status symbol 3130 indicates that the batteries 352a-352c, whose status are represented by graphical representation 3128, are used to power the multi-use module 650. The display area 3146 may also provide a numerical indication of the amount of time remaining for which the batteries 352a-352c can continue to run the system 1000 in the current mode of operation. Display area 3192 shows a graphical representation 3132 of the degree to which the user interface battery 368 is charged and a numerical indication 3194 of the amount of time remaining for which the user interface battery 368 can continue to run the user interface module 146. A battery status symbol 3134 indicates that the user interface battery 368, whose status is represented by the graphical representation 3132, is used to power the user interface 146. Display area 3136 identifies whether the operator interface module 146 is operating in a wireless fashion 3196, along with a graphical representation 3198 of the quality of the wireless connection between the operator interface module 146 and the remainder of the system 1000. The display screen 3100 also includes an alarm image 3101 indicating whether any parameter of the system 1000 is outside of a preset operator threshold for that parameter (the alarm 3101 is shown as "off" in FIG. 52) or communicating a system-related alarm message. The display screen 3100 further includes a display area 3146 showing a time and date of system operation and a display area 3138 showing the amount of time elapsed since perfusion begins.

In other embodiments, the display screen 3100 also shows FiO$_2$ and FiCO$_2$ concentrations, which are fractional concentrations of oxygen and carbon dioxide, respectively, measured via sensors 1030 and 1031 across the trachea interface 1024. Moreover, the display screen 3100 can additionally show readings of weight and elasticity of the lungs 1004, PH of the perfusion fluid 108 circulating through the lungs 1004, partial pressures of gas components in the perfusion fluid, and positive end expiratory pressures (PEEP) of the lungs 1004 which indicate the pressure in the lungs 1004 at the end of an exhaled breath.

Having described specific features of the lung chamber assembly 1018, exemplary processes for cannulation at the pulmonary vein interface 1026, and the data acquisition and display modules of the system 1000, an exemplary lung transplantation procedure is described next with reference to FIGS. 53 and 54.

Figure 53:
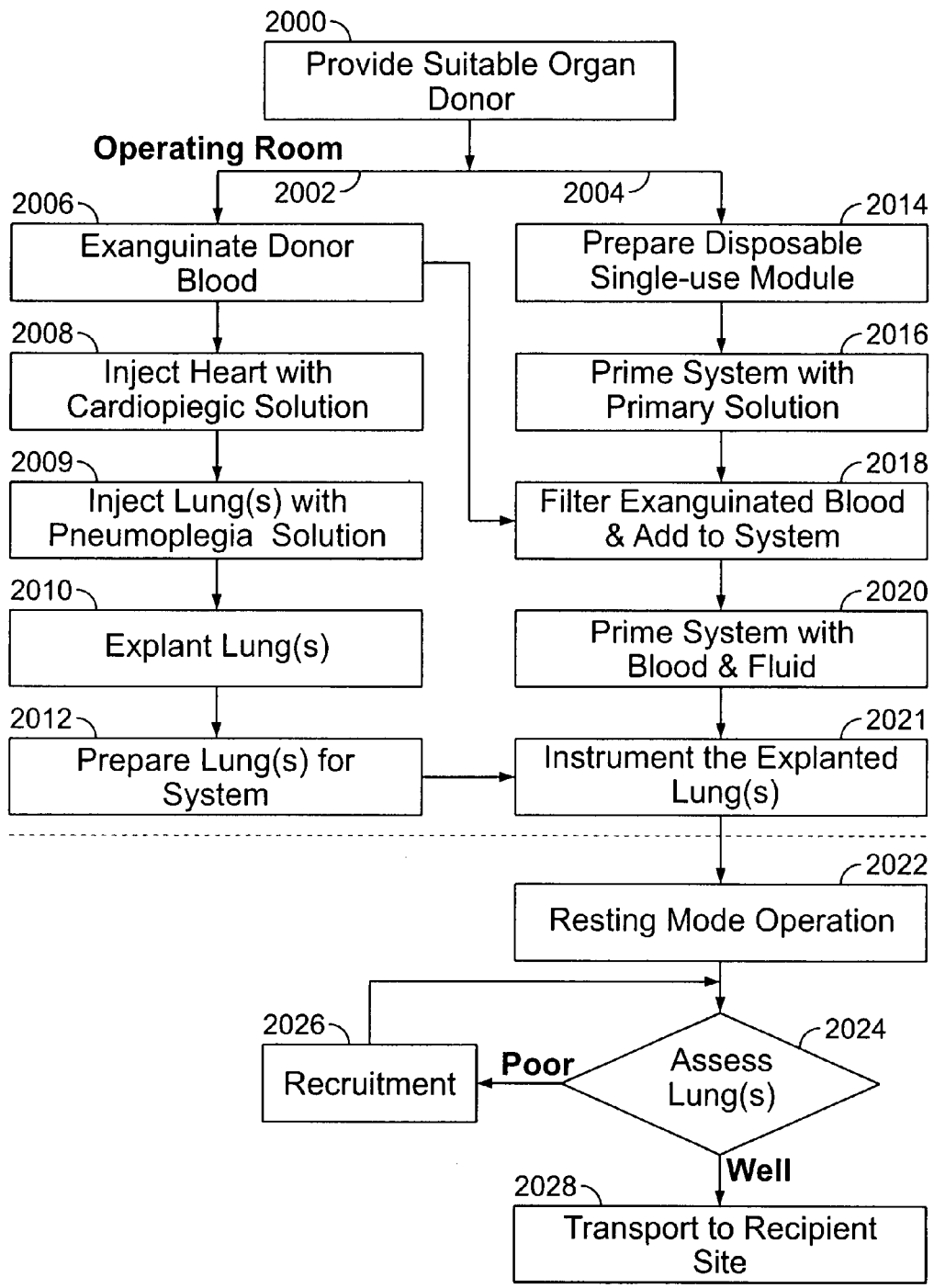
FIG. 53 is a flow diagram depicting a donor-side process for removing lungs from a donor and placing them into the lung care system of FIG. 34 according to an illustrative embodiment of the invention.

The process of obtaining and preparing the lungs 1004 for cannulation and transport as shown in FIG. 53 is similar to the steps shown in FIG. 29A for the care of a heart. This process begins by providing a suitable organ donor at step 2000. The organ donor is brought to a donor location, whereupon the process of receiving and preparing the donor lungs 1004 for cannulation and transport proceeds down two intersecting pathways. The pathways principally involve preparing the system 1000 to receive the donor lungs 1004 and then transport the lungs 1004 via system 1000 to a recipient site. In particular, pathway 2002 includes exsanguinating the donor, arresting the donor's heart, and preparing the lungs 1004 for cannulation into the system 1000. In particular, in the exsanguination step 2006, the donor's blood is removed and set aside so it can be used to perfuse the lungs 1004 during their maintenance on the system 1000. Steps involved in removing blood from the exanguinated donor are described above with respect to FIG. 29A. After the donor's blood is exanguinated, the donor heart is injected in step 2008 with a cardioplegic solution to temporarily halt its beating in preparation for harvesting the lungs 1004.

After the donor's heart is arrested, a pneumoplegia solution is administered to the lungs at step 2009 before the lungs 1004 are explanted from the donor at step 2010 and prepared for loading onto the system 1000 at step 2012. Processes involved in explanting a single lung or a pair of lungs 1004 are explained above with respect to FIGS. 35 and 36.

With continued reference to FIG. 53, after the lungs 1004 are explanted from the donor's body, they are instrumented onto the system 1000 at step 2021 by insertion into the lung chamber assembly 1018 and cannulation at the appropriate interfaces as described above with respect to FIGS. 34 and 48-51.

According to other illustrative embodiments, the lungs 1004 can be transferred directly from the donor to the system 1000 without the use of cardioplegia. In one particular implementation, the donor's lungs 1004 are removed without the donor's heart being arrested and are subsequently instrumented into the system 1000 for maintenance.

During the preparation of the lungs 1004 via path 2002, the system 1000 is prepared through the steps of path 2004 so it is primed and waiting to receive the lungs 1004 for cannulation and transport as soon as the lungs 1004 are prepared. In particular, the system 1000 is prepared in pathway 2004 through a series of steps including providing the single use module 1002 (step 2014), priming the system 1000 with a primary solution (step 2016), filtering the blood from the donor and adding it to the reservoir 160 (step 2018), and priming the system 1000 with a mixture of the blood and the perfusion fluid 108 (step 2020). In certain embodiments, the perfusion fluid 108 includes whole blood. In certain embodiments, the perfusion fluid 108 is partially or completely depleted of leukocytes. In certain embodiments, the perfusion fluid 108 is partially or completely depleted of platelets. The priming, supplemental, and preservative solutions utilized by the organ care system 100 for the maintenance of a heart may also be used in the system 1000. In certain embodiments, the solutions used with the system 100 are used, but new additives including prostaglandin E, Prostacycline, dextran, isuprel, flolan and nitric oxide donors are added while epinephrine is removed. The additives may be generally selected from anti-microbials, vasodilators, and anti-inflammatory drugs. The additives may be delivered to the system 1000 via ports 762 and 774 coupled to the reservoir 160 or via the tracheal interface 1024 through a nebulizer or a bronchoscope. The various solutions utilized by the organ care system 1000 will be described below in further detail.

At step 2022, the system 1000 is selected to operate in the maintenance mode. Different approaches of implementing the maintenance mode are described above with reference to FIGS. 37 and 38. In general, the explanted lungs 1004 are connected into the system 1000. The perfusion fluid 108 is pumped into the lungs 1004 through the pulmonary artery interface 1022 and pumped away from the lungs 1004 through the pulmonary vein interface 1026. A supply of gas, either as an isolated volume or a continuous flow, is provided to the lungs 1004 via the tracheal interface 1024. A flow of a respiratory gas, having a pre-determined composition of gas components, is also provided to the lungs 1004 for use in respiration by the lungs 1004 during perfusion. In addition, at a steady-state of the system 1000, a composition of gas components in the perfusion fluid 108 flowing into the lungs 1004 includes a substantially constant composition of components, and the perfusion fluid 108 flowing away from the lungs 1004 also includes a substantially constant composition of components. Moreover, at step 2024, the instrumented lungs 1004 may be monitored and assessed using a plurality of monitoring components coupled to the system 1000.

Based on the monitored parameters, in some instances, it is desirable to provide recruitment to the lungs 1004 during the maintenance mode (step 2026). For example, the lungs 1004 may be treated with antimicrobials or suctioned to remove fluid and alveoli debris in the trachea 1006. Collapsed alveoli in the lungs 1004 may be inflated using sigh breathing by causing the lungs 1004 to inhale breaths that are of variable volume, such as causing the lungs 1004 to inhale a first breath having a volume that is larger than the volumes of at least two next breaths. In some instances, an operator may perform surgery on the lungs 1004 or provide therapeutic or other treatment, such as immunosuppressive treatments, chemotherapy, genetic testing or irradiation therapy. Additional assessments of the lungs 1004 are described above with respect to FIGS. 37-40.

Figure 54:
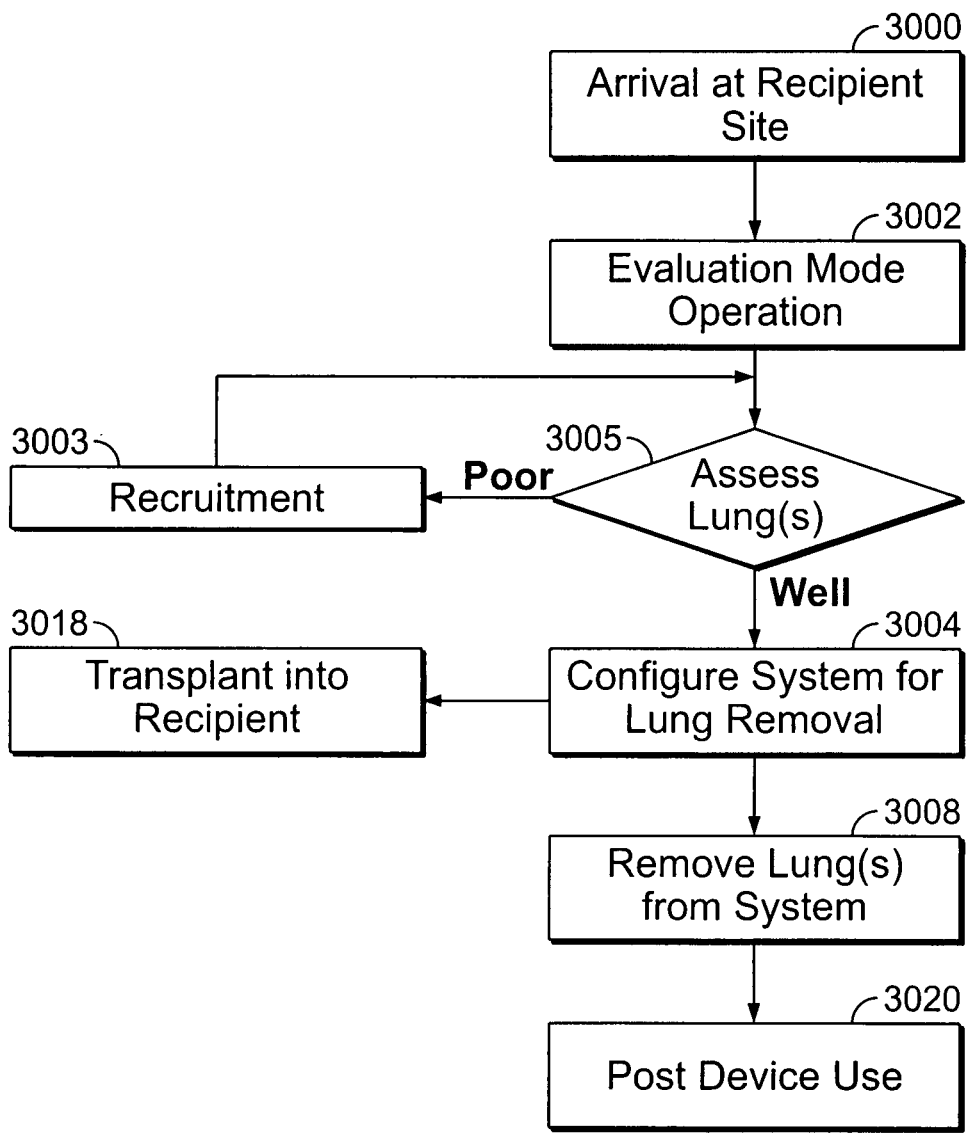
FIG. 54 is a flow diagram depicting a recipient-side process for removing lungs from the lung care system of FIG. 34 and transplanting them into a recipient according to an illustrative embodiment of the invention.

FIG. 54 provides an exemplary process for conducting additional tests on the lungs 1004 while the system 1000 is at the recipient site (step 3000). In particular, at step 3002, the system 1000 is set to operate in the evaluation mode in order to provide a perfusion condition that is suitable for the evaluation of the lungs 1004 to determine their gas-transfer capacity. Additional recruitment can be performed during the evaluation mode at step 3003 based on assessment of the lungs 1004 performed at step 3005. Steps involved in implementing the evaluation mode are described above in detail with reference to FIG. 39. After testing is complete at the recipient site, the lungs 1004 are prepared for implantation into the recipient. This includes configuring the system 1000 for lung removal by powering down the pump 106 to stop the flow of perfusion fluid 108 (step 3004) and, optionally, administering a pneumoplegia solution to the lungs 1004. Next, in step 3008, the lungs 1004 are de-cannulated and removed from the lung chamber assembly 1018. In step 3018, the lungs 1004 are transplanted into the recipient patient by inserting them into the recipient's chest cavity and suturing the various pulmonary connections to their appropriate mating connections within the recipient. In certain embodiments, a portion of the recipient's left atrium may be excised and replaced with one or more of the donor's left atrial cuff 1008 to which the donor's pulmonary veins are attached.

As described above, the system 1000 employs a priming solution, and also a perfusion fluid 108 that combines a nutritional supplement 116 solution and a preservative solution 118 with a blood product or synthetic blood product to form the perfusion fluid 108. The priming, supplement 116, and preservative 118 solutions are described next.

According to certain embodiments, solutions with particular solutes and concentrations are selected and proportioned for the perfusion fluid 108 to enable the lungs 1004 to function at physiologic or near physiologic conditions. For example, such conditions include maintaining lung function at or near a physiologic temperature and/or preserving a lung in a state that permits normal cellular metabolism, such as protein synthesis.

In certain embodiments solutions are formed from compositions by combining components with a fluid, from more concentrated solutions by dilution, or from more dilute solutions by concentration. In exemplary embodiments, suitable solutions include an energy source and one or more amino acids selected and proportioned so that the organ continues its cellular metabolism during perfusion. Cellular metabolism includes, for example conducting protein synthesis while functioning during perfusion. Some illustrative solutions are aqueous based, while other illustrative solutions are non-aqueous, for example organic solvent-based, ionic-liquid-based, or fatty-acid-based.

The solutions may include one or more energy-rich components to assist the organ in conducting its normal physiologic function. These components may include energy rich materials that are metabolizable, and/or components of such materials that an organ can use to synthesize energy sources during perfusion. Exemplary sources of energy-rich molecules include, for example, one or more carbohydrates. Examples of carbohydrates include monosaccharides, disaccharides, oligosaccharides, polysaccharides, or combinations thereof, or precursors or metabolites thereof. While not meant to be limiting, examples of monosaccharides suitable for the solutions include octoses; heptoses; hexoses, such as fructose, allose, altrose, glucose, mannose, gulose, idose, galactose, and talose; pentoses such as ribose, arabinose, xylose, and lyxose; tetroses such as erythrose and threose; and trioses such as glyceraldehyde. While not meant to be limiting, examples of disaccharides suitable for the solutions include (+)-maltose (4-O-(☐-D-glucopyranosyl)-☐-D-glucopyranose), (+)-cellobiose (4-O-(☐-D-glucopyranosyl)-D-glucopyranose), (+)-lactose (4-O-(☐-D-galactopyranosyl)-☐-D-glucopyranose), sucrose (2-O-(☐-D-glucopyranosyl)-☐-D-fructofuranoside). While not meant to be limiting, examples of polysaccharides suitable for the solutions include cellulose, starch, amylose, amylopectin, sulfomucopolysaccharides (such as dermatane sulfate, chondroitin sulfate, sulodexide, mesoglycans, heparan sulfates, idosanes, heparins and heparinoids), and glycogen. In some embodiments, monossacharides, disaccharides, and polysaccharides of both aldoses, ketoses, or a combination thereof are used. One or more isomers, including enantiomers, diastereomers, and/or tautomers of monossacharides, disaccharides, and/or polysaccharides, including those described and not described herein, may be employed in the solutions described herein. In some embodiments, one or more monossacharides, disaccharides, and/or polysaccharides may have been chemically modified, for example, by derivatization and/or protection (with protecting groups) of one or more functional groups. In certain embodiments, carbohydrates, such as dextrose or other forms of glucose are preferred.

Other possible energy sources include adenosine triphosphate (ATP), co-enzyme A, pyruvate, flavin adenine dinucleotide (FAD), thiamine pyrophosphate chloride (co-carboxylase), β-nicotinamide adenine dinucleotide (NAD), β-nicotinamide adenine dinucleotide phosphate (NADPH), and phosphate derivatives of nucleosides, i.e. nucleotides, including mono-, di-, and tri-phosphates (e.g., UTP, GTP, GDF, and UDP), coenzymes, or other bio-molecules having similar cellular metabolic functions, and/or metabolites or precursors thereof. For example, phosphate derivatives of adenosine, guanosine, thymidine (5-Me-uridine), cytidine, and uridine, as well as other naturally and chemically modified nucleosides are contemplated.

In certain embodiments, one or more carbohydrates are provided along with a phosphate source, such as a nucleotide. One exemplary carbohydrate is dextran. The carbohydrate helps enable the organ to produce ATP or other energy sources during perfusion. The phosphate source may be provided directly through ATP, ADP, AMP or other sources. In other illustrative embodiments, a phosphate is provided through a phosphate salt, such as glycerophosphate, sodium phosphate or other phosphate ions. A phosphate may include any form thereof in any ionic state, including protonated forms and forms with one or more counter ions In some instances, additional components are provided to assist the lungs 1004 in conducting its metabolism during perfusion. These components include, for example, forms or derivatives of adenine and/or adenosine, which may be used for ATP synthesis, for maintaining endothelial function, and/or for attenuating ischemia and/or reperfusion injury. According to certain implementations, a magnesium ion source is provided with a phosphate, and in certain embodiments, with adenosine to further enhance ATP synthesis within the cells of the perfused lungs 1004.

Solutions described herein may include one or more amino acids, preferably a plurality of amino acids, to support protein synthesis by the organ's cells. Suitable amino acids include, for example, any of the naturally-occurring amino acids. The amino acids may be, in various enantiomeric or diastereomeric forms. For example, solutions may employ either D- or L-amino acids, or a combination thereof, i.e. solutions enantioenriched in more of the D- or L-isomer or racemic solutions. Suitable amino acids may also be non-naturally occurring or modified amino acids, such as citrulline, orniithine, homocystein, homoserine, β-amino acids such as β-alanine, amino-caproic acid, or combinations thereof.

Certain exemplary solutions include some but not all naturally-occurring amino acids. In some embodiments, solutions include essential amino acids. For example, a solution may be prepared with one or more or all of the following amino-acids:

Glycine
Alanine
Arginine
Aspartic Acid
Glutamic Acid
Histidine
Isoleucine
Leucine
Methionine
Phenylalanine
Proline
Serine
Thereonine
Tryptophan
Tyrosine
Valine
Lysine acetate In certain embodiments, non-essential and/or semi-essential amino acids are not included in the solutions. For example, in some embodiments, asparagine, glutamine, and/ or cysteine are not included. In other embodiments, the solution contains one or more non-essential and/or semi-essential amino acids. Accordingly, in other embodiments, asparagine, glutamine, and/or cysteine are included.

The solutions may also contain electrolytes, particularly calcium ions for facilitating enzymatic reactions, and/or coagulation within the organ. Other electrolytes may be used, such as sodium, potassium, chloride, sulfate, magnesium and other inorganic and organic charged species, or combinations thereof. It should be noted that any component provided hereunder may be provided, where valence and stability permit, in an ionic form, in a protonated or unprotonated form, in salt or free base form, or as ionic or covalent substituents in combination with other components that hydrolyze and make the component available in aqueous solutions, as suitable and appropriate.

In certain embodiments, the solutions contain buffering components. For example, suitable buffer systems include 2-morpholinoethanesulfonic acid monohydrate (MES), cacodylic acid, $H_2CO_3/NaHCO_3$ ($pK_{a1}$), citric acid ($pK_{a3}$), bis(2-hydroxyethyl)-imino-tris-(hydroxymethyl)-methane (Bis-Tris), N-carbamoylmethylimidino acetic acid (ADA), 3-bis[tris(hydroxymethyl)methylamino]propane (Bis-Tris Propane) ($pK_{a1}$), piperazine-1,4-bis(2-ethanesulfonic acid) (PIPES), N-(2-Acetamido)-2-aminoethanesulfonic acid (ACES), imidazole, N,N-bis(2-hydroxyethyl)-2-aminoethanesulfonic acid (BES), 3-(N-morpholino)propanesulphonic acid (MOPS), $NaH_2PO_4/Na_2HPO_4$ ($pK_{a2}$), N-tris(hydroxymethyl)methyl-2-aminoethanesulfonic acid (TES), N-(2-hydroxyethyl)-piperazine-N'-2-ethanesulfonic acid (HEPES), N-(2-hydroxyethyl)piperazine-N'-(2-hydroxypropanesulfonic acid) (HEPPSO), triethanolamine, N-[tris(hydroxymethyl)methyl]glycine (Tricine), tris hydroxymethylaminoethane (Tris), glycineamide, N,N-bis(2-hydroxyethyl) glycine (Bicine), glycylglycine ($pK_{a2}$), N-tris(hydroxymethyl)methyl-3-aminopropanesulfonic acid (TAPS), or a combination thereof. In some embodiments, the solutions contain sodium bicarbonate, potassium phosphate, or TRIS buffer.

In another aspect, a blood product is provided with the solution to support the organ during metabolism. Exemplary suitable blood products may include whole blood, and/or one or more components thereof such as blood serum, plasma, albumin, and red blood cells. In embodiments where whole blood is used, the blood may be passed through a leukocyte and platelet depleting filter to reduce pyrogens, antibodies and/or other items that may cause inflammation in the organ. Thus, in some embodiments, the solution employs whole blood that has been at least partially depleted of leukocytes and/or whole blood that has been at least partially depleted of platelets.

The solutions are preferably provided at a physiologic temperature and maintained thereabout throughout perfusion and recirculation. As used herein, "physiologic temperature" is referred to as temperatures between about 25° C. and about 37° C., for example, between about 30° C. and about 37° C., such as between about 34° C. and about 37° C.

Table 1 sets forth components that are used in an exemplary aqueous priming solution. The component amounts in Table 1 are relative to each other and to the amount of aqueous solvent employed in the solution (about 500 mL in the exemplary embodiment) and may be scaled as appropriate. In certain embodiments, the quantity of aqueous solvent varies ± about 10%.

TABLE 1

Composition of Exemplary Priming Solution (about 500 mL aqueous solution)

| Component | Amount | Specification |
|---|---|---|
| Dextran | 20 g | ±about 50% |
| Sodium Chloride | 4.8 g | ±about 10% |
| Potassium Chloride | 185 mg | ±about 10% |
| Magnesium Sulfate heptahydrate | 185 mg | ±about 10% |
| Sodium Glycerophosphate | 900 mg | ±about 10% |

With regard to the nutritional supplement solution 116, in certain embodiments it includes one or more carbohydrates and may also include a phosphate source. The nutritional supplement solution 116 is typically maintained at a pH of about 5.0 to about 6.5, for example about 5.5 to about 6.0.

Table 2 sets forth components that are used in an exemplary nutritional supplement solution 116. In some embodiments, the nutritional solution 116 further includes sodium glycerol phosphate. The amount of components in Table 2 is relative to the amount of aqueous solvent employed in the solution 116 (about 500 mL) and may be scaled as appropriate. In some embodiments, the quantity of aqueous solvent varies ± about 10%.

TABLE 2

Components of Exemplary Nutritional Solution (about 500 mL)

| Component | Amount | Specification |
|---|---|---|
| Dextrose | 40 g | ±about 10% |

In certain embodiments the nutritional solution 116 includes one or more carbohydrates and may also include a phosphate source. The nutritional solution 116 is typically maintained at a pH of about 5.0 to about 6.5, for example of about 5.5 to about 6.0.

Other components may be added to the preservation solution 118, including, for example, adenosine, magnesium, phosphate, calcium, and/or sources thereof. In some instances, additional components are provided to assist the organ in conducting its metabolism during perfusion. These components include, for example, forms of adenosine, which may be used for ATP synthesis, for maintaining endothelial function, and/or for attenuating ischemia and/or reperfusion injury. Components may also include other nucleosides, such as guanosine, thymidine (5-Me-uridine), cytidine, and uridine, as well as other naturally and chemically modified nucleosides including nucleotides thereof. According to some implementations, a magnesium ion source is provided with a phosphate source, and in certain embodiments, with adenosine to further enhance ATP synthesis within the cells of the perfused organ. A plurality of amino acids may also be added to support protein synthesis by the heart's 102 cells. Applicable amino acids may include, for example, any of the naturally-occurring amino acids, as well as those mentioned above.

Table 3 sets forth components that may be used in a solution 118 for preserving an organ as described herein. The solution 118 may include one or more of the components described in Table 3.

TABLE 3

Component of Exemplary Composition for Preservative Solution

| Component | Exemplary Concentration Ranges in Preservative Solution |
|---|---|
| Alanine | about 1 mg/L-about 10 g/L |
| Arginine | about 1 mg/L-about 10 g/L |
| Asparagine | about 1 mg/L-about 10 g/L |
| Aspartic Acid | about 1 mg/L-about 10 g/L |
| Cysteine | about 1 mg/L-about 10 g/L |
| Cystine | about 1 mg/L-about 10 g/L |
| Glutamic Acid | about 1 mg/L-about 10 g/L |
| Glutamine | about 1 mg/L-about 10 g/L |
| Glycine | about 1 mg/L-about 10 g/L |
| Histidine | about 1 mg/L-about 10 g/L |
| Hydroxyproline | about 1 mg/L-about 10 g/L |
| Isoleucine | about 1 mg/L-about 10 g/L |
| Leucine | about 1 mg/L-about 10 g/L |
| Lysine | about 1 mg/L-about 10 g/L |
| Methionine | about 1 mg/L-about 10 g/L |
| Phenylalanine | about 1 mg/L-about 10 g/L |
| Proline | about 1 mg/L-about 10 g/L |
| Serine | about 1 mg/L-about 10 g/L |
| Threonine | about 1 mg/L-about 10 g/L |
| Tryptophan | about 1 mg/L-about 10 g/L |
| Tyrosine | about 1 mg/L-about 10 g/L |
| Valine | about 1 mg/L-about 10 g/L |
| Adenine | about 1 mg/L-about 10 g/L |
| ATP | about 10 ug/L-about 100 g/L |
| Adenylic Acid | about 10 ug/L-about 100 g/L |
| ADP | about 10 ug/L-about 100 g/L |
| AMP | about 10 ug/L-about 100 g/L |
| Ascorbic Acid | about 1 ug/L-about 10 g/L |
| D-Biotin | about 1 ug/L-about 10 g/L |
| Vitamin D-12 | about 1 ug/L-about 10 g/L |
| Cholesterol | about 1 ug/L-about 10 g/L |
| Dextrose (Glucose) | about 1 g/L-about 150 g/L |
| Multi-vitamin Adult | about 1 mg/L-about 20 mg/L or 1 unit vial |
| Folic Acid | about 1 ug/L-about 10 g/L |
| Glutathione | about 1 ug/L-about 10 g/L |
| Guanine | about 1 ug/L-about 10 g/L |
| Inositol | about 1 g/L-about 100 g/L |
| Riboflavin | about 1 ug/L-about 10 g/L |
| Ribose | about 1 ug/L-about 10 g/L |
| Thiamine | about 1 mg/L-about 10 g/L |
| Uracil | about 1 mg/L-about 10 g/L |
| Calcium Chloride | about 1 mg/L-about 100 g/L |
| NaHCO$_3$ | about 1 mg/L-about 100 g/L |
| Magnesium sulfate | about 1 mg/L-about 100 g/L |
| Potassium chloride | about 1 mg/L-about 100 g/L |
| Sodium glycerophosphate | about 1 mg/L-about 100 g/L |
| Sodium Chloride | about 1 mg/L-about 100 g/L |
| Sodium Phosphate | about 1 mg/L-about 100 g/L |
| Insulin | about 1 IU-about 150 IU |
| Serum albumin | about 1 g/L-about 100 g/L |
| Pyruvate | about 1 mg/L-about 100 g/L |
| Coenzyme A | about 1 ug/L-about 10 g/L |
| Serum | about 1 ml/L-about 100 ml/L |
| Heparin | about 500 U/L-about 1500 U/L |
| Solumedrol | about 200 mg/L-about 500 mg/L |
| Dexamethasone | about 1 mg/L-about 1 g/L |
| FAD | about 1 ug/L-about 10 g/L |
| NADP | about 1 ug/L-about 10 g/L |
| adenosine | about 1 mg/L-about 10 g/L |
| guanosine | about 1 mg/L-about 10 g/L |
| GTP | about 10 ug/L-about 100 g/L |
| GDP | about 10 ug/L-about 100 g/L |
| GMP | about 10 ug/L-about 100 g/L |

Table 4 sets forth components that are used in an exemplary preservative solution 118. The amounts provided in Table 4 describe preferred amounts relative to other components in the table and may be scaled to provide compositions of sufficient quantity. In some embodiments, the amounts listed in Table 4 can vary by ± about 10% and still be used in the solutions described herein.

TABLE 4

Components of Exemplary Preservative Solution

| Component | Amount |
|---|---|
| Adenosine | About 675 mg-About 825 mg |
| Calcium Chloride dihydrate | About 2100 mg-About 2600 mg |
| Glycine | About 315 mg-About 385 mg |
| L-Alanine | About 150 mg-About 200 mg |
| L-Arginine | About 600 mg-About 800 mg |
| L-Aspartic Acid | About 220 mg-About 270 mg |
| L-Glutamic Acid | About 230 mg-About 290 mg |
| L-Histidine | About 200 mg-About 250 mg |
| L-Isoleucine | About 100 mg about 130 mg |
| L-Leucine | About 300 mg-About 380 mg |
| L-Methionine | About 50 mg-About 65 mg |
| L-Phenylalanine | About 45 mg-About 60 mg |
| L-Proline | About 110 mg-About 140 mg |
| L-Serine | About 80 mg-About 105 mg |
| L-Thereonine | About 60 mg-About 80 mg |
| L-Tryptophan | About 30 mg-About 40 mg |
| L-Tyrosine | About 80 mg-About 110 mg |
| L-Valine | About 150 mg-About 190 mg |
| Lysine Acetate | About 200 mg-About 250 mg |
| Magnesium Sulfate Heptahydrate | About 350 mg-About 450 mg |
| Potassium Chloride | About 15 mg-About 25 mg |
| Sodium Chloride | About 1500 mg-About 2000 mg |
| Dextrose | About 25 gm-About 120 gm |
| Insulin | About 75 Units-About 150 Units |
| MVI-Adult | 1 unit vial |
| SoluMedrol | about 200 mg-500 mg |
| Sodium Bicarbonate | About 10-25 mEq |

In the exemplary embodiment of a solution 118, the components in Table 4 are combined in the relative amounts listed therein per about 1 L of aqueous fluid to form the solution 118. In some embodiments, the components in Table 4 are combined in the relative amounts listed therein per about 500 mL of aqueous fluid and then combined with the solution 116, also about 500 mL, to provide a maintenance solution 116/118 of about 1 L of aqueous fluid. In some embodiments the quantity of aqueous fluid in solutions 116, 118, and/or 116/118 can vary ± about 10%. The pH of the solution 118 may be adjusted to be between about 7.0 and about 8.0, for example about 7.3 and about 7.6. The solution 118 may be sterilized, for example by autoclaving, to provide for improved purity.

Table 5 sets forth another exemplary preservative solution 118, comprising a tissue culture media having the components identified in Table 5 and combined with an aqueous fluid, which may be used in the perfusion fluid 108 as described herein. The amounts of components listed in Table 5 are relative to each other and to the quantity of aqueous solution used. In some embodiments, about 500 mL of aqueous fluid is used. In other embodiments about 1 L of aqueous fluid is used. For example, combination of about 500 mL of preservative solution 118 with 500 mL of nutritional solution 116 affords a maintenance solution 116/118 of about 1 L. In some embodiments, the quantity of aqueous solution can vary ± about 10%. The component amounts and the quantity of aqueous solution may be scaled as appropriate for use. The pH of the preservative solution 118, in this embodiment, may be adjusted to be about 7.0 to about 8.0, for example about 7.3 to about 7.6.

TABLE 5

Composition of Another Exemplary Preservative Solution (about 500 mL aqueous solution)

| Tissue Culture Component | Amount | Specification |
| --- | --- | --- |
| Adenosine | 750 mg | ±about 10% |
| Calcium Chloride dihydrate | 2400 mg | ±about 10% |
| Glycine | 350 mg | ±about 10% |
| L-Alanine | 174 mg | ±about 10% |
| L-Arginine | 700 mg | ±about 10% |
| L-Aspartic Acid | 245 mg | ±about 10% |
| L-Glutamic Acid | 258 mg | ±about 10% |
| L-Histidine | 225 mg | ±about 10% |
| L-Isoleucine | 115.5 mg | ±about 10% |
| L-Leucine | 343 mg | ±about 10% |
| L-Methionine | 59 mg | ±about 10% |
| L-Phenylalanine | 52 mg | ±about 10% |
| L-Proline | 126 mg | ±about 10% |
| L-Serine | 93 mg | ±about 10% |
| L-Thereonine | 70 mg | ±about 10% |
| L-Tryptophan | 35 mg | ±about 10% |
| L-Tyrosine | 92 mg | ±about 10% |
| L-Valine | 171.5 mg | ±about 10% |
| Lysine Acetate | 225 mg | ±about 10% |
| Magnesium Sulfate Heptahydrate | 400 mg | ±about 10% |
| Potassium Chloride | 20 mg | ±about 10% |
| Sodium Chloride | 1750 mg | ±about 10% |

Since amino acids are the building blocks of proteins, the unique characteristics of each amino acid impart certain important properties on a protein such as the ability to provide structure and to catalyze biochemical reactions. The selection and concentrations of the amino acids provided in the preservative solutions provide support of normal physiologic functions such as metabolism of sugars to provide energy, regulation of protein metabolism, transport of minerals, synthesis of nucleic acids (DNA and RNA), regulation of blood sugar and support of electrical activity, in addition to providing protein structure. Additionally, the concentrations of specific amino acids found in the preservative solutions can be used to predictably stabilize the pH of the maintenance solution 116/118 and perfusion fluid 108.

In one embodiment, a maintenance solution 116/118 is made from a combination of the preservative solution 118, including one or more amino acids, and the nutritional solution 116, including one or more carbohydrates, such as glucose or dextrose. The maintenance solution 116/118 may also have additives, such as those described herein, administered at the point of use just prior to infusion into the organ perfusion system. For example, additional additives that can be included with the solution or added at the point of use by the user include hormones and steroids, such as dexamethasone and insulin, prostacycline and other members of the prostoglandine family, beta-1-agonists (e.g., albuterol, isopreternaol), vitamins, such as an adult multi-vitamin, for example adult multivitamins for infusion, such as MVI-Adult. Additional small molecules and large bio-molecules may also be included with the solution or added at the point of use by the user at port 762, for example, therapeutics and/or components typically associated with blood or blood plasma, such as albumin.

The solutions may include therapeutic components to help maintain the lungs 1004 and protect them against ischemia, reperfusion injury and other ill effects during perfusion, to help mitigate edema, or provide general endothelial tissue support for the lungs 1004. In certain exemplary embodiments these components may include hormones (e.g., insulin), vitamins (e.g., an adult multi-vitamin, such as multi-vitamin MVI-Adult), and/or steroids (e.g., dexamethasone and SoluMedrol). In some embodiments, therapeutics that are included in the compositions and solutions for organ maintenance to help mitigate edema, provide endothelial support, and otherwise provide preventative or prophylactic treatment to the lungs 1004. In certain embodiments, the systems described herein include hormones, such as thyroid hormones, for example $T_3$ and/or $T_4$ thyroid hormones added to the nutritional solution 116, the preservative solution 118, and/or the maintenance solutions 116/118 either before or during perfusion of the organ. Additional exemplary therapeutics include isuprel, flolan, prostacyclin or other prostaglandin, beta-1-agonists, beta-2-antagonists, brochodilators, isoproterenol, pentoxifylline, and nitric oxide donors (e.g., L-arginine, nitroglycerine, nitroprusside). The above therapeutics may also be added directly to the system, for example, to the perfusion fluid 108, before or during perfusion of the organ. In certain embodiments, colloids are added, such as dextran, albumin, hydroxyethyl starches, or gelatins. Other components that may be added include anti-microbial agents, anti-fungal agents, anti-viral agents, vasodilators, surfactants adapted to resist collapsing of alveoli within the lung and anti-inflammatory drugs.

In particular, the addition of dextran offers numerous benefits including improving erythrocyte deformability, preventing erythrocyte aggregation, inducing disbanding of already aggregated cells, improving pulmonary circulation and preserving endothelial-epithelial membrane. Dextran also has anti-thrombotic effects by being able to coat endothelial surfaces and platelets. The addition of prostaglandins into various solutions induce effects such as vasodilation of pulmonary vascular bed, inhibition of platelet aggregation, bronchilation, reducing endothelia permeability and reducing neutrophil adhesion. In addition, nitric oxide is used to treat ischemia-reperfusion injury of the lungs 1004 because it can improve ventilation-perfusion mismatch and decrease pulmonary artery pressures. Isoproterenol, as a therapeutic agent, acts a non-selective beta-adrenergic agonist. It is adapted to relax almost all varieties of smooth muscles, hence preventing or relieving broncho-constriction and producing pulmonary vasodilation. Moreover, therapeutics such as surfactants prevent the collapsing of alveoli within the lungs 1004 during the breathing cycle as well as protect the lungs 1004 from injuries and infections caused by foreign bodies and pathogens. Pentoxifylline, as a therapeutic agent, ameliorates ischemia-reperfusion injury by, for example, inhibiting leukocyte sequestration in the lungs 1004, thus preventing the release of free radicals and cytokin.

The one or more therapeutics or other additives may be delivered to the lung through the tracheal interface 1024 via a nebulizer, or added to the perfusion fluid 108 through the maintenance solution, or added by injection directly into the perfusion fluid reservoir at the point of use. In certain embodiments, therapeutic agents such as nitric oxide are provided indirectly to the explanted lungs 1004 through the administration of an upstream precursor molecule such as L-arginine or through the infusion of a nitric oxide donor such as nitroglycerin or nitroprusside. In certain embodiments, therapeutics such as bronchodilators are provided to the lungs 1004 in an injectable form into the perfusion fluid 108 or through the tracheal interface 1024 in a nebulized form. In certain embodiments, exogenous surfactants are delivered to the lungs 1004 through the tracheal interface 1024 or provided to different sections of the lungs 1004 using bronchoscopy. In certain embodiments, pentoxifylline is added to the perfusion fluid 108 in an injectable form.

With further reference to Table 4, certain components used in the exemplary preservation solution 118 are molecules, such as small organic molecules or large bio-molecules, that would be inactivated, for example through decomposition or denaturing, if passed through sterilization. According to the system 100, the inactivatable components of the solution 118 may be prepared separately from the remaining components of the solution 118. The separate preparation involves separately purifying each component through known techniques. The remaining components of the solution 118 are sterilized, for example through an autoclave, then combined with the biological components.

Table 6 lists certain biological components that may be separately purified and added to the solutions described herein after sterilization, according to this two-step process. These additional or supplemental components may be added to solutions 118, 116, 116/118, the priming solution or a combination thereof individually, in various combinations, all at once as a composition, or as a combined solution. For example, in certain embodiments, the epinephrine, insulin, and MVI-Adult, listed in Table 6, are added to the maintenance solution 116/118. In another example, the SoluMedrol and the sodium bicarbonate, listed in Table 6, are added to the priming solution. The additional components may also be combined in one or more combinations or all together and placed in solution before being added to solutions 116, 118, 116/118, and/or the priming solution. In some embodiments, the additional components are added directly to the perfusion fluid 108 through port 762. The component amounts listed in Table 6 are relative to each other and/or to the amounts of components listed in one or more of Tables 1-5 as well as the amount of aqueous solution used in preparing solutions 116, 118, 116/118, and/or the priming solution and may be scaled as appropriate for the amount of solution required.

TABLE 6

Exemplary Biological Components Added Prior to Use

| Component | Amount | Type | Specification |
|---|---|---|---|
| Insulin | about 100 Units | Hormone | ±about 10% |
| MVI-Adult | 1 mL unit vial | Vitamin | ±about 10% |
| SoluMedrol | About 250 mg | Steroid | ±about 10% |
| Sodium Bicarbonate | About 20 mEq | Buffer | ±about 10% |

In one embodiment, a composition for use in a maintenance solution 116/118 is provided comprising one or more carbohydrates, one or more organ stimulants, and a plurality of amino acids that do not include asparagine, glutamine, or cysteine. The composition may also include other substances, such as those used in solutions described herein.

In another embodiment, a system for perfusing an organ, such as a heart, is provided comprising an organ and a substantially cell-free composition, comprising one or more carbohydrates, one or more organ stimulants, and a plurality of amino acids that do not include asparagine, glutamine, or cysteine. Substantially cell-free includes systems that are substantially free from cellular matter; in particular, systems that are not derived from cells. For example, substantially cell-free includes compositions and solutions prepared from non-cellular sources.

In another aspect, the solutions 116 and 118 may be provided in the form of a kit that includes one or more organ maintenance solutions. An exemplary maintenance solution may include components identified above in one or more fluid solutions for use in an organ perfusion fluid 108. In certain embodiments, the maintenance solution 116/118 may include multiple solutions, such as a preservation solution 118 and a nutritional solution 116 and/or a supplemental composition or solution, or may include dry components that may be regenerated in a fluid to form one or more solutions 116/118. The kit may also comprise components from the solutions 116 and/or 118 in one or more concentrated solutions which, on dilution, provide a preservation, nutritional, and/or supplemental solution as described herein. The kit may also include a priming solution. In an exemplary embodiment, the maintenance solution includes a preservation solution 118 and a nutritional solution 116 such as those described above, and a priming solution such as that described above.

In certain embodiments, the kit is provided in a single package, wherein the kit includes one or more solutions (or components necessary to formulate the one or more solutions by mixing with an appropriate fluid), and instructions for sterilization, flow and temperature control during perfusion and use and other information necessary or appropriate to apply the kit to organ perfusion. In certain embodiments, a kit is provided with only a single solution 116, 118 and/or 116/118 (or set of dry components for use in a solution upon mixing with an appropriate fluid), and the single solution 116, 118 and/or 116/118 (or set of dry components) is provided along with a set of instructions and other information or materials necessary or useful to operate the solution 116, 118 and/or 116/118 in the system 100.

In another aspect, the systems, solutions and methods may be used to deliver therapeutics to an organ during perfusion. For example, one or more of the solutions and/or systems described above may include one or more drugs, biologics, gene therapy vectors, or other therapeutics which are delivered to the organ during perfusion. Suitable exemplary therapeutics may include drugs, biologics, or both. Suitable drugs may include, for example, anti fungals, anti-microbials or anti-biotics, anti-inflamatories, anti-proliferatives, anti-virals, steroids, retinoids, NSAIDs, vitamin D3 and vitamin D3 analogs, calcium channel blockers, complement neutralizers, ACE inhibitors, immuno-suppressants, and other drugs. Suitable biologics may include proteins; suitable biologics may also include vectors loaded with one or more genes for gene therapy application.

For example, suitable steroids include but are not limited to androgenic and estrogenic steroid hormones, androgen receptor antagonists and 5-α-reductase inhibitors, and corticosteroids. Specific examples include but are not limited to alclometasone, clobetasol, fluocinolone, fluocortolone, diflucortolone, fluticasone, halcinonide, mometasone, prednisone, prednisolone, methylprednisolone, triamcinolone, betamethasone, and dexamethasone, and various esters and acetonides thereof.

Suitable retinoids include but are not limited to retinol, retinal, isotretinoin, acitretin, adapalene, tazarotene, and bexarotene.

Suitable NSAIDs include but are not limited to naproxen, suprofen, ketoprofen, ibuprofen, flurbiprofen, diclofenac, indomethacin, celecoxib, and rofecoxib.

Suitable vitamin D3 analogues include but are not limited to doxercalciferol, seocalcitol, calcipotriene, tacalcitol, calcitriol, ergocalciferol, and calcifediol.

Suitable anti-viral agents include but are not limited to trifluridine, cidofovir, acyclovir, penciclovir, famciclovir, valcyclovir, gancyclovir, and docosanol.

Suitable human carbonic anhydrase inhibitors include but are not limited to methazoliamide, acetazolamide, and dorzolamide.

Suitable anti-proliferative agents include but are not limited to 5-FU, taxol, daunorubicin, and mitomycin.

Suitable antibiotic (antimicrobial) agents include but are not limited to bacitracin, chlorhexidine, chlorhexidine digluconate, ciprofloxacin, clindamycin, erythromycin, gentamicin, lomefloxacin, metronidazole, minocycline, moxifloxacin, mupirocin, neomycin, ofloxacin, polymyxin B, rifampicin, ruflozacin, tetracycline, tobramycin, triclosan, and vancomycin. The antiviral and antibacterial prodrugs described herein may be used to treat appropriately responsive systemic infections.

In certain embodiments, a solution system for use in a perfusion fluid 108, comprising a first chamber containing a first solution, such as a preservation solution 118, that includes one or more cardio stimulants and a plurality of amino acids that do not include asparagine, glutamine, or cysteine, and a second chamber, containing a second solution, such as a nutritional solution 116, that includes one or more carbohydrates, such as dextrose. The system may also include a sterilization system for sterilizing the first solution and the second solution prior to using the solutions to perfuse a heart. In some embodiments, one or more of the solutions 118 and 116 includes one or more therapeutics. In some embodiments the solution system includes a third chamber comprising a priming solution, such as is described above, which may have one or more carbohydrates. In certain embodiments, the first solution 118 includes adenosine, insulin, one or more immuno-suppressants, a multi-vitamin, and/or one or more electrolytes.

It is to be understood that while the invention has been described in conjunction with the various illustrative embodiments, the forgoing description is intended to illustrate and not limit the scope of the invention, which is defined by the scope of the appended claims. For example, a variety of systems and/or methods may be implemented based on the disclosure and still fall within the scope of the invention. Other aspects, advantages, and modifications are within the scope of the following claims. All references cited herein are incorporated by reference in their entirety and made part of this application.

What is claimed is:

1. A lung care system comprising:
   a portable multiple use module including a portable chassis;
   a first electromechanical connector disposed on the portable multiple use module;
   a single use disposable module including:
      a disposable structure including a second electromechanical connector disposed thereon that is sized and shaped for interlocking the single use disposable module with the multiple use module for electromechanical inter-operation with the multiple use module, wherein the second electromechanical connector is configured to electromechanically couple to the first electromechanical connector, and
      a lung chamber assembly having a first interface for allowing a flow of perfusion fluid into the lung, a second interface for allowing ventilation of the lung, and a third interface for allowing a flow of the perfusion fluid away from the lung;
      a pump adapted to flow the perfusion fluid into and away from the lung; and
      a respiratory gas source having a predetermined composition of oxygen;
   a ventilator coupled to the respiratory gas source and the second interface;
   a gas exchange device configured to controllably alter a composition of a first gas component in the perfusion fluid;
   at least one processor coupled to a non-transitory memory storing instructions that, when executed by the at least one processor:
      cause the ventilator to ventilate the lung by flowing respiratory gas into the lung via the second interface in periodic breaths containing a predetermined volume of and pressure of the respiratory gas;
      cause the ventilator to maintain a predetermined minimum positive end-expiratory pressure, and
      cause the gas exchange device to modulate the composition of the first gas component in the perfusion fluid as a function of the amount of oxygen in the respiratory gas provided to the lung;
   wherein the lung chamber assembly includes a flexible membrane that suspends the lung within the lung chamber assembly for supporting the lung and maintaining a shape of the lung.

2. The system of claim 1, wherein the first interface includes a pulmonary artery cannula, and the second interface includes a cannula disposed within a tracheal conduit of the lung.

3. The system of claim 1, wherein the third interface includes a cup shaped interface and the cup-shaped interface includes a plurality of openings at respective heights along a sidewall of the interface.

4. The system of claim 3, wherein the third interface includes a selector valve in fluid communication with the plurality of openings for controllably drawing the perfusion fluid in the cup-shaped interface away from the lung chamber assembly via a selected one of the plurality of openings and an outlet conduit.

5. The system of claim 1, wherein the flexible membrane substantially prevents the lung from contacting at least one wall of the lung chamber assembly.

6. The system of claim 1, wherein the flexible membrane is a netting.

7. The system of claim 1, wherein the lung chamber assembly has a shape of a ribcage.

8. The system of claim 1, wherein the lung chamber assembly includes a diaphragm structure.

9. The system of claim 1, comprising a heater for maintaining the perfusion fluid provided to the lung chamber assembly at a near physiologic temperature.

10. The system of claim 9, wherein the temperature is between about 30° C. and about 37° C.

11. The system of claim 10, wherein the temperature is between about 34° C. and about 37° C.

12. The system of claim 1, wherein the gas exchange device includes a gas select switch for selecting from a plurality of gas supplies to modulate the composition of a gas component in the perfusion fluid.

13. The system of claim 1, comprising an isolated volume compartment cannulated to a tracheal conduit of the lung and adapted to ventilate the lung during perfusion.

14. The system of claim 1, comprising an oxygenation sensor for measuring an oxygen content in the perfusion fluid.

15. The system of claim 1, comprising an oxygenation sensor adapted to provide a signal indicative of a hematocrit measurement of the perfusion fluid.

16. A lung care system comprising:
   a portable multiple use module including a portable chassis;
   a first electromechanical connector disposed on the portable multiple use module;
   a single use disposable module including,
      a disposable structure including a second electromechanical connector disposed thereon that is sized and shaped for interlocking the single use disposable module with the multiple use module for electromechanical inter-operation with the multiple use module, wherein the second electromechanical connector is configured to electromechanically couple to the first electromechanical connector, and
      a lung chamber assembly having a first conduit for allowing a flow of perfusion fluid into the lung, a second conduit for allowing ventilation of the lung, and a third conduit for allowing a flow of the perfusion fluid away from the lung;
   a pump adapted to flow the perfusion fluid into and away from the lungs; and
   a respiratory gas source in communication with the second conduit;
   a ventilator coupled to the respiratory gas source and the second conduit;
   a gas exchange device configured to controllably alter a composition of a first gas component in the perfusion fluid; and
   at least one processor coupled to a non-transitory memory storing instructions that, when executed by the at least one processor:
      cause the ventilator to ventilate the lung by flowing respiratory gas into the lung via the second conduit in periodic breaths containing a predetermined volume of and pressure of the respiratory gas;
      cause the ventilator to maintain a predetermined minimum positive end-expiratory pressure, and
      cause the gas exchange device to modulate the composition of the first gas component in the perfusion fluid as a function of the amount of oxygen in the respiratory gas provided to the lung;
   a perfusion circuit in communication with the first and third conduits wherein the third conduit is configured to connect to pulmonary veins of a lung and a left atrial cuff.

17. The system of claim 16, wherein the third conduit has a funnel shaped end.

18. The system of claim 1 wherein the single use disposable module further includes an optical interconnection configured to be coupled to a corresponding connection on the multiple use module.

19. The system of claim 16 wherein the single use disposable module further includes an optical interconnection configured to be coupled to a corresponding connection on the multiple use module.

* * * * *